US011129890B1

United States Patent
Sun

(10) Patent No.: US 11,129,890 B1
(45) Date of Patent: Sep. 28, 2021

(54) **NON-INTEGRATING *HIV-1* COMPRISING MUTANT RT/IN PROTEINS AND THE SARS-COV-2 SPIKE PROTEIN**

(71) Applicant: Vigene Biosciences Inc., Rockville, MD (US)

(72) Inventor: Zairen Sun, Rockville, MD (US)

(73) Assignee: Vigene Biosciences, Inc., Rockville, MD (US)

( * ) Notice: Subject to any disclaimer, the term of this patent is extended or adjusted under 35 U.S.C. 154(b) by 0 days.

(21) Appl. No.: 16/877,839

(22) Filed: May 19, 2020

(51) Int. Cl.
| | |
|---|---|
| *A61K 39/21* | (2006.01) |
| *C12N 7/00* | (2006.01) |
| *C12N 15/86* | (2006.01) |
| *A61K 39/215* | (2006.01) |
| *A61K 39/00* | (2006.01) |

(52) U.S. Cl.
CPC ............ *A61K 39/21* (2013.01); *A61K 39/215* (2013.01); *C12N 7/00* (2013.01); *C12N 15/86* (2013.01); *A61K 2039/543* (2013.01); *C12N 2740/15034* (2013.01); *C12N 2740/15041* (2013.01); *C12N 2740/15051* (2013.01); *C12N 2740/16041* (2013.01); *C12N 2740/16061* (2013.01); *C12N 2740/16062* (2013.01); *C12N 2740/16211* (2013.01); *C12N 2740/16222* (2013.01)

(58) Field of Classification Search
CPC ...... A61K 39/21; A61K 39/215; C12N 15/86; C12N 2740/16041; C12N 2740/15041; C12N 2740/16061; C12N 2740/16211; C12N 2740/16222; C12N 2740/16062; C12N 2740/15034; C12N 2740/15051
See application file for complete search history.

(56) References Cited

FOREIGN PATENT DOCUMENTS

CN 111088283 A * 5/2020

OTHER PUBLICATIONS

Negri, D. R. M., et al., Sep. 2007, Successful immunization with a single injection of non-integrating lentiviral vector, Mol. Ther. 15(9):1716-1723.*

(Continued)

*Primary Examiner* — Jeffrey S Parkin
(74) *Attorney, Agent, or Firm* — Jeffrey I. Auerbach; AuerbachSchrot LLC

(57) ABSTRACT

The present invention is directed to recombinant lentiviral particles that array the SARS-CoV-2 spike (S) protein on their surface ("SARS-CoV-2 S Protein Lentiviral Particles"), and that optionally comprise an additional copy of a polynucleotide encoding the SARS-CoV-2 spike (S) protein in their viral genome, and to methods for the production of such lentiviral particles. The invention particularly pertains to such SARS-CoV-2 S Protein Lentiviral Particles that have been engineered to be incapable of mediating the integration of their lentiviral genome into the chromosomes of infected cells and/or to be incapable of mediating the reverse transcription of their lentiviral genome. The present invention is also directed to "SARS-CoV-2 S Protein Lentiviral Vaccine" pharmaceutical compositions that comprise such SARS-CoV-2 S Protein Lentiviral Particles. The present invention is additionally directed to the use of such SARS-CoV-2 S Protein Lentiviral Vaccine pharmaceutical compositions for providing immunity to COVID-19 infection to humans and other mammals, either directly or as an inactivated form.

22 Claims, 14 Drawing Sheets

Specification includes a Sequence Listing.

(56) References Cited

OTHER PUBLICATIONS

Wu, F., et al., Feb. 2020, A new coronavirus associated with human respiratory disease in China, Nature 579:265-283.*

He, Y., et al., Jun. 2006, Antigenic and immunogenic characterization of recombinant baculovirus-expressed severe acute respiratory syndrome coronavirus spike protein: Implication for vaccine design, J. Virol. 80(12):5757-5767.*

Moore, M. J., et al., Oct. 2004, Retrovirus pseudotyped with the severe acute respiratory syndrome coronavirus spike protein efficiently infect cells expressing angiotensin-converting enzyme 2, J. Virol. 78(19): 10628-1635.*

Saeed, M. Q., et al., Dec. 2014, Comparison between several integrase-defective lentiviral vectors reveals increased integration of an HIV vector bearing a D167H mutant, Mol. Ther. Nucleic Acids 3, e213, pp. 1-12.*

Gandara, C., et al., 2018, Manufacture of third-generation lentivirus for preclinical use, with process development considerations for translation to good manufacturing practice, Human Gene Therapy Methods 29(1): 1-15.*

NCBI BLAST Alignment of GenBank Y_009724390.1 and Polymorphic Variants Thereof (2020) https://blast.ncbi.nlm.nih.gov/BLAST.cgi#; pp. 1-100.

Addgene (2014) "*Plasmids 101: The Promoter Region—Let's Go!*," Addgene; pp. 1-22.

Al Ali, S. et al.(2016) "*Use of Reporter Genes in the Generation of Vaccinia Virus-Derived Vectors*," Viruses 8(5):1-18.
Arce, F. et al. (2011) "*Targeting Lentiviral Vectors for Cancer Immunotherapy*," Curr. Cancer Ther. Rev. 7(4):248-260.
Banasik, M.B. el al. (2010) "*Integrase-Defective Lentiviral Vectors: Progress and Applications*," Gene Ther 17:150-157.
Bauler, M. et al. (2020) "*Production of Lentiviral Vectors Using Suspension Cells Grown in Serum-Free Media*," Molec. Ther.: Meth. Clin. Develop. 17:58-68.
Busatto, S. et al. (2018) "*Tangential Flow Filtration for Highly Efficient Concentration of Extracellular Vesicles from Large Volumes of Fluid*," Cells 7(12):1-11.
Chen, S.-H. et al. (2019) "*Overview: Recombinant Viral Vectors as Neuroscience Tools*," Curr. Protoc. Neurosci. 87(1):e67:1-16.
Colosimo, A. et al. (2000) "*Transfer and Expression of Foreign Genes in Mammalian Cells*," BioTechniques 29(2):314-331.
Cooper, A.R. et al. (2011) "Highly Efficient Large-Scale Lentiviral Vector Concentration by Tandem Tangential Flow Filtration," J. Virol. Methods. 177(1):1-9.
Craigo, J.K. et al. (2013) "*Envelope Determinants of Equine Lentiviral Vaccine Protection*," Plos One 8(6):e66093:1-11.
Cullen, B.R. (1991) "*Regulation of HIV-I Gene Expression*" FASEB J. 5:2361-2368.
Danforth, K. et al. (2017) "*Global Mortality and Morbidity of HIV/AIDS*," In: Major Infectious Diseases, vol. 6 (Holmes, K.K. et al. (Eds.)) The World Bank, Washington, DC (18 pages).
Dogbevia, G.K. et al. (2015) "*Inducible and Combinatorial Gene Manipulation in Mouse Brain*," Front. Cell. Neurosci. 9:142:1-8.
Dogbevia, G.K. et al. (2016) "*Flexible, AAV-equipped Genetic Modules for Inducible Control of Gene Expression in Mammalian Brain*," Molec. Ther. Nucl. Acids 5:e309:1-8.
Elsingcr, R.W. et al. (2018) "*Ending the HIV/AIDS Pandemic*," Emerg. Infect. dis. 24(3):413-416.
Engelman, A. et al. (2012) "*The Structural Biology of HIV-I: Mechanistic and Therapeutic Insights*," Nat. Rev. Microbiol. 10(4):279-290.
Escors, D. et al. (2011) "*Lentiviral Vectors in Gene Therapy: Their Current Status and Future* Potential," Arch. Immunol. Ther. Exp. (Warsz.) 58(2):107-119.
Fontana, J.M. et al. (2014) "*Mucosal Immunization With Integrase Defective Lentiviral Vectors Protects Against Influenza Virus Challenge in Mice*," PLoS One 9(5):1-12.
Freed, E.O. (2015) "*HIV-1 Assembly, Release and Maturation*," Nat. Rev. Microbiol. 13(8):484-496.
Gallinaro, A. et al. (2018) "*Integrase Defective Lentiviral Vector as a Vaccine Platform for Delivering Influenza Antigens*," Front. Immunol. 9:171 (pp. 1-11).
Gandara, C. et al. (2018) "*Manufacture of Third-Generation Lentivirus for Preclinical Use, with Process Development Considerations for Translation to Good Manufacturing Practice*," Hum. Gene Ther. Meth. 29(1):1-15.
Gaspar, H.B. et al. (2011) "*Long-Term Persistence of a Polyclonal T Cell Repertoire After Gene Therapy for X-Linked Severe Combined Immunodeficiency*," Sci. Transl. Med. 3:97ra79:1-7.
Glum, C.M. et al. (2010) "*The Art of Reporter Proteins in Science: Past, Present and Future Applications*," BMB Rcp. 43(7):451-460.
Gottlingcr, H.G. et al. (1989) "*Role of Capsid Precursor Processing and Myristoylation in Morphogenesis and Infectivity of Human Immunodeficiency Virus Type 1*," Proc. Natl. Acad. Sci. (U.S.A.) 86:5781-5785.
Guler-Gane, G. et al. (2016) "*Overcoming the Refractory Expression of Secreted Recombinant Proteins in Mammalian Cells through Modification of the Signal Peptide and Adjacent Amino Acids*," Plos One 11(5):1-15.
Hacein-Bey-Abina, S. et al. (2003) "*LMO2-Associated Clonal T Cell Proliferation in Two Patients After Gene Therapy for SCID-X1*" Science 302:415-419.
Heinzinger, N. K. et al. (1994) "*The vpr Protein of Human Immunodeficiency Virus Type 1 Influences Nuclear Localization of Viral Nucleic Acids in Nondividing Host Cells*," Proc. Natl. Acad. Sci. (U.S.A.) 91(15):7311-7315.
Higashimoto, T. et al. (2007) "*The Woodchuck Hepatitis Virus Post-Transcriptional Regulatory Element Reduces Readthrough Transcription From Retroviral Vectors*," Gene Ther. 14:1298-1304.
Hope, T.J. et al. (2000) "*Structure, Expression, and Regulation of the HIV Genome*," HIV InSite Knowledge Base Chapter, pp. 1-12.
Hu, B. (2011) "Immunization Delivered by Lentiviral Vectors for Cancer and Infectious Diseases," Immunol. Rev. 239(1):45-61.
Huisman, W. et al. (2009) "*Vaccine-Induced Enhancement of Viral Infections*," Vaccine 27(4):505-512.
Kammler, S. et al. (2006) "*The Strength of the HIV-1 3' Splice Sites Affects Rev Function*," Retrovirol. 3:89:1-20.
Keeler, A.M. et al. (2017) "*Gene Therapy 2017: Progress and Future Directions*," Clin. Trasl. Sci. 10:242-248.
Klimatcheva, E. et al. (1999) "*Lentiviral Vectors and Gene Therapy*," Front. Biosci. 4:D481-D496.
Kozak, M. (1987) "*An Analysis of 5'-Noncoding Sequences From 699 Vertebrate Messenger RNAs*" Nucl. Acids Res. 15(20):8125-8148.
Leavitt. A,D, et al. (1996) "*Human Immunodeficiency Virus Type 1 Integrase Mutants Retain In Vitro Integrase Activity Yet Fail to Integrate Viral DNA Efficiently During Infection*," J. Virol. 70(2):721-728.
Li, X. et al. (2011) "*Structural Biology of Retroviral DNA Integration*" Virol. 411(2):194-205.
Li, Y. et al. (1992) " *Complete Nucleotide Sequence, Genome Organization, and Biological Properties of Human Immunodeficiency Virus Type 1 In Vivo: Evidence for Limited Defectiveness and Complementation*," J. Virol. 66(11):6587-6600.
Lundstrom, K. (2019) "*RNA Viruses as Tools in Gene Therapy and Vaccine Development*." Genes (Basel) 10(3):1-24.
McBride, C.E. et al. (2007) "*The Cytoplasmic Tail of the Severe Acute Respiratory Syndrome Coronavirus Spike Protein Contains a Novel Endoplasmic Reticulum Retrieval Signal That Binds COPI and Promotes Interaction with Membrane Protein*," J. Virol. 81(5):2418-2428.
Merten, O.-W. et al. (2016) "*Production of Lentiviral Vectors*," Molec. Ther. Meth. Clin. Develop. 3:16017:1-14.
Milone, M.C. et al. (2018) "*Clinical Use of Lentiviral Vectors*," Leukemia 32:1529-1541.
Miyoshi, H. (1998) "*Development of A Self-Inactivating Lentivirus Vector*," J. Virol. 72(10):8150-8157.
Norton, T.D. et al. (2016) "*Recent Advances in Lentiviral Vaccines for HIV-1 Infection*," Front. Immunol. 7:243:1-8.
O'Keefe, B.R. et al. (2010) "*Broad-Spectrum in vitro Activity and in vivo Efficacy of the Antiviral Protein Griffithsin Against Emerging Viruses of the Family Coronaviridae*," J. Virol. 84(5):2511-2521.

(56) References Cited

OTHER PUBLICATIONS

Pincha, M. et al. (2010) "*Lentiviral Vectors for Immunization: An Inflammatory Field*," Expert Rev. Vaccines 9(3):309-321.
Pollard, V.W. et al. (1998) "*The HIV-1 Rev Protein*," Annu. Rev. Microbiol. 52:491-532.
Sayasith, K. et al. (2000) "*Characterization of Mutant HIV-1 Integrase Carrying Amino Acid Changes in the Catalytic Domain*," Mol. Cells 10(5):525-532.
Schambach, A. et al. (2013) "*Biosafety Features of Lentiviral Vectors*," Human Gene Ther. 24:132-142.
Schubert, U. et al. (1996) "*The Two Biological Activities of Human Immunodeficiency Virus Type I Vpu Protein Involve Two Separable Structural Domains*," J. Virol. 70(2):809-819.
Selig, L. et al. (1999) "*Interaction with the p6 Domain of the Gag Precursor Mediates Incorporation into Virions of Vpr and Vpx Proleins from Primate Lentiviruses*," J. Virol. 73(1):592-600.
Selvam, C. (2017) "*Therapeutic Potential of Chemically Modified siRNA: Recent Trends*," Chem. Biol. Drug Des. 90(5):665-678.
Shirley, J.L. et al. (2020) "*Immune Responses to Viral Gene Therapy Vectors*," Molec. Ther. 28(3):709-722.
Soliman, M. et al. (2017) "*Mechanisms of HIV-1 Control*," Curr. HIV/AIDS Rep. 14(3):101-109.
Strebel, K. et al. (1987) "*The HIV 'A' (sor) Gene Product is Essential for Virus Infectivity*" Nature 328(6132):728-730.
Vaccari, M. et al. (2018) "*HIV Vaccine Candidate Activation of Hypoxia and the Inflammasome in CD14+ Monocytes is Associated with a Decreased Risk of SIV $_{mac251}$ Acquisition*," Nat. Med. 24(6):847-856.
Wang, C. et al. (2020) "*The Establishment of Reference Sequence for SARS-CoV-2 and Variation Analysis*," J. Med. Virol. 92:667-674.
Wang, Y. et al. (2019) "*Tangential Flow Microfiltration for Viral Separation and Concentration*," Micromachines 10:320 (pp. 1-13).
Willey, R.L. et al. (1992) "*Human Immunodeficiency Virus Type 1 Vpu Protein Induces Rapid Degradation of CD4*," J. Virol. 66(12):7193-7200.
Wu, F. et al. (2020) "*A New Coronavirus Associated With Human Respiratory Disease in China*," Nature 579(7798):265-269.
Yaguchi, M. et al. (2013) "Characterization of the Properties of Seven Promoters in the Motor Cortex of Rats and Monkeys After Lentiviral Vector-Mediated Gene Transfer," Hum. Gene Ther. Methods 24(6):333-344.
Zhao, X. (2013) "*Several Affinity Tags Commonly Used in Chromatographic Purification*," J. Anal. Meth. Chem. 2013:581093:1-8.
Bona, R. et al. (2006) "*Development of a Human Immunodeficiency Virus Vector-Based, Single-Cycle Assay for Evaluation of Anti-Integrase Compounds*," Antimicrob. Agents Chemother. 50(10):3407-3417.

\* cited by examiner

Figure 5

NON-INTEGRATING *HIV-1* COMPRISING MUTANT RT/IN PROTEINS AND THE SARS-COV-2 SPIKE PROTEIN

REFERENCE TO SEQUENCE LISTING

This application includes one or more Sequence Listings pursuant to 37 C.F.R. 1.821 et seq., which are disclosed in computer-readable media (file name: 2650-0005US1_ST25.txt, created on May 18, 2020, and having a size of 206,750 bytes), which file is herein incorporated by reference in its entirety.

FIELD OF THE INVENTION

The present invention is directed to recombinant lentiviral particles that array the SARS-CoV-2 spike (S) protein on their surface ("SARS-CoV-2 S Protein Lentiviral Particles"), and that optionally comprise an additional copy of a polynucleotide encoding the SARS-CoV-2 spike (S) protein in their viral genome, and to methods for the production of such lentiviral particles. The invention particularly pertains to such SARS-CoV-2 S Protein Lentiviral Particles that have been engineered to be incapable of mediating the integration of their lentiviral genome into the chromosomes of infected cells and/or to be incapable of mediating the reverse transcription of their lentiviral genome. The present invention is also directed to "SARS-CoV-2 S Protein Lentiviral Vaccine" pharmaceutical compositions that comprise such SARS-CoV-2 S Protein Lentiviral Particles. The present invention is additionally directed to the use of such SARS-CoV-2 S Protein Lentiviral Vaccine pharmaceutical compositions for providing immunity to COVID-19 infection to humans and other mammals, either directly or as an inactivated form.

BACKGROUND OF THE INVENTION

I. Lentiviruses

Lentiviruses are members of the retroviridae family of viruses. They include primate and non-primate retroviruses (such as HIV and SIV (simian immunodeficiency virus), FIV (feline immunodeficiency virus), BIV (bovine immunodeficiency virus), CAEV (caprine arthritis-encephalitis virus), EIAV (equine infectious anemia virus) and visnavirus) (Escors, D. et al. (2011) "*Lentiviral Vectors In Gene Therapy: Their Current Status And Future Potential*," Arch. Immunol. Ther. Exp. (Warsz.) 58(2):107-119). The most widely studied lentivirus is HIV-1, the causative agent of AIDS (Danforth, K. et al. (2017) "*Global Mortality and Morbidity of HIV/AIDS*," In: MAJOR INFECTIOUS DISEASES, Vol. 6 (Holmes, K. K. et al. (Eds.)) The World Bank, Washington, D.C.; Engelman, A. et al. (2012) "*The Structural Biology Of HIV-1: Mechanistic And Therapeutic Insights*," Nat. Rev. Microbiol. 10(4):279-290; Freed, E. O. (2015) "*HIV-1 Assembly, Release And Maturation*," Nat. Rev. Microbiol. 13(8):484-496; Soliman, M. et al. (2017) "*Mechanisms of HIV-1 Control*," Curr. HIV/AIDS Rep. 14(3):101-109; Elsinger, R. W. et al. (2018) "*Ending the HIV/AIDS Pandemic*," Emerg. Infect. dis. 24(3):413-416).

Although wildtype lentiviruses are capable of causing disease, it has been possible to modify their genomes to produce lentiviral vectors and vaccines that have proven to be safe and effective in the laboratory and therapeutically (Keeler, A. M. et al. (2017) "*Gene Therapy 2017: Progress and Future Directions*," Clin. Trasl. Sci. 10:242-248; Milone, M. C. et al. (2018) "*Clinical Use of Lentiviral Vectors*," Leukemia 32:1529-1541; Escors, D. et al. (2011) "*Lentiviral Vectors In Gene Therapy: Their Current Status And Future Potential*," Arch. Immunol. Ther. Exp. (Warsz.) 58(2):107-119; Schambach, A. et al. (2013) "*Biosafety Features of Lentiviral Vectors*," Human Gene Ther. 24:132-142; Shirley, J. L. et al. (2020) "*Immune Responses to Viral Gene Therapy Vectors*," Molec. Ther. 28(3):709-722). Lentiviruses have thus evolved into highly efficient vehicles for in vivo gene delivery (Chen, S.-H. et al. (2019) "*Overview: Recombinant Viral Vectors as Neuroscience Tools*," Curr. Protoc. Neurosci. 87(1):e67:1-16; Lundstrom, K. (2019) "*RNA Viruses as Tools in Gene Therapy and Vaccine Development*." Genes (Basel) 10(3):1-24).

The wildtype lentiviral genome consists of two linear, single-stranded, positive-sense RNA molecules of 9.75 kb, whose ends are flanked by long terminal repeated sequences (LTR). These 5' and 3' LTR sequences are required for viral transcription, reverse transcription, and integration of the viral genome. The lentiviral genome comprises at least nine genes: gag, pol, env, tat, rev, vpu, vpr, vif and nef (Hope, T. J. et al. (2000) "*Structure, Expression, and Regulation of the HIV Genome*," HIV InSite Knowledge Base Chapter, pages 1-12). The basic structure of the lentivirus genome is shown in FIG. 1.

The lentiviral LTRs are composed of three subregions: U3 (for unique 3' sequence), R (for repeated sequence), and U5 (for unique 5' sequence) (Starcich, B. et al. (1985) "*Characterization Of Long Terminal Repeat Sequences Of HTLV-III*," Science 227(4686):538-540). The U3 region is approximately 450-basepairs (bp) in length and is located at the 5' end of each LTR. The U3 region contains cis-acting binding sites for cellular transcription factors. The R region of each LTR contains a 100-bp repeated sequence. Transcription begins at the first base of the R region and polyadenylation occurs immediately after the last base of R. The U5 region is 180-bp in length and contains the Tat binding site and packaging sequences of HIV. The 3' end of the U5 region is defined by the location of a lysyl tRNA binding site. The lysyl tRNA acts as a primer for the reverse transcription of the lentivirus.

Transcription of the gag gene occurs in two reading frames at a ratio of approximately 20:1 due to a ribosomal frame-shifting event that is triggered by a specific cis-acting RNA motif in the distal region of the gag RNA. The more abundant gag transcript encodes a 55 kD Gag precursor protein that is cleaved into four smaller proteins, designated MA (matrix (p17)), CA (capsid (p24)), NC (nucleocapsid (p9)), and p6, by a virally encoded protease (p10; PRO)) (Gottlinger, H. G. et al. (1989) "*Role Of Capsid Precursor Processing And Myristoylation In Morphogenesis And Infectivity Of Human Immunodeficiency Virus Type 1*," Proc. Natl. Acad. Sci. (U.S.A.) 86:5781-5785. The frame-shifting causes the less abundant gag transcript to include pol gene sequences, so that a 160 kD Gag-Pol fusion protein is expressed. This fusion protein is cleaved into Gag and Pol proteins by the viral protease (p10 (PRO)). The Pol cleavage product is further digested to yield the viral protease (p10 (PRO)), a reverse transcriptase (p50; RT) that is needed for the reverse transcription of the genomic RNA into DNA, an RNase H (p15), and an integrase (p31, IN)) that is needed to effect the integration of the lentivirus into the chromosome of infected cells. The env gene encodes 160 kD protein that is cleaved by cellular enzymes into a gp120 surface glycoprotein (SU) and a gp41 transmembrane protein (TM). These proteins associate with one another to form trimeric structures on the surface of the mature lentivirus. Tat encodes a transcriptional trans-activator critical for activating viral transcription. Rev encodes a 13-kD sequence-specific RNA binding protein that regulates the splicing and export of viral transcripts (Pollard, V. W. et al. (1998) "*The HIV-1 Rev Protein*," Annu. Rev. Microbiol. 52:491-532). The rev and tat genes both contain untranscribed intervening sequences. Tat and rev are the first proteins to be synthesized following integration and are required to accelerate the production of viral mRNAs. The vpu, vpr, vif and nef genes encode accessory proteins, and are not required for viral replication in in vitro systems (Klimatcheva, E. et al. (1999) "*Lentiviral Vectors And Gene Therapy*," Front. Biosci. 4:D481-D496). Among these gene, vpr is a virion-associated protein present only in primate lentiviruses. Vpr can act as a weak transcriptional trans-activator of the LTRs and participates in enabling infection of non-dividing cells (Heinzinger, N. K. et al. (1994) "*The vpr Protein Of Human Immunodeficiency Virus Type 1 Influences Nuclear Localization Of Viral Nucleic Acids In Nondividing Host Cells*," Proc. Natl. Acad. Sci. (U.S.A.) 91(15):7311-7315). The 16-kD Vpu polypeptide is an integral membrane phosphoprotein that is primarily localized in the internal membranes of the cell. It functions to down-modulate CD4 and to enhance virion release (Willey, R. L. et al. (1992) "*Human Immunodeficiency Virus Type 1 Vpu Protein Induces Rapid Degradation Of CD4*," J. Virol. 66(12):7193-7200; Schubert, U. et al. (1996) "*The Two Biological Activities Of Human Immunodeficiency Virus Type 1 Vpu Protein Involve Two Separable Structural Domains*," J. Virol. 70(2):809-819). Nef acts post-translationally to decrease the cell-surface expression of CD4, the primary receptor for HIV (Foster, J. L. et al. (2011) "*Mechanisms Of HIV-1 Nef Function And Intracellular Signaling*," J. Neuroimmune Pharmacol. 6(2):230-246; Garcia, J. V. et al. (1992) "*Down-regulation of Cell Surface CD4 by nef*," Res. Virol. 143(1):52-55). Vif is a 23-kD polypeptide that is essential for the replication of HIV in peripheral blood lymphocytes, macrophages, and certain cell lines (Strebel, K. et al. (1987) "*The HIV 'A' (sor) Gene Product Is Essential For Virus Infectivity*," Nature 328(6132):728-730).

Located between the 5'-LTR and the gag gene is ψ, which is a region that serves as a signal for genome dimerization and packaging. In addition to these major genes, the viral genome also contains regulatory genes (tat and rev) as well as accessory genes (e.g., vif, vpr, vpu, p7, and nef).

Lentiviral particles are highly structured. FIG. 2 illustrates the structure of a wildtype lentivirus particle. The particle is composed of a central core that contains two copies of the viral RNA genome complexed with the nucleocapsid proteins. The central core also contains the viral integrase, reverse transcriptase, and accessory proteins. The central core is enclosed within a protein shell that is formed through the self-assembly of lentiviral p24 capsid proteins. A layer of matrix proteins surrounds the capsid shell. Envelope glycoproteins (env proteins) are incorporated into the matrix protein layer. When the virus is released from infected cells ("budding"), a portion of the cell's lipid membrane envelopes the matrix protein layer. The envelope glycoproteins extend beyond this lipid membrane envelope and are capable of binding to receptor molecules that are present on the surfaces of new potential host cells, thereby enabling the infection of such cells. The nature of a lentivirus' env proteins thus determines the lentivirus' host range (i.e., the species that the virus are capable of infecting) and tropism (i.e., the specific cell types that the virus is capable of infecting).

The Lentivirus lifecycle can be summarized by six major steps: First, envelope glycoproteins on the surface of the lentiviral particle bind to cell receptors, permitting the virus to enter into the cell. Then, the matrix and capsid proteins disassemble, releasing the viral genome and viral proteins into the cytoplasm of the infected cell. The reverse transcriptase then uses the viral RNA as a template for the synthesis of viral DNA. The viral DNA is then transported to the nucleus where it is integrated into the host genome via the action of viral integrase (Fanales-Belasio, E. et al. (2010) "*HIV Virology And Pathogenetic Mechanisms Of Infection: A Brief Overview*," Ann. I. Super. Sanita. 46(1):5-14). The 5' LTR of the integrated viral genome acts as a combined enhancer and promoter, enabling the host cell's RNA polymerase II to begin transcription of the viral genome. The 3' LTR stabilizes newly synthesized transcripts by regulating their polyadenylation. Tat, Rev, and Nef proteins are produced that facilitate the production of other viral transcripts necessary for progression through the viral lifecycle (Wei, P. et al. (1998) "*A Novel CDK9-Associated C-Type Cyclin Interacts Directly With HIV-1 Tat And Mediates Its High-Affinity, Loop-Specific Binding To TAR RNA*," Cell 92(4):451-462). Rev facilitates the nuclear export of the viral mRNA molecules by binding to a Rev-responsive element (RRE) on such transcripts (Malim, M. H. et al. (1989) "*The HIV-1 Rev Trans-Activator Acts Through A Structured Target Sequence To Activate Nuclear Export Of Unspliced Viral mRNA*," Nature 338(6212):254-257). Finally, the exported viral genome and proteins are assembled at the cell's plasma membrane and released from the host cell (Fanales-Belasio, E. et al. (2010) "*HIV Virology And Pathogenetic Mechanisms Of Infection: A Brief Overview*," Annali Dell'istituto Superiore Di Sanita. 46(1):5-14).

II. Lentiviral Vectors

Lentiviruses cannot be directly employed as vaccines because their capacity to integrate into cellular chromosomes of infected cells is potentially oncogenic. Thus, lentiviral vector systems have been developed that do not permit chromosomal integration to occur. Most recombinant lentivirus vectors are derived from HIV-1. In order to comport with the constraints that certain lentiviral elements, such as the LTRs, ψ, and RRE (Rev response element required for processing and transport of viral RNAs) are required in cis, whereas other lentiviral elements, such as genes: gag, pol, env, tat, rev, vpu, vpr, vif and nef function in trans, such vector systems entail the co-transfection of multiple plasmids.

Multiple generations of such lentiviral vector systems have been described (Pincha, M. et al. (2010) "*Lentiviral Vectors For Immunization: An Inflammatory Field*," Expert Rev. Vaccines 9(3):309-321). Their basic principle is to avoid the formation of replication-competent species (Schambach, A. et al. (2013) "*Biosafety Features of Lentiviral Vectors*," Human Gene Ther. 24:132-142). To accomplish these goals, sequences that encode lentiviral proteins are deleted from the transgene-containing vector, and sequences that are required for highly efficient packaging into nascent particles are moved to a separate plasmid. In order to be able to more easily vary tropism, sequences encoding the envelope protein are provided on a further plasmid.

Thus, in the first generation of lentiviral vectors, three vectors were employed to produce lentiviral particles:

(1) a packaging plasmid that encoded the required gag and pol sequences, the viral regulatory genes tat and rev and the accessory genes vif, vpr, vpu and nef;
(2) an envelope vector that encoded a non-lentiviral, heterogenous envelope protein ("pseudotyped" envelope protein) that determines the host range (tropism) of the lentiviral particle; and
(3) a transfer vector that comprised the 5' and 3' LTR sequences, W, the RRE, the central polypurine tract (cPPT) (derived from the Pol reading frame) that increases the efficiency of reverse transcription (RT), and a desired exogenous gene for expression (transgene) under the control of a promoter, such as the cytomegalovirus (CMV) immediate-early enhancer and promoter (Barrow, K. M. (2006) "*Use Of The Cytomegalovirus Promoter For Transient And Stable Transgene Expression In Mouse Embryonic Stem Cells*," Methods Mol Biol. 329:283-294) or the Rous sarcoma virus (RSV) (Yaguchi, M. et al. (2013) "*Characterization Of The Properties Of Seven Promoters In The Motor Cortex Of Rats And Monkeys After Lentiviral Vector-Mediated Gene Transfer*," Hum. Gene Ther. Methods 24(6):333-344).

Co-transfection with all three vectors thus results in the production of lentiviral particles that express the pseudo-envelope protein on their surfaces. By replacing the native lentiviral envelope protein with a heterogenous "pseudotyped" envelope protein, such vector systems alter the tropism of the lentivirus so that it targets desired host cells. For example, the native lentiviral envelope protein can be replaced with the vesicular stomatitis virus glycoprotein G (VSV-G) to create a pseudotyped lentiviral vectors having extensive host cell infectivity (see, Gruber, A. et al. (2000) "*Dendritic Cells Transduced By Multiply Deleted HIV-1 Vectors Exhibit Normal Phenotypes And Functions And Elicit An HIV-Specific Cytotoxic T-Lymphocyte Response in vitro*," Blood 96:1327-1333; Zufferey, R. et al. (1997) "*Multiply Attenuated Lentiviral Vector Achieves Efficient Gene Delivery in vivo*," Nat. Biotechnol. 15:871-875).

Second generation lentiviral vector systems deleted the four accessory genes, vif, vpr, vpu and nef, thereby improving the safety profile of the lentiviral vector, since any replication-competent lentivirus would be devoid of all virulence factors (Hope, T. J. et al. (2000) "*Structure, Expression, and Regulation of the HIV Genome*," HIV InSite Knowledge Base Chapter, pages 1-12; Escors, D. et al. (2011) "*Lentiviral Vectors In Gene Therapy: Their Current Status And Future Potential*," Arch. Immunol. Ther. Exp. (Warsz.) 58(2):107-119).

Third generation lentiviral systems further improved the safety profile of the lentiviral vector by deleting the U3 region of the 3'-LTR (Pincha, M. et al. (2010) "*Lentiviral Vectors For Immunization: An Inflammatory Field*," Expert Rev. Vaccines 9(3):309-321). The deletion results in the Transcriptional Self-Inactivation (SIN) of potentially packageable viral genomes in transduced cells (Schambach, A. et al. (2013) "*Biosafety Features of Lentiviral Vectors*," Human Gene Ther. 24:132-142; Yu, S. F. et al. (1986) "*Self-Inactivating Retroviral Vectors Designed For Transfer Of Whole Genes Into Mammalian Cells*," Proc. Natl. Acad. Sci. (U.S.A.) 83(10):3194-3198; Miyoshi, H. (1998) "*Development Of A Self-Inactivating Lentivirus Vector*," J. Virol. 72(10):8150-8157). Additionally, the rev gene (which encodes a gene product that promotes the transport of unspliced and singly spliced viral transcripts into the cytoplasm, thereby allowing late viral proteins to be produced) is expressed from a separate plasmid. The 5' LTR is modified to delete its U3 region and to place the 5' LTR under the control of a strong tat-independent constitutive promoter (Dull, T. et al. (1998) "*A Third-Generation Lentivirus Vector With A Conditional Packaging System*," J. Virol. 72:8463-8471). FIG. 3 illustrates the four vectors of third generation lentiviral systems.

III. Lentiviral Vaccines

Lentiviral vectors have been primarily employed as delivery vehicles for gene therapy due to the low incidence of pre-existing anti-lentivirus immunity in the population and their capacity to integrate into the genome of recipient cells (thus providing persistent, long term expression of the therapeutic gene being delivered by the vector) (Keeler, A. M. et al. (2017) "*Gene Therapy 2017: Progress and Future Directions*," Clin. Trasl. Sci. 10:242-248; Milone, M. C. et al. (2018) "*Clinical Use of Lentiviral Vectors*," Leukemia 32:1529-1541; Shirley, J. L. et al. (2020) "*Immune Responses to Viral Gene Therapy Vectors*," Molec. Ther. 28(3):709-722; Escors, D. et al. (2011) "*Lentiviral Vectors In Gene Therapy: Their Current Status And Future Potential*," Arch. Immunol. Ther. Exp. (Warsz.) 58(2):107-119; Chen, S.-H. et al. (2019) "*Overview: Recombinant Viral Vectors as Neuroscience Tools*," Curr. Protoc. Neurosci. 87(1):e67:1-16; Klimatcheva, E. et al. (1999) "*Lentiviral Vectors And Gene Therapy*," Front. Biosci. 4:D481-D496).

The use of lentiviral vectors as vaccines for providing long term active immunity against pathogens has been encumbered by low infectivity (Huisman, W. et al. (2009) "*Vaccine-Induced Enhancement Of Viral Infections*," Vaccine 27(4):505-512) and by concerns regarding that lentiviral integration into the chromosomes of recipient cells may be oncogenic. Although the risk of insertional mutagenesis is considered to be very low (Norton, T. D. et al. (2016) "*Recent Advances in Lentiviral Vaccines for HIV-1 Infection*," Front. Immunol. 7:243:1-8), incidences of leukemia were observed when a retroviral vector derived from the Murine Moloney Leukemia Virus (MoMLV) was used in two SCID-X1 lentiviral gene therapy trials (Gaspar, H. B. et al. (2011) "*Long-Term Persistence Of A Polyclonal T Cell Repertoire After Gene Therapy For X-Linked Severe Combined Immunodeficiency*," Sci. Transl. Med. 3:97ra79:1-7; Hacein-Bey-Abina, S. et al. (2003) "*LMO2-Associated Clonal T Cell Proliferation In Two Patients After Gene Therapy For SCID-X1*," Science 302:415-419).

In order to address such concerns, integrase-defective lentiviral vectors (IDLV) have been developed (Fontana, J. M. et al. (2014) "*Mucosal Immunization With Integrase Defective Lentiviral Vectors Protects Against Influenza Virus Challenge In Mice*," PLoS One 9(5):1-12; Banasik, M. B. et al. (2010) "*Integrase-Defective Lentiviral Vectors: Progress And Applications*," Gene Ther 17:150-157; Michelini, Z. et al. (2009) "*Development And Use Of SIV-Based Integrase Defective Lentiviral Vector For Immunization*," Vaccine (2009) 27(34):4622-4629; Norton, T. D. et al. (2016) "*Recent Advances in Lentiviral Vaccines for HIV-1 Infection*," Front. Immunol. 7:243:1-8). A number of mutations in the HIV integrase gene have been described, particularly within the protein's catalytic triad (Banasik, M. B. et al. (2010) "*Integrase-Defective Lentiviral Vectors: Progress And Applications*," Gene Ther 17:150-157). As a result, IDLV accumulate in the nuclei of transduced cells as stable, transcriptionally-active, episomal DNA circles that persist in slowly dividing and terminally differentiated cells. A single immunization with an IDLV capable of delivering influenza hemagglutinin (HA) and nucleoprotein (NP) antigens provided high and persistent levels of antiviral neutralizing antibodies in mice (Fontana, J. M. et al. (2014) "*Mucosal Immunization With Integrase Defective Lentiviral Vectors Protects Against Influenza Virus Challenge In Mice*," PLoS One 9(5):1-12; Gallinaro, A. et al. (2018) "*Integrase Defective Lentiviral Vector as a Vaccine Platform for Delivering Influenza Antigens*," Front. Immunol. 9:171). Measles virus glycoproteins (MVGs), hemagglutinin (H) and fusion (F), have also been used to pseudotype lentiviral vectors for vaccines targeting dendritic cells (Norton, T. D. et al. (2016) "*Recent Advances in Lentiviral Vaccines for HIV-1 Infection*," Front. Immunol. 7:243:1-8). Lentiviral vectors that are designed to target dendritic cells have been developed as cancer vaccines (Arce, F. et al. (2011) "*Targeting Lentiviral Vectors For Cancer Immunotherapy*," Curr. Cancer Ther. Rev. 7(4):248-260).

IV. SARS-CoV-2 Coronavirus

Coronaviruses (CoVs) are enveloped, single-stranded, RNA viruses that possess a positive-sense RNA genome of 26 to 32 kilobases in length. Coronaviruses belong to the subfamily Orthocoronavirinae in the family Coronaviridae and the order Nidovirales. Four genera of coronaviruses have been identified, namely, Alphacoronavirus (αCoV), Betacoronavirus (βCoV), Deltacoronavirus (δCoV), and Gammacoronavirus (γCoV) (Chan, J. F. et al. (2013) "*Interspecies Transmission And Emergence Of Novel Viruses: Lessons From Bats And Birds*," Trends Microbiol. 21(10): 544-555). Evolutionary analyses have shown that bats and rodents are the gene sources of most αCoVs and βCoVs, while avian species are the gene sources of most δCoVs and γCoVs. Prior to 2019, only six coronavirus species were known to be pathogenic to humans. Four of these species were associated with mild clinical symptoms, but two coronaviruses, Severe Acute Respiratory Syndrome (SARS) coronavirus (SARS-CoV) (Marra, M. A. et al. (2003) "*The Genome Sequence of the SARS-Associated Coronavirus*," Science 300(5624):1399-1404) and Middle East Respiratory Syndrome (MERS) coronavirus (MERS-CoV) (Mackay, I. M. (2015) "*MERS Coronavirus: Diagnostics, Epidemiology And Transmission*," Virol. J. 12:222. doi: 10.1186/s12985-015-0439-5) were associated with human mortalities approaching 10% (Su, S. et al. (2016) "*Epidemiology, Genetic Recombination, And Pathogenesis Of Coronaviruses*," Trends Microbiol. 24:490-502; Al Johani, S. et al. (2016) "*MERS-CoV Diagnosis: An Update*," J. Infect. Public Health 9(3):216-219).

Severe Acute Respiratory Syndrome Coronavirus 2 (SARS-CoV-2) is a newly identified coronavirus species (the virus was previously provisionally named "2019 novel coronavirus" or "2019-nCoV") (Fang, Y. et al. (2020) "*Transmission Dynamics Of The COVID-19 Outbreak And Effectiveness Of Government Interventions: A Data-Driven Analysis*," J. Med. Virol. doi: 10.1002/jmv.25750; Zhao, W. M. et al. (2020) "*The 2019 Novel Coronavirus Resource*," Yi Chuan. 42(2):212-221; Zhu, N. et al. (2020) "*A Novel Coronavirus from Patients with Pneumonia in China, 2019*," New Engl. J. Med. 382(8):727-733).

The SARS-CoV-2 genome has been sequenced from at least 170 isolates. The reference sequence is GenBank NC_045512 (Wang, C. et al. (2020) "*The Establishment Of Reference Sequence For SARS-CoV-2 And Variation Analysis*," J. Med. Virol. 92:667-674; Chan, J. F. et al. (2020) "*Genomic Characterization Of The 2019 Novel Human-Pathogenic Coronavirus Isolated From A Patient With Atypical Pneumonia After Visiting Wuhan*," Emerg. Microbes. Infect. 9(1):221-236). Comparisons of the sequences of multiple isolates of the virus (MN988668 and NC_045512, isolated from Wuhan, China, and MN938384.1, MN975262.1, MN985325.1, MN988713.1, MN994467.1, MN994468.1, and MN997409.1) reveal greater than 99.99% identity (Sah, R. et al. (2020) "*Complete Genome Sequence of a 2019 Novel Coronavirus (SARS-CoV-2) Strain Isolated in Nepal*," Microbiol. Resource Announcements 9(11): e00169-20, pages 1-3; Brüssow, H. (2020) "*The Novel Coronavirus—A Snapshot of Current Knowledge*," Microbial Biotechnology 0:(0):1-6). The SARS-CoV-2 genome is highly similar to that of human SARS-CoV, with an overall nucleotide identity of approximately 82% (Chan, J. F. et al. (2020) "*Genomic Characterization Of The 2019 Novel Human-Pathogenic Corona Virus Isolated From A Patient With Atypical Pneumonia After Visiting Wuhan*," Emerg Microbes Infect 9:221-236; Chan, J. F. et al. (2020) "*Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens*," J Clin. Microbiol. JCM.00310-20. doi: 10.1128/JCM.00310-20). Based on its homology to related coronaviruses, SARS-CoV-2 is predicted to encode 12 open reading frame (ORFs) coding regions (ORF1ab, S (spike), 3, E (envelope protein), M (matrix), 7, 8, 9, 10b, N, 13 and 14.

The coronavirus spike or S protein, which is arrayed on the virus surface, is considered crucial for determining host tropism and transmission capacity (Lu, G. et al. (2015) "*Bat-To-Human: Spike Features Determining 'Host Jump' Of Coronaviruses SARS-CoV, MERS-CoV, And Beyond*," Trends Microbiol. 23:468-478; Wang, Q. et al. (2016) "*MERS-CoV Spike Protein: Targets For Vaccines And Therapeutics*," Antiviral. Res. 133:165-177). Studies of the S protein of SARS-CoV have found it to be functionally cleaved into two subunits: an S1 domain that mediates receptor binding, and an S2 domain that mediates membrane fusion (He, Y. et al. (2004) "*Receptor-Binding Domain Of SARS-CoV Spike Protein Induces Highly Potent Neutralizing Antibodies: Implication For Developing Subunit Vaccine*," Biochem. Biophys. Res. Commun. 324:773-781; Li, F. (2016) "*Structure, Function, And Evolution Of Coronavirus Spike Proteins*," Annu. Rev. Virol. 3:237-261; He, Y. et al. (2004) "*Receptor-Binding Domain Of SARS-CoV Spike Protein Induces Highly Potent Neutralizing Antibodies: Implication For Developing Subunit Vaccine*, Biochem. Biophys. Res. Commun. 324:773-781). The S protein of SARS-CoV-2 shares 76% identity with the S protein of SARS-CoV (Lu, R. et al. (2020) "*Genomic Characterisation And Epidemiology Of 2019 Novel Coronavirus: Implications For Virus Origins And Receptor Binding*," Lancet 395(10224): 565-574). In light of such similarity, it has been proposed that these S proteins may have similar functions. FIG. 4 illustrates the structure of the SARS-CoV-2 viral particle. The structure is similar to that of lentiviruses in that a glycoprotein spike (the S protein) extends out of the viral particle and is responsible for viral tropism.

Patients infected with SARS-CoV-2 exhibit COVID-19, a condition characterized by fever and cough (Kong, I. et al. (2020) "*Early Epidemiological and Clinical Characteristics of 28 Cases of Coronavirus Disease in South Korea*," Osong Public Health Res Perspect. 11(1):8-14). In approximately 20% of patients, COVID-19 progresses to a severe respiratory disease and pneumonia that has a mortality of 5-10% (1-2% overall mortality). No cure for COVID-19 yet exists, and no vaccine is currently available. These deficiencies are exacerbated by the wide susceptibility of individuals to infection (reflecting the absence of prior herd immunity). Since no therapies have been proven to be effective thus far, management of COVID-19 presently consists of a "Four-Anti and Two-Balance" strategy included antivirus, anti-shock, anti-hyoxemia, anti-secondary infection, and maintaining water, electrolyte and acid-base balance and micro-ecological balance (Xu, K. et al. (2020) "*Management Of Corona Virus Disease*-19 (*COVID*-19): *The Zhejiang Experience*," Zhejiang Da Xue Bao Yi Xue Ban. 49(1):0). In 2020, COVID-19 became a pandemic accounting for over 300,000 ascribed deaths.

In sum, an urgent need exists for a vaccine that could protect populations from COVID-19. The present invention is directed to this and other goals.

SUMMARY OF THE INVENTION

The present invention is directed to recombinant lentiviral particles that array the SARS-CoV-2 spike (S) protein on their surface ("SARS-CoV-2 S Protein Lentiviral Particles"), and that optionally comprise an additional copy of a polynucleotide encoding the SARS-CoV-2 spike (S) protein in their viral genome, and to methods for the production of such lentiviral particles. The invention particularly pertains to such SARS-CoV-2 S Protein Lentiviral Particles that have been engineered to be incapable of mediating the integration of their lentiviral genome into the chromosomes of infected cells and/or to be incapable of mediating the reverse transcription of their lentiviral genome. The present invention is also directed to "SARS-CoV-2 S Protein Lentiviral Vaccine" pharmaceutical compositions that comprise such SARS-CoV-2 S Protein Lentiviral Particles. The present invention is additionally directed to the use of such SARS-CoV-2 S Protein Lentiviral Vaccine pharmaceutical compositions for providing immunity to COVID-19 infection to humans and other mammals, either directly or as an inactivated form.

In detail, the invention provides a lentiviral particle that comprises a recombinantly engineered lentiviral genome and that arrays a SARS-CoV-2 spike (S) protein on its surface.

The invention further provides the embodiment of such lentiviral particle wherein the recombinantly engineered lentiviral genome is non-integrating.

The invention further provides the embodiment of such lentiviral particle wherein the recombinantly engineered lentiviral genome is incapable of being reverse transcribed.

The invention further provides the embodiment of such lentiviral particle wherein the recombinantly engineered lentiviral genome is non-integrating and incapable of being reverse transcribed.

The invention further provides the embodiment of such lentiviral particles wherein the recombinantly engineered lentiviral genome encodes a heterologous transgene protein.

The invention further provides the embodiment of such lentiviral particles wherein the encoded heterologous transgene protein is an antibiotic resistance determinant, a reporter protein, a protein drug effective in treating SARS-CoV-2 infection, or a protein that comprises the epitope binding domain of an antibody that binds to a SARS-CoV-2 antigen.

The invention further provides the embodiment of such lentiviral particles wherein the encoded heterologous transgene protein is a SARS-CoV-2 protein.

The invention further provides the embodiment of such lentiviral particles wherein the encoded SARS-CoV-2 heterologous transgene protein is a SARS-CoV-2 Spike (S) protein or a SARS-CoV-2 Nucleocapsid (N) protein.

The invention further provides a vaccine for the treatment of COVID-19, wherein the vaccine comprises a prophylactically effective dose of a pharmaceutical composition that comprises any of the above-described lentiviral particles and a pharmaceutically acceptable carrier.

The invention further provides the embodiment of such vaccine wherein the recombinantly engineered lentiviral genome of the lentiviral particle is non-integrating.

The invention further provides the embodiment of such vaccine wherein the recombinantly engineered lentiviral genome of the lentiviral particle is incapable of being reverse transcribed.

The invention further provides the embodiment of such vaccine wherein the recombinantly engineered lentiviral genome of the lentiviral particle is non-integrating and incapable of being reverse transcribed.

The invention further provides the embodiment of such vaccine wherein the recombinantly engineered lentiviral genome of the lentiviral particle encodes a heterologous transgene protein.

The invention further provides the embodiment of such vaccines wherein the encoded heterologous transgene protein is a SARS-CoV-2 Spike (S) protein or a SARS-CoV-2 Nucleocapsid (N) protein.

The invention further provides the embodiment of such vaccines wherein the pharmaceutically acceptable carrier is adapted for intramuscular administration.

The invention further provides the embodiment of such vaccines wherein the pharmaceutically acceptable carrier is adapted for intranasal administration.

The invention further provides a method for producing any of the above-described recombinant lentiviral particles, wherein the method comprises:
(A) transfecting HEK293 cells with:
  (1) an LTR-containing vector that comprises a deleted 5' LTR U3 region and a self-inactivating 3' LTR region;
  (2) a packaging vector that comprises a polynucleotide that encodes the gag and pol proteins;
  (3) a REV vector that comprises a polynucleotide that encodes a rev protein; and
  (4) an envelope vector that comprises a polynucleotide that encodes a SARS-CoV-2 spike (S) protein; and
(B) permitting the cells to produce the recombinant lentiviral particle.

The invention further provides the embodiment of such method wherein the packaging vector comprises a genome that encodes a mutated integrase, wherein the transfection produces a recombinant lentiviral particle that comprises a genome that is non-integrating.

The invention further provides the embodiment of such method wherein the packaging vector comprises a genome that encodes a mutated reverse transcriptase, wherein the transfection produces a recombinant lentiviral particle that comprises a genome that is incapable of being reverse transcribed.

The invention further provides the embodiment of such method wherein the packaging vector comprises a genome that additionally encodes a mutated integrase, wherein the transfection produces a recombinant lentiviral particle that comprises a genome that is non-integrating and incapable of being reverse transcribed.

The invention further provides the embodiment of such methods wherein the LTR-containing vector comprises the features of any of the LTR-containing vectors:
  pLenti-SV40-puro (SEQ ID NO:27);
  pLenti-SV40-puro (-att) (SEQ ID NO:28);
  pLenti-CMV-IRES-empty (-att) (SEQ ID NO:67);
  pLenti-CMV-IRES-Spike (SEQ ID NO:70);

pLenti-IgGκ-nCoV-Spike-CD8-TM (-att) (SEQ ID NO:83);

pLenti-IgGκ-nCoV-N-CD8-TM (-att) (SEQ ID NO:84); or pLenti-IL-2 n-CoV-N(-att) (SEQ ID NO:85).

The invention further provides the embodiment of such methods wherein the packaging vector comprises the features of pGAG (SEQ ID NO:44).

The invention further provides the embodiment of such methods wherein the REV vector comprises the features of pREV (SEQ ID NO:49).

The invention further provides the embodiment of such methods wherein the envelope vector comprises the features of pCMV-SARS-CoV-2 S Protein (SEQ ID NO:61).

BRIEF DESCRIPTION OF THE DRAWINGS

FIG. 5 illustrates the structure of the four plasmids employed to produce the SARS-CoV-2 S Protein Lentiviral Vaccine compositions of the present invention.

DETAILED DESCRIPTION OF THE INVENTION

The present invention is directed to recombinant lentiviral particles that array the SARS-CoV-2 spike (S) protein on their surface ("SARS-CoV-2 S Protein Lentiviral Particles"), and that optionally comprise an additional copy of a polynucleotide encoding the SARS-CoV-2 spike (S) protein in their viral genome, and to methods for the production of such lentiviral particles. The invention particularly pertains to such SARS-CoV-2 S Protein Lentiviral Particles that have been engineered to be incapable of mediating the integration of their lentiviral genome into the chromosomes of infected cells and/or to be incapable of mediating the reverse transcription of their lentiviral genome. The present invention is also directed to "SARS-CoV-2 S Protein Lentiviral Vaccine" pharmaceutical compositions that comprise such SARS-CoV-2 S Protein Lentiviral Particles. The present invention is additionally directed to the use of such SARS-CoV-2 S Protein Lentiviral Vaccine pharmaceutical compositions for providing immunity to COVID-19 infection to humans and other mammals, either directly or as an inactivated form.

The SARS-CoV-2 S Protein Lentiviral Particles of the present invention are lentiviral particle that have been pseudotyped to express and/or array the spike (S) protein of SARS-CoV-2 on their outer surface so as to permit the SARS-CoV-2 S protein to be recognized as an antigen by the immune system of a "recipient subject" (e.g., a mammal, and especially, a human, a non-human primate, or a non-human mammal (e.g., a canine, feline, bovine, equine, ovine, porcine, rodent, bat, pangolin, etc.)). Such SARS-CoV-2 S Protein Lentiviral Particles can be used in SARS-CoV-2 S Protein Lentiviral Vaccine pharmaceutical compositions that can be administered to recipient subjects to thereby cause such subjects to elicit neutralizing antibodies against the SARS-CoV-2 S protein. The binding of such antibodies to SARS-CoV-2 viral particles decreases the infectivity of SARS-CoV-2 and/or the severity of COVID-19 in such recipients. As used herein, "SARS-CoV-2 infectivity" is defined as the capacity of SARS-CoV-2 to enter a host cell and exploit its resources to replicate and produce progeny infectious viral particles. SARS-CoV-2 infectivity will preferably be decreased by the SARS-CoV-2 S Protein Lentiviral Vaccine pharmaceutical compositions of the present invention by at least about one order of magnitude, by at least about two orders of magnitude, by at least about three orders of magnitude, by at least about four orders of magnitude, or by more than at least five orders of magnitude. In one embodiment, such administration is implemented so as to elicit secretory IgA2 antibodies. In a second embodiment, such administration is implemented so as to elicit IgM and/or IgG antibodies.

Figure 1:
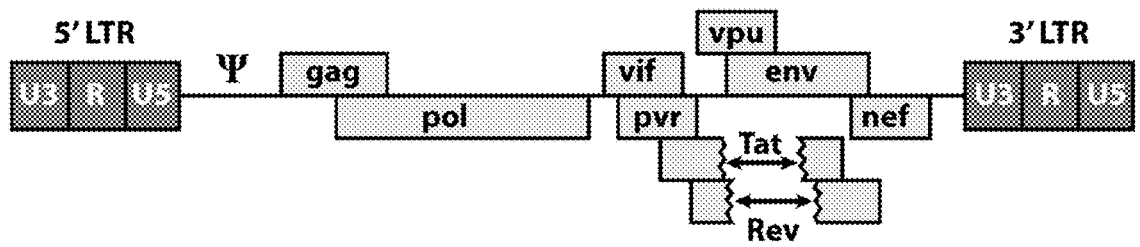
FIG. 1 illustrates the structure of a wildtype lentivirus genome.
Figure 2:
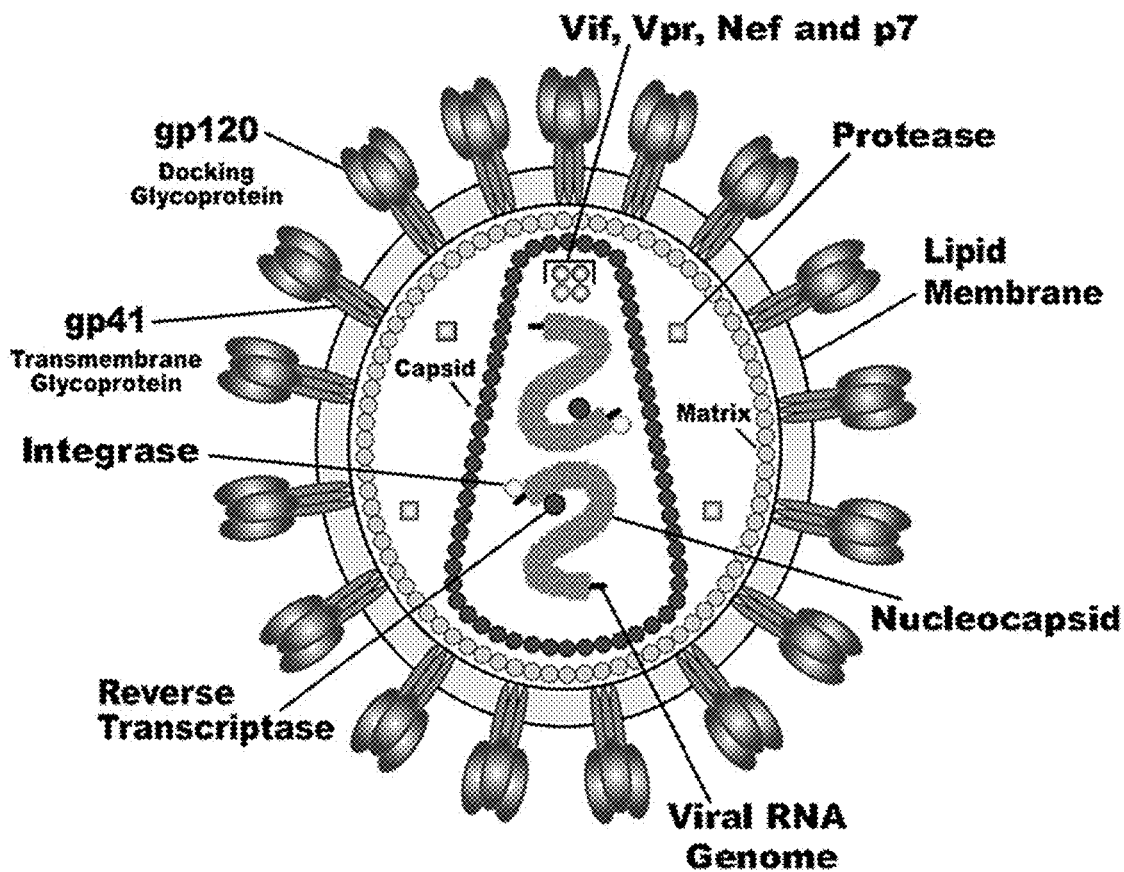
FIG. 2 illustrates the structure of a wildtype lentivirus particle.
Figure 3:
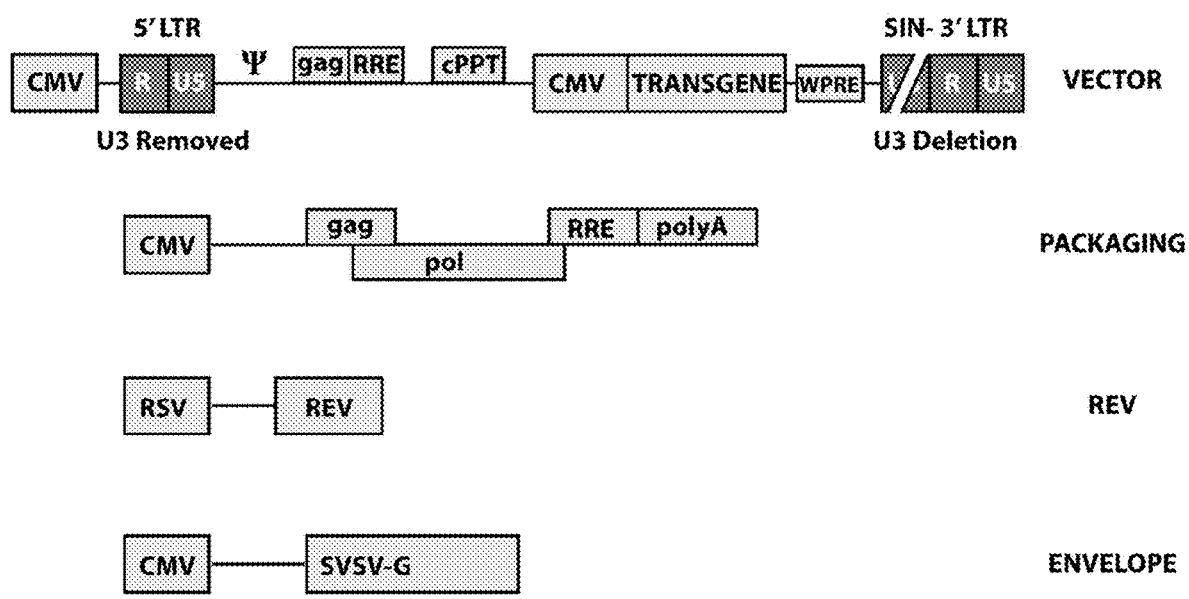
FIG. 3 illustrates the four plasmids of third generation lentiviral systems: the transgene-containing vector, the packaging vector, the rev-expressing vector and the envelope protein containing vector. CMV and RSV denote the cytomegalovirus immediate-early enhancer and promoter and the Rous sarcoma virus (RSV) promoter, respectively.
Figure 4:
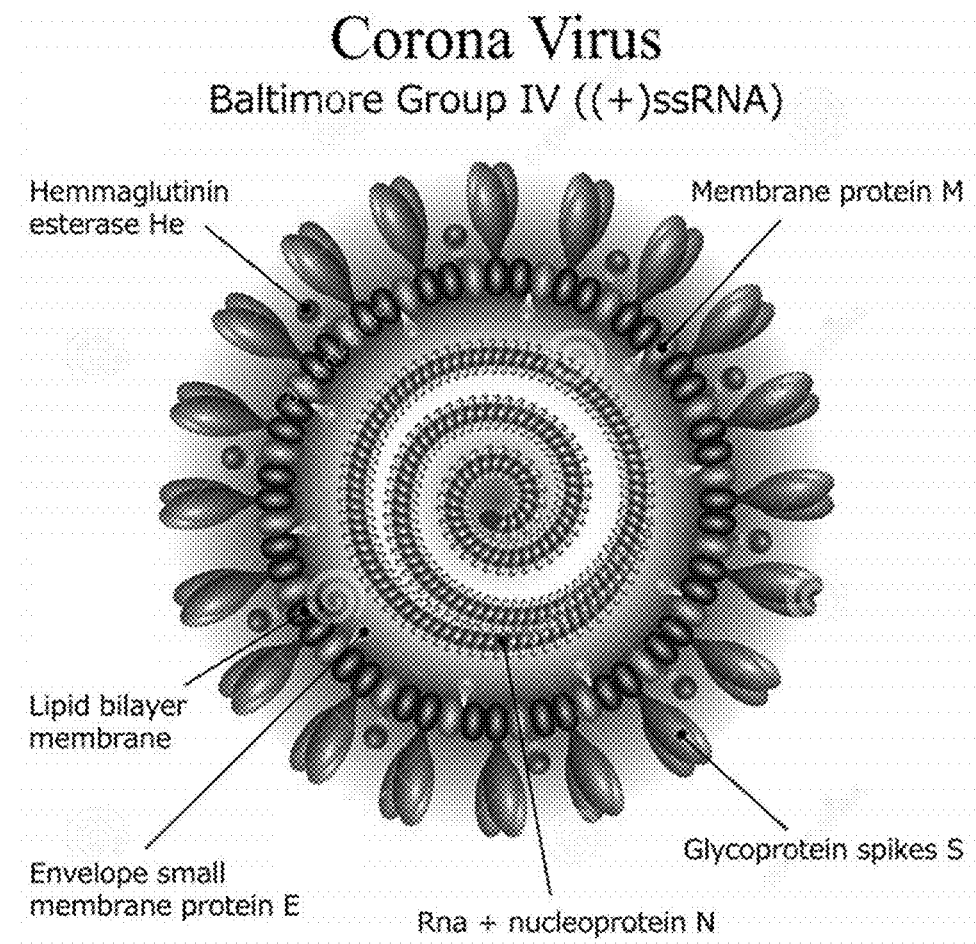
FIG. 4 illustrates the structure of the SARS-CoV-2 viral particle.

The present invention provides SARS-CoV-2 S Protein Lentiviral Particles that have been engineered to be incapable of mediating the integration of the lentiviral genome into the chromosomes of infected cells. As discussed above, and as illustrated in FIG. 2, mature lentiviral particles contain the lentiviral integrase protein (encoded by one of the pol gene transcripts). Thus, even though third generation lentiviral vector systems have moved the pol gene to a separate packaging vector, the lentiviral particles produced by such vector systems contain functional integrase proteins.

Thus, the LTR-containing genome of the mature lentiviral particles produced by such vector systems is capable of being integrated into the chromosomes of infected cells. In contrast, as discussed below, in one embodiment, the present invention employs packaging vectors whose pol gene has been mutated to render the expressed integrase non-functional. As a consequence, the lentiviral particles that are produced do not contain functional integrase proteins. Accordingly, in such embodiment, the genome present in the LTR-containing vectors of the present invention are non-integrating. As used herein, a genome contained within a lentiviral particle is said to be "non-integrating" if the integrase present within such particle exhibits an ability to mediate integration into the chromosome of an infected cells that is at least two orders of magnitude, more preferably at least three orders of magnitude, more preferably still at least four orders of magnitude less than the ability of a wildtype lentiviral integrase, or most preferably, if integration is undetectable under conditions in which the integration of a wildtype lentiviral genome is detectable. SARS-CoV-2 S Protein Lentiviral Particles of the present invention that comprise such mutated integrase proteins are effectively incapable of inserting their genomes into the chromosomes of transfected cells, and are thus much less likely to cause oncogenic events. Accordingly, such SARS-CoV-2 S Protein Lentiviral Particles of the present invention are safer than wildtype lentiviral vectors.

The present invention also provides SARS-CoV-2 S Protein Lentiviral Particles that have been engineered to be incapable of mediating the reverse transcription of their genome. As discussed above, and as illustrated in FIG. 2, mature lentiviral particles contain the lentiviral reverse transcriptase protein (encoded by one of the pol gene transcripts). Thus, the LTR-containing genome of the mature lentiviral particles produced by such vector systems is capable of being reverse transcribed into DNA upon entry into infected cells. In contrast, as discussed below, in one embodiment, the present invention employs packaging vectors whose pol gene has been mutated to render the expressed reverse transcriptase non-functional. As a consequence, the lentiviral particles that are produced do not contain functional reverse transcriptase integrase. Accordingly, in such embodiment, the genome present in the LTR-containing vectors of the present invention are incapable of being reverse transcribed. As used herein, a genome contained within a lentiviral particle is said to be "incapable of being reverse transcribed" if the reverse transcriptase present within such particle exhibits an ability to mediate reverse transcription within infected cells that is at least two orders of magnitude, more preferably at least three orders of magnitude, more preferably still at least four orders of magnitude less than the ability of a wildtype lentiviral reverse transcriptase, or most preferably, if reverse transcription is undetectable under conditions in which the reverse transcription of a wildtype lentiviral genome is detectable. As discussed below, the lentiviral RT proteins of such lentiviral particles comprise mutations that block reverse transcriptase function. Reverse transcription is required in order for the lentiviral genome to integrate into the chromosomes of transfected cells. Thus, by being incapable of mediating reverse transcription, the SARS-CoV-2 S Protein Lentiviral Particles of the present invention are effectively incapable of inserting their genomes into the chromosomes of transfected cells, and are thus much less likely to cause oncogenic events than wildtype lentiviral particles. Accordingly, such SARS-CoV-2 S Protein Lentiviral Particles of the present invention are safer than wildtype lentiviral vectors.

Additionally, reverse transcription is required for lentiviral replication. Thus, the SARS-CoV-2 S Protein Lentiviral Particles of the present invention that are incapable of mediating reverse transcription are effectively incapable of self-propagation. The genomes of such lentiviral particles will thus be capable of being transcribed and of expressing viral proteins, but will in time passively diminish in recipient subjects (due to cellular aging, cell division, apoptosis, RNA processing and other natural processes). As such, the SARS-CoV-2 S Protein Lentiviral Particles of the present invention are much less likely to be associated with long term adverse consequences than wildtype lentiviral vectors.

The present invention specifically contemplates SARS-CoV-2 S Protein Lentiviral Particles that are both non-integrating and additionally incapable of mediating reverse transcription. Such lentiviral particles are synergistically safer than either lentiviral particles having non-integrating genomes or lentiviral particles having genomes that are incapable of mediating reverse transcription.

Figure 5:
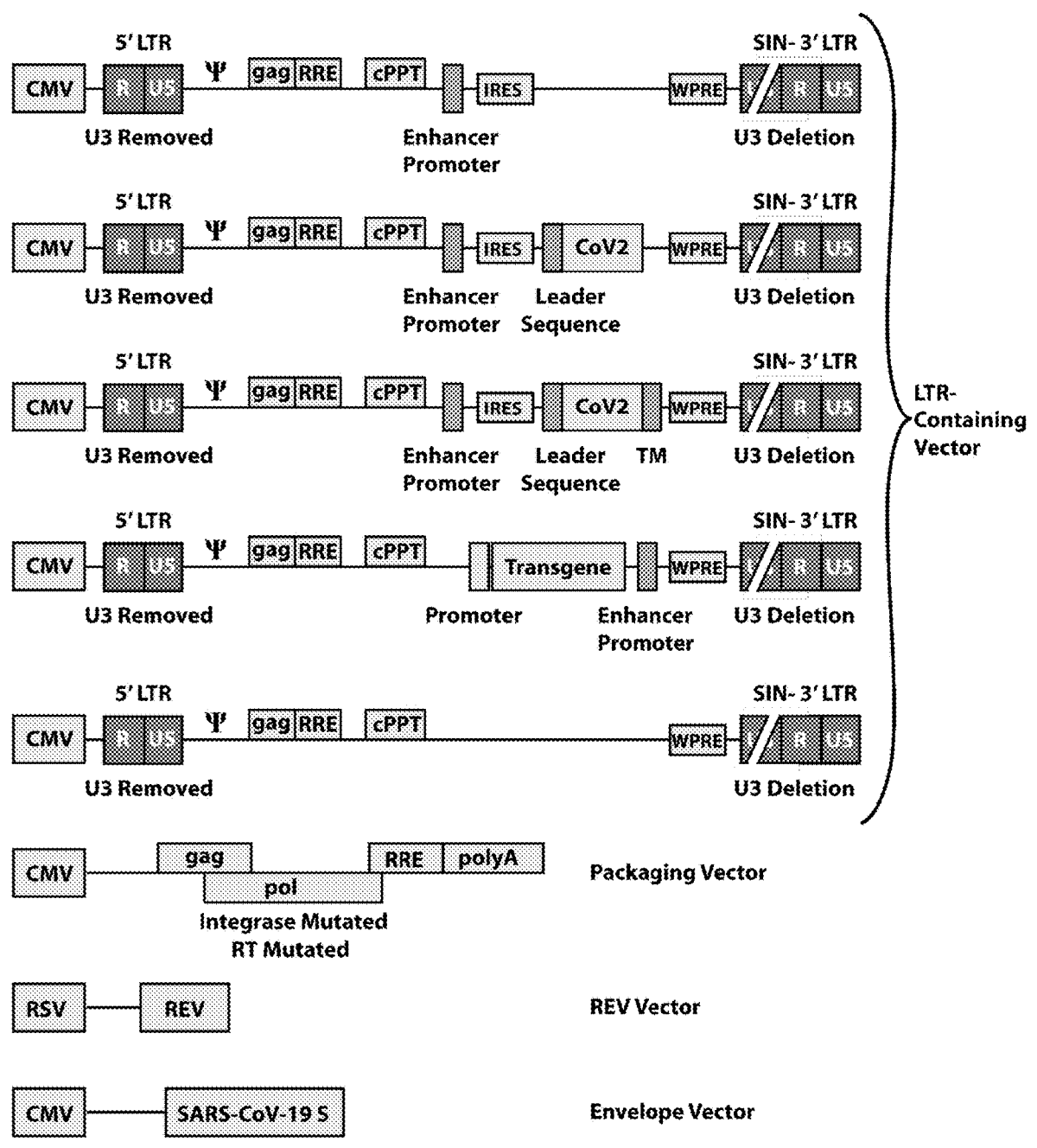

I. Preferred Vectors for Producing the SARS-CoV-2 S Protein Lentiviral Particles of the Present Invention The SARS-CoV-2 S Protein Lentiviral Particles of the present invention are preferably produced by co-transfecting a cell with four plasmids (FIG. 5): (1) an LTR-Containing vector; (2) a packaging vector; (3) a REV vector; and (4) an envelope vector.

A. LTR-Containing Vectors of the Present Invention

Figure 6:
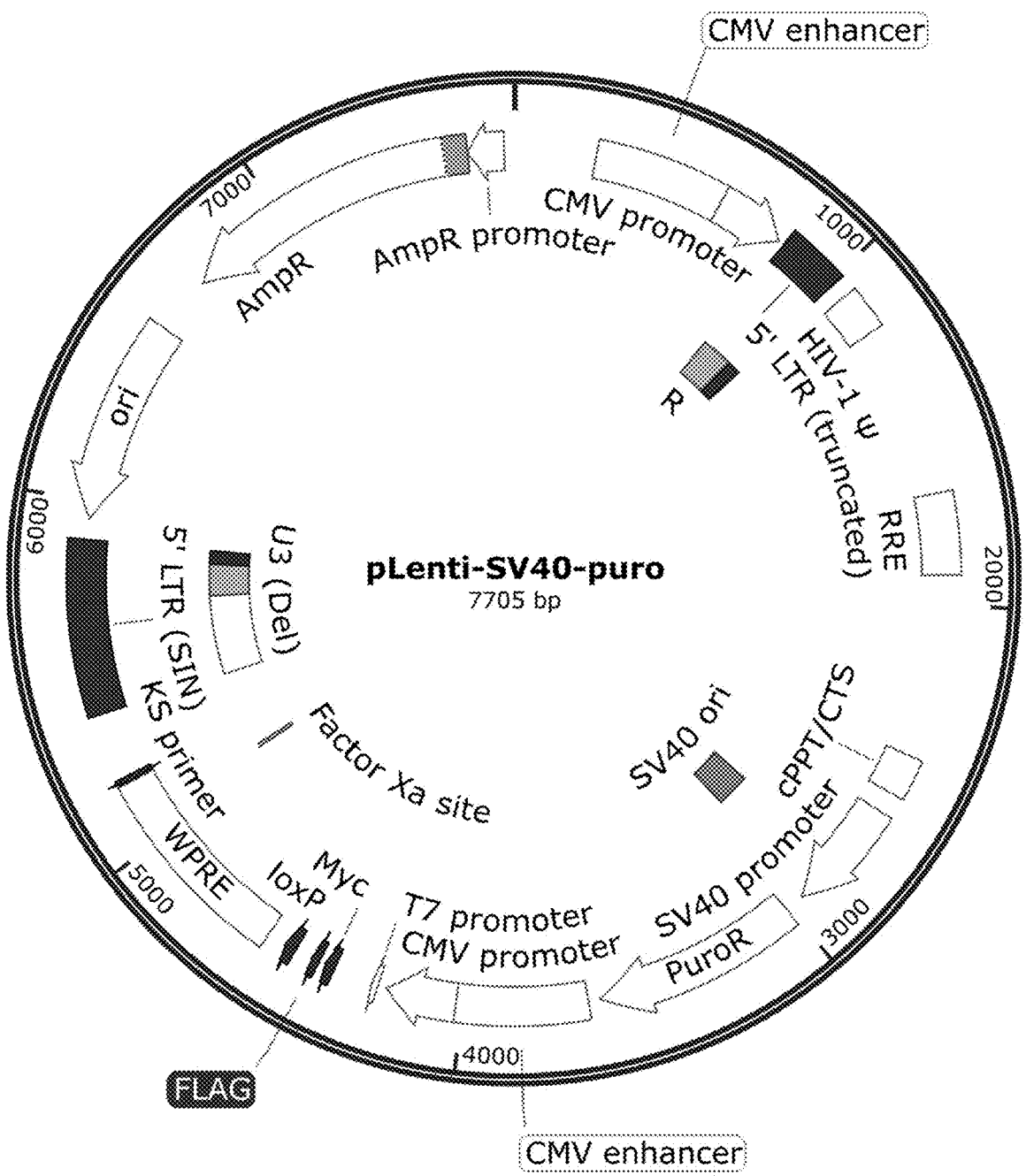
FIG. 6 provides the structure of pLenti-SV40-puro (SEQ ID NO:27) (7705 nucleotide residues), which is an example of an LTR-containing vector of the present invention.
Figure 7:
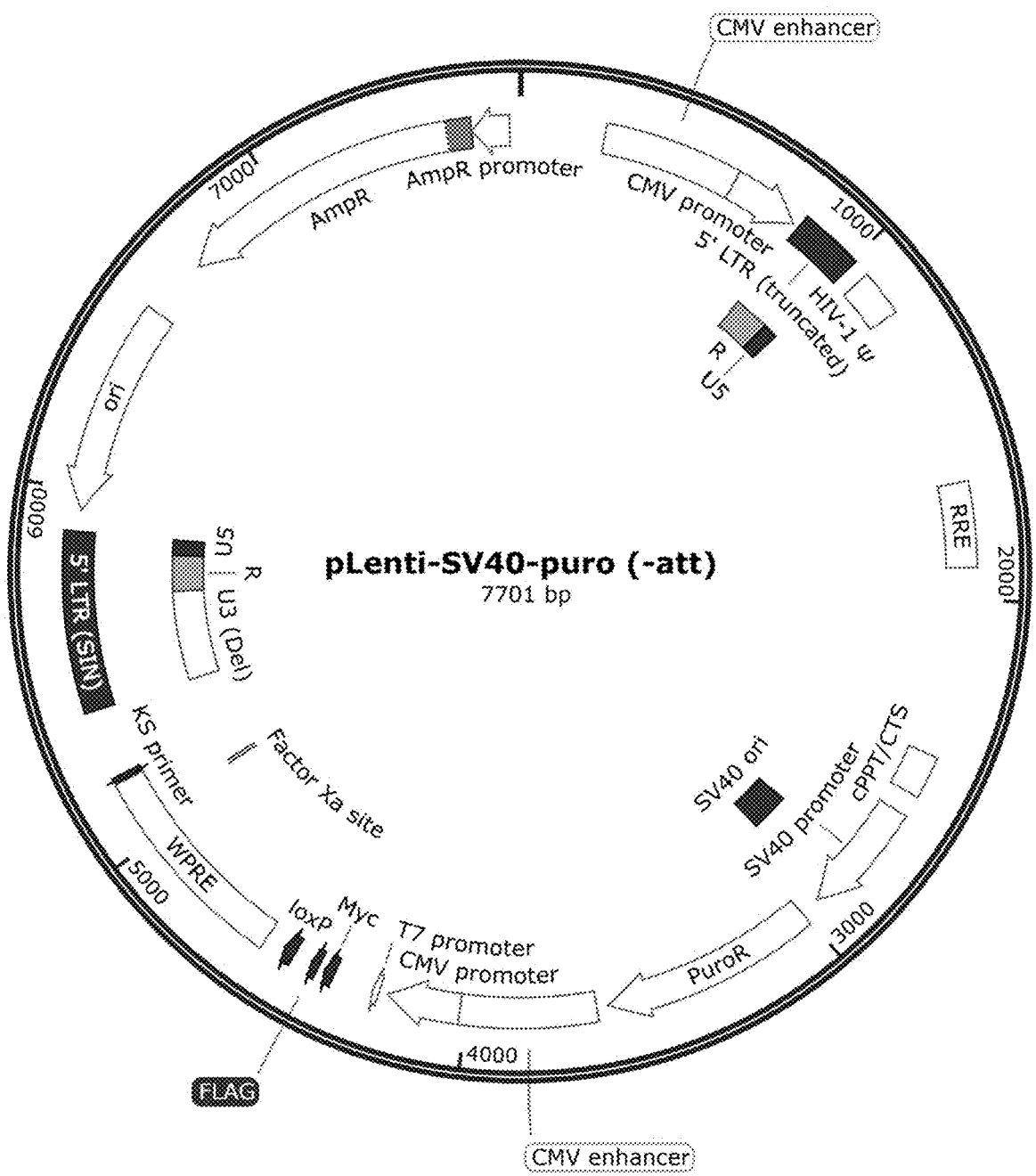
FIG. 7 provides the structure of pLenti-SV40-puro (-att) (SEQ ID NO:28) (7701 nucleotide residues), which is an example of an LTR-containing vector of the present invention.
Figure 8:
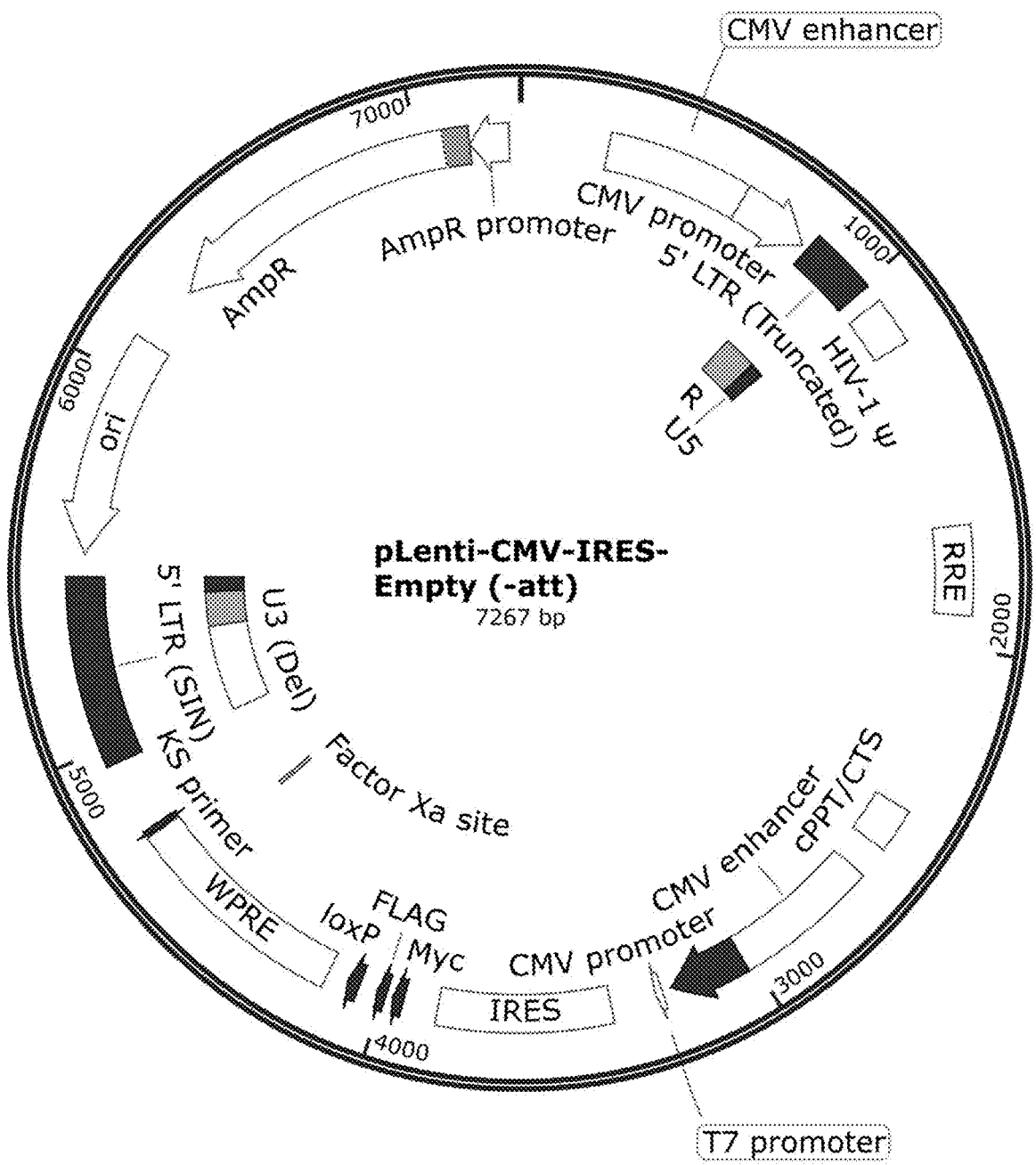
FIG. 8 provides the structure of pLenti-CMV-IRES-empty (-att) (SEQ ID NO:67) (7267 nucleotide residues), which is an example of an LTR-containing vector of the present invention.
Figure 9:
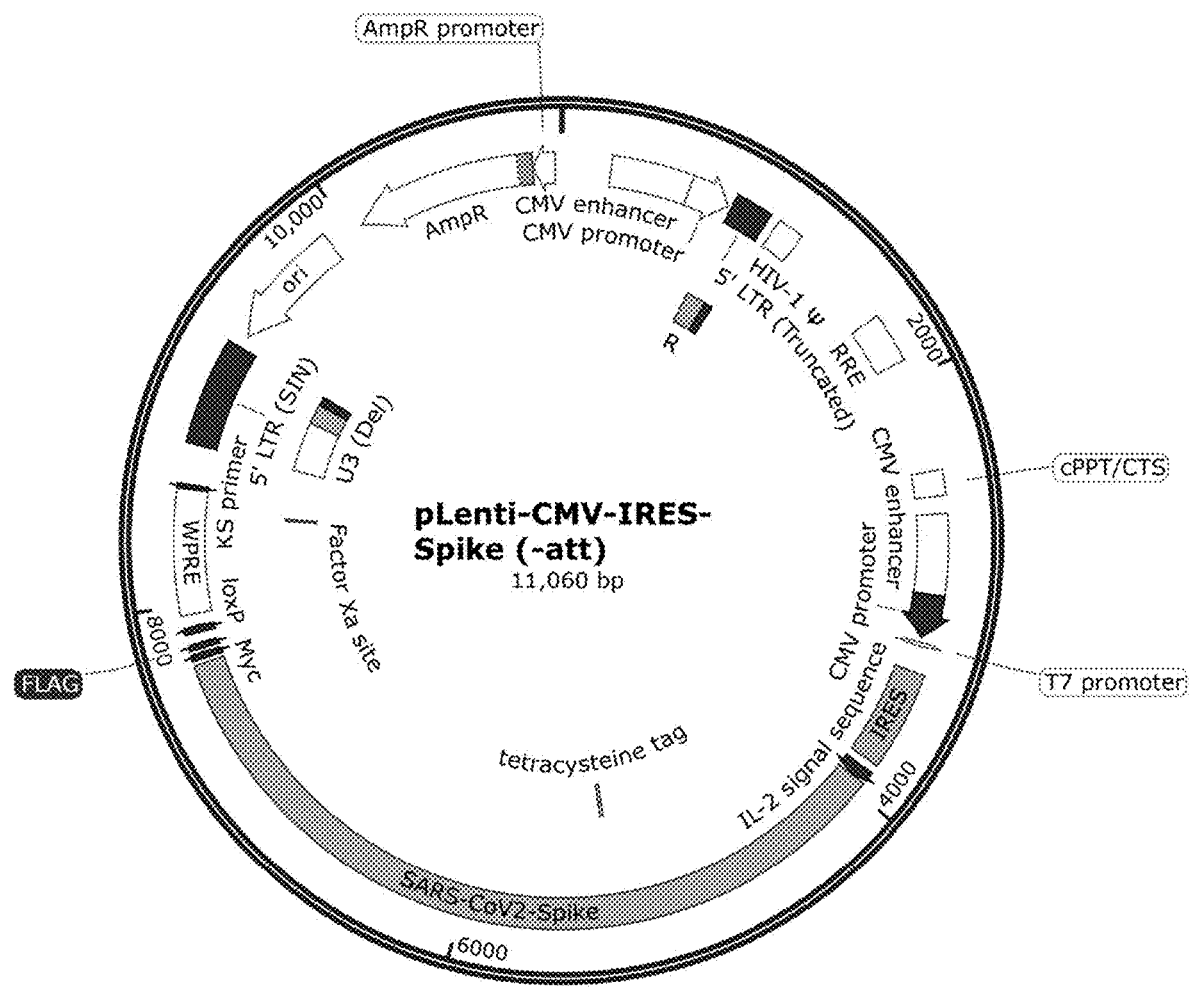
FIG. 9 provides the structure of pLenti-CMV-IRES-Spike (-att) (SEQ ID NO:70) (11060 nucleotide residues), which is an example of an LTR-containing vector of the present invention.
Figure 10:
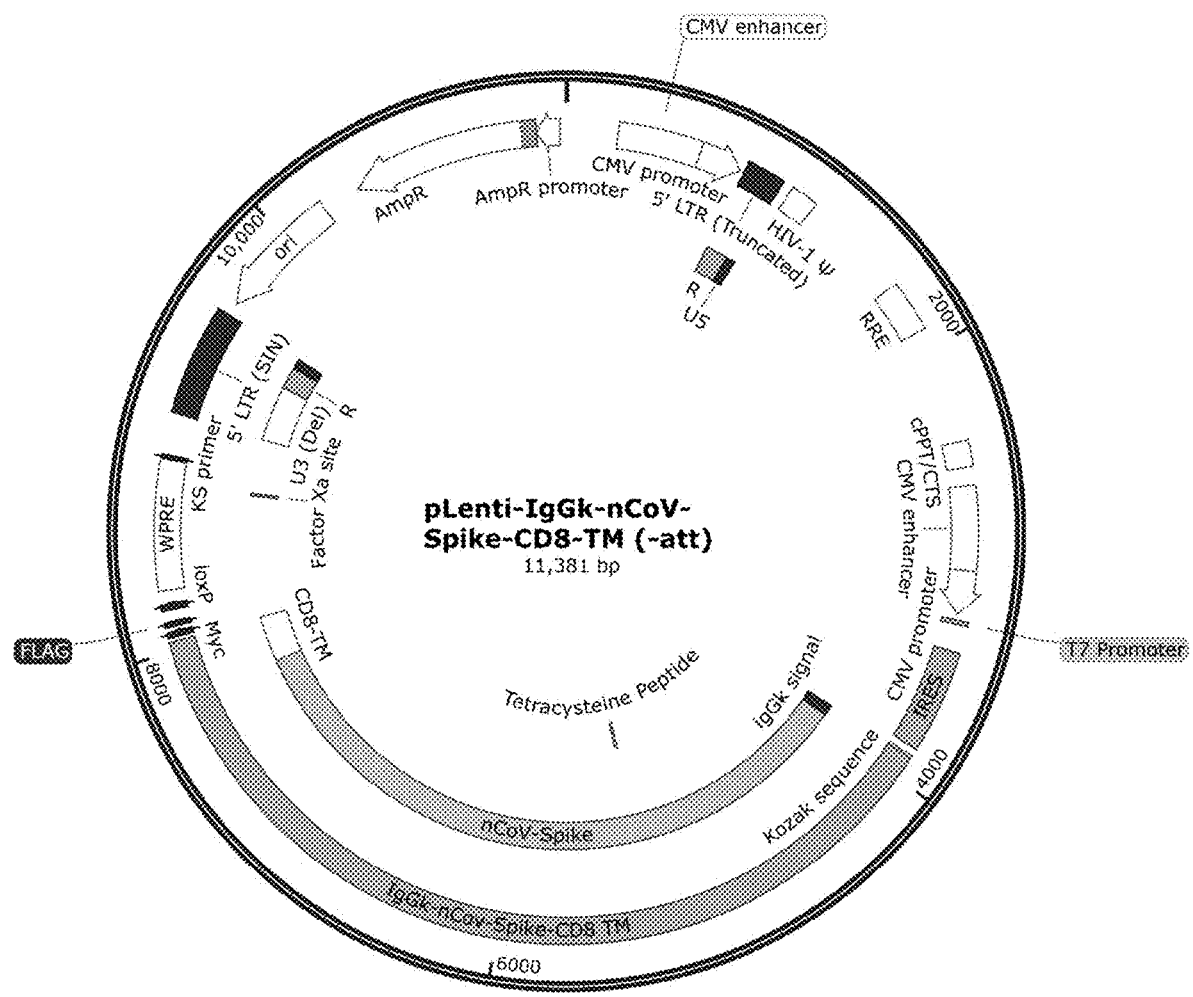
FIG. 10 provides the structure of pLenti-IgGκ-nCoV-Spike-CD8-TM (-att) (SEQ ID NO:83) (11381 nucleotide residues), which is an example of an LTR-containing vector of the present invention.
Figure 11:
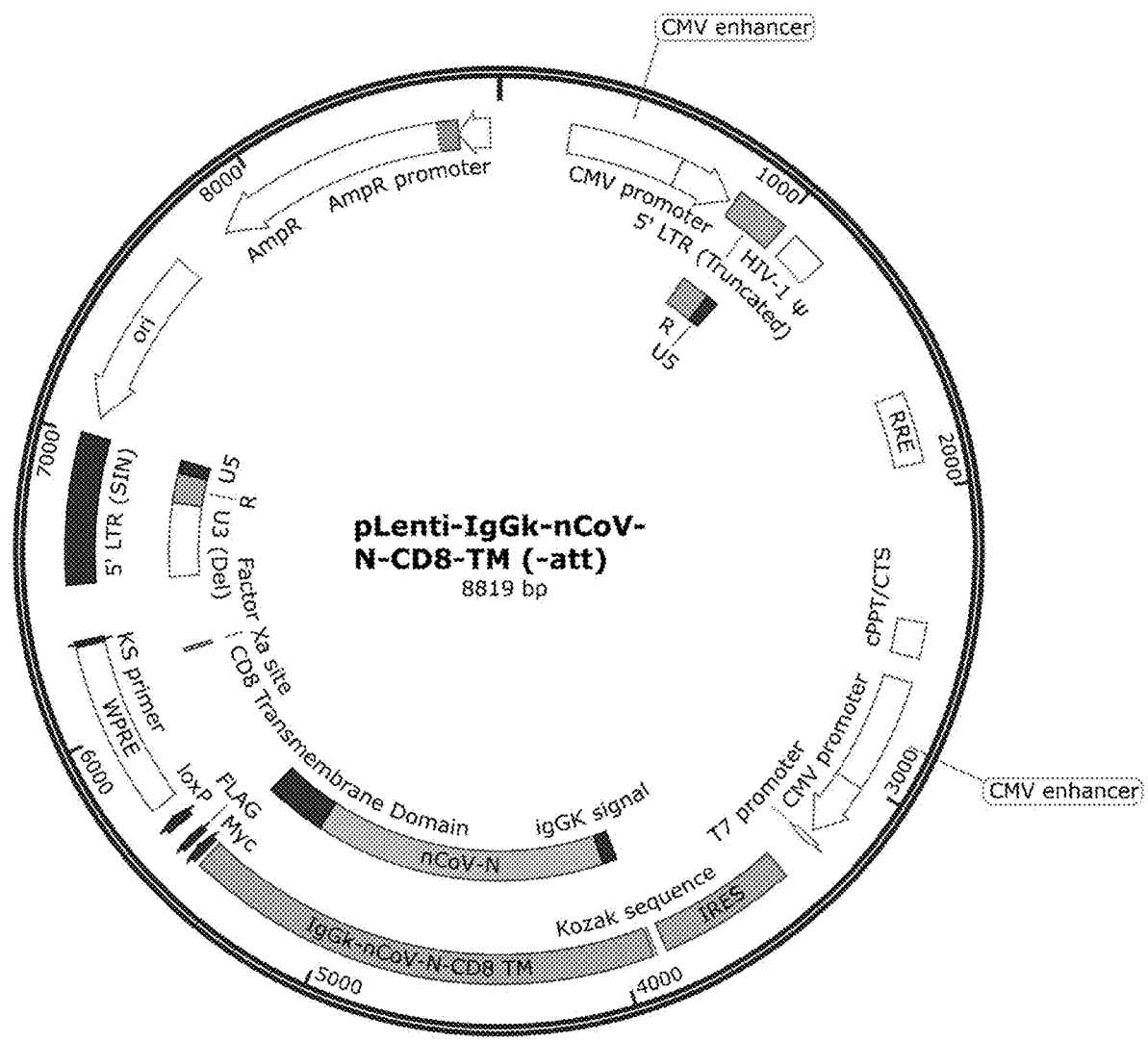
FIG. 11 provides the structure of pLenti-IgGκ-nCoV-N-CD8-TM (-att) (SEQ ID NO:84) (8819 nucleotide residues), which is an example of an LTR-containing vector of the present invention.

1. Features and Components of the LTR-Containing Vectors of the Present Invention As used herein, the term "LTR-containing vector" is intended to denote a vector that comprises at least one lentiviral LTR regions (which region may be intact, truncated, or contain an internal deletion, relative to a wildtype lentiviral LTR region). Such vectors will additionally comprise a promoter capable of mediating transcription of an R region and U5 region of a 5' lentiviral LTR, a lentiviral ψ region, a lentiviral Rev response element (RRE), a lentiviral central polypurine tract and central termination sequence (cPPT/CTS), and a self-inactivating 3' LTR region. The vectors: pLenti-SV40-puro (FIG. 6), pLenti-SV40-puro (-att) (FIG. 7), pLenti-CMV-IRES-empty (-att) (FIG. 8), pLenti-CMV-IRES-Spike (FIG. 9), pLenti-IgGκ-nCoV-Spike-CD8-TM (-att) (FIG. 10), pLenti-IgGκ-nCoV-N-CD8-TM (-att) (FIG. 11) and pLenti-IL-2 n-CoV-N(-att) (FIG. 12) illustrate the LTR-containing vectors of the present invention.

The LTR-containing vectors of the present invention comprise multiple preferred features. The first of such preferred features of the LTR vectors of the present invention is a first promoter (and an optional upstream transcriptional enhancer site) that will facilitate and mediate transcription in a mammalian host cell. Suitable promoters include the human cytomegalovirus (CMV) immediate early enhancer site and promoter, the EF1a promoter, the SV40 promoter, the human or murine PGK1 promoter, the α-fetoprotein promoter, the β-interferon promoter, the metallothionein II (MT II) promoter, the mouse mammary tumor virus (MMTV) promoter, the murine leukemia virus (MuLV) long terminal repeat promoter, the Ubc promoter, the human beta-actin promoter, the CAG promoter, the Rous sarcoma virus (RSV) promoter, the tetracycline response element (TRE) promoter, the Ca2+/calmodulin-dependent protein kinase II promoter, the human polymerase III RNA promoter, and the human or murine U6 small nuclear promoter (Colosimo, A. et al. (2000) "*Transfer and Expression of Foreign Genes in Mammalian Cells*," BioTechniques 29(2): 314-331; Addgene (2014) "*Plasmids* 101: *The Promoter Region—Let's Go!*," Addgene). Illustrative polynucleotides for such purpose comprise the human cytomegalovirus (CMV) immediate early enhancer site and the CMV immediate early promoter site. An illustrative CMV immediate early enhancer site comprises the sequence (SEQ ID NO:1):

```
gacattgatt attgactagt tattaatagt aatcaattac ggggtcatta gttcatagcc catatatgga gttccgcgtt acataactta cggtaaatgg cccgcctggc tgaccgccca acgaccccg cccattgacg tcaataatga cgtatgttcc catagtaacg ccaataggga ctttccattg acgtcaatgg gtggagtatt tacggtaaac tgcccacttg gcagtacatc aagtgtatca tatgccaagt acgccccta ttgacgtcaa tgacggtaaa tggcccgcct ggcattatgc ccagtacatg accttatggg actttcctac ttggcagtac atctacgtat tagtcatcgc tattaccatg
```

A suitable variant CMV immediate early enhancer site comprises the sequence (SEQ ID NO:2) (differences are shown underlined):

```
gacattgatt attgactagt tattaatagt aatcaattac ggggtcatta gttcatagcc catatatgga gttccgcgtt acataactta cggtaaatgg cccgcctggc tgaccgccca acgaccccg cccattgacg tcaataatga cgtatgttcc catagtaacg ccaataggga ctttccattg acgtcaatgg gtggagtatt tacggtaaac tgcccacttg gcagtacatc aagtgtatca tatgccaagt ccgccccta ttgacgtcaa tgacggtaaa tggcccgcct ggcattatgc ccagtacatg accttacggg actttcctac ttggcagtac atctacgtat tagtcatcgc tattaccatg
```

Truncated variants of such illustrative CMV immediate early enhancer sites that lack the first 76 residues of SEQ ID NO:1 or SEQ ID NO:2 may alternatively be employed.

An illustrative CMV immediate early promoter site for the LTR-containing vectors of the present invention comprises the sequence (SEQ ID NO:3):

```
gtgatgcggt tttggcagta catcaatggg cgtggatagc ggtttgactc acggggattt ccaagtctcc acccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag
```

A suitable variant CMV immediate early promoter site comprises the sequence (SEQ ID NO:4) (differences are shown underlined):

```
gtgatgcggt tttggcagta caccaatggg cgtggatagc ggtttgactc acggggattt ccaagtctcc acccattga cgtcaatggg agtttgtttt ggcaccaaaa tcaacgggac tttccaaaat gtcgtaataa ccccgccccg ttgacgcaaa tgggcggtag gcgtgtacgg tgggaggtct atataagcag agct
```

Additional suitable CMV immediate early promoter sites (e.g., SEQ ID NO:52) are discussed below.

A further preferred feature of the LTR-containing vectors of the present invention is a lentiviral 5' LTR region that has been truncated to delete its U3 region. The lentiviral 5' LTR region is natively composed of a U3 region, an R region (SEQ ID NO:76) and a U5 region (SEQ ID NO:77).

```
                                SEQ ID NO: 76
gggtctctct ggttagacca gatctgagcc tgggagctct
ctggctaact agggaaccca ctgcttaagc ctcaataaag
cttgccttga gtgcttca
```

```
                                SEQ ID NO: 77
agtagtgtgt gcccgtctgt tgtgtgactc tggtaactag
agatccctca gacccttta gtcagtgtgg aaaatctcta
gca
```

As discussed above, the deletion of the U3 region results in the transcriptional self-inactivation (SIN) of potentially packageable viral genomes in transduced cells. In preferred embodiments, such lentiviral 5' LTR region is derived from the 5' LTR of HIV-1, and comprises the sequence of SEQ ID NO:5, which is composed of an R region (SEQ ID NO:76) (shown in bold) and a U5 region (SEQ ID NO:77) (single underlined).

```
                                SEQ ID NO: 5
gggtctctct ggttagacca gatctgagcc tgggagctct ctggctaact agggaaccca ctgcttaagc ctcaataaag cttgccttga gtgcttcaag tagtgtgtgc ccgtctgttg tgtgactctg gtaactagag atccctcaga ccctttagt cagtgtggaa aatctctagc a
```

An alternative lentiviral 5' LTR region lacks the two 3' terminal residues of SEQ ID NO:5, and comprises the sequence of SEQ ID NO:68:

```
gggtctctct ggttagacca gatctgagcc tgggagctct ctggctaact agggaaccca ctgcttaagc ctcaataaag cttgccttga gtgcttcaag tagtgtgtgc ccgtctgttg tgtgactctg gtaactagag atccctcaga ccctttagt cagtgtggaa aatctctag
```

A further preferred feature of the LTR-containing vectors of the present invention is a lentiviral ψ region. In preferred embodiments, such lentiviral ψ region is derived from HIV-1, and comprises the sequence of (SEQ ID NO:6):

```
ctctctcgac gcaggactcg gcttgctgaa gcgcgcacgg caagaggcga ggggcggcga ctggtgagta cgccaaaaat tttgactagc ggaggctaga aggagagaga tgggtgcgag agcgtc
```

A further preferred feature of the LTR-containing vectors of the present invention is a lentiviral Rev response element (RRE), which allows for Rev-dependent mRNA export from the nucleus to the cytoplasm. In preferred embodiments, such lentiviral RRE region is derived from HIV-1, and comprises the sequence of (SEQ ID NO:7):

```
aggagctttg ttccttgggt tcttgggagc agcaggaagc actatgggcg cagcgtcaat gacgctgacg gtacaggcca gacaattatt gtctggtata gtgcagcagc agaacaattt gctgagggct attgaggcgc aacagcatct gttgcaactc acagtctggg gcatcaagca gctccaggca agaatcctgg ctgtggaaag atacctaaag gatcaacagc tcct
```

A further preferred feature of the LTR-containing vectors of the present invention is a lentiviral central polypurine tract and central termination sequence (cPPT/CTS). In preferred embodiments, such lentiviral cPPT/CTS region is derived from HIV-1, and comprises the sequence of (SEQ ID NO:8):

```
ttttaaaaga aaaggggggga ttggggggta cagtgcaggg gaaagaatag tagacataat agcaacagac atacaaacta aagaattaca aaaacaaatt acaaaaattc aaaatttt
```

In one embodiment, the LTR-containing vectors of the present invention will contain as a further preferred feature a second promoter that will be operably-linked to a non-lentiviral (i.e., "heterologous") transgene, so as to be capable of mediating the transcription and expression of the protein encoded by such transgene in a mammalian host cell. Suitable promoters are described above, and particularly include the CMV promoter (with or without its enhancer site). However, an illustrative such second promoter is an SV40 promoter that comprises the sequence of (SEQ ID NO:9), and which comprises an SV40 origin of replication (shown underlined):

```
gtgtgtcagt tagggtgtgg aaagtcccca ggctcccag caggcagaag tatgcaaagc atgcatctca attagtcagc aaccaggtgt ggaaagtccc caggctcccc agcaggcaga agtatgcaaa gcatgcatct caattagtca gcaaccatag tcccgcccct aactccgccc atcccgccc taactccgcc cagttccgcc cattctccgc cccatggctg actaattttt tttatttatg cagaggccga ggccgcctcg gcctctgagc tattccagaa gtagtgagga ggcttttttg gaggcctagg cttttgcaaa
```

In one embodiment, the second promoter will be a regulatable promoter, such that the extent of transcription in a transfected subject may be increased or decreased via the provision of an inducer or repressor agent. Any of numerous regulatable promoters, for example, the EF1a or CAG promoters or the tetracycline(tet) inducible systems (Dogbevia, G. K. et al. (2015) "Inducible And Combinatorial Gene Manipulation In Mouse Brain," Front. Cell. Neurosci. 9:142:1-8; Dogbevia, G. K. et al. (2016) "Flexible, AAV-Equipped Genetic Modules for Inducible Control of Gene Expression in Mammalian Brain," Molec. Ther. Nucl. Acids 5:e309:1-8) described in the art may be employed in such manner.

In one embodiment, such operably-linked heterologous transgene may encode an antibiotic resistance determinant, for example an N-acetyltransferase capable of providing recipient host cells with resistance to puromycin. An illustrative antibiotic resistance determinant for such purpose is the N-acetyltransferase of *Streptomyces alboniger*, which comprises the sequence (SEQ ID NO:10):

```
MTEYKPTVRL ATRDDVPRAV RTLAAAFADY PATRHTVDPD

RHIERVTELQ ELFLTRVGLD IGKVWVADDG AAVAVWTTPE

SVEAGAVFAE IGPRMAELSG SRLAAQQQME GLLAPHRPKE

PAWFLATVGV SPDHQGKGLG SAVVLPGVEA AERAGVPAFL

ETSAPRNLPF YERLGFTVTA DVEVPEGPRT WCMTRKPGA
```

An illustrative polynucleotide that encodes such N-acetyl-transferase of *Streptomyces alboniger* comprises the sequence (SEQ ID NO:11):

```
atgaccgagt acaagcccac ggtgcgcctc gccacccgcg acgacgtccc ccgggcagta cgcaccctcg ccgccgcgtt cgccgactac cccgccacgc gccacaccgt cgatccagac cgccacatcg agcgggtcac cgagctgcaa gaactcttcc tcacgcgcgt cgggctcgac atcggcaagg tgtgggtcgc ggacgacggc gccgcggtgg cggtctggac cacgccggag agcgtcgaag cggggggcggt gttcgccgag atcggcccgc gcatggccga gttgagcggt tcccggctgg ccgcgcagca acagatggaa ggcctcctgg cgccgcaccg gcccaaggag cccgcgtggt tcctggccac cgtcggcgtc tcgcccgacc accagggcaa gggtctgggc agcgccgtcg tgctcccgg agtggaggcg gccgagcgcg ccggggtgcc cgccttcctg gagacctccg cgccccgcaa cctcccttc tacgagcggc tcggcttcac cgtcaccgcc gacgtcgagg tgcccgaagg accgcgcacc tggtgcatga cccgcaagcc cggtgcctga
```

In an alternative embodiment, such operably-linked heterologous transgene may encode a reporter protein, such that the presence of the LTR-containing vector in a recipient cell can be more readily assessed. Examples of suitable reporter genes are well-known and include β-galactosidase, β-glucuronidase, chloramphenicol acetyltransferase, green fluorescent protein, red fluorescent protein, luciferase, etc. (Al Ali, S. et al. (2016) "*Use of Reporter Genes in the Genera-* tion of Vaccinia Virus-Derived Vectors," Viruses 8(5):1-18; Thakur, B. et al. (2015) "Molecular Imaging of Therapeutic Potential of Reporter Probes," Curr. Drug Targets 16(6): 645-657; Ghim, C. M. et al. (2010) "The Art Of Reporter Proteins In Science: Past, Present And Future Applications," BMB Rep. 43(7):451-460; Liu, A. M. et al. (2009) "Reporter Gene Assays," Meth. Mol. Biol. 486:109-123; Jansson, J. K. (2003) "Marker And Reporter Genes: Illuminating Tools For Environmental Microbiologists," Curr. Opin. Microbiol. 6(3):310-316; Lewis, J. C. et al. (1998) "Applications Of Reporter Genes," Anal. Chem. 70(17): 579A-585A).

In a further embodiment, such operably-linked heterologous transgene may encode a protein pharmaceutical agent, such as a protein drug (especially a protein drug that is effective in treating a coronavirus infection (especially SARS-CoV-2), e.g., β-interferon, griffithsin (GRFT), etc.) (Spiegel, M. et al. (2004) "The Antiviral Effect Of Interferon-Beta Against SARS-Coronavirus Is Not Mediated By mXA Protein," J. Clin. Virol. 30(3):211-213; (O'Keefe, B. R. et al. (2010) "Broad-Spectrum in vitro Activity and in vivo Efficacy Of The Antiviral Protein Griffthsin Against Emerging Viruses Of The Family Coronaviridae," J. Virol. 84(5):2511-2521), a protein that comprises the epitope binding domain of an antibody (e.g., an antibody light or heavy chain, a single chain antibody, etc.), especially a protein that comprises the epitope binding domain of an antibody that binds to a SARS-CoV-2 antigen). For example, a lentiviral particle that arrays the SARS-CoV-2 S protein on its surface will exhibit a tropism for cells that possess the cellular receptor capable of binding such protein. By administering such lentiviral particles that are additionally capable of transcribing a pharmaceutical agent effective against SARS-CoV-2, the present invention provides a means for targeting the pharmaceutical agent to loci of potential infection by actual SARS-CoV-2 viruses.

In a further embodiment, such operably-linked heterologous transgene may encode a viral protein, for example, an influenza HA protein (e.g., GenBank Accession Nos.: QJI52636.1, CY147342.1, etc.), a SARS-CoV S protein (e.g., GenBank Accession Nos.: AB263618.1, BAF42873.1, AAR23250.1, etc.), a MERS-CoV S protein (e.g., GenBank Accession Nos.: QGW51898.1, QGW51909.1, QGW51920.1, etc.), or a SARS-CoV-2 protein, and especially a SARS-CoV-2 S or N protein. In this embodiment of the invention, it is desired that the expressed viral protein be released by the transfected cell into the extracellular environment so that it may be detected by the immune system and aid in developing immunity against the virus. Thus, where the viral protein possesses an endoplasmic reticulum binding site, it is desirable that the encoding polynucleotide be truncated so as to not encode such site.

In a preferred embodiment, the polynucleotide that encodes the viral protein will be preceded by an in-frame signal sequence, such as the IL-2 signal sequence (SEQ ID NO:72):

```
MYRMQLLSCIALSLALVTNS,
``` or the IgGκ signal sequence (SEQ ID NO:81) (Guler-Gane, G. et al. (2016) "Overcoming the Refractory Expression of Secreted Recombinant Proteins in Mammalian Cells through Modification of the Signal Peptide and Adjacent Amino Acids," Plos One 11(5):1-15)

```
MDMRVPAQLLGLLLLWLSGARC
``` so as to form a fusion protein. The IL-2 signal (SEQ ID NO:72) may be encoded by a polynucleotide that comprises the sequence (SEQ ID NO:73):

```
atgtacagga tgcaactcct gtcttgcatt gcactaagtc
ttgcacttgt cacaaacagt
```

The IgGκ signal sequence (SEQ ID NO:81) may be encoded by a polynucleotide that comprises the sequence (SEQ ID NO:82):

```
atggacatga gggtccctgc tcagctcctg gggctcctgc
tgctctggct ctcaggtgcc agatgt
```

The presence of such a signal sequence promotes secretion of the viral protein (Zhang, L. et al. (2005) "Alteration In The IL-2 Signal Peptide Affects Secretion Of Proteins in vitro And in vivo," J. Gene Med. 7(3):354-365; Owji, H. et al. (2018) "A Comprehensive Review Of Signal Peptides: Structure, Roles, And Applications," Eur. J. Cell. Biol. 97(6):422-441; Nothwehr, S. F. et al. (1990) "Targeting Of Proteins Into The Eukaryotic Secretory Pathway: Signal Peptide Structure/Function Relationships," Bioessays 12(10):479-484). The in-frame signal sequence may be preceded by a consensus sequence for strong initiation of translation, such as a Kozak sequence, (Kozak, M. (1987) "An Analysis Of 5'-Noncoding Sequences From 699 Vertebrate Messenger RNAs," Nucl. Acids Res. 15(20):8125-8148). An illustrative Kozak sequence is (SEQ ID NO:85)

```
gccaccatgg.
```

Figure 12:
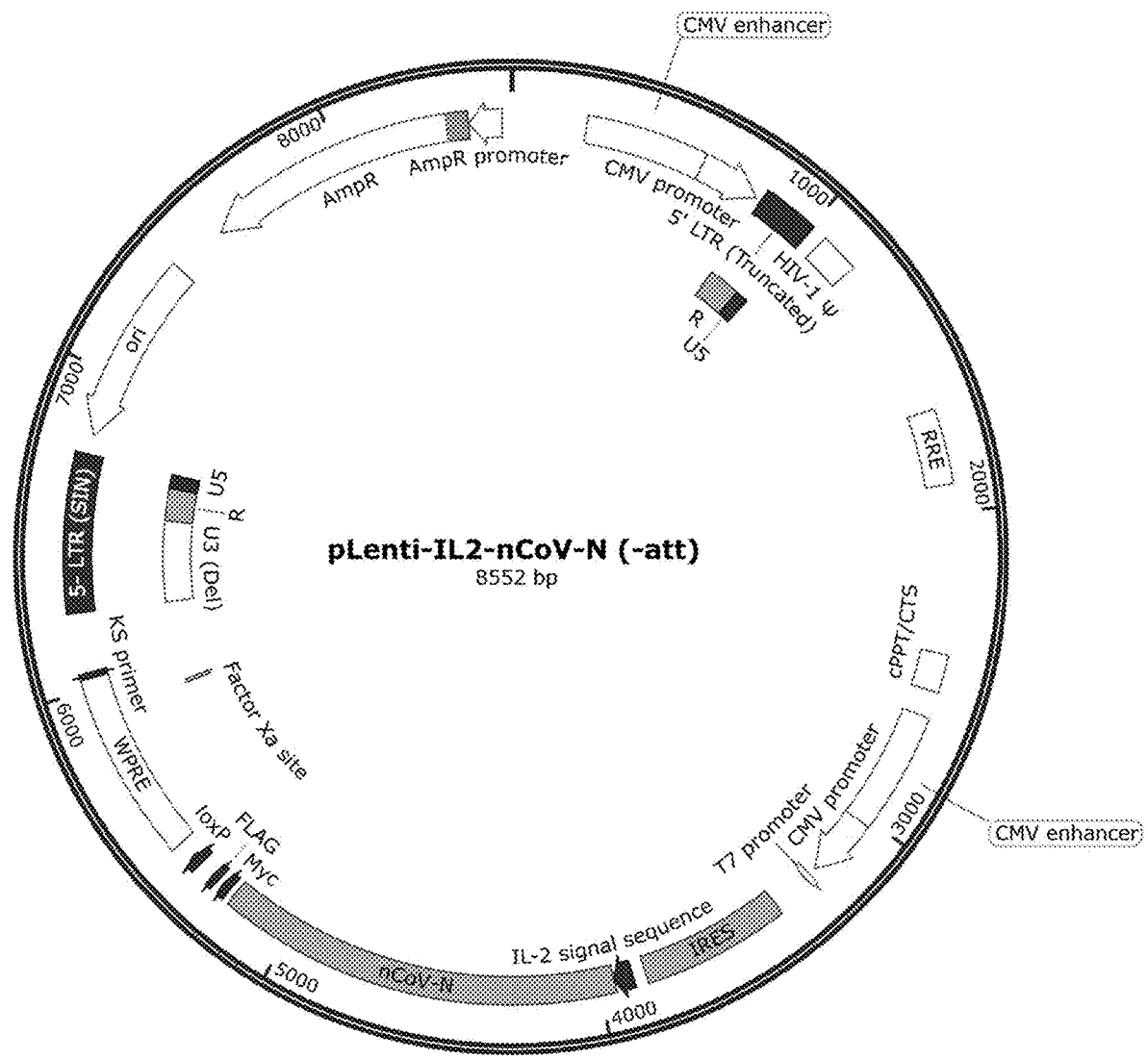
FIG. 12 provides the structure of pLenti-IL-2 n-CoV-N(-att) (SEQ ID NO:85) (8552 nucleotide residues), which is an example of an LTR-containing vector of the present invention.

In a particularly preferred embodiment, such operably-linked heterologous transgene will encode all or part of one or more proteins of SARS-CoV-2, e.g., all or part of the SARS-CoV-2 S protein, all or part of the SARS-CoV-2 nucleocapsid (N) protein, etc. Alternatively, transfection can be conducted using two different LTR-containing vectors, one of which comprises a transgene that encodes all or a portion of the SARS-CoV-2 S gene and the second of which comprises a transgene that encodes all or a portion of the SARS-CoV-2 N gene. The resulting lentiviral particles will array a mixture of S and N proteins on their surface. For example, transfection may be conducted in the presence of the LTR-containing vector pLenti-CMV-IRES-Spike (-att) (FIG. 9) or pLenti-IgG-nCoV-Spike-CD8-TM (-att) (FIG. 10) and in the presence of the LTR-containing vector pLenti-IgGκ-nCoV-N-CD8-TM (FIG. 11) or pLenti-IL-2 n-CoV-N (-att) (FIG. 12).

Polynucleotides encoding SARS-CoV-2 S proteins are described below. The SARS-CoV-2 N protein has the sequence (SEQ ID NO:78):

```
MSDNGPQNQR NAPRITFGGP SDSTGSNQNG ERSGARSKQR
RPQGLPNNTA SWFTALTQHG KEDLKFPRGQ GVPINTNSSP
DDQIGYYRRA TRRIRGGDGK MKDLSPRWYF YYLGTGPEAG
LPYGANKDGI IWVATEGALN TPKDHIGTRN PANNAAIVLQ
LPQGTTLPKG FYAEGSRGGS QASSRSSSRS RNSSRNSTPG
SSRGTSPARM AGNGGDAALA LLLLDRLNQL ESKMSGKGQQ
```

-continued

QQGQTVTKKS AAEASKKPRQ KRTATKAYNV TQAFGRRGPE

QTQGNFGDQE LIRQGTDYKH WPQIAQFAPS ASAFFGMSRI

GMEVTPSGTW LTYTGAIKLD DKDPNFKDQV ILLNKHIDAY

KTFPPTEPKK DKKKKADETQ ALPQRQKKQQ TVTLLPAADL

DDFSKQLQQS MSSADSTQA

The SARS-CoV-2 N protein (SEQ ID NO:78) may be encoded by the polynucleotide sequence (SEQ ID NO:79):

```
atgtctgata atggacccca aaatcagcga aatgcaccc
gcattacgtt tggtggaccc tcagattcaa ctggcagtaa
ccagaatgga gaacgcagtg gggcgcgatc aaaacaacgt
cggccccaag gtttacccaa taatactgcg tcttggttca
ccgctctcac tcaacatggc aaggaagacc ttaaattccc
tcgaggacaa ggcgttccaa ttaacaccaa tagcagtcca
gatgaccaaa ttggctacta ccgaagagct accagacgaa
ttcgtggtgg tgacggtaaa atgaaagatc tcagtccaag
atggtatttc tactacctag gaactgggcc agaagctgga
cttccctatg gtgctaacaa agacggcatc atatgggttg
caactgaggg agccttgaat acaccaaaag atcacattgg
caccgcaat cctgctaaca atgctgcaat cgtgctacaa
cttcctcaag gaacaacatt gccaaaaggc ttctacgcag
aagggagcag aggcggcagt caagcctctt ctcgttcctc
atcacgtagt cgcaacagtt caagaaattc aactccaggc
agcagtaggg gaacttctcc tgctagaatg gctggcaatg
gcggtgatgc tgctcttgct ttgctgctgc ttgacagatt
gaaccagctt gagagcaaaa tgtctggtaa aggccaacaa
caacaaggcc aaactgtcac taagaaatct gctgctgagg
cttctaagaa gcctcggcaa aaacgtactg ccactaaagc
atacaatgta acacaagctt tcggcagacg tggtccagaa
caaacccaag gaaattttgg ggaccaggaa ctaatcagac
aaggaactga ttacaaacat tggccgcaaa ttgcacaatt
tgcccccagc gcttcagcgt tcttcggaat gtcgcgcatt
ggcatggaag tcacaccttc gggaactgtg ttgacctaca
caggtgccat caaattggat gacaaagatc caaatttcaa
agatcaagtc attttgctga ataagcatat tgacgcatac
aaaacattcc caccaacaga gcctaaaaag gacaaaaaga
agaaggctga tgaaactcaa gccttaccgc agagacagaa
gaaacagcaa actgtgactc ttcttcctgc tgcagatttg
gatgatttct ccaaacaatt gcaacaatcc atgagcagtg
ctgactcaac tcaggcc
``` or by a codon-optimized variant thereof (SEQ ID NO:80):

```
atgtctgata atggaccaca aaaccagcgc aatgctccga
ggataacatt cggtgggccc tccgactcta ctggaagcaa
tcaaaatggg gagcggtcag gagccaggtc taaacagagg
cgacctcagg ggctgcctaa taatactgcc agctggttca
ctgctctgac ccagcatggc aaggaggact gaagttccc
caggggtcag ggtgtaccaa tcaacactaa ttcttcccca
gacgaccaga ttggttatta cagaagggct acccggagga
ttaggggagg ggatggcaag atgaaggatc ttagtccacg
ctggtatttt tactaccttg gtacaggacc agaggctgga
cttccttatg gagcaaacaa agatggaatc atctgggtgg
ccacggaggg agccctcaat accccaaaag accatatcgg
gacccggaac ccgccaata atgccgcgat agtactgcaa
ttgccccaag ggactactct gccaaaaggc ttttatgcag
aagggtctcg aggagggtct caggcctcca gtcgctcatc
ttcccggtcc agaaacagca gccggaattc cacacccggg
agtagcagag gcactagccc tgcacgaatg gctggcaatg
gaggagatgc cgcccttgca ctgctgcttc tggatcgcct
gaaccagttg gagtccaaaa tgagtggcaa ggggcagcaa
cagcagggcc agacagtcac caagaagtct gccgcagaag
cttccaaaaa gccaaggcag aagaggacag caactaaagc
ttataacgtg acgcaggctt cggtaggcg gggaccagaa
cagacccagg gtaacttcgg cgatcaggag cttattagac
aggggacaga ctataaacac tggccccaga tcgcccaatt
tgcccccagt gcatccgcct tcttcgggat gagtagaatc
ggcatggagg tgactcctag tggcacgtgg ctcacctata
ccggcgctat caagcttgat gacaaagatc ctaatttcaa
agatcaggtc atactgctga ataagcacat tgacgcatac
aaaacctttc ccctaccga accgaagaag gacaagaaga
aaaaggccga tgagacgcaa gctctgcctc agaggcagaa
gaaacagcaa acagtcactc tgttgcctgc ggcggacctt
gatgactttt ctaaacagct gcagcagagt atgagcagcg
ccgactccac ccaggcg
```

Such vectors will thus cause the SARS-CoV-2 spike (S) protein or nucleocapsid (N) protein to be produced in infected cells. Export of such protein will thus serve to provide such antigens to recipient subjects so that they may elicit neutralizing antibodies to SARS-CoV-2 and become immunized to COVID-19. It is preferred that the polynucleotide be codon optimized for translation in human cells. When the transgene encodes the SARS-CoV-2 S protein, it is preferred that its sequence be different from the sequence of the SARS-CoV-2 S protein-encoding polynucleotide used in the envelope vectors of the present invention in order to minimize recombination between these two sequences. Thus, it is preferred to employ the codon-optimized polynucleotide sequence of SEQ ID NO:71 to encode the SARS-CoV-2 spike protein (SEQ ID NO:54) in the LTR-containing vector embodiment that expresses a SARS-CoV-2 spike protein transgene.

SEQ ID NO: 71

```
atgtttgtgt tcctggtgct gctgccactg gtgtccagcc
agtgtgtgaa cctgaccacc aggacccaac ttcctcctgc
ctacaccaac tccttcacca ggggagtcta ctaccctgac
aaggtgttca ggtcctctgt gctgcacagc acccaggacc
tgttcctgcc attcttcagc aatgtgacct ggttccatgc
catccatgtg tctggcacca atggcaccaa gaggtttgac
aaccctgtgc tgccattcaa tgatggagtc tactttgcca
gcacagagaa gagcaacatc atcaggggct ggatttttgg
caccaccctg acagcaaga cccagtccct gctgattgtg
aacaatgcca ccaatgtggt gattaaggtg tgtgagttcc
agttctgtaa tgacccattc ctgggagtct actaccacaa
gaacaacaag tcctggatgg agtctgagtt cagggtctac
tcctctgcca acaactgtac ctttgaatat gtgagccaac
cattcctgat ggacttggag ggcaagcagg gcaacttcaa
gaacctgagg gagtttgtgt tcaagaacat tgatggctac
ttcaagattt acagcaaaca cacaccaatc aacctggtga
gggacctgcc acagggcttc tctgccttgg aaccactggt
ggacctgcca attggcatca acatcaccag gttccagacc
ctgctggctc tgcacaggtc ctacctgaca cctggagact
cctcctctgg ctggacagca ggagcagcag cctactatgt
gggctacctc caaccaagga ccttcctgct gaaatacaat
gagaatggca ccatcacaga tgctgtggac tgtgccctgg
acccactgtc tgagaccaag tgtaccctga atccttcac
agtggagaag ggcatctacc agaccagcaa cttcagggtc
caaccaacag agagcattgt gaggtttcca aacatcacca
acctgtgtcc atttggagag gtgttcaatg ccaccaggtt
tgcctctgtc tatgcctgga acaggaagag gattagcaac
tgtgtggctg actactctgt gctctacaac tctgcctcct
tcagcacctt caagtgttat ggagtgagcc caaccaaact
gaatgacctg tgtttcacca atgtctatgc tgactccttt
gtgattaggg gagatgaggt gagacagatt gcccctggac
aaacaggcaa gattgctgac tacaactaca aactgcctga
tgacttcaca ggctgtgtga ttgcctggaa cagcaacaac
ctggacagca aggtgggagg caactacaac tacctctaca
gactgttcag gaagagcaac ctgaaaccat tgagaggga
catcagcaca gagatttacc aggctgcag cacaccatgt
aatggagtgg agggcttcaa ctgttactt ccactccaat
```

-continued

```
cctatggctt ccaaccaacc aatggagtgg gctaccaacc
atacagggtg gtggtgctgt cctttgaact gctccatgcc
cctgccacag tgtgtggacc aaagaagagc accaacctgg
tgaagaacaa gtgtgtgaac ttcaacttca tggactgac
aggcacagga gtgctgacag agagcaacaa gaagttcctg
ccattccaac agtttggcag ggacattgct gacaccacag
atgctgtgag ggacccacag accttggaga ttctggacat
cacaccatgt tcctttggag gagtgtctgt gattacacct
ggcaccaaca ccagcaacca ggtggctgtg ctctaccagg
atgtgaactg tactgaggtg cctgtggcta tccatgctga
ccaacttaca ccaacctgga gggtctacag cacaggcagc
aatgtgttcc agaccagggc tggctgtctg attggagcag
agcatgtgaa caactcctat gagtgtgaca tcccaattgg
agcaggcatc tgtgcctcct accagaccca gaccaacagc
ccaggagggg caaggtctgt ggcaagccag agcatcattg
cctacacaat gagtctggga gcagagaact ctgtggctta
cagcaacaac agcattgcca tcccaaccaa cttcaccatc
tctgtgacca cagagattct gcctgtgagt atgaccaaga
cctctgtgga ctgtacaatg tatatctgtg gagacagcac
agagtgtagc aacctgctgc tccaatatgg ctccttctgt
acccaactta caggggctct gacaggcatt gctgtggaac
aggacaagaa cacccaggag gtgtttgccc aggtgaagca
gatttacaag acacctccaa tcaaggactt tggaggcttc
aacttcagcc agattctgcc tgacccaagc aagccaagca
agaggtcctt cattgaggac ctgctgttca acaaggtgac
cctggctgat gctggcttca tcaagcaata tggagactgt
ctgggagaca ttgctgccag ggacctgatt tgtgcccaga
agttcaatgg actgacagtg ctgcctccac tgctgacaga
tgagatgatt gcccaataca cctctgccct gctggctggc
accatcacct ctggctggac ctttggagca ggagcagccc
tccaaatccc atttgctatg cagatggctt acaggttcaa
tggcattgga gtgacccaga atgtgctcta tgaaaccag
aaactgattg ccaaccagtt caactctgcc attggcaaga
ttcaggactc cctgtccagc acagcctctg ccctgggcaa
actccaagat gtggtgaacc agaatgccca ggctctgaac
accctggtga agcaactttc cagcaacttt ggagccatct
cctctgtgct gaatgacatc ctgagcagac tggacaaggt
ggaggctgag gtccagattg acagactgat tacaggcaga
ctccaatccc tccaaaccta tgtgacccaa caacttatca
gggctgctga gattagggca tctgccaacc tggctgccac
caagatgagt gagtgtgtgc tgggacaaag caagagggtg
```

```
gacttctgtg gcaagggcta ccacctgatg agttttccac agtctgcccc tcatggagtg gtgttcctgc atgtgaccta tgtgcctgcc caggagaaga acttcaccac agccctgcc atctgccatg atggcaaggc tcactttcca agggagggag tgtttgtgag caatggcacc cactggtttg tgacccagag gaacttctat gaaccacaga ttatcaccac agacaacacc tttgtgtctg gcaactgtga tgtggtgatt ggcattgtga acaacacagt ctatgaccca ctccaacctg aactggactc cttcaaggag gaactggaca aatacttcaa gaaccacacc agccctgatg tggacctggg agacatctct ggcatcaatg cctctgtggt gaacatccag aaggagatta acagactgaa tgaggtggct aagaacctga atgagtccct gattgacctc caagaactgg gcaaatatga acaatacatc aagtggccat ggtacatctg gctgggcttc attgctggac tgattgccat tgtgatggtg accataatgc tgtgttgtat gacctcctgt tgttcctgtc tgaaaggctg ttgttcctgt ggctcctgtt gtaag
```

The transgene may be fused to a transmembrane domain, such as the CD8 transmembrane domain in order to promote the anchoring of the transgene protein in the lentiviral membrane. The sequence of the CD8 transmembrane domain is (SEQ ID NO:87):

```
ALSNSIMYFS HFVPVFLPAK PTTTPAPRPP TPAPTIASQP

LSLRPEACRP AAGGAVHTRG LDFACDIYIW APLAGTCGVL

LLSLVIT
```

A polynucleotide that encodes the CD8 transmembrane domain comprises the sequence (SEQ ID NO:88).

```
gccctgagca actccatcat gtacttcagc cacttcgtgc cggtcttcct gccagcgaag cccaccacga cgccagcgcc gcgaccacca acaccggcgc ccaccatcgc gtcgcagccc ctgtccctgc gcccagaggc gtgccggcca gcggcggggg gcgcagtgca cacgaggggg ctggacttcg cctgtgatat ctacatctgg gcgcccttgg ccgggacttg tggggtcctt ctcctgtcac tggttatcac ctga
```

In a further embodiment, the LTR-containing vector of the present invention comprise the above-discussed second promoter and comprise a heterologous transgene that is not translated into a protein. For example, such LTR-containing vector may comprise a polynucleotide that upon transcription provides an siRNA molecule capable of silencing an essential SARS-CoV-2 gene (e.g., the SARS-CoV-2 reverse transcriptase or integrase) (Kanasty, R. et al. (2013) "*Delivery Materials for siRNA Therapeutics*," Nat. Mater. 12(11): 967-977; Selvam, C. (2017) "*Therapeutic Potential Of Chemically Modified siRNA: Recent Trends*," Chem. Biol. Drug Des. 90(5):665-678; Gavrilov, K. et al. (2012) "*Therapeutic siRNA: Principles, Challenges, And Strategies*," Yale J. Biol. Med. 85(2):187-200).

In a further alternative embodiment, illustrated by the LTR-containing vector pLenti-CMV-IRES-empty (-att) (FIG. 8), the LTR-containing vector of the present invention lack the above-discussed second promoter and/or lack a heterologous transgene.

A further preferred feature of the LTR-containing vectors of the present invention is a third promoter (and an optional upstream transcriptional enhancer site) that will facilitate and mediate transcription in a mammalian host cell. Promoters for suitable for such use are discussed above. An illustrative transcriptional enhancer site is the variant CMV immediate early enhancer site (SEQ ID NO:2) and the variant CMV immediate early promoter site (SEQ ID NO:4).

A further preferred feature of the LTR-containing vectors of the present invention is a first promoter that will direct transcription in a bacterial host. Suitable promoters include the T7 promoter, the T7 lac promoter, the Sp6 promoter, the araBAD promoter, the trp promoter, the lac promoter, the Ptac promoter, the lambda pL promoter, and the T3 promoter. Sources of such promoters are well known in the art (Zheng, C. et al. (2008) "*Evaluation of Promoters for Use in Tissue-Specifc Gene Delivery*," In: GENE THERAPY PROTOCOLS, Humana Press; pp. 205-219; Pance, A. (2013) "*Tailoring The Models Of Transcription*," Int. J. Mol. Sci. 14(4):7583-7597; Tolmachov, O. (2009) "*Designing Plasmid Vectors*;" Methods Mol. Biol. 542:117-129; Addgene (2014) "*Plasmids 101: The Promoter Region—Let's Go!*," Addgene). An exemplary polynucleotide for such purpose comprises a T7 promoter site. An illustrative T7 promoter site comprises the sequence (SEQ ID NO:12):

```
taatacgactcactatagg.
```

A further preferred feature of the LTR-containing vectors of the present invention is an internal ribosome entry site (IRES), such as the internal ribosome entry site of the encephalomyocarditis virus (EMCV) (SEQ ID NO:69):

```
gagggcccgg aaacctggcc ctgtcttctt gacgagcatt cctagggtc tttcccctct cgccaaagga atgcaaggtc tgttgaatgt cgtgaaggaa gcagttcctc tggaagcttc ttgaagacaa acaacgtctg tagcgaccct ttgcaggcag cggaaccccc cacctggcga caggtgcctc tgcggccaaa agccacgtgt ataagataca cctgcaaagg cggcacaacc ccagtgccac gttgtgagtt ggatagttgt ggaaagagtc aaatggctct cctcaagcgt attcaacaag gggctgaagg atgcccagaa ggtaccccat tgtatgggat ctgatctggg gcctcggtgc acatgcttta catgtgttta gtcgaggtta aaaaacgtct aggcccccccg aaccacgggg acgtggtttt cctttgaaaa acacgatgat aa
```

A further preferred, but optional, feature of the LTR-containing vectors of the present invention comprises one or more epitope tags that facilitate the recovery of product by immunoadsorption or affinity chromatography (Zhao, X. (2013) "*Several Affinity Tags Commonly Used In Chromatographic Purification*," J. Anal. Meth. Chem. 2013:581093: 1-8). Illustrative epitope tags include a Myc (human c-Myc oncogene) or FLAG® epitope tag, a combined Myc-FLAG® tag that comprises the sequence (SEQ ID NO:13):

EQKLISEEDL AANDILDYKD DDDKV

(the FLAG® epitope tag portion thereof is underlined) An exemplary polynucleotide encoding such combined epitope tag comprises the sequence (SEQ ID NO:14):

gagcagaaac tcatctcaga agaggatctg gcagcaaatg atatcctgga ttacaaggat gacgacgata aggtt A further preferred, but optional, feature of the LTR-containing vectors of the present invention comprises a LoxP site, which permits recombination in the presence of Cre recombinase (McLellan, M. A. (2017) "*Cre-LoxP-Mediated Recombination: General Principles And Experimental Considerations*," Curr. Protoc. Mouse Biol. 7(1):1-12), and thus facilitates cloning and modification of the vector. An exemplary polynucleotide encoding such LoxP site comprises the sequence (SEQ ID NO:15):

ataacttcgtatagcatacattatacgaagttat.

A further preferred feature of the LTR-containing vectors of the present invention, optionally present when the LTR-containing vector comprises a heterologous transgene, comprises a woodchuck hepatitis virus post-transcriptional regulatory element (WPRE) (Higashimoto, T. et al. (2007) "*The Woodchuck Hepatitis Virus Post-Transcriptional Regulatory Element Reduces Readthrough Transcription From Retroviral Vectors*," Gene Ther. 14:1298-1304). An illustrative polynucleotide encoding such WPRE comprises the sequence (SEQ ID NO:16):

aatcaacctc tggattacaa aatttgtgaa agattgactg gtattcttaa ctatgttgct cctttttacgc tatgtggata cgctgcttta atgcctttgt atcatgctat tgcttcccgt atggctttca ttttctcctc cttgtataaa tcctggttgc tgtctcttta tgaggagttg tggcccgttg tcaggcaacg tggcgtggtg tgcactgtgt ttgctgacgc aacccccact ggttggggca ttgccaccac ctgtcagctc ctttccggga ctttcgcttt ccccctccct attgccacgg cggaactcat cgccgcctgc cttgcccgct gctggacagg ggctcggctg ttgggcactg acaattccgt ggtgttgtcg gggaaatcat cgtcctttcc ttggctgctc gcctgtgttg ccacctggat tctgcgcggg acgtccttct gctacgtccc ttcggccctc aatccagcgg accttccttc ccgcggcctg ctgccggctc tgcggcctct tccgcgtctt cgccttcgcc ctcagacgag tcggatctcc ctttgggccg cctccccgc A further preferred feature of the LTR-containing vectors of the present invention, optionally present when the LTR-containing vector comprises a heterologous transgene, comprises a Factor Xa cleavage site that mediates the cleavage of fusion proteins by Factor Xa protease (Block, H. et al. (2015) "*Proteolytic Affinity Tag Cleavage*," Methods Enzymol. 559:71-97). An illustrative polynucleotide encoding such Factor Xa cleavage site comprises the sequence (SEQ ID NO:17):

tcggccctcaat.

A further preferred optional feature of the LTR-containing vectors of the present invention comprises a primer binding site for sequencing. An illustrative polynucleotide encoding such a site is a KS primer binding site that comprises the sequence (SEQ ID NO:18):

cgaggtcgacggtatcg.

Preferably, the primer binding site is introduced into the strand of the vector that does not comprise the transgene-encoding sequences (i.e., it is introduced into the "second" strand of the vector).

A further preferred feature of the LTR-containing vectors of the present invention is a second lentiviral 5' LTR region that has been truncated to delete its U3 region. In preferred embodiments, such lentiviral 5' LTR region is derived from the 5' LTR of HIV-1, and comprises the same sequence (SEQ ID NO:5) as the above-discussed first lentiviral 5' LTR region.

A further preferred feature of the LTR-containing vectors of the present invention is an origin of replication capable of mediating the replication of the vector in prokaryotic cells. An exemplary origin or replication site for this purpose is the high-copy-number ColE1/pMB1/pBR322/pUC origin of replication that comprises the sequence of SEQ ID NO:19, and is preferably positioned on the second strand of the vector:

ttgagatcct ttttttctgc gcgtaatctg ctgcttgcaa acaaaaaaac caccgctacc agcggtggtt tgtttgccgg atcaagagct accaactctt tttccgaagg taactggctt cagcagagcg cagataccaa atactgttct tctagtgtag ccgtagttag gccaccactt caagaactct gtagcaccgc ctacatacct cgctctgcta atcctgttac cagtggctgc tgccagtggc gataagtcgt gtcttaccgg gttggactca agacgatagt taccggataa ggcgcagcgg tcgggctgaa cggggggttc gtgcacacag cccagcttgg agcgaacgac ctacaccgaa ctgagatacc tacagcgtga gctatgagaa agcgccacgc ttcccgaagg gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga tttttgtgat gctcgtcagg ggggcggagc ctatggaaa A variant of such high-copy-number ColE1/pMB1/pBR322/pUC origin of replication comprises the sequence (SEQ ID NO:20) (the difference with respect to SEQ ID NO:19 is underlined):

ttgagatcct ttttttctgc gcgtaatctg ctgcttgcaa acaaaaaaac caccgctacc agcggtggtt tgtttgccgg

```
atcaagagct accaactctt tttccgaagg taactggctt cagcagagcg cagataccaa atactgtcct tctagtgtag ccgtagttag gccaccactt caagaactct gtagcaccgc ctacatacct cgctctgcta atcctgttac cagtggctgc tgccagtggc gataagtcgt gtcttaccgg gttggactca agacgatagt taccggataa ggcgcagcgg tcgggctgaa cgggggggttc gtgcacacag cccagcttgg agcgaacgac ctacaccgaa ctgagatacc tacagcgtga gctatgagaa agcgccacgc ttcccgaagg gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga tttttgtgat gctcgtcagg ggggcggagc ctatggaaa
```

A further preferred feature of the LTR-containing vectors of the present invention is a gene that encodes an antibiotic resistance determinant, such as AmpR, which confers resistance to ampicillin, carbenicillin, and related antibiotics to bacterial cells transfected with the vector. The antibiotic resistance determinant is operably controlled by a promoter, such as the AmpR promoter, and both polynucleotide sequences are preferably positioned on the second stand of the vector. An illustrative AmpR antibiotic resistance determinant comprises the sequence (SEQ ID NO:21) (signal sequence shown underlined):

```
MSIQHFRVAL IPFFAAFCLP VFAEPETLVK VKDAEDQLGA

RVGYIELDLN SGKILESFRP EERFPMMSTF KVLLCGAVLS

RIDAGQEQLG RRIHYSQNDL VEYSPVTEKH LTDGMTVREL

CSAAITMSDN TAANLLLTTI GGPKELTAFL HNMGDHVTRL

DRWEPELNEA IPNDERDTTM PVAMATTLRK LLTGELLTLA

SRQQLIDWME ADKVAGPLLR SALPAGWFIA DKSGAGERGS

RGIIAALGPD GKPSRIVVIY TTGSQATMDE RNRQIAEIGA

SLIKHW
```

An illustrative polynucleotide that encodes the AmpR antibiotic resistance determinant of SEQ ID NO:21 has the sequence of SEQ ID NO:22:

```
atgagtattc aacatttccg tgtcgccctt attccttttt ttgcggcatt ttgccttcct gttttgctc acccagaaac gctggtgaaa gtaaaagatg ctgaagatca gttgggtgca cgagtgggtt acatcgaact ggatctcaac agcggtaaga tccttgagag ttttcgcccc gaagaacgtt ttccaatgat gagcactttt aaagttctgc tatgtggcgc ggtattatcc cgtattgacg ccgggcaaga gcaactcggt cgccgcatac actattctca gaatgacttg gttgagtact caccagtcac agaaaagcat cttacggatg gcatgacagt aagagaatta
```

```
tgcagtgctg ccataaccat gagtgataac actgcggcca acttacttct gacaacgatc ggaggaccga aggagctaac cgcttttttg cacaacatgg gggatcatgt aactcgcctt gatcgttggg aaccggagct gaatgaagcc ataccaaacg acgagcgtga caccacgatg cctgtagcaa tggcaacaac gttgcgcaaa ctattaactg gcgaactact tactctagct tcccggcaac aattaataga ctggatggag gcggataaag ttgcaggacc acttctgcgc tcggcccttc cggctggctg gtttattgct gataaatctg gagccggtga gcgtgggtct cgcggtatca ttgcagcact ggggccagat ggtaagccct cccgtatcgt agttatctac acgacgggga gtcaggcaac tatggatgaa cgaaatagac agatcgctga gataggtgcc tcactgatta agcattgg
```

A variant AmpR antibiotic resistance determinant comprises the sequence (SEQ ID NO:23) (signal sequence shown underlined; difference between SEQ ID NO:21 shown double underlined):

```
MSIQHFRVAL IPFFAAFCLP VFAHPETLVK VKDAEDQLGA

RVGYIELDLN SGKILESFRP EERFPMMSTF KVLLCGAVLS

RVDAGQEQLG RRIHYSQNDL VEYSPVTEKH LTDGMTVREL

CSAAITMSDN TAANLLLTTI GGPKELTAFL HNMGDHVTRL

DRWEPELNEA IPNDERDTTM PAAMATTLRK LLTGELLTLA

SRQQLIDWME ADKVAGPLLR SALPAGWFIA DKSGAGERGS

RGIIAALGPD GKPSRIVVIY TTGSQATMDE RNRQIAEIGA
SLIKHW
```

An illustrative polynucleotide that encodes the variant AmpR antibiotic resistance determinant of SEQ ID NO:23 comprises the sequence (SEQ ID NO:24) (differences relative to SEQ ID NO:22 are underlined):

```
atgagtattc aacatttccg tgtcgccctt attccttttt ttgcggcatt ttgccttcct gttttgctc acccagaaac gctggtgaaa gtaaaagatg ctgaagatca gttgggtgca cgagtgggtt acatcgaact ggatctcaac agcggtaaga tccttgagag ttttcgcccc gaagaacgtt ttccaatgat gagcactttt aaagttctgc tatgtggcgc ggtattatcc cgtgttgacg ccgggcaaga gcaactcggt cgccgcatac actattctca gaatgacttg gttgagtact caccagtcac agaaaagcat cttacggatg gcatgacagt aagagaatta tgcagtgctg ccataaccat gagtgataac actgcggcca acttacttct gacaacgatc ggaggaccga aggagctaac cgcttttttg cacaacatgg gggatcatgt aactcgcctt gatcgttggg aaccggagct gaatgaagcc ataccaaacg
```

```
acgagcgtga caccacgatg cctgcagcaa tggcaacaac gttgcgcaaa ctattaactg gcgaactact tactctagct tcccggcaac aattaataga ctggatggag gcggataaag ttgcaggacc acttctgcgc tcggcccttc cggctggctg gtttattgct gataaatctg gagccggtga gcgtgggtct cgcggtatca ttgcagcact ggggccagat ggtaagccct cccgtatcgt agttatctac acgacgggga gtcaggcaac tatggatgaa cgaaatagac agatcgctga gataggtgcc tcactgatta agcattgg
```

An illustrative AmpR promoter-containing polynucleotide has the sequence of SEQ ID NO:25:

```
cgcgggaccc ctatttgttt atttttctaa atacattcaa atatgtatcc gctcatgaga cataaccct gataaatgct tcaataatat tgaaaaagga agagt
```

A variant AmpR promoter-containing polynucleotide has the sequence of SEQ ID NO:26 (differences relative to SEQ ID NO:25 are underlined):

```
cgcggaaccc ctatttgttt atttttctaa atacattcaa atatgtatcc gctcatgaga caataaccct gataaatgct tcaataatat tgaaaaagga agagt
```

The double-stranded vector pLenti-SV40-puro (FIG. 6) (7,705 base pairs) is a preferred LTR-containing vector of the present invention that may be used with the packaging vectors, REV vectors and envelope vectors of the present invention to produce lentiviral particles that array a SARS-CoV-2 S protein on their surface. The double-stranded vector pLenti-SV40-puro (-att) (FIG. 7) (7,701 base pairs) is an alternate preferred LTR-containing vector of the present invention that may be used with the packaging, REV and envelope vectors of the present invention to produce lentiviral particles that array a SARS-CoV-2 S protein on their surface. Vector pLenti-SV40-puro (-att) differs in sequence from vector pLenti-SV40-puro in containing:
(1) a deletion of the CA residues found at positions 1013-1014 of SEQ ID NO:27, which positions correspond to the two 3' terminal nucleotides of the 5' LTR;
(2) a deletion of the TG residues found at positions 5391-5392 of SEQ ID NO:27, which correspond to residues 1-2 of the 3' terminus of the U3 region;
(3) an A to C substitution at position 5426, which correspond to residues within the U3 region; and
(4) a C to G substitution at position 5428, which correspond to residues within the U3 region.

Such modifications further reduce the ability of the vector to integrate into a chromosome of a transfected mammalian cell.

The sequence of the native 3' LTR U3 region is SEQ ID NO:62:

```
tggaagggct aattcactcc caacgaagac aagatatcct tgatctgtgg atctaccaca cacaaggcta cttccctgat tggcagaact acacaccagg gccagggatc agatatccac
```

```
tgacctttgg atggtgctac aagctagtac cagttgagca agagaaggta gaagaagcca atgaaggaga gaacacccgc ttgttacacc ctgtgagcct gcatgggatg gatgacccgg agagagaagt attagagtgg aggtttgaca gccgcctagc atttcatcac atggcccgag agctgcatcc ggagtacttc aagaactgct gacatcgagc ttgctacaag ggactttccg ctggggactt tccagggagg cgtggcctgg gcgggactgg ggagtggcga gccctcagat cctgcatata agcagctgct ttttgcctgt act
```

The U3 region of vector pLenti-SV40-puro (SEQ ID NO:63) comprises a deletion of 133 residues (corresponding to residues 312-444 of SEQ ID NO:62).

SEQ ID NO: 63:
```
tggaagggct aattcactcc caacgaagac aagatatcct tgatctgtgg atctaccaca cacaaggcta cttccctgat tggcagaact acacaccagg gccagggatc agatatccac tgacctttgg atggtgctac aagctagtac cagttgagca agagaaggta gaagaagcca atgaaggaga gaacacccgc ttgttacacc ctgtgagcct gcatgggatg gatgacccgg agagagaagt attagagtgg aggtttgaca gccgcctagc atttcatcac atggcccgag agctgcatcc ggactgtact
```

The U3 region of vector pLenti-SV40-puro (-att) (SEQ ID NO:64) comprises a deletion of the first two U3 residues and substitutions at positions 36 and 38 relative to SEQ ID NO:62 (underlined below) and the deletion of 133 residues (corresponding to residues 312-444 of SEQ ID NO:62).

SEQ ID NO: 64:
```
  gaagggct aattcactcc caacgaagac aagatctgct tgatctgtgg atctaccaca cacaaggcta cttccctgat tggcagaact acacaccagg gccagggatc agatatccac tgacctttgg atggtgctac aagctagtac cagttgagca agagaaggta gaagaagcca atgaaggaga gaacacccgc ttgttacacc ctgtgagcct gcatgggatg gatgacccgg agagagaagt attagagtgg aggtttgaca gccgcctagc atttcatcac atggcccgag agctgcatcc ggactgtact
```

2. Illustrative LTR-Containing Vectors (a) pLenti-SV40-Puro

The vector pLenti-SV40-puro (FIG. 6) illustrates the LTR-containing vectors of the present invention. The first strand of vector pLenti-SV40-puro has 7705 nucleotide residues and has the sequence of SEQ ID NO:27 (differences relative to the polynucleotide sequence of the first strand of vector pLenti-SV40-puro (-att) are underlined):

| | |
|---|---|
| gtcgacggat cgggagatct cccgatcccc tatggtgcac tctcagtaca | 50 |
| atctgctctg atgccgcata gttaagccag tatctgctcc ctgcttgtgt | 100 |
| gttggaggtc gctgagtagt gcgcgagcaa aatttaagct acaacaaggc | 150 |
| aaggcttgac cgacaattgc atgaagaatc tgcttagggt taggcgtttt | 200 |
| gcgctgcttc gcgatgtacg ggccagatat cgcgttgaca ttgattattg | 250 |
| actagttatt aatagtaatc aattacgggg tcattagttc atagcccata | 300 |
| tatggagttc cgcgttacat aacttacggt aaatggcccg cctggctgac | 350 |
| cgcccaacga cccccgccca ttgacgtcaa taatgacgta tgttcccata | 400 |
| gtaacgccaa tagggacttt ccattgacgt caatgggtgg agtatttacg | 450 |
| gtaaactgcc cacttggcag tacatcaagt gtatcatatg ccaagtacgc | 500 |
| cccctattga cgtcaatgac ggtaaatggc ccgcctggca ttatgcccag | 550 |
| tacatgacct tatgggactt tcctacttgg cagtacatct acgtattagt | 600 |
| catcgctatt accatggtga tgcggttttg gcagtacatc aatgggcgtg | 650 |
| gatagcggtt tgactcacgg ggatttccaa gtctccaccc cattgacgtc | 700 |
| aatgggagtt tgttttggca ccaaaatcaa cgggactttc caaaatgtcg | 750 |
| taacaactcc gccccattga cgcaaatggg cggtaggcgt gtacggtggg | 800 |
| aggtctatat aagcagcgcg ttttgcctgt actgggtctc tctggttaga | 850 |
| ccagatctga gcctgggagc tctctggcta actagggaac ccactgctta | 900 |
| agcctcaata aagcttgcct tgagtgcttc aagtagtgtg tgcccgtctg | 950 |
| ttgtgtgact ctggtaacta gagatccctc agaccctttt agtcagtgtg | 1000 |
| gaaaatctct agcagtggcg cccgaacagg gacttgaaag cgaaagggaa | 1050 |
| accagaggag ctctctcgac gcaggactcg gcttgctgaa gcgcgcacgg | 1100 |
| caagaggcga gggcggcga ctggtgagta cgccaaaaat tttgactagc | 1150 |
| ggaggctaga aggagagaga tgggtgcgag agcgtcagta ttaagcgggg | 1200 |
| gagaattaga tcgcgatggg aaaaaattcg gttaaggcca gggggaaaga | 1250 |
| aaaaatataa attaaaacat atagtatggg caagcaggga gctagaacga | 1300 |
| ttcgcagtta atcctggcct gttagaaaca tcagaaggct gtagacaaat | 1350 |
| actgggacag ctacaaccat cccttcagac aggatcagaa gaacttagat | 1400 |
| cattatataa tacagtagca accctctatt gtgtgcatca aaggatagag | 1450 |
| ataaaagaca ccaaggaagc tttagacaag atagaggaag agcaaaacaa | 1500 |
| aagtaagacc accgcacagc aagcggccgg ccgctgatct tcagacctgg | 1550 |
| aggaggagat atgagggaca attggagaag tgaattatat aaatataaag | 1600 |
| tagtaaaaat tgaaccatta ggagtagcac ccaccaaggc aaagagaaga | 1650 |
| gtggtgcaga gagaaaaaag agcagtggga ataggagctt tgttccttgg | 1700 |
| gttcttggga gcagcaggaa gcactatggg cgcagcgtca atgacgctga | 1750 |
| cggtacaggc cagacaatta ttgtctggta tagtgcagca gcagaacaat | 1800 |
| ttgctgaggg ctattgaggc gcaacagcat ctgttgcaac tcacagtctg | 1850 |
| gggcatcaag cagctccagg caagaatcct ggctgtggaa agatacctaa | 1900 |
| aggatcaaca gctcctgggg atttggggtt gctctggaaa actcatttgc | 1950 |
| accactgctg tgccttggaa tgctagttgg agtaataaat ctctggaaca | 2000 |
| gatttggaat cacacgacct ggatggagtg ggacagagaa attaacaatt | 2050 |

```
acacaagctt aatacactcc ttaattgaag aatcgcaaaa ccagcaagaa      2100
aagaatgaac aagaattatt ggaattagat aaatgggcaa gtttgtggaa      2150
ttggtttaac ataacaaatt ggctgtggta tataaaatta ttcataatga      2200
tagtaggagg cttggtaggt ttaagaatag tttttgctgt actttctata      2250
gtgaatagag ttaggcaggg atattcacca ttatcgtttc agacccacct      2300
cccaaccccg aggggacccg acaggcccga aggaatagaa gaagaaggtg      2350
gagagagaga cagagacaga tccattcgat tagtgaacgg atcggcactg      2400
cgtgcgccaa ttctgcagac aaatggcagt attcatccac aattttaaaa      2450
gaaaaggggg gattgggggg tacagtgcag gggaaagaat agtagacata      2500
atagcaacag acatacaaac taagaatta caaaaacaaa ttacaaaaat      2550
tcaaaatttt cgggtttatt acagggacag cagagatcca gtttggttag      2600
taccgggccc gctctagaat gtgtgtcagt tagggtgtgg aaagtcccca      2650
ggctccccag caggcagaag tatgcaaagc atgcatctca attagtcagc      2700
aaccaggtgt ggaaagtccc caggctcccc agcaggcaga agtatgcaaa      2750
gcatgcatct caattagtca gcaaccatag tcccgcccct aactccgccc      2800
atcccgcccc taactccgcc cagttccgcc cattctccgc ccatggctg       2850 actaattttt tttatttatg cagaggccga ggccgcctcg gcctctgagc      2900
tattccagaa gtagtgagga ggcttttttg gaggcctagg cttttgcaaa      2950
aagctcccgg gagcttgtat atccattttc ggatctgatc aagagacacg      3000
tacgaccatg accgagtaca agcccacggt gcgcctcgcc acccgcgacg      3050
acgtcccccg ggcagtacgc accctcgccc cgcgttcgc cgactacccc       3100 gccacgcgcc acaccgtcga tccagaccgc cacatcgagc gggtcaccga      3150
gctgcaagaa ctcttcctca cgcgcgtcgg gctcgacatc ggcaaggtgt      3200
gggtcgcgga cgacggcgcc gcggtggcgg tctggaccac gccggagagc      3250
gtcgaagcgg gggcggtgtt cgccgagatc ggcccgcgca tggccgagtt      3300
gagcggttcc cggctggccg cgcagcaaca gatggaaggc ctcctggcgc      3350
cgcaccggcc caaggagccc gcgtggttcc tggccaccgt cggcgtctcg      3400
cccgaccacc agggcaaggg tctgggcagc gccgtcgtgc tccccggagt      3450
ggaggcggcc gagcgcgccg gggtgcccgc cttcctggag acctccgcgc      3500
cccgcaacct ccccttctac gagcggctcg gcttcaccgt caccgccgac      3550
gtcgaggtgc ccgaaggacc gcgcacctgg tgcatgaccc gcaagcccgg      3600
tgcctgattt ctagacatgt ccaatatgac cgccatgttg acattgatta      3650
ttgactagtt attaatagta atcaattacg gggtcattag ttcatagccc      3700
atatatggag ttccgcgtta cataacttac ggtaaatggc ccgcctggct      3750
gaccgcccaa cgacccccgc ccattgacgt caataatgac gtatgttccc      3800
atagtaacgc caatagggac tttccattga cgtcaatggg tggagtattt      3850
acggtaaact gcccacttgg cagtacatca agtgtatcat atgccaagtc      3900
cgccccctat tgacgtcaat gacggtaaat ggcccgcctg gcattatgcc      3950
cagtacatga ccttacggga ctttcctact tggcagtaca tctacgtatt      4000
agtcatcgct attaccatgg tgatgcggtt ttggcagtac accaatgggc      4050
gtggatagcg gtttgactca cggggatttc caagtctcca ccccattgac      4100
```

```
gtcaatggga gtttgttttg gcaccaaaat caacgggact ttccaaaatg    4150
tcgtaataac cccgccccgt tgacgcaaat gggcggtagg cgtgtacggt    4200
gggaggtcta tataagcaga gctcgtttag tgaaccgtca gaattttgta    4250
atacgactca ctatagggcg gccgggaatt cgtcgactgg atccggtacc    4300
gaggagatct gccgccgcga tcgccggcgc gccagatctc aagcttaact    4350
agctagcgga ccgacgcgta cgcggccgct cgagcagaaa ctcatctcag    4400
aagaggatct ggcagcaaat gatatcctgg attacaagga tgacgacgat    4450 aaggttttaaa cggccggccg cggtctgtac aagtaggatt cgtcgaggga    4500
cctaataact tcgtatagca tacattatac gaagttatac atgtttaagg    4550
gttccggttc cactaggtac aattcgatat caagcttatc gataatcaac    4600
ctctggatta caaaatttgt gaaagattga ctggtattct taactatgtt    4650 gctccttta cgctatgtgg atacgctgct ttaatgcctt tgtatcatgc    4700
tattgcttcc cgtatggctt tcattttctc ctccttgtat aaatcctggt    4750
tgctgtctct ttatgaggag ttgtggcccg ttgtcaggca acgtggcgtg    4800
gtgtgcactg tgtttgctga cgcaaccccc actggttggg gcattgccac    4850
cacctgtcag ctcctttccg ggactttcgc tttccccctc cctattgcca    4900
cggcggaact catcgccgcc tgccttgccc gctgctggac aggggctcgg    4950
ctgttgggca ctgacaattc cgtggtgttg tcggggaaat catcgtcctt    5000
tccttggctg ctcgcctgtg ttgccacctg gattctgcgc gggacgtcct    5050
tctgctacgt cccttcggcc ctcaatccag cggaccttcc ttcccgcggc    5100
ctgctgccgg ctctgcggcc tcttccgcgt cttcgccttc gccctcagac    5150
gagtcggatc tccctttggg ccgcctcccc gcatcgatac cgtcgacctc    5200
gatcgagacc tagaaaaaca tggagcaatc acaagtagca atacagcagc    5250
taccaatgct gattgtgcct ggctagaagc acaagaggag gaggaggtgg    5300
gttttccagt cacacctcag gtacctttaa gaccaatgac ttacaaggca    5350
gctgtagatc ttagccactt tttaaaagaa aaggggggac tggaagggct    5400
aattcactcc caacgaagac aagatatcct tgatctgtgg atctaccaca    5450
cacaaggcta cttccctgat tggcagaact acacaccagg gccagggatc    5500
agatatccac tgacctttgg atggtgctac aagctagtac cagttgagca    5550
agagaaggta gaagaagcca atgaaggaga gaacacccgc ttgttacacc    5600
ctgtgagcct gcatgggatg gatgacccgg agagagaagt attagagtgg    5650
aggtttgaca gccgcctagc atttcatcac atggcccgag agctgcatcc    5700
ggactgtact gggtctctct ggttagacca gatctgagcc tgggagctct    5750
ctggctaact agggaaccca ctgcttaagc ctcaataaag cttgccttga    5800
gtgcttcaag tagtgtgtgc ccgtctgttg tgtgactctg gtaactagag    5850
atccctcaga cccttttagt cagtgtggaa aatctctagc agcatgtgag    5900
caaaaggcca gcaaaggcc aggaaccgta aaaaggccgc gttgctggcg    5950
ttttttcata ggctccgccc ccctgacgag catcacaaaa atcgacgctc    6000
aagtcagagg tggcgaaacc cgacaggact ataaagatac caggcgtttc    6050
cccctggaag ctccctcgtg cgctctcctg ttccgaccct gccgcttacc    6100
ggatacctgt ccgcctttct cccttcggga agcgtggcgc tttctcatag    6150
```

```
ctcacgctgt aggtatctca gttcggtgta ggtcgttcgc tccaagctgg    6200
gctgtgtgca cgaaccccc  gttcagcccg accgctgcgc cttatccggt    6250
aactatcgtc ttgagtccaa cccggtaaga cacgacttat cgccactggc    6300
agcagccact ggtaacagga ttagcagagc gaggtatgta ggcggtgcta    6350
cagagttctt gaagtggtgg cctaactacg gctacactag aagaacagta    6400
tttggtatct gcgctctgct gaagccagtt accttcggaa aaagagttgg    6450
tagctcttga tccggcaaac aaaccaccgc tggtagcggt ggttttttg     6500 tttgcaagca gcagattacg cgcagaaaaa aaggatctca agaagatcct    6550
ttgatctttt ctacggggtc tgacgctcag tggaacgaaa actcacgtta    6600
agggattttg gtcatgagat tatcaaaaag gatcttcacc tagatccttt    6650
taaattaaaa atgaagtttt aaatcaatct aaagtatata tgagtaaact    6700
tggtctgaca gttaccaatg cttaatcagt gaggcaccta tctcagcgat    6750
ctgtctattt cgttcatcca tagttgcctg actccccgtc gtgtagataa    6800
ctacgatacg ggagggctta ccatctggcc ccagtgctgc aatgataccg    6850
cgagacccac gctcaccggc tccagattta tcagcaataa accagccagc    6900
cggaagggcc gagcgcagaa gtggtcctgc aactttatcc gcctccatcc    6950
agtctattaa ttgttgccgg gaagctagag taagtagttc gccagttaat    7000
agtttgcgca acgttgttgc cattgctaca ggcatcgtgg tgtcacgctc    7050
gtcgtttggt atggcttcat tcagctccgg ttcccaacga tcaaggcgag    7100
ttacatgatc ccccatgttg tgcaaaaaag cggttagctc cttcggtcct    7150
ccgatcgttg tcagaagtaa gttggccgca gtgttatcac tcatggttat    7200
ggcagcactg cataattctc ttactgtcat gccatccgta agatgctttt    7250
ctgtgactgg tgagtactca accaagtcat tctgagaata gtgtatgcgg    7300
cgaccgagtt gctcttgccc ggcgtcaata cgggataata ccgcgccaca    7350
tagcagaact ttaaaagtgc tcatcattgg aaaacgttct cggggcgaa     7400 aactctcaag gatcttaccg ctgttgagat ccagttcgat gtaacccact    7450
cgtgcaccca actgatcttc agcatctttt actttcacca gcgtttctgg    7500
gtgagcaaaa acaggaaggc aaaatgccgc aaaaaaggga ataagggcga    7550
cacggaaatg ttgaatactc atactcttcc tttttcaata ttattgaagc    7600
atttatcagg gttattgtct catgagcgga tacatatttg aatgtattta    7650
gaaaaataaa caaatagggg tcccgcgcac atttccccga aaagtgccac    7700
ctgac                                                     7705
```

As will be noted, residues 237-616 of pLenti-SV40-puro (SEQ ID NO:27) correspond to the CMV immediate early enhancer site (SEQ ID NO:1). Residues 618-816 of SEQ ID NO:27 correspond to the CMV immediate early promoter site (SEQ ID NO:3). Residues 834-1014 of SEQ ID NO:27 correspond to the truncated lentiviral 5' LTR region (SEQ ID NO:5). Residues 1061-1186 of SEQ ID NO:27 correspond to the lentiviral ψ region (SEQ ID NO:6). Residues 1683-1916 of SEQ ID NO:27 correspond to the lentiviral Rev response element (RRE) (SEQ ID NO:7). Residues 2443-2560 of SEQ ID NO:27 correspond to the lentiviral cPPT/CTS region (SEQ ID NO:8). Residues 2621-2950 of SEQ ID NO:27 correspond to the SV40 promoter and origin of replication (SEQ ID NO:9). Residues 3008-3607 of SEQ ID NO:27 correspond to a polynucleotide sequence (SEQ ID NO:11) that encodes the N-acetyltransferase of Streptomyces alboniger (SEQ ID NO:10). Residues 3640-4019 of SEQ ID NO:27 correspond to the variant CMV immediate early enhancer site (SEQ ID NO:2). Residues 4020-4223 of SEQ ID NO:27 correspond to the variant CMV immediate early promoter site (SEQ ID NO:4). Residues 4249-4267 of SEQ ID NO:27 correspond to a T7 promoter site (SEQ ID NO:12). Residues 4382-4453 of SEQ ID NO:27 correspond to a polynucleotide sequence (SEQ ID NO:14) that encodes a combined Myc (human c-Myc oncogene) and FLAG® epitope tag (SEQ ID NO:13). Residues 4505-4538 of SEQ ID NO:27 correspond to a LoxP site (SEQ ID NO:15). Residues 4594-5182 of SEQ ID NO:27 correspond to a woodchuck hepatitis virus post-transcriptional regulatory element (WPRE) (SEQ ID NO:16). Residues 5065-5076 of SEQ ID NO:27 correspond to a Factor Xa cleavage site (SEQ ID NO:17). Residues 5185-5201 of SEQ ID NO:27 correspond to a polynucleotide whose sequence is complementary to the sequence a KS primer binding site (SEQ ID NO:18). Residues 5391-5891 correspond to a 5' LTR that has been modified to be self-inactivating (SIN) of which residues 5391-5710 correspond to a modified U3 region (SEQ ID NO:62), residues 5711-5891 correspond to R and the U5 regions of the 5' LTR (SEQ ID NO:5). Residues 5953-6541 of SEQ ID NO:27 correspond to a polynucleotide whose sequence is complementary to the sequence of the high-copy-number ColE1/pMB1/pBR322/pUC origin of replication (SEQ ID NO:19). Residues 6712-7572 of SEQ ID NO:27 correspond to a polynucleotide whose sequence is complementary to the sequence encoding the AmpR antibiotic resistance determinant (SEQ ID NO:22) (i.e., such encoding sequence is on the second strand of the vector). Residues 7573-7677 of SEQ ID NO:27 correspond to a polynucleotide whose sequence is complementary to the sequence of the AmpR promoter (SEQ ID NO:25) (i.e., such promoter sequence is on the second strand of the vector).

(b) pLenti-SV40-Puro (-Att)

The vector pLenti-SV40-puro (-att) (FIG. 7) further illustrates the LTR-containing vectors of the present invention. The first strand of vector pLenti-SV40-puro (-att) has 7701 nucleotide residues and has the sequence of SEQ ID NO:28:

```
gtcgacggat cgggagatct cccgatcccc tatggtgcac tctcagtaca      50
atctgctctg atgccgcata gttaagccag tatctgctcc ctgcttgtgt     100
gttggaggtc gctgagtagt gcgcgagcaa aatttaagct acaacaaggc     150
aaggcttgac cgacaattgc atgaagaatc tgcttagggt taggcgtttt     200
gcgctgcttc gcgatgtacg ggccagatat cgcgttgaca ttgattattg     250
actagttatt aatagtaatc aattacgggg tcattagttc atagcccata     300
tatggagttc cgcgttacat aacttacggt aaatggcccg cctggctgac     350
cgcccaacga ccccgccca ttgacgtcaa taatgacgta tgttcccata     400
gtaacgccaa tagggacttt ccattgacgt caatgggtgg agtatttacg     450
gtaaactgcc cacttggcag tacatcaagt gtatcatatg ccaagtacgc     500
cccctattga cgtcaatgac ggtaaatggc ccgcctggca ttatgcccag     550
tacatgacct tatgggactt tcctacttgg cagtacatct acgtattagt     600
catcgctatt accatggtga tgcggttttg gcagtacatc aatgggcgtg     650
gatagcggtt tgactcacgg ggatttccaa gtctccaccc cattgacgtc     700
aatgggagtt tgttttggca ccaaaatcaa cgggactttc caaaatgtcg     750
taacaactcc gccccattga cgcaaatggg cggtaggcgt gtacggtggg     800
aggtctatat aagcagcgcg ttttgcctgt actgggtctc tctggttaga     850
ccagatctga gcctgggagc tctctggcta actagggaac ccactgctta     900
agcctcaata aagcttgcct tgagtgcttc aagtagtgtg tgcccgtctg     950
ttgtgtgact ctggtaacta gagatccctc agacccttt agtcagtgtg    1000 gaaaatctct aggtggcgcc cgaacaggga cttgaaagcg aaagggaaac    1050
cagaggagct ctctcgacgc aggactcggc ttgctgaagc gcgcacggca    1100
agaggcgagg ggcggcgact ggtgagtacg ccaaaaattt tgactagcgg    1150
aggctagaag gagagagatg ggtgcgagag cgtcagtatt aagcggggga    1200
gaattagatc gcgatgggaa aaaattcggt taaggccagg gggaaagaaa    1250
aaatataaat taaaacatat agtatgggca agcagggagc tagaacgatt    1300
cgcagttaat cctggcctgt tagaaacatc agaaggctgt agacaaatac    1350
tgggacagct acaaccatcc cttcagacag gatcagaaga acttagatca    1400
ttatataata cagtagcaac cctctattgt gtgcatcaaa ggatagagat    1450
aaaagacacc aaggaagctt tagacaagat agaggaagag caaaacaaaa    1500
gtaagaccac cgcacagcaa gcggccggcc gctgatcttc agacctggag    1550
gaggagatat gagggacaat tggagaagtg aattatataa atataaagta    1600
```

-continued

```
gtaaaaattg aaccattagg agtagcaccc accaaggcaa agagaagagt      1650
ggtgcagaga gaaaaaagag cagtgggaat aggagctttg ttccttgggt      1700
tcttgggagc agcaggaagc actatgggcg cagcgtcaat gacgctgacg      1750
gtacaggcca gacaattatt gtctggtata gtgcagcagc agaacaattt      1800
gctgagggct attgaggcgc aacagcatct gttgcaactc acagtctggg      1850
gcatcaagca gctccaggca agaatcctgg ctgtggaaag atacctaaag      1900
gatcaacagc tcctggggat ttggggttgc tctggaaaac tcatttgcac      1950
cactgctgtg ccttggaatg ctagttggag taataaatct ctggaacaga      2000 tttgaatca cacgacctgg atggagtggg acagagaaat taacaattac       2050
acaagcttaa tacactcctt aattgaagaa tcgcaaaacc agcaagaaaa      2100
gaatgaacaa gaattattgg aattagataa atgggcaagt tgtggaatt       2150 ggtttaacat aacaaattgg ctgtggtata taaaattatt cataatgata      2200
gtaggaggct tggtaggttt aagaatagtt tttgctgtac tttctatagt      2250
gaatagagtt aggcagggat attcaccatt atcgtttcag acccacctcc      2300
caaccccgag gggacccgac aggcccgaag gaatagaaga agaaggtgga      2350
gagagagaca gagacagatc cattcgatta gtgaacggat cggcactgcg      2400
tgcgccaatt ctgcagacaa atggcagtat tcatccacaa ttttaaaaga      2450 aaaggggga ttgggggta cagtgcaggg gaaagaatag tagacataat        2500
agcaacagac atacaaacta aagaattaca aaaacaaatt acaaaaattc      2550
aaaattttcg ggtttattac agggacagca gagatccagt ttggttagta      2600
ccgggcccgc tctagaatgt gtgtcagtta gggtgtggaa agtccccagg      2650 ctcccccagca ggcagaagta tgcaaagcat gcatctcaat tagtcagcaa     2700
ccaggtgtgg aaagtcccca ggctccccag caggcagaag tatgcaaagc      2750
atgcatctca attagtcagc aaccatagtc ccgcccctaa ctccgcccat      2800 cccgcccta actccgccca gttccgccca ttctccgccc catggctgac       2850 taatttttt tatttatgca gaggccgagg ccgcctcggc ctctgagcta       2900
ttccagaagt agtgaggagg cttttttgga ggcctaggct tttgcaaaaa      2950
gctcccggga gcttgtatat ccatttttcgg atctgatcaa gagacacgta     3000
cgaccatgac cgagtacaag cccacggtgc gcctcgccac ccgcgacgac      3050
gtcccccggg cagtacgcac cctcgccgcc gcgttcgccg actacccgc       3100 cacgcgccac accgtcgatc cagaccgcca catcgagcgg gtcaccgagc      3150
tgcaagaact cttcctcacg cgcgtcgggc tcgacatcgg caaggtgtgg      3200
gtcgcggacg acggcgccgc ggtggcggtc tggaccacgc cggagagcgt      3250
cgaagcgggg gcggtgttcg ccgagatcgg cccgcgcatg gccgagttga      3300
gcggttcccg gctggccgcg cagcaacaga tggaaggcct cctggcgccg      3350
caccggccca aggagcccgc gtggttcctg gccaccgtcg gcgtctcgcc      3400
cgaccaccag ggcaagggtc tgggcagcgc cgtcgtgctc cccggagtgg      3450
aggcggccga gcgcgccggg gtgcccgcct tcctggagac ctccgcgccc      3500
cgcaacctcc ccttctacga gcggctcggc ttcaccgtca ccgccgacgt      3550
cgaggtgccc gaaggaccgc gcacctggtg catgacccgc aagcccggtg      3600
cctgatttct agacatgtcc aatatgaccg ccatgttgac attgattatt      3650
```

```
gactagttat taatagtaat caattacggg gtcattagtt catagcccat    3700
atatggagtt ccgcgttaca taacttacgg taaatggccc gcctggctga    3750
ccgcccaacg acccccgccc attgacgtca ataatgacgt atgttcccat    3800
agtaacgcca atagggactt tccattgacg tcaatgggtg gagtatttac    3850
ggtaaactgc ccacttggca gtacatcaag tgtatcatat gccaagtccg    3900 cccctattg acgtcaatga cggtaaatgg cccgcctggc attatgccca     3950
gtacatgacc ttacgggact tcctacttg gcagtacatc tacgtattag     4000
tcatcgctat taccatggtg atgcggtttt ggcagtacac caatgggcgt    4050
ggatagcggt ttgactcacg gggatttcca agtctccacc ccattgacgt    4100
caatgggagt ttgttttggc accaaaatca acgggacttt ccaaaatgtc    4150
gtaataaccc cgccccgttg acgcaaatgg gcggtaggcg tgtacggtgg    4200
gaggtctata taagcagagc tcgtttagtg aaccgtcaga attttgtaat    4250
acgactcact atagggcggc cgggaattcg tcgactggat ccggtaccga    4300
ggagatctgc cgccgcgatc gccggcgcgc cagatctcaa gcttaactag    4350
ctagcggacc gacgcgtacg cggccgctcg agcagaaact catctcagaa    4400
gaggatctgg cagcaaatga tatcctggat tacaaggatg acgacgataa    4450
ggtttaaacg gccggccgcg gtctgtacaa gtaggattcg tcgagggacc    4500
taataacttc gtatagcata cattatacga agttatacat gtttaagggt    4550
tccggttcca ctaggtacaa ttcgatatca agcttatcga taatcaacct    4600
ctggattaca aaatttgtga aagattgact ggtattctta actatgttgc    4650
tccttttacg ctatgtggat acgctgcttt aatgcctttg tatcatgcta    4700
ttgcttcccg tatggctttc attttctcct ccttgtataa atcctggttg    4750
ctgtctcttt atgaggagtt gtggcccgtt gtcaggcaac gtggcgtggt    4800
gtgcactgtg tttgctgacg caacccccac tggttggggc attgccacca    4850
cctgtcagct ccttccggg actttcgctt tccccctccc tattgccacg     4900
gcggaactca tcgccgcctg ccttgcccgc tgctggacag gggctcggct    4950
gttgggcact gacaattccg tggtgttgtc ggggaaatca tcgtcctttc    5000
cttggctgct cgcctgtgtt gccacctgga ttctgcgcgg gacgtccttc    5050
tgctacgtcc cttcggccct caatccagcg gaccttcctt cccgcggcct    5100
gctgccggct ctgcggcctc ttccgcgtct tcgccttcgc cctcagacga    5150
gtcggatctc cctttgggcc gcctccccgc atcgataccg tcgacctcga    5200
tcgagaccta gaaaaacatg gagcaatcac aagtagcaat acagcagcta    5250
ccaatgctga ttgtgcctgg ctagaagcac aagaggagga ggaggtgggt    5300
tttccagtca cacctcaggt acctttaaga ccaatgactt acaaggcagc    5350
tgtagatctt agccactttt taaaagaaaa ggggggacga agggctaatt    5400
cactcccaac gaagacaaga tctgcttgat ctgtggatct accacacaca    5450
aggctacttc cctgattggc agaactacac accagggcca gggatcagat    5500
atccactgac ctttggatgg tgctacaagc tagtaccagt tgagcaagag    5550
aaggtagaag aagccaatga aggagagaac accgcttgt tacaccctgt    5600 gagcctgcat gggatggatg acccggagag agaagtatta gagtggaggt    5650
ttgacagccg cctagcattt catcacatgg cccgagagct gcatccggac    5700
```

-continued

```
tgtactgggt ctctctggtt agaccagatc tgagcctggg agctctctgg     5750
ctaactaggg aacccactgc ttaagcctca ataaagcttg ccttgagtgc     5800
ttcaagtagt gtgtgcccgt ctgttgtgtg actctggtaa ctagagatcc     5850
ctcagaccct tttagtcagt gtggaaaatc tctagcagca tgtgagcaaa     5900
aggccagcaa aaggccagga accgtaaaaa ggccgcgttg ctggcgtttt     5950
tccataggct ccgccccct dacgagcatc acaaaaatcg acgctcaagt     6000
cagaggtggc gaaacccgac aggactataa agataccagg cgtttccccc     6050
tggaagctcc ctcgtgcgct ctcctgttcc gaccctgccg cttaccggat     6100
acctgtccgc ctttctccct tcgggaagcg tggcgctttc tcatagctca     6150
cgctgtaggt atctcagttc ggtgtaggtc gttcgctcca agctgggctg     6200
tgtgcacgaa ccccccgttc agcccgaccg ctgcgcctta tccggtaact     6250
atcgtcttga gtccaacccg gtaagacacg acttatcgcc actggcagca     6300
gccactggta acaggattag cagagcgagg tatgtaggcg gtgctacaga     6350
gttcttgaag tggtggccta actacggcta cactagaaga acagtatttg     6400
gtatctgcgc tctgctgaag ccagttacct tcggaaaaag agttggtagc     6450
tcttgatccg gcaaacaaac caccgctggt agcggtggtt tttttgtttg     6500
caagcagcag attacgcgca gaaaaaaagg atctcaagaa gatcctttga     6550
tcttttctac ggggtctgac gctcagtgga acgaaaactc acgttaaggg     6600
attttggtca tgagattatc aaaaaggatc ttcacctaga tccttttaaa     6650
ttaaaaatga agttttaaat caatctaaag tatatatgag taaacttggt     6700
ctgacagtta ccaatgctta atcagtgagg cacctatctc agcgatctgt     6750
ctatttcgtt catccatagt tgcctgactc cccgtcgtgt agataactac     6800
gatacgggag ggcttaccat ctggccccag tgctgcaatg ataccgcgag     6850
acccacgctc accggctcca gatttatcag caataaacca gccagccgga     6900
agggccgagc gcagaagtgg tcctgcaact ttatccgcct ccatccagtc     6950
tattaattgt tgccgggaag ctagagtaag tagttcgcca gttaatagtt     7000
tgcgcaacgt tgttgccatt gctacaggca tcgtggtgtc acgctcgtcg     7050
tttggtatgg cttcattcag ctccggttcc caacgatcaa ggcgagttac     7100
atgatccccc atgttgtgca aaaaagcggt tagctccttc ggtcctccga     7150
tcgttgtcag aagtaagttg gccgcagtgt tatcactcat ggttatggca     7200
gcactgcata attctcttac tgtcatgcca tccgtaagat gcttttctgt     7250
gactggtgag tactcaacca agtcattctg agaatagtgt atgcggcgac     7300
cgagttgctc ttgcccggcg tcaatacggg ataataccgc gccacatagc     7350
agaactttaa aagtgctcat cattggaaaa cgttcttcgg ggcgaaaact     7400
ctcaaggatc ttaccgctgt tgagatccag ttcgatgtaa cccactcgtg     7450
cacccaactg atcttcagca tcttttactt tcaccagcgt ttctgggtga     7500
gcaaaaacag gaaggcaaaa tgccgcaaaa aagggaataa gggcgacacg     7550
gaaatgttga atactcatac tcttcctttt tcaatattat tgaagcattt     7600
atcagggtta ttgtctcatg agcggataca tatttgaatg tatttagaaa     7650
aataaacaaa tagggggtccc gcgcacattt ccccgaaaag tgccacctga     7700
c                                                          7701
```

As will be noted, residues 237-616 of pLenti-SV40-puro (-att) (SEQ ID NO:28) correspond to the CMV immediate early enhancer site (SEQ ID NO:1). Residues 618-816 of SEQ ID NO:28 correspond to the CMV immediate early promoter site (SEQ ID NO:3). Residues 834-1012 of SEQ ID NO:28 correspond to the truncated lentiviral 5' LTR region (SEQ ID NO:68). Residues 1059-1184 of SEQ ID NO:28 correspond to the lentiviral ψ region (SEQ ID NO:6). Residues 1681-1914 of SEQ ID NO:28 correspond to the lentiviral Rev response element (RRE) (SEQ ID NO:7). Residues 2441-2558 of SEQ ID NO:28 correspond to the lentiviral cPPT/CTS region (SEQ ID NO:8). Residues 2619-2948 of SEQ ID NO:28 correspond to the SV40 promoter and origin of replication (SEQ ID NO:9). Residues 3006-3605 of SEQ ID NO:28 correspond to a polynucleotide sequence (SEQ ID NO:11) that encodes the N-acetyltransferase of *Streptomyces alboniger* (SEQ ID NO:10). Residues 3638-4017 of SEQ ID NO:28 correspond to the variant CMV immediate early enhancer site (SEQ ID NO:2). Residues 4018-4221 of SEQ ID NO:28 correspond to the variant CMV immediate early promoter site (SEQ ID NO:4). Residues 4247-4265 of SEQ ID NO:28 correspond to a T7 promoter site (SEQ ID NO:12). Residues 4380-4450 of SEQ ID NO:28 correspond to a polynucleotide sequence (SEQ ID NO:14) that encodes a combined Myc (human c-Myc oncogene) and FLAG® epitope tag (SEQ ID NO:13). Residues 4503-4536 of SEQ ID NO:28 correspond to a LoxP site (SEQ ID NO:15). Residues 4592-5180 of SEQ ID NO:28 correspond to a woodchuck hepatitis virus post-transcriptional regulatory element (WPRE) (SEQ ID NO:16). Residues 5063-5074 of SEQ ID NO:28 correspond to a Factor Xa cleavage site (SEQ ID NO:17). Residues 5183-5199 of SEQ ID NO:28 correspond to a polynucleotide whose sequence is complementary to the sequence a KS primer binding site (SEQ ID NO:18). Residues 5389-5887 correspond to a 5' LTR that has been modified to be self-inactivating (SIN) of which residues 5389-5706 correspond to a modified U3 region (SEQ ID NO:64), residues 5707-5888 correspond to R and the U5 regions of the 5' LTR (SEQ ID NO:5). Residues 5949-6537 of SEQ ID NO:28 correspond to a polynucleotide whose sequence is complementary to the sequence of the high-copy-number ColE1/pMB1/pBR322/pUC origin of replication (SEQ ID NO:19). Residues 6708-7568 of SEQ ID NO:28 correspond to a polynucleotide whose sequence is complementary to the sequence encoding the AmpR antibiotic resistance determinant (SEQ ID NO:22) (i.e., such encoding sequence is on the second strand of the vector). Residues 7569-7673 of SEQ ID NO:28 correspond to a polynucleotide whose sequence is complementary to the sequence of the AmpR promoter (SEQ ID NO:25) (i.e., such promoter sequence is on the second strand of the vector).

(c) pLenti-CMV-IRES-Empty (-Att)

The vector pLenti-CMV-IRES-empty (-att) (FIG. 8) further illustrates the LTR-containing vectors of the present invention. The first strand of vector pLenti-CMV-IRES-empty (-att) has 7267 nucleotide residues and has the sequence of SEQ ID NO:67:

```
gtcgacggat cgggagatct cccgatcccc tatggtgcac tctcagtaca      50
atctgctctg atgccgcata gttaagccag tatctgctcc ctgcttgtgt     100
gttggaggtc gctgagtagt gcgcgagcaa aatttaagct acaacaaggc     150
aaggcttgac cgacaattgc atgaagaatc tgcttagggt taggcgtttt     200
gcgctgcttc gcgatgtacg ggccagatat cgcgttgaca ttgattattg     250
actagttatt aatagtaatc aattacgggg tcattagttc atagcccata     300
tatggagttc cgcgttacat aacttacggt aaatggcccg cctggctgac     350
cgcccaacga cccccgccca ttgacgtcaa taatgacgta tgttcccata     400
gtaacgccaa tagggacttt ccattgacgt caatgggtgg agtatttacg     450
gtaaactgcc cacttggcag tacatcaagt gtatcatatg ccaagtacgc     500
cccctattga cgtcaatgac ggtaaatggc ccgcctggca ttatgcccag     550
tacatgacct tatgggactt tcctacttgg cagtacatct acgtattagt     600
catcgctatt accatggtga tgcggttttg gcagtacatc aatgggcgtg     650
gatagcggtt tgactcacgg ggatttccaa gtctccaccc cattgacgtc     700
aatgggagtt tgttttggca ccaaaatcaa cgggactttc caaaatgtcg     750
taacaactcc gccccattga cgcaaatggg cggtaggcgt gtacggtggg     800
aggtctatat aagcagcgcg ttttgcctgt actgggtctc tctggttaga     850
ccagatctga gcctgggagc tctctggcta actagggaac ccactgctta     900
agcctcaata aagcttgcct tgagtgcttc aagtagtgtg tgcccgtctg     950
ttgtgtgact ctggtaacta gagatccctc agacccttt agtcagtgtg    1000
gaaaatctct aggtggcgcc cgaacaggga cttgaaagcg aaagggaaac    1050
cagaggagct ctctcgacgc aggactcggc ttgctgaagc gcgcacggca    1100
```

```
-continued
agaggcgagg ggcggcgact ggtgagtacg ccaaaaattt tgactagcgg      1150
aggctagaag gagagagatg ggtgcgagag cgtcagtatt aagcgggga       1200 gaattagatc gcgatgggaa aaaattcggt taaggccagg gggaaagaaa      1250
aaatataaat taaacatat agtatgggca agcagggagc tagaacgatt       1300
cgcagttaat cctggcctgt tagaaacatc agaaggctgt agacaaatac      1350
tgggacagct acaaccatcc cttcagacag gatcagaaga acttagatca      1400
ttatataata cagtagcaac cctctattgt gtgcatcaaa ggatagagat      1450
aaaagacacc aaggaagctt tagacaagat agaggaagag caaaacaaaa      1500
gtaagaccac cgcacagcaa gcggccggcc gctgatcttc agacctggag      1550
gaggagatat gagggacaat tggagaagtg aattatataa atataaagta      1600
gtaaaaattg aaccattagg agtagcaccc accaaggcaa agagaagagt      1650
ggtgcagaga gaaaaaagag cagtgggaat aggagctttg ttccttgggt      1700
tcttgggagc agcaggaagc actatgggcg cagcgtcaat gacgctgacg      1750
gtacaggcca gacaattatt gtctggtata gtgcagcagc agaacaattt      1800
gctgagggct attgaggcgc aacagcatct gttgcaactc acagtctggg      1850
gcatcaagca gctccaggca agaatcctgg ctgtggaaag atacctaaag      1900
gatcaacagc tcctggggat ttggggttgc tctggaaaac tcatttgcac      1950
cactgctgtg ccttggaatg ctagttggag taataaatct ctggaacaga      2000
tttggaatca cacgacctgg atggagtggg acagagaaat taacaattac      2050
acaagcttaa tacactcctt aattgaagaa tcgcaaaacc agcaagaaaa      2100
gaatgaacaa gaattattgg aattagataa atgggcaagt ttgtggaatt      2150
ggtttaacat aacaaattgg ctgtggtata taaaattatt cataatgata      2200
gtaggaggct tggtaggttt aagaatagtt tttgctgtac tttctatagt      2250
gaatagagtt aggcagggat attcaccatt atcgtttcag acccacctcc      2300
caaccccgag gggacccgac aggcccgaag gaatagaaga agaaggtgga      2350
gagagagaca gagacagatc cattcgatta gtgaacggat cggcactgcg      2400
tgcgccaatt ctgcagacaa atggcagtat tcatccacaa ttttaaaaga      2450 aaaggggggga ttgggggta cagtgcaggg gaaagaatag tagacataat      2500
agcaacagac atacaaacta agaattaca aaaacaaatt acaaaaattc      2550
aaaattttcg ggtttattac agggacagca gagatccagt ttggttagta      2600
ccgggcccgc tctagacatg tccaatatga ccgccatgtt gacattgatt      2650
attgactagt tattaatagt aatcaattac ggggtcatta gttcatagcc      2700
catatatgga gttccgcgtt acataactta cggtaaatgg cccgcctggc      2750
tgaccgccca acgacccccg cccattgacg tcaataatga cgtatgttcc      2800
catagtaacg ccaatagggA ctttccattg acgtcaatgg gtggagtatt      2850
tacggtaaac tgcccacttg gcagtacatc aagtgtatca tatgccaagt      2900
ccgcccccta ttgacgtcaa tgacggtaaa tggcccgcct ggcattatgc      2950
ccagtacatg accttacggg actttcctac ttggcagtac atctacgtat      3000
tagtcatcgc tattaccatg gtgatgcggt tttggcagta caccaatggg      3050
cgtggatagc ggtttgactc acggggattt ccaagtctcc accccattga      3100
cgtcaatggg agtttgtttt ggcaccaaaa tcaacgggac tttccaaaat      3150
```

```
gtcgtaataa ccccgccccg ttgacgcaaa tgggcgtag  gcgtgtacgg    3200 tgggaggtct atataagcag agctcgttta gtgaaccgtc agaattttgt    3250
aatacgactc actatagggc ggccgggaat tcgtcgactg ccccccccccc   3300 taacgttact ggccgaagcc gcttggaata aggccggtgt gcgtttgtct    3350
atatgttatt ttccaccata ttgccgtctt ttggcaatgt gagggcccgg    3400
aaacctggcc ctgtcttctt gacgagcatt cctaggggtc tttcccctct    3450
cgccaaagga atgcaaggtc tgttgaatgt cgtgaaggaa gcagttcctc    3500
tggaagcttc ttgaagacaa acaacgtctg tagcgaccct ttgcaggcag    3550
cggaaccccc cacctggcga caggtgcctc tgcggccaaa agccacgtgt    3600
ataagataca cctgcaaagg cggcacaacc ccagtgccac gttgtgagtt    3650
ggatagttgt ggaaagagtc aaatggctct cctcaagcgt attcaacaag    3700
gggctgaagg atgcccagaa ggtaccccat tgtatgggat ctgatctggg    3750
gcctcggtgc acatgcttta catgtgttta gtcgaggtta aaaaacgtct    3800 aggcccccccg aaccacgggg acgtggtttt cctttgaaaa acacgatgat   3850
aatgatccgg taccgaggag atctgccgcc gcgatcgccg gcgcgccaga    3900
tctcaagctt aactagctag cggaccgacg cgtacgcggc cgctcgagca    3950
gaaactcatc tcagaagagg atctggcagc aaatgatatc ctggattaca    4000
aggatgacga cgataaggtt taaacggccg ccgcggtct gtacaagtag     4050 gattcgtcga gggacctaat aacttcgtat agcatacatt atacgaagtt    4100
atacatgttt aagggttccg gttccactag gtacaattcg atatcaagct    4150
tatcgataat caacctctgg attacaaaat ttgtgaaaga ttgactggta    4200
ttcttaacta tgttgctcct tttacgctat gtggatacgc tgctttaatg    4250
cctttgtatc atgctattgc ttcccgtatg gctttcatt  tctcctcctt    4300 gtataaatcc tggttgctgt ctctttatga ggagttgtgg cccgttgtca    4350
ggcaacgtgg cgtggtgtgc actgtgtttg ctgacgcaac ccccactggt    4400
tggggcattg ccaccacctg tcagctcctt ccgggactt  tcgctttccc    4450 cctccctatt gccacggcgg aactcatcgc cgcctgcctt gcccgctgct    4500
ggacaggggc tcggctgttg ggcactgaca attccgtggt gttgtcgggg    4550
aaatcatcgt cctttccttg gctgctcgcc tgtgttgcca cctggattct    4600
gcgcgggacg tccttctgct acgtcccttc ggccctcaat ccagcggacc    4650
ttccttcccg cggcctgctg ccggctctgc ggcctcttcc gcgtcttcgc    4700
cttcgccctc agacgagtcg atctcccctt gggccgcct  ccccgcatcg    4750 ataccgtcga cctcgatcga gacctagaaa aacatggagc aatcacaagt    4800
agcaatacag cagctaccaa tgctgattgt gcctggctag aagcacaaga    4850
ggaggaggag gtgggttttc cagtcacacc tcaggtacct ttaagaccaa    4900
tgacttacaa ggcagctgta gatcttagcc actttttaaa agaaaagggg    4950
ggacgaaggg ctaattcact cccaacgaag acaagatctg cttgatctgt    5000
ggatctacca cacacaaggc tacttccctg attggcagaa ctacacacca    5050
gggccaggga tcagatatcc actgacctt  ggatggtgct acaagctagt    5100
accagttgag caagagaagg tagaagaagc caatgaagga gagaacaccc    5150
gcttgttaca ccctgtgagc ctgcatggga tggatgaccc ggagagagaa    5200
```

-continued

```
gtattagagt ggaggtttga cagccgccta gcatttcatc acatggcccg       5250
agagctgcat ccggactgta ctgggtctct ctggttagac cagatctgag       5300
cctgggagct ctctggctaa ctagggaacc cactgcttaa gcctcaataa       5350
agcttgcctt gagtgcttca agtagtgtgt gcccgtctgt tgtgtgactc       5400
tggtaactag agatccctca gacccttta gtcagtgtgg aaaatctcta        5450
gcagcatgtg agcaaaaggc cagcaaaagg ccaggaaccg taaaaaggcc       5500
gcgttgctgg cgttttttcca taggctccgc ccccctgacg agcatcacaa      5550
aaatcgacgc tcaagtcaga ggtggcgaaa cccgacagga ctataaagat      5600
accaggcgtt ccccctgga agctccctcg tgcgctctcc tgttccgacc       5650
ctgccgctta ccggatacct gtccgccttt ctcccttcgg gaagcgtggc      5700
gctttctcat agctcacgct gtaggtatct cagttcggtg taggtcgttc      5750
gctccaagct gggctgtgtg cacgaacccc ccgttcagcc cgaccgctgc      5800
gccttatccg gtaactatcg tcttgagtcc aacccggtaa gacacgactt      5850
atcgccactg gcagcagcca ctggtaacag gattagcaga gcgaggtatg     5900
taggcggtgc tacagagttc ttgaagtggt ggcctaacta cggctacact      5950
agaagaacag tatttggtat ctgcgctctg ctgaagccag ttaccttcgg      6000
aaaaagagtt ggtagctctt gatccggcaa acaaaccacc gctggtagcg     6050
gtggtttttt tgtttgcaag cagcagatta cgcgcagaaa aaaggatct       6100 caagaagatc ctttgatctt ttctacgggg tctgacgctc agtggaacga     6150
aaactcacgt taagggattt tggtcatgag attatcaaaa aggatcttca     6200
cctagatcct tttaaattaa aaatgaagtt ttaaatcaat ctaaagtata     6250
tatgagtaaa cttggtctga cagttaccaa tgcttaatca gtgaggcacc     6300
tatctcagcg atctgtctat ttcgttcatc catagttgcc tgactccccg     6350
tcgtgtagat aactacgata cgggagggct taccatctgg ccccagtgct     6400
gcaatgatac cgcgagaccc acgctcaccg gctccagatt tatcagcaat     6450
aaaccagcca gccggaaggg ccgagcgcag aagtggtcct gcaactttat     6500
ccgcctccat ccagtctatt aattgttgcc gggaagctag agtaagtagt     6550
tcgccagtta atagtttgcg caacgttgtt gccattgcta caggcatcgt     6600
ggtgtcacgc tcgtcgtttg gtatggcttc attcagctcc ggttcccaac     6650
gatcaaggcg agttacatga tcccccatgt tgtgcaaaaa agcggttagc     6700
tccttcggtc ctccgatcgt tgtcagaagt aagttggccg cagtgttatc     6750
actcatggtt atggcagcac tgcataattc tcttactgtc atgccatccg     6800
taagatgctt ttctgtgact ggtgagtact caaccaagtc attctgagaa     6850
tagtgtatgc ggcgaccgag ttgctcttgc ccggcgtcaa tacgggataa    6900
taccgcgcca catagcagaa ctttaaaagt gctcatcatt ggaaaacgtt     6950
cttcggggcg aaaactctca aggatcttac cgctgttgag atccagttcg     7000
atgtaaccca ctcgtgcacc caactgatct tcagcatctt ttactttcac     7050
cagcgtttct gggtgagcaa aaacaggaag gcaaaatgcc gcaaaaaagg     7100
gaataagggc gacacggaaa tgttgaatac tcatactctt ccttttttcaa    7150 tattattgaa gcatttatca gggttattgt ctcatgagcg gatacatatt    7200
```

```
tgaatgtatt tagaaaaata aacaaatagg ggtcccgcgc acatttcccc         7250
gaaaagtgcc acctgac                                            7267
```

As will be noted, residues 237-616 of pLenti-CMV-IRES-empty (-att) (SEQ ID NO:67) correspond to the CMV immediate early enhancer site (SEQ ID NO:1). Residues 618-816 of SEQ ID NO:67 correspond to the CMV immediate early promoter site (SEQ ID NO:3). Residues 834-1012 of SEQ ID NO:67 correspond to the alternative truncated lentiviral 5' LTR region (SEQ ID NO:68). Residues 1059-1184 of SEQ ID NO:67 correspond to the lentiviral ψ region (SEQ ID NO:6). Residues 1681-1914 of SEQ ID NO:67 correspond to the lentiviral Rev response element (RRE) (SEQ ID NO:7). Residues 2441-2558 of SEQ ID NO:67 correspond to the lentiviral cPPT/CTS region (SEQ ID NO:8). Residues 2641-3020 of SEQ ID NO:67 correspond to the variant CMV immediate early enhancer site (SEQ ID NO:2). Residues 3021-3224 of SEQ ID NO:67 correspond to the variant CMV immediate early promoter site (SEQ ID NO:4). Residues 3250-3268 of SEQ ID NO:67 correspond to a T7 promoter site (SEQ ID NO:12). Residues 3391-3852 of SEQ ID NO:67 correspond to the internal ribosome entry site of the encephalomyocarditis virus (EMCV) (SEQ ID NO:69). Residues 3946-4020 of SEQ ID NO:67 correspond to a polynucleotide sequence (SEQ ID NO:14) that encodes a combined Myc (human c-Myc oncogene) and FLAG® epitope tag (SEQ ID NO:13). Residues 4069-4102 of SEQ ID NO:67 correspond to a LoxP site (SEQ ID NO:15). Residues 4158-4746 of SEQ ID NO:67 correspond to a woodchuck hepatitis virus post-transcriptional regulatory element (WPRE) (SEQ ID NO:16). Residues 4629-4640 of SEQ ID NO:67 correspond to a Factor Xa cleavage site (SEQ ID NO:17). Residues 4749-4765 of SEQ ID NO:67 correspond to a polynucleotide whose sequence is complementary to the sequence a KS primer binding site (SEQ ID NO:18). Residues 4955-5453 correspond to a 5' LTR that has been modified to be self-inactivating (SIN) of which residues 4955-5272 correspond to a modified U3 region (SEQ ID NO:64), residues 5273-5400 correspond to R and the U5 regions of the 5' LTR (SEQ ID NO:5). Residues 5515-6103 of SEQ ID NO:67 correspond to a polynucleotide whose sequence is complementary to the sequence of the high-copy-number ColE1/pMB1/pBR322/pUC origin of replication (SEQ ID NO:19). Residues 6274-7134 of SEQ ID NO:67 correspond to a polynucleotide whose sequence is complementary to the sequence encoding the AmpR antibiotic resistance determinant (SEQ ID NO:22) (i.e., such encoding sequence is on the second strand of the vector). Residues 7135-7239 of SEQ ID NO:67 correspond to a polynucleotide whose sequence is complementary to the sequence of the AmpR promoter (SEQ ID NO:25) (i.e., such promoter sequence is on the second strand of the vector).

(d) pLenti-CMV-IRES-Spike (-Att)

The vector pLenti-CMV-IRES-Spike (-att) (FIG. 9) further illustrates the LTR-containing vectors of the present invention. The first strand of vector pLenti-CMV-IRES-Spike (-att) has 11060 nucleotide residues and has the sequence of SEQ ID NO:70:

```
gtcgacggat cgggagatct cccgatcccc tatggtgcac tctcagtaca         50
atctgctctg atgccgcata gttaagccag tatctgctcc ctgcttgtgt        100
gttggaggtc gctgagtagt gcgcgagcaa aatttaagct acaacaaggc        150
aaggcttgac cgacaattgc atgaagaatc tgcttagggt taggcgtttt        200
gcgctgcttc gcgatgtacg ggccagatat cgcgttgaca ttgattattg        250
actagttatt aatagtaatc aattacgggg tcattagttc atagcccata        300
tatggagttc cgcgttacat aacttacggt aaatggcccg cctggctgac        350
cgcccaacga cccccgccca ttgacgtcaa taatgacgta tgttcccata        400
gtaacgccaa tagggacttt ccattgacgt caatgggtgg agtatttacg        450
gtaaactgcc cacttggcag tacatcaagt gtatcatatg ccaagtacgc        500
cccctattga cgtcaatgac ggtaaatggc ccgcctggca ttatgcccag        550
tacatgacct tatgggactt tcctacttgg cagtacatct acgtattagt        600
catcgctatt accatggtga tgcggttttg gcagtacatc aatgggcgtg        650
gatagcggtt tgactcacgg ggatttccaa gtctccaccc cattgacgtc        700
aatgggagtt tgttttggca ccaaaatcaa cgggactttc caaaatgtcg        750
taacaactcc gccccattga cgcaaatggg cggtaggcgt gtacggtggg        800
aggtctatat aagcagcgcg ttttgcctgt actgggtctc tctggttaga        850
ccagatctga gcctgggagc tctctggcta actagggaac ccactgctta        900
agcctcaata aagcttgcct tgagtgcttc aagtagtgtg tgcccgtctg        950
ttgtgtgact ctggtaacta gagatccctc agacccttt agtcagtgtg       1000
```

```
-continued
gaaaatctct aggtggcgcc cgaacaggga cttgaaagcg aaagggaaac    1050
cagaggagct ctctcgacgc aggactcggc ttgctgaagc gcgcacggca    1100
agaggcgagg ggcggcgact ggtgagtacg ccaaaaattt tgactagcgg    1150
aggctagaag gagagagatg ggtgcgagag cgtcagtatt aagcggggga    1200
gaattagatc gcgatgggaa aaaattcggt taaggccagg gggaaagaaa    1250
aaatataaat taaacatat agtatgggca agcagggagc tagaacgatt    1300
cgcagttaat cctggcctgt tagaaacatc agaaggctgt agacaaatac    1350
tgggacagct acaaccatcc cttcagacag gatcagaaga acttagatca    1400
ttatataata cagtagcaac cctctattgt gtgcatcaaa ggatagagat    1450
aaaagacacc aaggaagctt tagacaagat agaggaagag caaaacaaaa    1500
gtaagaccac cgcacagcaa gcggccggcc gctgatcttc agacctggag    1550
gaggagatat gagggacaat tggagaagtg aattatataa atataaagta    1600
gtaaaaattg aaccattagg agtagcaccc accaaggcaa agaagagt     1650 ggtgcagaga gaaaaaagag cagtgggaat aggagctttg ttccttgggt    1700
tcttgggagc agcaggaagc actatgggcg cagcgtcaat gacgctgacg    1750
gtacaggcca gacaattatt gtctggtata gtgcagcagc agaacaattt    1800
gctgagggct attgaggcgc aacagcatct gttgcaactc acagtctggg    1850
gcatcaagca gctccaggca agaatcctgg ctgtggaaag atacctaaag    1900
gatcaacagc tcctggggat ttggggttgc tctggaaaac tcatttgcac    1950
cactgctgtg ccttggaatg ctagttggag taataaatct ctggaacaga    2000
tttggaatca cacgacctgg atggagtggg acagagaaat taacaattac    2050
acaagcttaa tacactcctt aattgaagaa tcgcaaaacc agcaagaaaa    2100
gaatgaacaa gaattattgg aattagataa atgggcaagt ttgtggaatt    2150
ggtttaacat aacaaattgg ctgtggtata taaaattatt cataatgata    2200
gtaggaggct tggtaggttt aagaatagtt tttgctgtac tttctatagt    2250
gaatagagtt aggcagggat attcaccatt atcgtttcag acccacctcc    2300
caaccccgag gggacccgac aggcccgaag gaatagaaga agaaggtgga    2350
gagagagaca gagacagatc cattcgatta gtgaacggat cggcactgcg    2400
tgcgccaatt ctgcagacaa atggcagtat tcatccacaa ttttaaaaga    2450 aaaggggggga ttggggggta cagtgcaggg gaaagaatag tagacataat    2500
agcaacagac atacaaacta agaattaca aaaacaaatt acaaaaattc    2550
aaaattttcg ggtttattac agggacagca gagatccagt ttggttagta    2600
ccgggcccgc tctagacatg tccaatatga ccgccatgtt gacattgatt    2650
attgactagt tattaatagt aatcaattac gggtcatta gttcatagcc    2700 catatatgga gttccgcgtt acataactta cggtaaatgg cccgcctggc    2750
tgaccgccca acgacccccg cccattgacg tcaataatga cgtatgttcc    2800
catagtaacg ccaatagggga cttttccattg acgtcaatgg gtggagtatt    2850
tacggtaaac tgcccacttg gcagtacatc aagtgtatca tatgccaagt    2900
ccgcccccta ttgacgtcaa tgacggtaaa tggcccgcct ggcattatgc    2950
ccagtacatg accttacggg actttcctac ttggcagtac atctacgtat    3000
tagtcatcgc tattaccatg gtgatgcggt tttggcagta caccaatggg    3050
```

```
cgtggatagc ggtttgactc acggggattt ccaagtctcc accccattga    3100
cgtcaatggg agtttgtttt ggcaccaaaa tcaacgggac tttccaaaat    3150
gtcgtaataa ccccgccccg ttgacgcaaa tgggcggtag gcgtgtacgg    3200
tgggaggtct atataagcag agctcgttta gtgaaccgtc agaattttgt    3250
aatacgactc actatagggc ggccgggaat tcgtcgactg ccccccccc    3300 taacgttact ggccgaagcc gcttggaata aggccggtgt gcgtttgtct    3350
atatgttatt ttccaccata ttgccgtctt ttggcaatgt gagggcccgg    3400
aaacctggcc ctgtcttctt gacgagcatt cctaggggtc tttcccctct    3450
cgccaaagga atgcaaggtc tgttgaatgt cgtgaaggaa gcagttcctc    3500
tggaagcttc ttgaagacaa acaacgtctg tagcgaccct ttgcaggcag    3550
cggaaccccc cacctggcga caggtgcctc tgcggccaaa agccacgtgt    3600
ataagataca cctgcaaagg cggcacaacc ccagtgccac gttgtgagtt    3650
ggatagttgt ggaaagagtc aaatggctct cctcaagcgc attcaacaag    3700
gggctgaagg atgcccagaa ggtaccccat tgtatgggat ctgatctggg    3750
gcctcggtgc acatgcttta catgtgttta gtcgaggtta aaaaacgtct    3800
aggccccccg aaccacgggg acgtggtttt cctttgaaaa acacgatgat    3850
aatgatccgg taccgaggag atctgccgcc gcgatcgcca ccatgtacag    3900
gatgcaactc ctgtcttgca ttgcactaag tcttgcactt gtcacaaaca    3950
gtatgtttgt gttcctggtg ctgctgccac tggtgtccag ccagtgtgtg    4000
aacctgacca ccaggaccca acttcctcct gcctacacca actccttcac    4050
caggggagtc tactaccctg acaaggtgtt caggtcctct gtgctgcaca    4100
gcacccagga cctgttcctg ccattcttca gcaatgtgac ctggttccat    4150
gccatccatg tgtctggcac caatggcacc aagaggtttg acaaccctgt    4200
gctgccattc aatgatggag tctactttgc cagcacagag aagagcaaca    4250
tcatcagggg ctggattttt ggcaccaccc tggacagcaa gacccagtcc    4300
ctgctgattg tgaacaatgc caccaatgtg gtgattaagg tgtgtgagtt    4350
ccagttctgt aatgacccat tcctgggagt ctactaccac aagaacaaca    4400
agtcctggat ggagtctgag ttcagggtct actcctctgc caacaactgt    4450
acctttgaat atgtgagcca accattcctg atggacttgg agggcaagca    4500
gggcaacttc aagaacctga gggagtttgt gttcaagaac attgatggct    4550
acttcaagat ttacagcaaa cacacaccaa tcaacctggt gagggacctg    4600
ccacagggct tctctgcctt ggaaccactg gtggacctgc caattggcat    4650
caacatcacc aggttccaga ccctgctggc tctgcacagg tcctacctga    4700
cacctggaga ctcctcctct ggctggacag caggagcagc agcctactat    4750
gtgggctacc tccaaccaag gaccttcctg ctgaaataca atgagaatgg    4800
caccatcaca gatgctgtgg actgtgccct ggacccactg tctgagacca    4850
agtgtaccct gaaatccttc acagtggaga agggcatcta ccagaccagc    4900
aacttcaggg tccaaccaac agagagcatt gtgaggtttc caaacatcac    4950
caacctgtgt ccatttggag aggtgttcaa tgccaccagg tttgcctctg    5000
tctatgcctg gaacaggaag aggattagca actgtgtggc tgactactct    5050
gtgctctaca actctgcctc cttcagcacc ttcaagtgtt atggagtgag    5100
```

-continued

```
cccaaccaaa ctgaatgacc tgtgtttcac caatgtctat gctgactcct      5150
ttgtgattag gggagatgag gtgagacaga ttgcccctgg acaaacaggc      5200
aagattgctg actacaacta caaactgcct gatgacttca caggctgtgt      5250
gattgcctgg aacagcaaca acctggacag caaggtggga ggcaactaca      5300
actacctcta cagactgttc aggaagagca acctgaaacc atttgagagg      5350
gacatcagca cagagattta ccaggctggc agcacaccat gtaatggagt      5400
ggagggcttc aactgttact ttccactcca atcctatggc ttccaaccaa      5450
ccaatggagt gggctaccaa ccatacaggg tggtggtgct gtcctttgaa      5500
ctgctccatg cccctgccac agtgtgtgga ccaaagaaga gcaccaacct      5550
ggtgaagaac aagtgtgtga acttcaactt caatggactg acaggcacag      5600
gagtgctgac agagagcaac aagaagttcc tgccattcca acagtttggc      5650
agggacattg ctgacaccac agatgctgtg agggacccac agaccttgga      5700
gattctggac atcacaccat gttcctttgg aggagtgtct gtgattacac      5750
ctggcaccaa caccagcaac caggtggctg tgctctacca ggatgtgaac      5800
tgtactgagg tgcctgtggc tatccatgct gaccaactta caccaacctg      5850
gagggtctac agcacaggca gcaatgtgtt ccagaccagg gctggctgtc      5900
tgattggagc agagcatgtg aacaactcct atgagtgtga catcccaatt      5950
ggagcaggca tctgtgcctc ctaccagacc cagaccaaca gcccaaggag      6000
ggcaaggtct gtggcaagcc agagcatcat tgcctacaca atgagtctgg      6050
gagcagagaa ctctgtggct tacagcaaca acagcattgc catcccaacc      6100
aacttcacca tctctgtgac cacagagatt ctgcctgtga gtatgaccaa      6150
gacctctgtg gactgtacaa tgtatatctg tggagacagc acagagtgta      6200
gcaacctgct gctccaatat ggctccttct gtacccaact taacagggct      6250
ctgacaggca ttgctgtgga acaggacaag aacacccagg aggtgtttgc      6300
ccaggtgaag cagatttaca agacacctcc aatcaaggac tttggaggct      6350
tcaacttcag ccagattctg cctgacccaa gcaagccaag caagaggtcc      6400
ttcattgagg acctgctgtt caacaaggtg accctggctg atgctggctt      6450
catcaagcaa tatggagact gtctgggaga cattgctgcc agggacctga      6500
tttgtgccca gaagttcaat ggactgacag tgctgcctcc actgctgaca      6550
gatgagatga ttgcccaata cacctctgcc ctgctggctg gcaccatcac      6600
ctctggctgg acctttggag caggagcagc cctccaaatc ccatttgcta      6650
tgcagatggc ttacaggttc aatggcattg gagtgaccca gaatgtgctc      6700
tatgagaacc agaaactgat tgccaaccag ttcaactctg ccattggcaa      6750
gattcaggac tccctgtcca gcacagcctc tgccctgggc aaactccaag      6800
atgtggtgaa ccagaatgcc caggctctga acacccctggt gaagcaactt      6850 tccagcaact ttggagccat ctcctctgtg ctgaatgaca tcctgagcag      6900
actggacaag gtggaggctg aggtccagat tgacagactg attacaggca      6950
gactccaatc cctccaaacc tatgtgaccc aacaacttat cagggctgct      7000
gagattaggg catctgccaa cctggctgcc accaagatga gtgagtgtgt      7050
gctgggacaa agcaagaggg tggacttctg tggcaagggc taccacctga      7100
tgagttttcc acagtctgcc cctcatggag tggtgttcct gcatgtgacc      7150
```

-continued

```
tatgtgcctg cccaggagaa gaacttcacc acagccctg ccatctgcca      7200 tgatggcaag gctcactttc caagggaggg agtgtttgtg agcaatggca      7250
cccactggtt tgtgacccag aggaacttct atgaaccaca gattatcacc      7300
acagacaaca cctttgtgtc tggcaactgt gatgtggtga ttggcattgt      7350
gaacaacaca gtctatgacc cactccaacc tgaactggac tccttcaagg      7400
aggaactgga caaatacttc aagaaccaca ccagccctga tgtggacctg      7450
ggagacatct ctggcatcaa tgcctctgtg gtgaacatcc agaaggagat      7500
tgacagactg aatgaggtgg ctaagaacct gaatgagtcc ctgattgacc      7550
tccaagaact gggcaaatat gaacaataca tcaagtggcc atggtacatc      7600
tggctgggct tcattgctgg actgattgcc attgtgatgg tgaccataat      7650
gctgtgttgt atgacctcct gttgttcctg tctgaaaggc tgttgttcct      7700
gtggctcctg ttgtaagtga acgcgtacgc ggccgctcga gcagaaactc      7750
atctcagaag aggatctggc agcaaatgat atcctggatt acaaggatga      7800
cgacgataag gtttaaacgg ccggccgcgg tctgtacaag taggattcgt      7850
cgagggacct aataacttcg tatagcatac attatacgaa gttatacatg      7900
tttaagggtt ccggttccac taggtacaat tcgatatcaa gcttatcgat      7950
aatcaacctc tggattacaa aatttgtgaa agattgactg gtattcttaa      8000
ctatgttgct ccttttacgc tatgtggata cgctgcttta atgcctttgt      8050
atcatgctat tgcttcccgt atggctttca ttttctcctc cttgtataaa      8100
tcctggttgc tgtctcttta tgaggagttg tggcccgttg tcaggcaacg      8150
tggcgtggtg tgcactgtgt ttgctgacgc aaccccact ggttggggca      8200 ttgccaccac ctgtcagctc ctttccggga ctttcgcttt ccccctccct      8250
attgccacgg cggaactcat cgccgcctgc cttgcccgct gctggacagg      8300
ggctcggctg ttgggcactg acaattccgt ggtgttgtcg gggaaatcat      8350
cgtccttttc cttggctgct ccctgtgttg ccacctggat tctgcgcggg      8400
acgtccttct gctacgtccc ttcggccctc aatccagcgg accttccttc      8450
ccgcggcctg ctgccggctc tgcggcctct tccgcgtctt cgccttcgcc      8500
ctcagacgag tcggatctcc ctttgggccg cctccccgca tcgataccgt      8550
cgacctcgat cgagacctag aaaaacatgg agcaatcaca agtagcaata      8600
cagcagctac caatgctgat tgtgcctggc tagaagcaca agaggaggag      8650
gaggtgggtt ttccagtcac acctcaggta cctttaagac caatgactta      8700
caaggcagct gtagatctta gccactttt aaaagaaaag ggggacgaa       8750 gggctaattc actcccaacg aagacaagat ctgcttgatc tgtggatcta      8800
ccacacacaa ggctacttcc ctgattggca gaactacaca ccagggccag      8850
ggatcagata tccactgacc tttggatggt gctacaagct agtaccagtt      8900
gagcaagaga aggtagaaga agccaatgaa ggagagaaca cccgcttgtt      8950
acaccctgtg agcctgcatg ggatggatga cccggagaga gaagtattag      9000
agtggaggtt tgacagccgc ctagcatttc atcacatggc ccgagagctg      9050
catccggact gtactgggtc tctctggtta gaccagatct gagcctggga      9100
gctctctggc taactaggga acccactgct taagcctcaa taaagcttgc      9150
cttgagtgct tcaagtagtg tgtgcccgtc tgttgtgtga ctctggtaac      9200
```

```
                                                  -continued
tagagatccc tcagaccctt ttagtcagtg tggaaaatct ctagcagcat    9250
gtgagcaaaa ggccagcaaa aggccaggaa ccgtaaaaag gccgcgttgc    9300
tggcgttttt ccataggctc cgcccccctg acgagcatca caaaaatcga    9350
cgctcaagtc agaggtggcg aaacccgaca ggactataaa gataccaggc    9400
gtttccccct ggaagctccc tcgtgcgctc tcctgttccg accctgccgc    9450
ttaccggata cctgtccgcc tttctccctt cgggaagcgt ggcgctttct    9500
catagctcac gctgtaggta tctcagttcg gtgtaggtcg ttcgctccaa    9550
gctgggctgt gtgcacgaac cccccgttca gcccgaccgc tgcgccttat    9600
ccggtaacta tcgtcttgag tccaacccgg taagacacga cttatcgcca    9650
ctggcagcag ccactggtaa caggattagc agagcgaggt atgtaggcgg    9700
tgctacagag ttcttgaagt ggtggcctaa ctacggctac actagaagaa    9750
cagtatttgg tatctgcgct ctgctgaagc cagttacctt cggaaaaaga    9800
gttggtagct cttgatccgg caaacaaacc accgctggta gcggtggttt    9850
ttttgtttgc aagcagcaga ttacgcgcag aaaaaaagga tctcaagaag    9900
atcctttgat cttttctacg gggtctgacg ctcagtggaa cgaaaactca    9950
cgttaaggga ttttggtcat gagattatca aaaaggatct tcacctagat   10000
ccttttaaat taaaaatgaa gttttaaatc aatctaaagt atatatgagt   10050
aaacttggtc tgacagttac caatgcttaa tcagtgaggc acctatctca   10100
gcgatctgtc tatttcgttc atccatagtt gcctgactcc ccgtcgtgta   10150
gataactacg atacgggagg gcttaccatc tggccccagt gctgcaatga   10200
taccgcgaga cccacgctca ccggctccag atttatcagc aataaaccag   10250
ccagccggaa gggccgagcg cagaagtggt cctgcaactt tatccgcctc   10300
catccagtct attaattgtt gccgggaagc tagagtaagt agttcgccag   10350
ttaatagttt gcgcaacgtt gttgccattg ctacaggcat cgtggtgtca   10400
cgctcgtcgt ttggtatggc ttcattcagc tccggttccc aacgatcaag   10450
gcgagttaca tgatccccca tgttgtgcaa aaaagcggtt agctccttcg   10500
gtcctccgat cgttgtcaga agtaagttgg ccgcagtgtt atcactcatg   10550
gttatggcag cactgcataa ttctcttact gtcatgccat ccgtaagatg   10600
cttttctgtg actggtgagt actcaaccaa gtcattctga aatagtgta    10650 tgcggcgacc gagttgctct tgcccggcgt caatacggga taataccgcg   10700
ccacatagca gaactttaaa agtgctcatc attggaaaac gttcttcggg   10750
gcgaaaactc tcaaggatct taccgctgtt gagatccagt tcgatgtaac   10800
ccactcgtgc acccaactga tcttcagcat cttttacttt caccagcgtt   10850
tctgggtgag caaaaacagg aaggcaaaat gccgcaaaaa agggaataag   10900
ggcgacacgg aaatgttgaa tactcatact cttcctttt caatattatt    10950 gaagcattta tcagggttat tgtctcatga gcggatacat atttgaatgt   11000
atttagaaaa ataaacaaat aggggtcccg cgcacatttc cccgaaaagt   11050
gccacctgac                                                11060
```

As will be noted, residues 237-616 of pLenti-CMV-IRES-Spike (-att) (SEQ ID NO:70) correspond to the CMV immediate early enhancer site (SEQ ID NO:1). Residues 618-816 of SEQ ID NO:70 correspond to the CMV immediate early promoter site (SEQ ID NO:3). Residues 834-1012 of SEQ ID NO:70 correspond to the alternative truncated lentiviral 5' LTR region (SEQ ID NO:68). Residues 1059-1184 of SEQ ID NO:70 correspond to the lentiviral ψ region (SEQ ID NO:6). Residues 1681-1914 of SEQ ID NO:70 correspond to the lentiviral Rev response element (RRE) (SEQ ID NO:7). Residues 2441-2558 of SEQ ID NO:70 correspond to the lentiviral cPPT/CTS region (SEQ ID NO:8). Residues 2641-3020 of SEQ ID NO:70 correspond to the variant CMV immediate early enhancer site (SEQ ID NO:2). Residues 3021-3224 of SEQ ID NO:70 correspond to the variant CMV immediate early promoter site (SEQ ID NO:4). Residues 3250-3268 of SEQ ID NO:70 correspond to a T7 promoter site (SEQ ID NO:12). Residues 3391-3852 of SEQ ID NO:70 correspond to the internal ribosome entry site of the encephalomyocarditis virus (EMCV) (SEQ ID NO:69). Residues 3893-3952 of SEQ ID NO:70 correspond to a polynucleotide sequence (SEQ ID NO:73) that encodes an TL-2 signal sequence (SEQ ID NO:72). Residues 3953-7717 of SEQ ID NO:70 correspond to a polynucleotide sequence (SEQ ID NO:71) that encodes the SARS-CoV-2 spike protein (SEQ ID NO:54). Residues 5265-5282 (gcaacaacctggacagca; SEQ ID NO:74) correspond to a sequence that is complementary to a polynucleotide that encodes a tetracysteine peptide (CCPGCC; SEQ ID NO:75) that binds biarsenical labeling reagents. Residues 7739-7813 of SEQ ID NO:70 correspond to a polynucleotide sequence (SEQ ID NO:14) that encodes a combined Myc (human c-Myc oncogene) and FLAG® epitope tag (SEQ ID NO:13). Residues 7862-7895 of SEQ ID NO:70 correspond to a LoxP site (SEQ ID NO:15). Residues 7951-8539 of SEQ ID NO:70 correspond to a woodchuck hepatitis virus post-transcriptional regulatory element (WPRE) (SEQ ID NO:16). Residues 8422-8433 of SEQ ID NO:70 correspond to a Factor Xa cleavage site (SEQ ID NO:17). Residues 8542-8558 of SEQ ID NO:70 correspond to a polynucleotide whose sequence is complementary to the sequence a KS primer binding site (SEQ ID NO:18). Residues 8748-9247 correspond to a 5' LTR that has been modified to be self-inactivating (SIN) of which residues 8748-9065 correspond to a modified U3 region (SEQ ID NO:64), residues 9066-9247 correspond to R and the U5 regions of the 5' LTR (SEQ ID NO:5). Residues 9308-9896 of SEQ ID NO:70 correspond to a polynucleotide whose sequence is complementary to the sequence of the high-copy-number ColE1/pMB1/pBR322/pUC origin of replication (SEQ ID NO:19). Residues 10067-10927 of SEQ ID NO:70 correspond to a polynucleotide whose sequence is complementary to the sequence encoding the AmpR antibiotic resistance determinant (SEQ ID NO:22) (i.e., such encoding sequence is on the second strand of the vector). Residues 10928-11032 of SEQ ID NO:70 correspond to a polynucleotide whose sequence is complementary to the sequence of the AmpR promoter (SEQ ID NO:25) (i.e., such promoter sequence is on the second strand of the vector).

(e) pLenti-IgGκ-nCoV-Spike-CD8-TM (-att)

The vector pLenti-IgGκ-nCoV-Spike-CD8-TM (-att) (FIG. 10) further illustrates the LTR-containing vectors of the present invention. The first strand of vector pLenti-IgGκ-nCoV-Spike-CD8-TM (-att) has 11381 nucleotide residues and has the sequence of SEQ ID NO:83:

```
gtcgacggat cgggagatct cccgatcccc tatggtgcac tctcagtaca        50
atctgctctg atgccgcata gttaagccag tatctgctcc ctgcttgtgt       100
gttggaggtc gctgagtagt gcgcgagcaa aatttaagct acaacaaggc       150
aaggcttgac cgacaattgc atgaagaatc tgcttagggt taggcgtttt       200
gcgctgcttc gcgatgtacg ggccagatat cgcgttgaca ttgattattg       250
actagttatt aatagtaatc aattacgggg tcattagttc atagcccata       300
tatggagttc cgcgttacat aacttacggt aaatggcccg cctggctgac       350
cgcccaacga cccccgccca ttgacgtcaa taatgacgta tgttcccata       400
gtaacgccaa tagggacttt ccattgacgt caatgggtgg agtatttacg       450
gtaaactgcc cacttggcag tacatcaagt gtatcatatg ccaagtacgc       500
cccctattga cgtcaatgac ggtaaatggc ccgcctggca ttatgcccag       550
tacatgacct tatgggactt tcctacttgg cagtacatct acgtattagt       600
catcgctatt accatggtga tgcggttttg gcagtacatc aatgggcgtg       650
gatagcggtt tgactcacgg ggatttccaa gtctccaccc cattgacgtc       700
aatgggagtt tgttttggca ccaaaatcaa cgggactttc caaaatgtcg       750
taacaactcc gccccattga cgcaaatggg cggtaggcgt gtacggtggg       800
aggtctatat aagcagcgcg ttttgcctgt actgggtctc tctggttaga       850
ccagatctga gcctgggagc tctctggcta actagggaac ccactgctta       900
agcctcaata aagcttgcct tgagtgcttc aagtagtgtg tgcccgtctg       950
ttgtgtgact ctggtaacta gagatccctc agacccttt agtcagtgtg      1000 gaaaatctct aggtggcgcc cgaacaggga cttgaaagcg aaagggaaac      1050
cagaggagct ctctcgacgc aggactcggc ttgctgaagc gcgcacggca      1100
```

-continued

```
agaggcgagg ggcggcgact ggtgagtacg ccaaaaattt tgactagcgg      1150
aggctagaag gagagagatg ggtgcgagag cgtcagtatt aagcgggga       1200 gaattagatc gcgatgggaa aaaattcggt taaggccagg gggaaagaaa      1250
aaatataaat taaaacatat agtatgggca agcagggagc tagaacgatt      1300
cgcagttaat cctggcctgt tagaaacatc agaaggctgt agacaaatac      1350
tgggacagct acaaccatcc cttcagacag gatcagaaga acttagatca      1400
ttatataata cagtagcaac cctctattgt gtgcatcaaa ggatagagat      1450
aaaagacacc aaggaagctt tagacaagat agaggaagag caaaacaaaa      1500
gtaagaccac cgcacagcaa gcggccggcc gctgatcttc agacctggag      1550
gaggagatat gagggacaat tggagaagtg aattatataa atataaagta      1600
gtaaaaattg aaccattagg agtagcaccc accaaggcaa agagaagagt      1650
ggtgcagaga gaaaaaagag cagtgggaat aggagctttg ttccttgggt      1700
tcttgggagc agcaggaagc actatgggcg cagcgtcaat gacgctgacg      1750
gtacaggcca gacaattatt gtctggtata gtgcagcagc agaacaattt      1800
gctgagggct attgaggcgc aacagcatct gttgcaactc acagtctggg      1850
gcatcaagca gctccaggca agaatcctgg ctgtggaaag atacctaaag      1900
gatcaacagc tcctggggat ttggggttgc tctggaaaac tcatttgcac      1950
cactgctgtg ccttggaatg ctagttggag taataaatct ctggaacaga      2000
tttggaatca cacgacctgg atggagtggg acagagaaat taacaattac      2050
acaagcttaa tacactcctt aattgaagaa tcgcaaaacc agcaagaaaa      2100
gaatgaacaa gaattattgg aattagataa atgggcaagt ttgtggaatt      2150
ggtttaacat aacaaattgg ctgtggtata taaaattatt cataatgata      2200
gtaggaggct tggtaggttt aagaatagtt tttgctgtac tttctatagt      2250
gaatagagtt aggcagggat attcaccatt atcgtttcag acccacctcc      2300
caaccccgag gggaccccgac aggcccgaag gaatagaaga agaaggtgga      2350
gagagagaca gagacagatc cattcgatta gtgaacggat cggcactgcg      2400
tgcgccaatt ctgcagacaa atggcagtat tcatccacaa ttttaaaaga      2450 aaaggggggga ttgggggggta cagtgcaggg gaaagaatag tagacataat      2500
agcaacagac atacaaacta aagaattaca aaaacaaatt acaaaaattc      2550
aaaattttcg ggtttattac agggacagca gagatccagt ttggttagta      2600
ccgggcccgc tctagacatg tccaatatga ccgccatgtt gacattgatt      2650
attgactagt tattaatagt aatcaattac ggggtcatta gttcatagcc      2700
catatatgga gttccgcgtt acataactta cggtaaatgg cccgcctggc      2750
tgaccgccca acgacccccg cccattgacg tcaataatga cgtatgttcc      2800
catagtaacg ccaatagggact ttccattg acgtcaatgg gtggagtatt       2850
tacggtaaac tgcccacttg gcagtacatc aagtgtatca tatgccaagt      2900
ccgcccccta ttgacgtcaa tgacggtaaa tggcccgcct ggcattatgc      2950
ccagtacatg accttacggg actttcctac ttggcagtac atctacgtat      3000
tagtcatcgc tattaccatg gtgatgcggt tttggcagta caccaatggg      3050
cgtggatagc ggtttgactc acggggattt ccaagtctcc accccattga      3100
cgtcaatggg agtttgtttt ggcaccaaaa tcaacgggac tttccaaaat      3150
```

-continued

```
gtcgtaataa ccccgccccg ttgacgcaaa tgggcggtag gcgtgtacgg      3200
tgggaggtct atataagcag agctcgttta gtgaaccgtc agaattttgt      3250
aatacgactc actatagggc ggccgggaat tcgtcgactg ccccccccc       3300 taacgttact ggccgaagcc gcttggaata aggccggtgt gcgtttgtct      3350
atatgttatt ttccaccata ttgccgtctt ttggcaatgt gagggcccgg      3400
aaacctggcc ctgtcttctt gacgagcatt cctaggggtc tttcccctct      3450
cgccaaagga atgcaaggtc tgttgaatgt cgtgaaggaa gcagttcctc      3500
tggaagcttc ttgaagacaa acaacgtctg tagcgaccct ttgcaggcag      3550
cggaaccccc cacctggcga caggtgcctc tgcggccaaa agccacgtgt      3600
ataagataca cctgcaaagg cggcacaacc ccagtgccac gttgtgagtt      3650
ggatagttgt ggaaagagtc aaatggctct cctcaagcgt attcaacaag      3700
gggctgaagg atgcccagaa ggtacccat tgtatgggat ctgatctggg       3750
gcctcggtgc acatgcttta catgtgttta gtcgaggtta aaaaacgtct      3800 aggcccccg aaccacgggg acgtggtttt cctttgaaaa acacgatgat       3850
aatgatccgg taccgaggag atctgccgcc gcgatcgcca ccatggacat      3900
gagggtccct gctcagctcc tggggctcct gctgctctgg ctctcaggtg      3950
ccagatgtat gtttgtgttc ctggtgctgc tgccactggt gtccagccag      4000
tgtgtgaacc tgaccaccag gacccaactt cctcctgcct acaccaactc      4050
cttcaccagg ggagtctact accctgacaa ggtgttcagg tcctctgtgc      4100
tgcacagcac ccaggacctg ttcctgccat tcttcagcaa tgtgacctgg      4150
ttccatgcca tccatgtgtc tggcaccaat ggcaccaaga ggtttgacaa      4200
ccctgtgctg ccattcaatg atggagtcta ctttgccagc acagagaaga      4250
gcaacatcat cagggctgg attttttggca ccaccctgga cagcaagacc      4300
cagtccctgc tgattgtgaa caatgccacc aatgtggtga ttaaggtgtg      4350
tgagttccag ttctgtaatg acccattcct gggagtctac taccacaaga      4400
acaacaagtc ctggatggag tctgagttca gggtctactc ctctgccaac      4450
aactgtacct ttgaatatgt gagccaacca ttcctgatgg acttggaggg      4500
caagcagggc aacttcaaga acctgaggga gtttgtgttc aagaacattg      4550
atggctactt caagatttac agcaaacaca ccaccaatca cctggtgagg      4600
gacctgccac agggcttctc tgccttggaa ccactggtgg acctgccaat      4650
tggcatcaac atcaccaggt tccagaccct gctggctctg cacaggtcct      4700
acctgacacc tggagactcc tcctctggct ggacagcagg agcagcagcc      4750
tactatgtgg gctacctcca accaaggacc ttcctgctga aatacaatga      4800
gaatggcacc atcacagatg ctgtggactg tgccctggac ccactgtctg      4850
agaccaagtg tacccctgaaa tccttcacag tggagaaggg catctaccag      4900
accagcaact tcagggtcca accaacagag agcattgtga ggtttccaaa      4950
catcaccaac ctgtgtccat ttggagaggt gttcaatgcc accaggtttg      5000
cctctgtcta tgcctggaac aggaagagga ttagcaactg tgtggctgac      5050
tactctgtgc tctacaactc tgcctccttc agcaccttca gtgttatgg       5100 agtgagccca accaaaactga atgacctgtg tttcaccaat gtctatgctg      5150 actccttgt gattagggga gatgaggtga acagattgc ccctggacaa        5200
```

```
acaggcaaga ttgctgacta caactacaaa ctgcctgatg acttcacagg    5250
ctgtgtgatt gcctggaaca gcaacaacct ggacagcaag gtgggaggca    5300
actacaacta cctctacaga ctgttcagga agagcaacct gaaaccattt    5350
gagagggaca tcagcacaga gatttaccag gctggcagca caccatgtaa    5400
tggagtggag ggcttcaact gttactttcc actccaatcc tatggcttcc    5450
aaccaaccaa tggagtgggc taccaaccat acagggtggt ggtgctgtcc    5500
tttgaactgc tccatgcccc tgccacagtg tgtggaccaa agaagagcac    5550
caacctggtg aagaacaagt gtgtgaactt caacttcaat ggactgacag    5600
gcacaggagt gctgacagag agcaacaaga agttcctgcc attccaacag    5650
tttggcaggg acattgctga caccacagat gctgtgaggg acccacagac    5700
cttggagatt ctggacatca caccatgttc ctttggagga gtgtctgtga    5750
ttacacctgg caccaacacc agcaaccagg tggctgtgct ctaccaggat    5800
gtgaactgta ctgaggtgcc tgtggctatc catgctgacc aacttacacc    5850
aacctggagg gtctacagca caggcagcaa tgtgttccag accagggctg    5900
gctgtctgat tggagcagag catgtgaaca actcctatga gtgtgacatc    5950
ccaattggag caggcatctg tgcctcctac cagacccaga ccaacagccc    6000
aaggagggca aggtctgtgg caagccagag catcattgcc tacacaatga    6050
gtctgggagc agagaactct gtggcttaca gcaacaacag cattgccatc    6100
ccaaccaact tcaccatctc tgtgaccaca gagattctgc ctgtgagtat    6150
gaccaagacc tctgtggact gtacaatgta tatctgtgga gacagcacag    6200
agtgtagcaa cctgctgctc caatatggct ccttctgtac ccaacttaac    6250
agggctctga caggcattgc tgtggaacag gacaagaaca cccaggaggt    6300
gtttgcccag gtgaagcaga tttacaagac acctccaatc aaggactttg    6350
gaggcttcaa cttcagccag attctgcctg acccaagcaa gccaagcaag    6400
aggtccttca ttgaggacct gctgttcaac aaggtgaccc tggctgatgc    6450
tggcttcatc aagcaatatg gagactgtct gggagacatt gctgccaggg    6500
acctgatttg tgcccagaag ttcaatggac tgacagtgct gcctccactg    6550
ctgacagatg agatgattgc ccaatacacc tctgccctgc tggctggcac    6600
catcacctct ggctggacct ttggagcagg agcagccctc caaatcccat    6650
ttgctatgca gatggcttac aggttcaatg gcattggagt gacccagaat    6700
gtgctctatg agaaccagaa actgattgcc aaccagttca actctgccat    6750
tggcaagatt caggactccc tgtccagcac agcctctgcc ctgggcaaac    6800
tccaagatgt ggtgaaccag aatgcccagg ctctgaacac cctggtgaag    6850
caactttcca gcaactttgg agccatctcc tctgtgctga atgacatcct    6900
gagcagactg gacaaggtgg aggctgaggt ccagattgac agactgatta    6950
caggcagact ccaatccctc caaacctatg tgacccaaca acttatcagg    7000
gctgctgaga ttagggcatc tgccaacctg gctgccacca gatgagtgaa    7050
gtgtgtgctg ggacaaagca agagggtgga cttctgtggc aagggctacc    7100
acctgatgag ttttccacag tctgcccctc atggagtggt gttcctgcat    7150
gtgacctatg tgcctgccca ggagaagaac ttcaccacag cccctgccat    7200
ctgccatgat ggcaaggctc actttccaag ggagggagtg tttgtgagca    7250
```

```
atggcaccca ctggtttgtg acccagagga acttctatga accacagatt      7300
atcaccacag acaacacctt tgtgtctggc aactgtgatg tggtgattgg      7350
cattgtgaac aacacagtct atgacccact ccaacctgaa ctggactcct      7400
tcaaggagga actggacaaa tacttcaaga accacaccag ccctgatgtg      7450
gacctgggag acatctctgg catcaatgcc tctgtggtga catccagaa       7500
ggagattgac agactgaatg aggtggctaa gaacctgaat gagtccctga      7550
ttgacctcca agaactgggc aaatatgaac aatacatcaa gtggccatgg      7600
tacatctggc tgggcttcat tgctggactg attgccattg tgatggtgac      7650
cataatgctg tgttgtatga cctcctgttg ttcctgtctg aaaggctgtt      7700
gttcctgtgg ctcctgttgt aagtttgatg aggatgactc tgaacctgtg      7750
ctgaaaggag tgaaactgca ctacaccgcc ctgagcaact ccatcatgta      7800
cttcagccac ttcgtgccgg tcttcctgcc agcgaagccc accacgacgc      7850
cagcgccgcg accaccaaca ccggcgccca ccatcgcgtc gcagcccctg      7900
tccctgcgcc cagaggcgtg ccggccagcg gcgggggcg cagtgcacac        7950
gaggggctg gacttcgcct gtgatatcta catctgggcg cccttggccg        8000
ggacttgtgg ggtccttctc ctgtcactgg ttatcacctg aacgcgtacg      8050
cggccgctcg agcagaaact catctcagaa gaggatctgg cagcaaatga      8100
tatcctggat tacaaggatg acgacgataa ggtttaaacg gccggccgcg      8150
gtctgtacaa gtaggattcg tcgagggacc taataacttc gtatagcata      8200
cattatacga agttatacat gtttaagggt tccggttcca ctaggtacaa      8250
ttcgatatca agcttatcga taatcaacct ctggattaca aaatttgtga      8300
aagattgact ggtattctta actatgttgc tccttttacg ctatgtggat      8350
acgctgcttt aatgcctttg tatcatgcta ttgcttcccg tatggctttc      8400
attttctcct ccttgtataa atcctggttg ctgtctcttt atgaggagtt      8450
gtggcccgtt gtcaggcaac gtggcgtggt gtgcactgtg tttgctgacg      8500
caaccccac tggttggggc attgccacca cctgtcagct cctttccggg       8550
actttcgctt ccccctccc tattgccacg gcggaactca tcgccgcctg       8600
ccttgcccgc tgctggacag gggctcggct gttgggcact gacaattccg      8650
tggtgttgtc ggggaaatca tcgtcctttc cttggctgct cgcctgtgtt      8700
gccacctgga ttctgcgcgg gacgtccttc tgctacgtcc cttcggccct      8750
caatccagcg gaccttcctt cccgcggcct gctgccggct ctgcggcctc      8800
ttccgcgtct tcgccttcgc cctcagacga gtcggatctc cctttgggcc      8850
gcctccccgc atcgataccg tcgacctcga tcgagaccta gaaaaacatg      8900
gagcaatcac aagtagcaat acagcagcta ccaatgctga ttgtgcctgg     8950
ctagaagcac aagaggagga ggaggtgggt tttccagtca cacctcaggt     9000
acctttaaga ccaatgactt acaaggcagc tgtagatctt agccactttt      9050
taaaagaaaa ggggggacga agggctaatt cactcccaac gaagacaaga     9100
tctgcttgat ctgtggatct accacacaca aggctacttc cctgattggc      9150
agaactacac accagggcca gggatcagat atccactgac ctttggatgg     9200
tgctacaagc tagtaccagt tgagcaagag aaggtagaag aagccaatga      9250
aggagagaac acccgcttgt tacaccctgt gagcctgcat gggatggatg      9300
```

```
acccggagag agaagtatta gagtggaggt tgacagccg cctagcattt    9350 catcacatgg cccgagagct gcatccggac tgtactgggt ctctctggtt    9400
agaccagatc tgagcctggg agctctctgg ctaactaggg aacccactgc    9450
ttaagcctca ataaagcttg ccttgagtgc ttcaagtagt gtgtgcccgt    9500
ctgttgtgtg actctggtaa ctagagatcc ctcagaccct tttagtcagt    9550
gtggaaaatc tctagcagca tgtgagcaaa aggccagcaa aaggccagga    9600
accgtaaaaa ggccgcgttg ctggcgtttt tccataggct ccgcccccct    9650
gacgagcatc acaaaaatcg acgctcaagt cagaggtggc gaaacccgac    9700
aggactataa agataccagg cgtttccccc tggaagctcc ctcgtgcgct    9750
ctcctgttcc gaccctgccg cttaccggat acctgtccgc ctttctccct    9800
tcgggaagcg tggcgctttc tcatagctca cgctgtaggt atctcagttc    9850
ggtgtaggtc gttcgctcca agctgggctg tgtgcacgaa ccccccgttc    9900
agcccgaccg ctgcgcctta tccggtaact atcgtcttga gtccaacccg    9950
gtaagacacg acttatcgcc actggcagca gccactggta acaggattag    10000
cagagcgagg tatgtaggcg tgctacagag ttcttgaag tggtggccta    10050 actacggcta cactagaaga acagtatttg gtatctgcgc tctgctgaag    10100
ccagttacct tcggaaaaag agttggtagc tcttgatccg gcaaacaaac    10150
caccgctggt agcggtggtt tttttgtttg caagcagcag attacgcgca    10200
gaaaaaaagg atctcaagaa gatcctttga tcttttctac ggggtctgac    10250
gctcagtgga acgaaaactc acgttaaggg attttggtca tgagattatc    10300
aaaaaggatc ttcacctaga tccttttaaa ttaaaaatga gttttaaat    10350 caatctaaag tatatatgag taaacttggt ctgacagtta ccaatgctta    10400
atcagtgagg cacctatctc agcgatctgt ctatttcgtt catccatagt    10450
tgcctgactc cccgtcgtgt agataactac gatacgggag ggcttaccat    10500
ctggccccag tgctgcaatg ataccgcgag acccacgctc accggctcca    10550
gatttatcag caataaacca gccagccgga agggccgagc gcagaagtgg    10600
tcctgcaact ttatccgcct ccatccagtc tattaattgt tgccgggaag    10650
ctagagtaag tagttcgcca gttaatagtt tgcgcaacgt tgttgccatt    10700
gctacaggca tcgtggtgtc acgctcgtcg tttggtatgg cttcattcag    10750
ctccggttcc caacgatcaa ggcgagttac atgatccccc atgttgtgca    10800
aaaaagcggt tagctccttc ggtcctccga tcgttgtcag aagtaagttg    10850
gccgcagtgt tatcactcat ggttatggca gcactgcata attctcttac    10900
tgtcatgcca tccgtaagat gcttttctgt gactggtgag tactcaacca    10950
agtcattctg agaatagtgt atgcggcgac cgagttgctc ttgcccggcg    11000
tcaatacggg ataataccgc gccacatagc agaactttaa aagtgctcat    11050
cattggaaaa cgttcttcgg ggcgaaaact ctcaaggatc ttaccgctgt    11100
tgagatccag ttcgatgtaa cccactcgtg cacccaactg atcttcagca    11150
tcttttactt tcaccagcgt ttctgggtga gcaaaaacag gaaggcaaaa    11200
tgccgcaaaa aagggaataa gggcgacacg gaaatgttga atactcatac    11250
tcttcctttt tcaatattat tgaagcattt atcagggtta ttgtctcatg    11300
```

```
                                    -continued
agcggataca tatttgaatg tatttagaaa aataaacaaa tagggtccc     11350 gcgcacattt ccccgaaaag tgccacctga c                        11381
```

As will be noted, residues 237-616 of pLenti-IgGκ-nCoV-Spike-CD8-TM (-att) (SEQ ID NO:83) correspond to the CMV immediate early enhancer site (SEQ ID NO:1). Residues 618-816 of SEQ ID NO:83 correspond to the CMV immediate early promoter site (SEQ ID NO:3). Residues 834-1012 of SEQ ID NO:83 correspond to the alternative truncated lentiviral 5' LTR region (SEQ ID NO:68). Residues 1059-1184 of SEQ ID NO:83 correspond to the lentiviral ψ region (SEQ ID NO:6). Residues 1681-1914 of SEQ ID NO:83 correspond to the lentiviral Rev response element (RRE) (SEQ ID NO:7). Residues 2441-2558 of SEQ ID NO:83 correspond to the lentiviral cPPT/CTS region (SEQ ID NO:8). Residues 2641-3020 of SEQ ID NO:83 correspond to the variant CMV immediate early enhancer site (SEQ ID NO:2). Residues 3021-3224 of SEQ ID NO:83 correspond to the variant CMV immediate early promoter site (SEQ ID NO:4). Residues 3250-3268 of SEQ ID NO:83 correspond to a T7 promoter site (SEQ ID NO:12). Residues 3391-3852 of SEQ ID NO:83 correspond to the internal ribosome entry site of the encephalomyocarditis virus (EMCV) (SEQ ID NO:69). Residues 3887-3896 of SEQ ID NO:83 correspond to a Kozak sequence (SEQ ID NO:85). Residues 3893-3958 of SEQ ID NO:83 correspond to an IgGκ signal sequence (SEQ ID NO:81). Residues 3959-7777 of SEQ ID NO:83 correspond to a polynucleotide sequence (SEQ ID NO:71) that encodes the SARS-CoV-2 spike protein (SEQ ID NO:54). Residues 5265-5282

(gcaacaacctggacagca, SEQ ID NO: 74)

correspond to a sequence that is complementary to a polynucleotide that encodes a tetracysteine peptide (CCPGCC; SEQ ID NO:75) that binds biarsenical labeling reagents. Residues 7778-8041 of SEQ ID NO:83 correspond to a polynucleotide (SEQ ID NO:88) that encodes a CD8 transmembrane domain (SEQ ID NO:87). Residues 8060-8134 of SEQ ID NO:83 correspond to a polynucleotide sequence (SEQ ID NO:14) that encodes a combined Myc (human c-Myc oncogene) and FLAG® epitope tag (SEQ ID NO:13). Residues 8183-8216 of SEQ ID NO:83 correspond to a LoxP site (SEQ ID NO:15). Residues 8272-8860 of SEQ ID NO:83 correspond to a woodchuck hepatitis virus post-transcriptional regulatory element (WPRE) (SEQ ID NO:16). Residues 8743-8754 of SEQ ID NO:83 correspond to a Factor Xa cleavage site (SEQ ID NO:17). Residues 8863-8879 of SEQ ID NO:83 correspond to a polynucleotide whose sequence is complementary to the sequence a KS primer binding site (SEQ ID NO:18). Residues 9069-9568 correspond to a 5' LTR that has been modified to be self-inactivating (SIN) of which residues 9069-9386 correspond to a modified U3 region (SEQ ID NO:64), residues 9387-9568 correspond to Rand the U5 regions of the 5' LTR (SEQ ID NO:5). Residues 9629-10,217 of SEQ ID NO:83 correspond to a polynucleotide whose sequence is complementary to the sequence of the high-copy-number ColE1/pMB1/pBR322/pUC origin of replication (SEQ ID NO:19). Residues 10388-11248 of SEQ ID NO:83 correspond to a polynucleotide whose sequence is complementary to the sequence encoding the AmpR antibiotic resistance determinant (SEQ ID NO:22) (i.e., such encoding sequence is on the second strand of the vector). Residues 11249-11353 of SEQ ID NO:83 correspond to a polynucleotide whose sequence is complementary to the sequence of the AmpR promoter (SEQ ID NO:25) (i.e., such promoter sequence is on the second strand of the vector).

(f) pLenti-IgGκ-nCoV-N-CD8-TM (-att)

The vector pLenti-IgGκ-nCoV-N-CD8-TM (-att) (FIG. 11) further illustrates the LTR-containing vectors of the present invention. The first strand of vector has 8819 nucleotide residues and has the sequence of SEQ ID NO:84:

```
gtcgacggat cgggagatct cccgatcccc tatggtgcac tctcagtaca     50
atctgctctg atgccgcata gttaagccaa tatctgctcc ctgcttgtgt    100
gttggaggtc gctgagtagt gcgcgagcaa aatttaagct acaacaaggc    150
aaggcttgac cgacaattgc atgaagaatc tgcttagggt taggcgtttt    200
gcgctgcttc gcgatgtacg ggccagatat cgcgttgaca ttgattattg    250
actagttatt aatagtaatc aattacgggg tcattagttc atagcccata    300
tatggagttc cgcgttacat aacttacggt aaatggcccg cctggctgac    350
cgcccaacga cccccgccca ttgacgtcaa taatgacgta tgttcccata    400
gtaacgccaa tagggacttt ccattgacgt caatgggtgg agtatttacg    450
gtaaactgcc cacttggcag tacatcaagt gtatcatatg ccaagtacgc    500 ccctattga cgtcaatgac ggtaaatggc ccgcctggca ttatgcccag     550
tacatgacct tatgggactt tcctacttgg cagtacatct acgtattagt    600
catcgctatt accatggtga tgcggttttg gcagtacatc aatgggcgtg    650
gatagcggtt tgactcacgg ggatttccaa gtctccaccc cattgacgtc    700
aatgggagtt tgttttggca ccaaaatcaa cgggactttc caaaatgtcg    750
```

-continued

```
taacaactcc gccccattga cgcaaatggg cggtaggcgt gtacggtggg      800
aggtctatat aagcagcgcg ttttgcctgt actgggtctc tctggttaga      850
ccagatctga gcctgggagc tctctggcta actagggaac ccactgctta      900
agcctcaata aagcttgcct tgagtgcttc aagtagtgtg tgcccgtctg      950
ttgtgtgact ctggtaacta gagatccctc agaccttttt agtcagtgtg     1000
gaaaatctct aggtggcgcc cgaacaggga cttgaaagcg aaagggaaac     1050
cagaggagct ctctcgacgc aggactcggc ttgctgaagc gcgcacggca     1100
agaggcgagg ggcggcgact ggtgagtacg ccaaaaattt tgactagcgg     1150
aggctagaag gagagagatg ggtgcgagag cgtcagtatt aagcggggga     1200
gaattagatc gcgatgggaa aaaattcggt taaggccagg gggaagaaaa     1250
aaatataaat taaaacatat agtatgggca agcagggagc tagaacgatt     1300
cgcagttaat cctggcctgt tagaaacatc agaaggctgt agacaaatac     1350
tgggacagct acaaccatcc cttcagacag gatcagaaga acttagatca     1400
ttatataata cagtagcaac cctctattgt gtgcatcaaa ggatagagat     1450
aaaagacacc aaggaagctt tagacaagat agaggaagag caaaacaaaa     1500
gtaagaccac cgcacagcaa gcggccggcc gctgatcttc agacctggag     1550
gaggagatat gagggacaat ggagaagtg aattatataa atataaagta      1600
gtaaaaattg aaccattagg agtagcaccc accaaggcaa agagaagagt     1650
ggtgcagaga gaaaaaagag cagtgggaat aggagctttg ttccttgggt     1700
tcttgggagc agcaggaagc actatgggcg cagcgtcaat gacgctgacg     1750
gtacaggcca gacaattatt gtctggtata gtgcagcagc agaacaattt     1800
gctgagggct attgaggcgc aacagcatct gttgcaactc acagtctggg     1850
gcatcaagca gctccaggca agaatcctgg ctgtggaaag atacctaaag     1900
gatcaacagc tcctggggat ttggggttgc tctggaaaac tcatttgcac     1950
cactgctgtg ccttggaatg ctagttggag taataaatct ctggaacaga     2000
tttggaatca cacgacctgg atggagtggg acagagaaat taacaattac     2050
acaagcttaa tacactcctt aattgaagaa tcgcaaaacc agcaagaaaa     2100
gaatgaacaa gaattattgg aattagataa atgggcaagt ttgtggaatt     2150
ggtttaacat aacaaattgg ctgtggtata taaaattatt cataatgata     2200
gtaggaggct tggtaggttt aagaatagtt tttgctgtac tttctatagt     2250
gaatagagtt aggcagggat attcaccatt atcgtttcag acccacctcc     2300
caaccccgag gggacccgac aggcccgaag gaatagaaga gaaggtgga      2350 gagagagaca gagacagatc cattcgatta gtgaacggat cggcactgcg     2400
tgcgccaatt ctgcagacaa atggcagtat tcatccacaa ttttaaaaga     2450
aaagggggga ttgggggta cagtgcaggg gaaagaatag tagacataat      2500
agcaacagac atacaaacta agaattaca aaaacaaatt acaaaaattc      2550
aaaattttcg ggtttattac agggacagca gagatccagt ttggttagta     2600
ccgggcccgc tctagacatg tccaatatga ccgccatgtt gacattgatt     2650
attgactagt tattaatagt aatcaattac ggggtcatta gttcatagcc     2700
catatatgga gttccgcgtt acataactta cggtaaatgg cccgcctggc     2750
tgaccgccca acgacccccg cccattgacg tcaataatga cgtatgttcc     2800
```

```
catagtaacg ccaataggga cttcccattg acgtcaatgg gtggagtatt    2850
tacggtaaac tgcccacttg gcagtacatc aagtgtatca tatgccaagt    2900 ccgccccta ttgacgtcaa tgacggtaaa tggcccgcct ggcattatgc     2950
ccagtacatg accttacggg actttcctac ttggcagtac atctacgtat    3000
tagtcatcgc tattaccatg gtgatgcggt tttggcagta caccaatggg    3050
cgtggatagc ggtttgactc acggggattt ccaagtctcc accccattga    3100
cgtcaatggg agtttgtttt ggcaccaaaa tcaacgggac tttccaaaat    3150
gtcgtaataa ccccgccccg ttgacgcaaa tgggcggtag gcgtgtacgg    3200
tgggaggtct atataagcag agctcgttta gtgaaccgtc agaattttgt    3250
aatacgactc actatagggc ggccgggaat tcgtcgactg ccccccccc    3300 taacgttact ggccgaagcc gcttggaata aggccggtgt gcgtttgtct    3350
atatgttatt ttccaccata ttgccgtctt ttggcaatgt gagggcccgg    3400
aaacctggcc ctgtcttctt gacgagcatt cctagggggt tttcccctct    3450
cgccaaagga atgcaaggtc tgttgaatgt cgtgaaggaa gcagttcctc    3500
tggaagcttc ttgaagacaa acaacgtctg tagcgaccct ttgcaggcag    3550
cggaaccccc cacctggcga caggtgcctc tgcggccaaa agccacgtgt    3600
ataagataca cctgcaaagg cggcacaacc ccagtgccac gttgtgagtt    3650
ggatagttgt ggaaagagtc aaatggctct cctcaagcgt attcaacaag    3700
gggctgaagg atgcccagaa ggtacccat tgtatgggat ctgatctggg     3750
gcctcggtgc acatgcttta catgtgttta gtcgaggtta aaaaacgtct    3800 aggcccccg aaccacgggg acgtggtttt cctttgaaaa acacgatgat     3850
aatgatccgg taccgaggag atctgccgcc gcgatcgcca ccatggacat    3900
gagggtccct gctcagctcc tggggctcct gctgctctgg ctctcaggtg    3950
ccagatgtat gtctgataat ggaccccaaa atcagcgaaa tgcaccccgc    4000
attacgtttg gtggaccctc agattcaact ggcagtaacc agaatggaga    4050
acgcagtggg gcgcgatcaa acaacgtcg gccccaaggt ttacccaata     4100
atactgcgtc ttggttcacc gctctcactc aacatggcaa ggaagacctt    4150
aaattccctc gaggacaagg cgttccaatt aacaccaata gcagtccaga    4200
tgaccaaatt ggctactacc gaagagctac cagacgaatt cgtggtggtg    4250
acggtaaaat gaaagatctc agtccaagat ggtatttcta ctacctagga    4300
actgggccag aagctggact tccctatggt gctaacaaag acggcatcat    4350
atgggttgca actgagggag ccttgaatac accaaaagat cacattggca    4400
cccgcaatcc tgctaacaat gctgcaatcg tgctacaact tcctcaagga    4450
acaacattgc caaaggctt ctacgcagaa gggagcagag gcggcagtca     4500
agcctcttct cgttcctcat cacgtagtcg caacagttca agaaattcaa    4550
ctccaggcag cagtagggga acttctcctg ctagaatggc tggcaatggc    4600
ggtgatgctg ctcttgcttt gctgctgctt gacagattga accagcttga    4650
gagcaaaatg tctggtaaag gccaacaaca acaaggccaa actgtcacta    4700
agaaatctgc tgctgaggct tctaagaagc ctcggcaaaa acgtactgcc    4750
actaaagcat acaatgtaac acaagctttc ggcagacgtg gtccagaaca    4800
aacccaagga aattttgggg accaggaact aatcagacaa ggaactgatt    4850
```

```
acaaacattg gccgcaaatt gcacaatttg cccccagcgc ttcagcgttc    4900
ttcggaatgt cgcgcattgg catggaagtc acaccttcgg gaacgtggtt    4950
gacctacaca ggtgccatca aattggatga caaagatcca aatttcaaag    5000
atcaagtcat tttgctgaat aagcatattg acgcatacaa acattccca    5050 ccaacagagc ctaaaaagga caaaaagaag aaggctgatg aaactcaagc    5100
cttaccgcag agacagaaga aacagcaaac tgtgactctt cttcctgctg    5150
cagatttgga tgatttctcc aaacaattgc aacaatccat gagcagtgct    5200
gactcaactc aggccgccct gagcaactcc atcatgtact tcagccactt    5250
cgtgccggtc ttcctgccag cgaagcccac cacgacgcca gcgccgcgac    5300
caccaacacc ggcgcccacc atcgcgtcgc agccctgtc cctgcgccca    5350 gaggcgtgcc ggccagcggc gggggcgca gtgcacacga gggggctgga    5400
cttcgcctgt gatatctaca tctgggcgcc cttggccggg acttgtgggg    5450
tccttctcct gtcactggtt atcacctgaa cgcgtacgcg gccgctcgag    5500
cagaaactca tctcagaaga ggatctggca gcaaatgata tcctggatta    5550
caaggatgac gacgataagg tttaaacggc cggccgcggt ctgtacaagt    5600
aggattcgtc gagggaccta ataacttcgt atagcataca ttatacgaag    5650
ttatacatgt ttaagggttc cggttccact aggtacaatt cgatatcaag    5700
cttatcgata atcaacctct ggattacaaa atttgtgaaa gattgactgg    5750
tattcttaac tatgttgctc cttttacgct atgtggatac gctgctttaa    5800
tgcctttgta tcatgctatt gcttcccgta tggctttcat tttctcctcc    5850
ttgtataaat cctggttgct gtctctttat gaggagttgt ggcccgttgt    5900
caggcaacgt ggcgtggtgt gcactgtgtt tgctgacgca acccccactg    5950 gttgggcat tgccaccacc tgtcagctcc tttccgggac tttcgctttc    6000
cccctcccta ttgccacggc ggaactcatc gccgcctgcc ttgcccgctg    6050
ctggacaggg gctcggctgt tgggcactga caattccgtg gtgttgtcgg    6100
ggaaatcatc gtccttttcct tggctgctcg cctgtgttgc cacctggatt    6150
ctgcgcggga cgtccttctg ctacgtccct tcggccctca atccagcgga    6200
ccttccttcc cgcggcctgc tgccggctct gcggcctctt ccgcgtcttc    6250
gccttcgccc tcagacgagt cggatctccc tttgggccgc ctccccgcat    6300
cgataccgtc gacctcgatc gagacctaga aaaacatgga gcaatcacaa    6350
gtagcaatac agcagctacc aatgctgatt gtgcctggct agaagcacaa    6400
gaggaggagg aggtgggttt tccagtcaca cctcaggtac ctttaagacc    6450
aatgacttac aaggcagctg tagatcttag ccactttta aaagaaaagg    6500 ggggacgaag ggctaattca ctcccaacga agacaagatc tgcttgatct    6550
gtggatctac cacacacaag gctacttccc tgattggcag aactacacac    6600
cagggccagg gatcagatat ccactgacct ttggatggtg ctacaagcta    6650
gtaccagttg agcaagagaa ggtagaagaa gccaatgaag gagagaacac    6700
ccgcttgtta caccctgtga gcctgcatgg gatggatgac ccggagagag    6750
aagtattaga gtggaggttt gacagccgcc tagcatttca tcacatggcc    6800
cgagagctgc atccggactg tactgggtct ctctggttag accagatctg    6850
agcctgggag ctctctggct aactagggaa cccactgctt aagcctcaat    6900
```

```
aaagcttgcc ttgagtgctt caagtagtgt gtgcccgtct gttgtgtgac      6950
tctggtaact agagatccct cagacccttt tagtcagtgt ggaaaatctc      7000
tagcagcatg tgagcaaaag gccagcaaaa ggccaggaac cgtaaaaagg      7050
ccgcgttgct ggcgttttc cataggctcc gcccccctga cgagcatcac       7100
aaaaatcgac gctcaagtca gaggtggcga acccgacag gactataaag       7150 ataccaggcg tttccccctg gaagctccct cgtgcgctct cctgttccga      7200
ccctgccgct taccggatac ctgtccgcct ttctcccttc gggaagcgtg      7250
gcgctttctc atagctcacg ctgtaggtat ctcagttcgg tgtaggtcgt      7300
tcgctccaag ctgggctgtg tgcacgaacc ccccgttcag cccgaccgct      7350
gcgccttatc cggtaactat cgtcttgagt ccaacccggt aagacacgac      7400
ttatcgccac tggcagcagc cactggtaac aggattagca gagcgaggta      7450
tgtaggcggt gctacagagt tcttgaagtg gtggcctaac tacggctaca      7500
ctagaagaac agtatttggt atctgcgctc tgctgaagcc agttaccttc      7550
ggaaaaagag ttggtagctc ttgatccggc aaacaaacca ccgctggtag      7600
cggtggtttt tttgtttgca agcagcagat tacgcgcaga aaaaaggat       7650 ctcaagaaga tcctttgatc ttttctacgg ggtctgacgc tcagtggaac      7700
gaaaactcac gttaagggat tttggtcatg agattatcaa aaaggatctt      7750
cacctagatc cttttaaatt aaaaatgaag ttttaaatca atctaaagta      7800
tatatgagta aacttggtct gacagttacc aatgcttaat cagtgaggca      7850
cctatctcag cgatctgtct atttcgttca tccatagttg cctgactccc      7900
cgtcgtgtag ataactacga tacgggaggg cttaccatct ggccccagtg      7950
ctgcaatgat accgcgagac ccacgctcac cggctccaga tttatcagca      8000
ataaaccagc cagccggaag ggccgagcgc agaagtggtc ctgcaacttt      8050
atccgcctcc atccagtcta ttaattgttg ccgggaagct agagtaagta      8100
gttcgccagt taatagtttg cgcaacgttg ttgccattgc tacaggcatc      8150
gtggtgtcac gctcgtcgtt tggtatggct tcattcagct ccggttccca      8200
acgatcaagg cgagttacat gatccccat gttgtgcaaa aaagcggtta       8250
gctccttcgg tcctccgatc gttgtcagaa gtaagttggc cgcagtgtta      8300
tcactcatgg ttatggcagc actgcataat tctcttactg tcatgccatc      8350
cgtaagatgc ttttctgtga ctggtgagta ctcaaccaag tcattctgag      8400
aatagtgtat gcggcgaccg agttgctctt gcccggcgtc aatacgggat      8450
aataccgcgc cacatagcag aactttaaaa gtgctcatca ttggaaaacg      8500
ttcttcgggg cgaaaactct caaggatctt accgctgttg agatccagtt      8550
cgatgtaacc cactcgtgca cccaactgat cttcagcatc ttttactttc      8600
accagcgttt ctgggtgagc aaaaacagga aggcaaaatg ccgcaaaaaa      8650
gggaataagg gcgacacgga aatgttgaat actcatactc ttcctttttc      8700
aatattattg aagcatttat cagggttatt gtctcatgag cggatacata      8750
tttgaatgta tttagaaaaa taaacaaata ggggtcccgc gcacatttcc      8800
ccgaaaagtg ccacctgac                                        8819
```

As will be noted, residues 237-616 of pLenti-IgGκ-nCoV-N-CD8-TM (-att) (SEQ ID NO:84) correspond to the CMV immediate early enhancer site (SEQ ID NO:1). Residues 618-816 of SEQ ID NO:84 correspond to the CMV immediate early promoter site (SEQ ID NO:3). Residues 834-1012 of SEQ ID NO:84 correspond to the truncated lentiviral 5' LTR region (SEQ ID NO:68). Residues 1059-1184 of SEQ ID NO:84 correspond to the lentiviral ψ region (SEQ ID NO:6). Residues 1681-1914 of SEQ ID NO:84 correspond to the lentiviral Rev response element (RRE) (SEQ ID NO:7). Residues 2441-2558 of SEQ ID NO:84 correspond to the lentiviral cPPT/CTS region (SEQ ID NO:8). Residues 2641-3020 of SEQ ID NO:84 correspond to the variant CMV immediate early enhancer site (SEQ ID NO:2). Residues 3021-3224 of SEQ ID NO:84 correspond to the variant CMV immediate early promoter site (SEQ ID NO:4). Residues 3250-3268 of SEQ ID NO:84 correspond to a T7 promoter site (SEQ ID NO:12). Residues 3391-3852 of SEQ ID NO:84 correspond to the internal ribosome entry site of the encephalomyocarditis virus (EMCV) (SEQ ID NO:69). Residues 3887-3896 of SEQ ID NO:84 correspond to a Kozak sequence (SEQ ID NO:85). Residues 3899-3958 of SEQ ID NO:84 correspond to an IgGκ signal sequence (SEQ ID NO:81). Residues 3959-5215 of SEQ ID NO:84 correspond to a polynucleotide sequence (SEQ ID NO:79) that encodes the SARS-CoV-2 N protein (SEQ ID NO:54). Residues 5216-5479 of SEQ ID NO:84 correspond to a polynucleotide (SEQ ID NO:88) that encodes a CD8 transmembrane domain (SEQ ID NO:87). Residues 5498-5572 of SEQ ID NO:84 correspond to a polynucleotide sequence (SEQ ID NO:14) that encodes a combined Myc (human c-Myc oncogene) and FLAG® epitope tag (SEQ ID NO:13). Residues 5621-5624 of SEQ ID NO:84 correspond to a LoxP site (SEQ ID NO:15). Residues 5710-6298 of SEQ ID NO:84 correspond to a woodchuck hepatitis virus post-transcriptional regulatory element (WPRE) (SEQ ID NO:16). Residues 6181-6192 of SEQ ID NO:84 correspond to a Factor Xa cleavage site (SEQ ID NO:17). Residues 6301-6317 of SEQ ID NO:84 correspond to a polynucleotide whose sequence is complementary to the sequence a KS primer binding site (SEQ ID NO:18). Residues 6507-7005 correspond to a 5' LTR that has been modified to be self-inactivating (SIN) of which residues 6507-6824 correspond to a modified U3 region (SEQ ID NO:64), residues 6825-7005 correspond to R and the U5 regions of the 5' LTR (SEQ ID NO:5). Residues 7067-7655 of SEQ ID NO:84 correspond to a polynucleotide whose sequence is complementary to the sequence of the high-copy-number ColE1/pMB1/pBR322/pUC origin of replication (SEQ ID NO:19). Residues 7826-9696 of SEQ ID NO:84 correspond to a polynucleotide whose sequence is complementary to the sequence encoding the AmpR antibiotic resistance determinant (SEQ ID NO:22) (i.e., such encoding sequence is on the second strand of the vector). Residues 8687-8791 of SEQ ID NO:84 correspond to a polynucleotide whose sequence is complementary to the sequence of the AmpR promoter (SEQ ID NO:25) (i.e., such promoter sequence is on the second strand of the vector).

(g) pLenti-IL2-nCoV-N(-att)

The vector pLenti-IL2-nCoV-N(-att) (FIG. 12) further illustrates the LTR-containing vectors of the present invention. The first strand of vector pLenti-IL2-nCoV-N(-att) has 8552 nucleotide residues and has the sequence of SEQ ID NO:85:

```
gtcgacggat cgggagatct cccgatcccc tatggtgcac tctcagtaca      50
atctgctctg atgccgcata gttaagccaa tatctgctcc ctgcttgtgt     100
gttggaggtc gctgagtagt gcgcgagcaa aatttaagct acaacaaggc     150
aaggcttgac cgacaattgc atgaagaatc tgcttagggt taggcgtttt     200
gcgctgcttc gcgatgtacg ggccagatat cgcgttgaca ttgattattg     250
actagttatt aatagtaatc aattacgggg tcattagttc atagcccata     300
tatggagttc cgcgttacat aacttacggt aaatggcccg cctggctgac     350
cgcccaacga ccccgccca  ttgacgtcaa taatgacgta tgttcccata     400
gtaacgccaa tagggacttt ccattgacgt caatgggtgg agtatttacg     450
gtaaactgcc cacttggcag tacatcaagt gtatcatatg ccaagtacgc     500
cccctattga cgtcaatgac ggtaaatggc ccgcctggca ttatgcccag     550
tacatgacct tatgggactt tcctacttgg cagtacatct acgtattagt     600
catcgctatt accatggtga tgcggttttg gcagtacatc aatgggcgtg     650
gatagcggtt tgactcacgg ggatttccaa gtctccaccc cattgacgtc     700
aatgggagtt tgttttggca ccaaaatcaa cgggactttc caaaatgtcg     750
taacaactcc gccccattga cgcaaatggg cggtaggcgt gtacggtggg     800
aggtctatat aagcagcgcg ttttgcctgt actgggtctc tctggttaga     850
ccagatctga gcctgggagc tctctggcta actagggaac ccactgctta     900
agcctcaata aagcttgcct tgagtgcttc aagtagtgtg tgcccgtctg     950
ttgtgtgact ctggtaacta gagatccctc agacccttt agtcagtgtg    1000
```

```
gaaaatctct aggtggcgcc cgaacaggga cttgaaagcg aaagggaaac    1050
cagaggagct ctctcgacgc aggactcggc ttgctgaagc gcgcacggca    1100
agaggcgagg ggcggcgact ggtgagtacg ccaaaaattt tgactagcgg    1150
aggctagaag gagagagatg ggtgcgagag cgtcagtatt aagcggggga    1200
gaattagatc gcgatgggaa aaaattcggt taaggccagg gggaaagaaa    1250
aaatataaat taaaacatat agtatgggca agcagggagc tagaacgatt    1300
cgcagttaat cctggcctgt tagaaacatc agaaggctgt agacaaatac    1350
tgggacagct acaaccatcc cttcagacag gatcagaaga acttagatca    1400
ttatataata cagtagcaac cctctattgt gtgcatcaaa ggatagagat    1450
aaaagacacc aaggaagctt tagacaagat agaggaagag caaaacaaaa    1500
gtaagaccac cgcacagcaa gcggccggcc gctgatcttc agacctggag    1550
gaggagatat gagggacaat tggagaagtg aattatataa atataaagta    1600
gtaaaaattg aaccattagg agtagcaccc accaaggcaa agaagagt     1650 ggtgcagaga gaaaaaagag cagtgggaat aggagctttg ttccttgggt    1700
tcttgggagc agcaggaagc actatgggcg cagcgtcaat gacgctgacg    1750
gtacaggcca gacaattatt gtctggtata gtgcagcagc agaacaattt    1800
gctgagggct attgaggcgc aacagcatct gttgcaactc acagtctggg    1850
gcatcaagca gctccaggca gaatcctgg ctgtggaaag atacctaaag    1900
gatcaacagc tcctggggat ttggggttgc tctggaaaac tcatttgcac    1950
cactgctgtg ccttggaatg ctagttggag taataaatct ctggaacaga    2000
tttggaatca cacgacctgg atggagtggg acagagaaat taacaattac    2050
acaagcttaa tacactcctt aattgaagaa tcgcaaaacc agcaagaaaa    2100
gaatgaacaa gaattattgg aattagataa atgggcaagt ttgtggaatt    2150
ggtttaacat aacaaattgg ctgtggtata taaaattatt cataatgata    2200
gtaggaggct tggtaggttt aagaatagtt tttgctgtac tttctatagt    2250
gaatagagtt aggcagggat attcaccatt atcgtttcag acccacctcc    2300
caaccccgag gggacccgac aggcccgaag gaatagaaga agaaggtgga    2350
gagagagaca gagacagatc cattcgatta gtgaacggat cggcactgcg    2400
tgcgccaatt ctgcagacaa atggcagtat tcatccacaa ttttaaaaga    2450
aaagggggga ttggggggta cagtgcaggg gaaagaatag tagacataat    2500
agcaacagac atacaaacta aagaattaca aaaacaaatt acaaaaattc    2550
aaaattttcg ggtttattac agggacagca gagatccagt ttggttagta    2600
ccgggcccgc tctagacatg tccaatatga ccgccatgtt gacattgatt    2650
attgactagt tattaatagt aatcaattac ggggtcatta gttcatagcc    2700
catatatgga gttccgcgtt acataactta cggtaaatgg cccgcctggc    2750
tgaccgccca acgacccccg cccattgacg tcaataatga cgtatgttcc    2800
catagtaacg ccaatagggA cttttccattg acgtcaatgg gtggagtatt    2850
tacggtaaac tgcccacttg gcagtacatc aagtgtatca tatgccaagt    2900
ccgcccccta ttgacgtcaa tgacggtaaa tggcccgcct ggcattatgc    2950
ccagtacatg accttacggg actttcctac ttggcagtac atctacgtat    3000
tagtcatcgc tattaccatg gtgatgcggt tttggcagta caccaatggg    3050
```

```
cgtggatagc ggtttgactc acggggattt ccaagtctcc accccattga    3100
cgtcaatggg agtttgtttt ggcaccaaaa tcaacgggac tttccaaaat    3150
gtcgtaataa ccccgccccg ttgacgcaaa tgggcggtag gcgtgtacgg    3200
tgggaggtct atataagcag agctcgttta gtgaaccgtc agaattttgt    3250
aatacgactc actatagggc ggccgggaat tcgtcgactg ccccccccc    3300 taacgttact ggccgaagcc gcttggaata aggccggtgt gcgtttgtct    3350
atatgttatt ttccaccata ttgccgtctt ttggcaatgt gagggcccgg    3400
aaacctggcc ctgtcttctt gacgagcatt cctaggggtc tttcccctct    3450
cgccaaagga atgcaaggtc tgttgaatgt cgtgaaggaa gcagttcctc    3500
tggaagcttc ttgaagacaa acaacgtctg tagcgaccct ttgcaggcag    3550
cggaaccccc cacctggcga caggtgcctc tgcggccaaa agccacgtgt    3600
ataagataca cctgcaaagg cggcacaacc ccagtgccac gttgtgagtt    3650
ggatagttgt ggaaagagtc aaatggctct cctcaagcgt attcaacaag    3700
gggctgaagg atgcccagaa ggtaccccat tgtatgggat ctgatctggg    3750
gcctcggtgc acatgcttta catgtgttta gtcgaggtta aaaaacgtct    3800 aggcccccg aaccacgggg acgtggtttt cctttgaaaa acacgatgat    3850
aatgatccgg taccgaggag atctgccgcc gcgatcgcca ccatgtacag    3900
gatgcaactc ctgtcttgca ttgcactaag tcttgcactt gtcacaaaca    3950
gtatgtctga taatggaccc caaaatcagc gaaatgcacc ccgcattacg    4000
tttggtggac cctcagattc aactggcagt aaccagaatg gagaacgcag    4050
tggggcgcga tcaaaacaac gtcggcccca aggtttaccc aataatactg    4100
cgtcttggtt caccgctctc actcaacatg gcaaggaaga ccttaaattc    4150
cctcgaggac aaggcgttcc aattaacacc aatagcagtc cagatgacca    4200
aattggctac taccgaagag ctaccagacg aattcgtggt ggtgacggta    4250
aaatgaaaga tctcagtcca agatggtatt tctactacct aggaactggg    4300
ccagaagctg gacttcccta tggtgctaac aaagacggca tcatatgggt    4350
tgcaactgag ggagccttga atacaccaaa agatcacatt ggcacccgca    4400
atcctgctaa caatgctgca atcgtgctac aacttcctca aggaacaaca    4450
ttgccaaaag gcttctacgc agaagggagc agaggcggca gtcaagcctc    4500
ttctcgttcc tcatcacgta gtcgcaacag ttcaagaaat tcaactccag    4550
gcagcagtag gggaacttct cctgctagaa tggctggcaa tggcggtgat    4600
gctgctcttg ctttgctgct gcttgacaga ttgaaccagc ttgagagcaa    4650
aatgtctggt aaaggccaac aacaacaagg ccaaactgtc actaagaaat    4700
ctgctgctga ggcttctaag aagcctcggc aaaaacgtac tgccactaaa    4750
gcatacaatg taacacaagc tttcggcaga cgtggtccag aacaaaccca    4800
aggaaatttt ggggaccagg aactaatcag acaaggaact gattacaaac    4850
attggccgca aattgcacaa tttgccccca gcgcttcagc gttcttcgga    4900
atgtcgcgca ttggcatgga agtcacacct tcgggaacgt ggttgaccta    4950
cacaggtgcc atcaaattgg atgacaaaga tccaaatttc aaagatcaag    5000
tcattttgct gaataagcat attgacgcat acaaaacatt cccaccaaca    5050
gagcctaaaa aggacaaaaa gaagaaggct gatgaaactc aagccttacc    5100
```

```
gcagagacag aagaaacagc aaactgtgac tcttcttcct gctgcagatt    5150
tggatgattt ctccaaacaa ttgcaacaat ccatgagcag tgctgactca    5200
actcaggcct aaacgcgtac gcggccgctc gagcagaaac tcatctcaga    5250
agaggatctg gcagcaaatg atatcctgga ttacaaggat gacgacgata    5300
aggtttaaac ggccggccgc ggtctgtaca agtaggattc gtcgagggac    5350
ctaataactt cgtatagcat acattatacg aagttataca tgtttaaggg    5400
ttccggttcc actaggtaca attcgatatc aagcttatcg ataatcaacc    5450
tctggattac aaaatttgtg aaagattgac tggtattctt aactatgttg    5500
ctccttttac gctatgtgga tacgctgctt taatgccttt gtatcatgct    5550
attgcttccc gtatggcttt cattttctcc tccttgtata atcctggtt    5600 gctgtctctt tatgaggagt tgtggcccgt tgtcaggcaa cgtggcgtgg    5650
tgtgcactgt gtttgctgac gcaaccccca ctggttgggg cattgccacc    5700
acctgtcagc tcctttccgg gactttcgct ttccccctcc ctattgccac    5750
ggcggaactc atcgccgcct gccttgcccg ctgctggaca ggggctcggc    5800
tgttgggcac tgacaattcc gtggtgttgt cggggaaatc atcgtccttt    5850
ccttggctgc tcgcctgtgt tgccacctgg attctgcgcg gacgtcctt    5900 ctgctacgtc ccttcggccc tcaatccagc ggaccttcct tcccgcggcc    5950
tgctgccggc tctgcggcct cttccgcgtc ttcgccttcg ccctcagacg    6000
agtcggatct ccctttgggc cgcctccccg catcgatacc gtcgacctcg    6050
atcgagacct agaaaaacat ggagcaatca caagtagcaa tacagcagct    6100
accaatgctg attgtgcctg gctagaagca caagaggagg aggaggtggg    6150 tttttccagtc acacctcagg tacctttaag accaatgact tacaaggcag    6200
ctgtagatct tagccacttt ttaaaagaaa aggggggacg aagggctaat    6250
tcactcccaa cgaagacaag atctgcttga tctgtggatc taccacacac    6300
aaggctactt ccctgattgg cagaactaca caccagggcc agggatcaga    6350
tatccactga ccttggatg gtgctacaag ctagtaccag ttgagcaaga    6400
gaaggtagaa gaagccaatg aaggagagaa cacccgcttg ttacaccctg    6450
tgagcctgca tgggatggat gacccggaga gagaagtatt agagtggagg    6500
tttgacagcc gcctagcatt tcatcacatg gcccgagagc tgcatccgga    6550
ctgtactggg tctctctggt tagaccagat ctgagcctgg gagctctctg    6600
gctaactagg gaacccactg cttaagcctc aataaagctt gccttgagtg    6650
cttcaagtag tgtgtgcccg tctgttgtgt gactctggta actagagatc    6700
cctcagaccc ttttagtcag tgtggaaaat ctctagcagc atgtgagcaa    6750
aaggccagca aaaggccagg aaccgtaaaa aggccgcgtt gctggcgttt    6800
ttccataggc tccgcccccc tgacgagcat cacaaaaatc gacgctcaag    6850
tcagaggtgg cgaaacccga caggactata agataccag gcgtttcccc    6900 ctggaagctc cctcgtgcgc tctcctgttc cgaccctgcc gcttaccgga    6950
tacctgtccg cctttctccc ttcgggaagc gtggcgcttt ctcatagctc    7000
acgctgtagg tatctcagtt cggtgtaggt cgttcgctcc aagctgggct    7050
gtgtgcacga accccccgtt cagcccgacc gctgcgcctt atccggtaac    7100
tatcgtcttg agtccaaccc ggtaagacac gacttatcgc cactggcagc    7150
```

```
agccactggt aacaggatta gcagagcgag gtatgtaggc ggtgctacag    7200
agttcttgaa gtggtggcct aactacggct acactagaag aacagtattt    7250
ggtatctgcg ctctgctgaa gccagttacc ttcggaaaaa gagttggtag    7300
ctcttgatcc ggcaaacaaa ccaccgctgg tagcggtggt ttttttgttt    7350
gcaagcagca gattacgcgc agaaaaaaag gatctcaaga agatcctttg    7400
atcttttcta cggggtctga cgctcagtgg aacgaaaact cacgttaagg    7450
gattttggtc atgagattat caaaaaggat cttcacctag atcctttta    7500 attaaaaatg aagttttaaa tcaatctaaa gtatatatga gtaaacttgg    7550
tctgacagtt accaatgctt aatcagtgag gcacctatct cagcgatctg    7600
tctatttcgt tcatccatag ttgcctgact ccccgtcgtg tagataacta    7650
cgatacggga gggcttacca tctggcccca gtgctgcaat gataccgcga    7700
gacccacgct caccggctcc agatttatca gcaataaacc agccagccgg    7750
aagggccgag cgcagaagtg gtcctgcaac tttatccgcc tccatccagt    7800
ctattaattg ttgccgggaa gctagagtaa gtagttcgcc agttaatagt    7850
ttgcgcaacg ttgttgccat tgctacaggc atcgtggtgt cacgctcgtc    7900
gtttggtatg gcttcattca gctccggttc ccaacgatca aggcgagtta    7950
catgatcccc catgttgtgc aaaaaagcgg ttagctcctt cggtcctccg    8000
atcgttgtca gaagtaagtt ggccgcagtg ttatcactca tggttatggc    8050
agcactgcat aattctctta ctgtcatgcc atccgtaaga tgcttttctg    8100
tgactggtga gtactcaacc aagtcattct gagaatagtg tatgcggcga    8150
ccgagttgct cttgcccggc gtcaatacgg gataataccg cgccacatag    8200
cagaacttta aaagtgctca tcattggaaa acgttcttcg gggcgaaaac    8250
tctcaaggat cttaccgctg ttgagatcca gttcgatgta acccactcgt    8300
gcacccaact gatcttcagc atcttttact ttcaccagcg tttctgggtg    8350
agcaaaaaca ggaaggcaaa atgccgcaaa aaagggaata agggcgacac    8400
ggaaatgttg aatactcata ctcttccttt ttcaatatta ttgaagcatt    8450
tatcagggtt attgtctcat gagcggatac atatttgaat gtatttagaa    8500
aaataaacaa atagggtcc cgcgcacatt tccccgaaaa gtgccacctg    8550
ac                                                       8552
```

As will be noted, residues 237-616 of pLenti-IL2-nCoV-N(-att) (SEQ ID NO:85) correspond to the CMV immediate early enhancer site (SEQ ID NO:1). Residues 618-816 of SEQ ID NO:85 correspond to the CMV immediate early promoter site (SEQ ID NO:3). Residues 834-1012 of SEQ ID NO:85 correspond to the truncated lentiviral 5' LTR region (SEQ ID NO:68). Residues 1059-1184 of SEQ ID NO:85 correspond to the lentiviral ψ region (SEQ ID NO:6). Residues 1681-1914 of SEQ ID NO:85 correspond to the lentiviral Rev response element (RRE) (SEQ ID NO:7). Residues 2441-2558 of SEQ ID NO:85 correspond to the lentiviral cPPT/CTS region (SEQ ID NO:8). Residues 2641-3020 of SEQ ID NO:85 correspond to the variant CMV immediate early enhancer site (SEQ ID NO:2). Residues 3021-3224 of SEQ ID NO:85 correspond to the variant CMV immediate early promoter site (SEQ ID NO:4). Residues 3250-3268 of SEQ ID NO:85 correspond to a T7 promoter site (SEQ ID NO:12). Residues 3391-3852 of SEQ ID NO:85 correspond to the internal ribosome entry site of the encephalomyocarditis virus (EMCV) (SEQ ID NO:69). Residues 3893-3952 of SEQ ID NO:85 correspond to a polynucleotide (SEQ ID NO:73) that encodes an IL-2 signal sequence (SEQ ID NO:72). Residues 3953-5209 of SEQ ID NO:85 correspond to a polynucleotide sequence (SEQ ID NO:79) that encodes the SARS-CoV-2 N protein (SEQ ID NO:54). Residues 5231-5302 of SEQ ID NO:85 correspond to a polynucleotide sequence (SEQ ID NO:14) that encodes a combined Myc (human c-Myc oncogene) and FLAG® epitope tag (SEQ ID NO:13). Residues 5354-5387 of SEQ ID NO:85 correspond to a LoxP site (SEQ ID NO:15). Residues 5443-6031 of SEQ ID NO:85 correspond to a woodchuck hepatitis virus post-transcriptional regulatory element (WPRE) (SEQ ID NO:16). Residues 5914-5925 of SEQ ID NO:85 correspond to a Factor Xa cleavage site (SEQ ID NO:17).

Residues 6034-6050 of SEQ ID NO:85 correspond to a polynucleotide whose sequence is complementary to the sequence a KS primer binding site (SEQ ID NO:18). Residues 6240-6738 correspond to a 5' LTR that has been modified to be self-inactivating (SIN) of which residues 6240-6557 correspond to a modified U3 region (SEQ ID NO:64), residues 6558-6738 correspond to R and the U5 regions of the 5' LTR (SEQ ID NO:5). Residues 6800-7388 of SEQ ID NO:85 correspond to a polynucleotide whose sequence is complementary to the sequence of the high-copy-number ColE1/pMB1/pBR322/pUC origin of replication (SEQ ID NO:19). Residues 7559-8419 of SEQ ID NO:85 correspond to a polynucleotide whose sequence is complementary to the sequence encoding the AmpR antibiotic resistance determinant (SEQ ID NO:22) (i.e., such encoding sequence is on the second strand of the vector). Residues 8420-8524 of SEQ ID NO:85 correspond to a polynucleotide whose sequence is complementary to the sequence of the AmpR promoter (SEQ ID NO:25) (i.e., such promoter sequence is on the second strand of the vector).

B. Packaging Vectors of the Present Invention

As used herein, the term "packaging vector" is intended to denote a vector that comprises a polynucleotide that encodes a gag protein, a polynucleotide that encodes a pol protein, a Rev response element (RRE), and a promoter sufficient to mediate the transcription of such genes in a mammalian cell.

Figure 13:
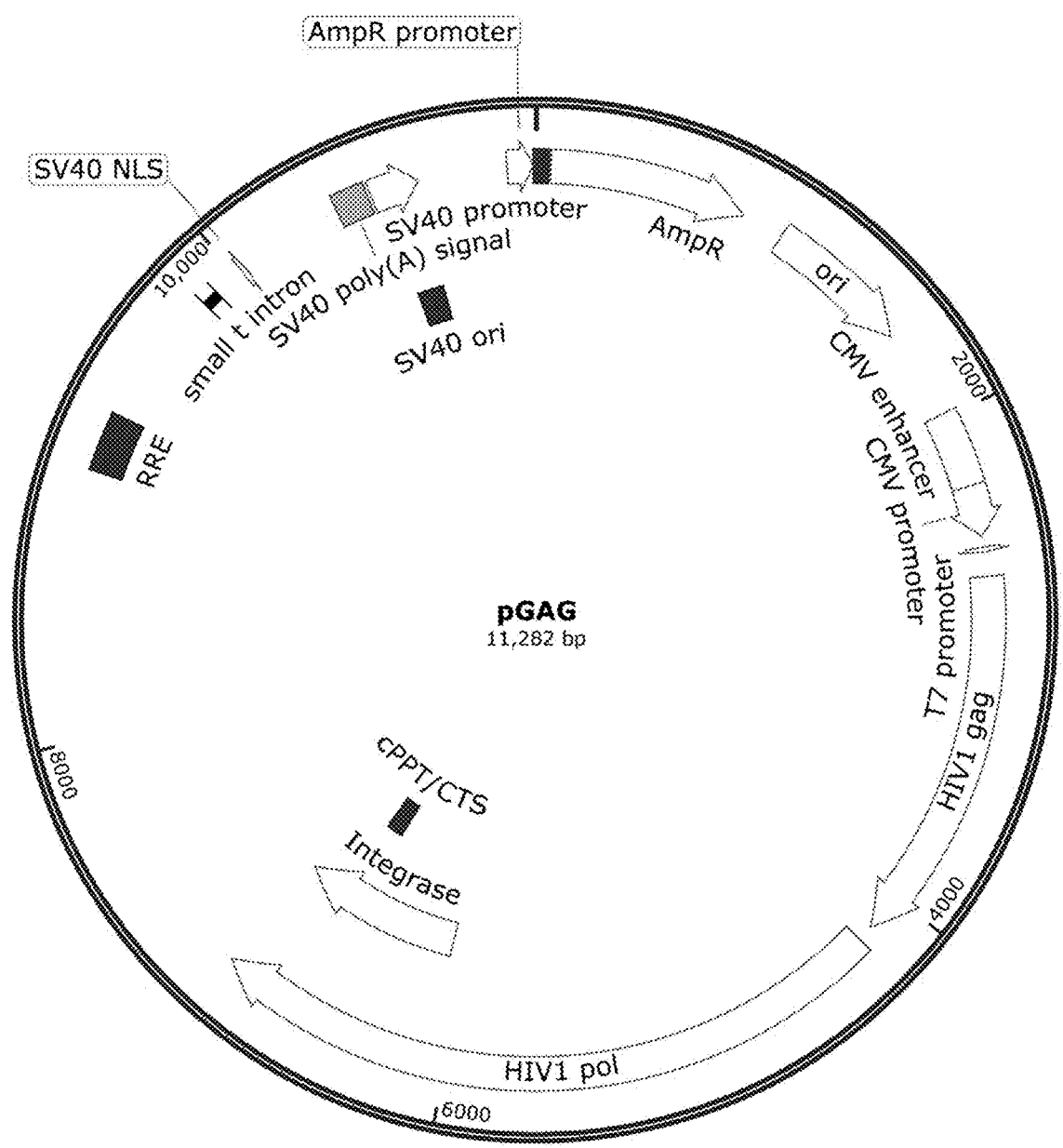
FIG. 13 provides the structure of pGAG (SEQ ID NO:44) (11282 nucleotide residues), which is an example of a packaging vector of the present invention.

Most preferably, the packaging vector of the present invention will be a double-stranded DNA plasmid. The structure of a preferred packaging vector (pGAG) is shown in FIG. 13, and comprises 11,282 base pairs. The preferred packaging vectors of the present invention comprise multiple features.

A first preferred feature of the packaging vectors of the present invention is an origin of replication capable of mediating the replication of the vector in prokaryotic cells, such as the high-copy-number ColE1/pMB1/pBR322/pUC origin of replication. Illustrative polynucleotides that comprise such an origin of replication are described above (e.g., SEQ ID NO:19, SEQ ID NO:20).

A further preferred feature of the packaging vectors of the present invention is a promoter (and an optional upstream transcriptional enhancer site) that will facilitate and mediate transcription in a mammalian host cell. Exemplary polynucleotides that comprise such an upstream transcriptional enhancer site include SEQ ID NO:1, SEQ ID NO:2, and their above-described truncated variants, such as the truncated variants SEQ ID NO:29 and SEQ ID NO:30:

```
                                                     SEQ ID NO: 29:
cgttacataa cttacggtaa atggcccgcc tggctgaccg cccaacgacc cccgcccatt gacgtcaata atgacgtatg ttcccatagt aacgccaata gggactttcc attgacgtca atgggtggag tatttacggt aaactgccca cttggcagta catcaagtgt atcatatgcc aagtacgccc cctattgacg tcaatgacgg taaatggccc gcctggcatt atgcccagta catgacctta tgggactttc ctacttggca gtacatctac gtattagtca tcgctattac catg
                                                     SEQ ID NO: 30:
cgttacataa cttacggtaa atggcccgcc tggctgaccg cccaacgacc cccgcccatt gacgtcaata atgacgtatg ttcccatagt aacgccaata gggactttcc attgacgtca atgggtggag tatttacggt aaactgccca cttggcagta catcaagtgt atcatatgcc aagtccgccc cctattgacg tcaatgacgg taaatggccc gcctggcatt atgcccagta catgacctta cgggactttc ctacttggca gtacatctac gtattagtca tcgctattac catg
```

Illustrative polynucleotides that comprise suitable promoter sites are described above, and include SEQ ID NO:3 and SEQ ID NO:4. Additional suitable promoter sites include the following variants of the CMV immediate early promoter site:

```
                                                     SEQ ID NO: 31
gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agct
                                                     SEQ ID NO: 32
gtgatgcggt tttggcagta caccaatggg cgtggatagc ggtttgactc acggggattt ccaagtctcc accccattga cgtcaatggg agtttgtttt
```

-continued

```
ggcaccaaaa tcaacgggac tttccaaaat gtcgtaataa ccccgcccg ttgacgcaaa tgggcggtag gcgtgtacgg tgggaggtct atataagcag
```

A further preferred feature of the packaging vectors of the present invention is a promoter that will facilitate and mediate transcription in a bacterial host. Illustrative polynucleotides, such as the exemplary T7 promoter site (SEQ ID NO:12) are described above.

A central feature of the packaging vectors of the present invention is a polynucleotide that encodes a gag protein, such as the HIV-1 gag protein (SEQ ID NO:33):

```
MGARASVLSG GELDRWEKIR LRPGGKKKYK LKHIVWASRE

LERFAVNPGL LETSEGCRQI LGQLQPSLQT GSEELRSLYN

TVATLYCVHQ RIEIKDTKEA LDKIEEEQNK SKKKAQQAAA

DTGHSNQVSQ NYPIVQNIQG QMVHQAISPR TLNAWVKVVE
```

-continued
```
EKAFSPEVIP MFSALSEGAT PQDLNTMLNT VGGHQAAMQM

LKETINEEAA EWDRVHPVHA GPIAPGQMRE PRGSDIAGTT

STLQEQIGWM TNNPPIPVGE IYKRWIILGL NKIVRMYSPT

SILDIRQGPK EPFRDYVDRF YKTLRAEQAS QEVKNWMTET

LLVQNANPDC KTILKALGPA ATLEEMMTAC QGVGGPGHKA

RVLAEAMSQV TNSATIMMQR GNFRNQRKIV KCFNCGKEGH

TARNCRAPRK KGCWKCGKEG HQMKDCTERQ ANFLGKIWPS

YKGRPGNFLQ SRPEPTAPPE ESFRSGVETT TPPQKQEPID

KELYPLTSLR SLFGNDPSSQ
```

An illustrative polynucleotide that encodes the HIV-1 gag protein is SEQ ID NO:34:

```
atgggtgcga gagcgtcagt attaagcggg ggagaattag atcgatggga aaaaattcgg ttaaggccag ggggaaagaa aaatatataa ttaaaacata tagtatgggc aagcagggag ctagaacgat tcgcagttaa tcctggcctg ttagaaacat cagaaggctg tagacaaata ctgggacagc tacaaccatc ccttcagaca ggatcagaag aacttagatc attatataat acagtagcaa ccctctattg tgtgcatcaa aggatagaga taaaagacac caaggaagct ttagacaaga tagaggaaga gcaaaacaaa agtaagaaaa aagcacagca agcagcagct gacacaggac acagcaatca ggtcagccaa aattacccta tagtgcagaa catccagggg caaatggtac atcaggccat atcacctaga actttaaatg catgggtaaa agtagtagaa gagaaggctt tcagcccaga agtgataccc atgttttcag cattatcaga aggagccacc ccacaagatt taaacaccat gctaaacaca gtggggggac atcaagcagc catgcaaatg ttaaaagaga ccatcaatga ggaagctgca gaatgggata gagtgcatcc agtgcatgca gggcctattg caccaggcca gatgagagaa ccaaggggaa gtgacatagc aggaactact agtacccttc aggaacaaat aggatggatg acaaataatc cacctatccc agtaggagaa atttataaaa gatggataat cctgggatta aataaaatag taagaatgta tagccctacc agcattctgg acataagaca aggaccaaaa gaacccttta gagactatgt agaccggttc tataaaactc taagagccga gcaagcttca caggaggtaa aaaattggat gacagaaacc ttgttggtcc aaaatgcgaa cccagattgt aagactattt taaaagcatt gggaccagcg gctacactag aagaaatgat gacagcatgt cagggagtag gaggacccgg ccataaggca agagtttgg ctgaagcaat gagccaagta acaaattcag ctaccataat gatgcagaga ggcaatttta ggaaccaaag aaagattgtt aagtgtttca attgtggcaa agaagggcac acagccagaa attgcagggc ccctaggaaa aagggctgtt ggaaatgtgg aaaggaagga caccaaatga aagattgtac tgagagacag gctaattttt
```

-continued
```
tagggaagat ctggccttcc tacaaggaa ggccagggaa ttttcttcag agcagaccag agccaacagc cccaccagaa gagagcttca ggtctgggt agagacaaca actcccctc agaagcagga gccgatagac aaggaactgt atcctttaac ttccctcaga tcactctttg gcaacgaccc ctcgtcacaa
```

A further central feature of the packaging vectors of the present invention is a polynucleotide that encodes a pol protein, such as the HIV-1 pol protein (SEQ ID NO:35):

```
MSLPGRWKPK MIGGIGGFIK VRQYDQILIE ICGHKAIGTV LVGPTPVNII

GRNLLTQIGC TLNFPISPIE TVPVKLKPGM DGPKVKQWPL TEEKIKALVE

ICTEMEKEGK ISKIGPENPY NTPVFAIKKK DSTKWRKLVD FRELNKRTQD

FWEVQLGIPH PAGLKKKKSV TVLDVGDAYF SVPLDEDFRK YTAFTIPSIN

NETPGIRYQY NVLPQGWKGS PAIFQSSMTK ILEPFRKQNP DIVIYQYMDD

LYVGSDLEIG QHRTKIEELR QHLLRWGLTT PDKKHQKEPP FLWMGYELHP

DKWTVQPIVL PEKDSWTVND IQKLVGKLNW ASQIYPGIKV RQLCKLLRGT

KALTEVIPLT EEAELELAEN REILKEPVHG VYYDPSKDLI AEIQKQGQGQ

WTYQIYQEPF KNLKTGKYAR MRGAHTNDVK QLTEAVQKIT TESIVIWGKT

PKFKLPIQKE TWETWWTEYW QATWIPEWEF VNTPPLVKLW YQLEKEPIVG

AETFYVDGAA NRETKLGKAG YVTNRGRQKV VTLTDTTNQK TELQAIYLAL

QDSGLEVNIV TDSQYALGII QAQPDQSESE LVNQIIEQLI KKEKVYLAWV

PAHKGIGGNE QVDKLVSAGI RKVLFLDGID KAQDEHEKYH SNWRAMASDF

NLPPVVAKEI VASCDKCQLK GEAMHGQVDC SPGIWQLDCT HLEGKVILVA

VHVASGYIEA EVIPAETGQE TAYFLLKLAG RWPVKTIHTD NGSNFTSATV

KAACWWAGIK QEFGIPYNPQ SQGVVESMNK ELKKIIGQVR DQAEHLKTAV

QMAVFIHNFK RKGGIGGYSA GERIVDIIAT DIQTKELQKQ ITKIQNFRVY

YRDSRNPLWK GPAKLLWKGE GAVVIQDNSD IKVVPRRKAK IIRDYGKQMA

GDDCVASRQD ED
```

An illustrative polynucleotide that encodes the HIV-1 pol protein has the sequence of SEQ ID NO:36:

```
atgagtttgc caggaagatg gaaaccaaaa atgataggg gaattggagg ttttatcaaa gtaagacagt atgatcagat actcatagaa atctgtggac ataaagctat aggtacagta ttagtaggac ctacacctgt caacataatt ggaagaaatc tgttgactca gattggttgc acttaaatt ttcccattag ccctattgag actgtaccag taaaattaaa gccaggaatg gatgcccaa aagttaaaca atggccattg acagaagaaa aaataaaagc attagtagaa atttgtacag agatggaaaa ggaagggaaa atttcaaaaa ttgggcctga aaatccatac aatactccag tatttgccat aaagaaaaaa gacagtacta aatggagaaa attagtagat ttcagagaac ttaataagag aactcaagac ttctgggaag ttcaattagg aataccacat cccgcagggt taaaaagaa aaaatcagta acagtactgg atgtgggtga tgcatatttt tcagttccct tagatgaaga cttcaggaaa tatactgcat ttaccatacc tagtataaac
```

-continued

```
aatgagacac cagggattag atatcagtac aatgtgcttc cacagggatg gaaaggatca ccagcaatat tccaaagtag catgacaaaa atcttagagc cttttagaaa acaaaatcca gacatagtta tctatcaata catggatgat ttgtatgtag gatctgactt agaaataggg cagcatagaa caaaaataga ggagctgaga caacatctgt tgaggtgggg acttaccaca ccagacaaaa aacatcagaa agaacctcca ttcctttgga tgggttatga actccatcct gataaatgga cagtacagcc tatagtgctg ccagaaaaag acagctggac tgtcaatgac atacagaagt tagtggggaa attgaattgg gcaagtcaga tttacccagg gattaaagta aggcaattat gtaaactcct tagaggaacc aaagcactaa cagaagtaat accactaaca gaagaagcag agctagaact ggcagaaaac agagagattc taaaagaacc agtacatgga gtgtattatg acccatcaaa agacttaata gcagaaatac agaagcaggg gcaaggccaa tggacatatc aaatttatca agagccattt aaaaatctga aaacaggaaa atatgcaaga atgaggggtg cccacactaa tgatgtaaaa caattaacag aggcagtgca aaaaataacc acagaaagca tagtaatatg gggaaagact cctaaattta aactgcccat acaaaaggaa acatgggaaa catggtggac agagtattgg caagccacct ggattcctga gtgggagttt gttaataccc ctcctttagt gaaattatgg taccagttag agaaagaacc catagtagga gcagaaacct tctatgtaga tggggcagct aacagggaga ctaaattagg aaaagcagga tatgttacta atagaggaag acaaaaagtt gtcaccctaa ctgacacaac aaatcagaag actgagttac aagcaattta tctagctttg caggattcgg gattagaagt aaacatagta acagactcac aatatgcatt aggaatcatt caagcacaac cagatcaaag tgaatcagag ttagtcaatc aaataataga gcagttaata aaaaaggaaa aggtctatct ggcatgggta ccagcacaca aaggaattgg aggaaatgaa caagtagata attagtcag tgctggaatc aggaaagtac tatttttaga tggaatagat aaggcccaag atgaacatga gaaatatcac agtaattgga gagcaatggc tagtgatttt aacctgccac ctgtagtagc aaaagaaata gtagccagct gtgataaatg tcagctaaaa ggagaagcca tgcatggaca agtagactgt agtccaggaa tatggcaact agattgtaca catttagaag gaaaagttat cctggtagca gttcatgtag ccagtggata tatagaagca gaagttattc cagcagaaac agggcaggaa acagcatatt ttcttttaaa attagcagga agatggccag taaaaacaat acatacagac aatggcagca atttcaccag tgctacggtt aaggccgcct gttggtgggc gggaatcaag caggaatttg gaattcccta caatccccaa agtcaaggag tagtagaatc tatgaataaa gaattaaaga aaattatagg acaggtaaga gatcaggctg aacatcttaa gacagcagta caaatggcag tattcatcca caatttta aagaaagggg ggattggggg
gtacagtgca ggggaaagaa tagtagacat aatagcaaca gacatacaaa
ctaaagaatt acaaaaacaa attacaaaaa ttcaaaattt tcgggtttat tacagggaca gcagaaatcc actttggaaa ggaccagcaa agctcctctg gaaaggtgaa ggggcagtag taatacaaga taatagtgac ataaaagtag
```

```
tgccaagaag aaaagcaaag atcattaggg attatggaaa acagatggca ggtgatgatt gtgtggcaag tagacaggat gaggat
```

The pol-encoding polynucleotide (SEQ ID NO:36) includes a central polypurine tract and central termination sequence (cPPT/CTS) (SEQ ID NO:8) (underlined above).

Improved safety can be obtained by employing a modified polynucleotide that encodes a pol protein that is substantially incapable of mediating reverse transcription of the lentiviral genome. Polynucleotides capable of encoding such proteins include modifications that encode D249V, D250V substitutions in the pol protein. The D249V and D250V substitutions attenuate the ability of the reverse transcriptase to mediate the reverse transcription of the lentiviral RNA into DNA. Thus, these mutations attenuate the ability of the lentiviral sequences to replicate.

Further improvements to safety can be obtained by employing a modified polynucleotide that encodes an IN integrase protein that is substantially incapable of mediating the reverse transcription of the lentiviral RNA into DNA. The amino acid sequence of the IN integrase protein is (SEQ ID NO:65):

```
FLDGIDKAQD EHEKYHSNWR AMASDFNLPP VVAKEIVASC DKCQLKGEAM

HGQVDCSPGI WQLDCTHLEG KVILVAVHVA SGYIEAEVIP AETGQETAYF

LLKLAGRWPV KTIHTDNGSN FTSATVKAAC WWAGIKQEFG IPYNPQSQGV

VESMNKELKK IIGQVRDQAE HLKTAVQMAV FIHNFKRKGG IGGYSAGERI

VDIIATDIQT KELQKQITKI QNFRVYYRDS RNPLWKGPAK LLWKGEGAVV

IQDNSDIKVV PRRKAKIIRD YGKQMAGDDC VASRQDED
```

A polynucleotide that encodes the IN integrase protein of SEQ ID NO:65 is SEQ ID NO:66 (corresponding to residues 1873-2736 of SEQ ID NO:36):

```
ttttagatg gaatagataa ggcccaagat gaacatgaga aatatcacag taattggaga gcaatggcta gtgattttaa cctgccacct gtagtagcaa aagaaatagt agccagctgt gataaatgtc agctaaaagg agaagccatg catggacaag tagactgtag tccaggaata tggcaactag attgtacaca tttagaagga aaagttatcc tggtagcagt tcatgtagcc agtggatata tagaagcaga agttattcca gcagaaacag ggcaggaaac agcatatttt cttttaaaat tagcaggaag atggccagta aaaacaatac atacagacaa tggcagcaat ttcaccagtg ctacggttaa ggccgcctgt tggtgggcgg gaatcaagca ggaatttgga attccctaca atccccaaag tcaaggagta gtagaatcta tgaataaaga attaaagaaa attataggac aggtaagaga tcaggctgaa catcttaaga cagcagtaca aatggcagta ttcatccaca atttttaaaag aaaaggggggg attgggggggt acagtgcagg ggaaagaata gtagacataa tagcaacaga catacaaact aaagaattac
```

```
aaaaacaaat tacaaaaatt caaaattttc gggtttatta cagggacagc agaaatccac tttggaaagg accagcaaag ctcctctgga aaggtgaagg ggcagtagta atacaagata atagtgacat aaaagtagtg ccaagaagaa aagcaaagat cattagggat tatggaaaac agatggcagg tgatgattgt gtggcaagta gacaggatga ggat
```

Polynucleotides capable of encoding mutated IN integrase proteins include those that cause mutations in the catalytic core of the lentiviral integrase (e.g., S81R, D64V, D116I, N120L, N120E, N120G, P145I, P145I/P90D, P145I/F185K, E152G, E152V, K156I, etc.). The D688V pol substitution creates the D64V mutated integrase protein, and is a preferred integrase mutation as it greatly impairs 3' processing, strand transfer, and disintegration in vitro, but permits the production of high infectious titer (Leavitt. A, D, et al. (1996) "*Human Immunodeficiency Virus Type 1 Integrase Mutants Retain In Vitro Integrase Activity Yet Fail To Integrate Viral DNA Efficiently During Infection*," J. Virol. 70(2):721-728; Sayasith, K. et al. (2000) "*Characterization Of Mutant HIV-1 Integrase Carrying Amino Acid Changes In The Catalytic Domain*," Mol. Cells 10(5):525-532). The D688V mutation thus attenuates the ability of the lentiviral sequences to integrate into the chromosomes of transfected mammalian cells, and thus attenuates the ability of the lentiviral sequences to integrate into the chromosomes of the cells of recipient subjects.

SEQ ID NO:37 provides the amino acid sequence of an variant pol protein that comprises D249V, D250V and D688V substitutions (relative to SEQ ID NO:35). The sequence of SEQ ID NO:37 is shown below (differences relative to SEQ ID NO:35 are underlined):

```
MSLPGRWKPK MIGGIGGFIK VRQYDQILIE ICGHKAIGTV

LVGPTPVNII GRNLLTQIGC TLNFPISPIE TVPVKLKPGM

DGPKVKQWPL TEEKIKALVE ICTEMEKEGK ISKIGPENPY

NTPVFAIKKK DSTKWRKLVD FRELNKRTQD FWEVQLGIPH

PAGLKKKKSV TVLDVGDAYF SVPLDEDFRK YTAFTIPSIN

NETPGIRYQY NVLPQGWKGS PAIFQSSMTK ILEPFRKQNP

DIVIYQYMVV LYVGSDLEIG QHRTKIEELR QHLLRWGLTT
```

-continued

```
PDKKHQKEPP FLWMGYELHP DKWTVQPIVL PEKDSWTVND
IQKLVGKLNW ASQIYPGIKV RQLCKLLRGT KALTEVIPLT
EEAELELAEN REILKEPVHG VYYDPSKDLI AEIQKQGQGQ
WTYQIYQEPF KNLKTGKYAR MRGAHTNDVK QLTEAVQKIT
TESIVIWGKT PKFKLPIQKE TWETWWTEYW QATWIPEWEF
VNTPPLVKLW YQLEKEPIVG AETFYVDGAA NRETKLGKAG
YVTNRGRQKV VTLTDTTNQK TELQAIYLAL QDSGLEVNIV
TDSQYALGII QAQPDQSESE LVNQIIEQLI KKEKVYLAWV
PAHKGIGGNE QVDKLVSAGI RKVLFLDGID KAQDEHEKYH
SNWRAMASDF NLPPVVAKEI VASCDKCQLK GEAMHGQVDC
SPGIWQLVCT HLEGKVILVA VHVASGYIEA EVIPAETGQE
TAYFLLKLAG RWPVKTIHTD NGSNFTSATV KAACWWAGIK
QEFGIPYNPQ SQGVVESMNK ELKKIIGQVR DQAEHLKTAV
QMAVFIHNFK RKGGIGGYSA GERIVDIIAT DIQTKELQKQ
ITKIQNFRVY YRDSRNPLWK GPAKLLWKGE GAVVIQDNSD
IKVVPRRKAK IIRDYGKQMA GDDCVASRQD ED
```

An exemplary polynucleotide that encodes the D249V/D250V/D688V HIV-1 pol protein has the sequence of SEQ ID NO:38:

```
atgagtttgc caggaagatg gaaaccaaaa atgatagggg
gaattggagg ttttatcaaa gtaagacagt atgatcagat
actcatagaa atctgtggac ataaagctat aggtacagta
ttagtaggac ctacacctgt caacataatt ggaagaaatc
tgttgactca gattggttgc actttaaatt ttcccattag
ccctattgag actgtaccag taaaattaaa gccaggaatg
gatggcccaa aagttaaaca atggccattg acagaagaaa
aaataaaagc attagtagaa atttgtacag agatggaaaa
ggaagggaaa atttcaaaaa ttgggcctga aaatccatac
aatactccag tatttgccat aaagaaaaaa gacagtacta
aatggagaaa attagtagat ttcagagaac ttaataagag
aactcaagac ttctgggaag ttcaattagg aataccacat
cccgcagggt taaaaaagaa aaaatcagta acagtactgg
atgtgggtga tgcatatttt tcagttccct tagatgaaga
cttcaggaaa tatactgcat ttaccatacc tagtataaac
aatgagacac cagggattag atatcagtac aatgtgcttc
cacagggatg gaaaggatca ccagcaatat tccaaagtag
catgacaaaa atcttagagc cttttagaaa acaaaatcca
gacatagtta tctatcaata catggtcgtg ttgtatgtag
gatctgactt agaaataggg cagcatagaa caaaaataga
ggagctgaga caacatctgt tgaggtgggg acttaccaca
ccagacaaaa aacatcagaa agaacctcca ttcctttgga
tgggttatga actccatcct gataaatgga cagtacagcc
tatagtgctg ccagaaaaag acagctggac tgtcaatgac
atacagaagt tagtggggaa attgaattgg gcaagtcaga
tttacccagg gattaaagta aggcaattat gtaaactcct
tagaggaacc aaagcactaa cagaagtaat accactaaca
gaagaagcag agctagaact ggcagaaaac agagagattc
taaaagaacc agtacatgga gtgtattatg acccatcaaa
agacttaata gcagaaatac agaagcaggg gcaaggccaa
tggacatatc aaatttatca agagccattt aaaaatctga
aaacaggaaa atatgcaaga atgaggggtg cccacactaa
tgatgtaaaa caattaacag aggcagtgca aaaaataacc
acagaaagca tagtaatatg gggaaagact cctaaattta
aactgcccat acaaaaggaa acatgggaaa catggtggac
agagtattgg caagccacct ggattcctga gtgggagttt
gttaataccc ctcctttagt gaaattatgg taccagttag
agaaagaacc catagtagga gcagaaacct tctatgtaga
tggggcagct aacagggaga ctaaattagg aaaagcagga
tatgttacta atagaggaag acaaaaagtt gtcaccctaa
ctgacacaac aaatcagaag actgagttac aagcaattta
tctagctttg caggattcgg gattagaagt aaacatagta
acagactcac aatatgcatt aggaatcatt caagcacaac
cagatcaaag tgaatcagag ttagtcaatc aaataataga
gcagttaata aaaaaggaaa aggtctatct ggcatgggta
ccagcacaca aaggaattgg aggaaatgaa caagtagata
aattagtcag tgctggaatc aggaaagtac tatttttaga
tggaatagat aaggcccaag atgaacatga gaaatatcac
agtaattgga gagcaatggc tagtgatttt aacctgccac
ctgtagtagc aaaagaaata gtagccagct gtgataaatg
tcagctaaaa ggagaagcca tgcatggaca agtagactgt
agtccaggaa tatggcaact agtctgtaca catttagaag
gaaaagttat cctggtagca gttcatgtag ccagtggata
tatagaagca gaagttattc cagcagaaac agggcaggaa
acagcatatt ttcttttaaa attagcagga agatggccag
taaaaacaat acatacagac aatggcagca atttcaccag
tgctacggtt aaggccgcct gttggtgggc gggaatcaag
caggaatttg gaattcccta caatccccaa agtcaaggag
tagtagaatc tatgaataaa gaattaaaga aaattatagg
acaggtaaga gatcaggctg aacatcttaa gacagcagta
caaatggcag tattcatcca caattttaaa agaaaagggg
ggattggggg gtacagtgca ggggaaagaa tagtagacat
aatagcaaca gacatacaaa ctaaagaatt acaaaaacaa
```

-continued

```
attacaaaaa ttcaaaattt tcgggtttat tacagggaca
gcagaaatcc actttggaaa ggaccagcaa agctcctctg
gaaaggtgaa ggggcagtag taatacaaga taatagtgac
ataaaagtag tgccaagaag aaaagcaaag atcattaggg
attatggaaa acagatggca ggtgatgatt gtgtggcaag
tagacaggat gaggattag
```

It will be noted that residues 2424-2541 of SEQ ID NO:36 and SEQ ID NO:38 each comprise a lentiviral central polypurine tract and central termination sequence (cPPT/CTS) (shown underlined above).

A further preferred feature of the packaging vectors of the present invention is a polynucleotide that comprises a Rev response element (RRE). An exemplary polynucleotide has the sequence of SEQ ID NO:7.

A further preferred feature of the packaging vectors of the present invention is a polynucleotide that comprises an SV40 small t intron. An exemplary polynucleotide has the sequence of SEQ ID NO:39:

```
gtaaatataa aatttttaag tgtataatgt gttaaactac
tgattctaat tgtttgtgta ttttag
```

A further preferred feature of the packaging vectors of the present invention is a polynucleotide that encodes a nuclear localization signal sufficient to promote localization of expressed proteins to the nucleus of a transfected mammalian cell. An exemplary nuclear localization signal is the nuclear localization signal of the SV40 large T antigen (SEQ ID NO:40):

PKKKRKV, which may be encoded by (SEQ ID NO:41):

ccaaaaaagaagagaaaggta.

A further preferred feature of the packaging vectors of the present invention is a polynucleotide that comprises a polyadenylation signal. An exemplary polynucleotide comprises the SV40 poly(A) signal site (SEQ ID NO:42):

```
aacttgttta ttgcagctta taatggttac aaataaagca
atagcatcac aaatttcaca aataaagcat ttttttcact
gcattctagt tgtggtttgt ccaaactcat caatgtatct
tatcatgtct ggatc
```

A further preferred feature of the packaging vectors of the present invention is a polynucleotide that comprises a promoter that will facilitate and mediate transcription in a mammalian host cell. An exemplary polynucleotide comprises the SV40 early promoter (SEQ ID NO:43):

```
gcatctcaat tagtcagcaa ccatagtccc gcccctaact
ccgcccatcc cgcccctaac tccgcccagt tccgcccatt
ctccgcccca tggctgacta attttttta tttatgcaga
ggccgaggcc gcctcggcct ctgagctatt ccagaagtag
tgaggaggct tttttggagg cctaggcttt tgcaaa
```

It will be noted that residues 47-182 of SEQ ID NO:43 (underlined above) correspond to an SV40 origin of replication.

A further preferred feature of the packaging vectors of the present invention is a polynucleotide that comprises a promoter that will facilitate and mediate transcription in a bacterial host. An illustrative polynucleotide that comprises the AmpR promoter has the sequence of SEQ ID NO:16.

A further preferred feature of the packaging vectors of the present invention is a gene that encodes an antibiotic resistance determinant, such as AmpR. Illustrative polynucleotides that encode such a determinant are described above (e.g., SEQ ID NO:22, SEQ ID NO:24).

The double-stranded vector pGAG (FIG. 13) is a preferred packaging vector of the present invention that may be used with the LTR-containing vectors, REV vectors and envelope vectors of the present invention to produce lentiviral particles that array a SARS-CoV-2 S protein on their surface. The polynucleotide sequence of the first strand of vector pGAG is SEQ ID NO:44:

```
ttcaacattt ccgtgtcgcc cttattccct tttttgcggc attttgcctt    50
cctgtttttg ctcacccaga aacgctggtg aaagtaaaag atgctgaaga   100
tcagttgggt gcacgagtgg gttacatcga actggatctc aacagcggta   150
agatccttga gagttttcgc cccgaagaac gttttccaat gatgagcact   200
tttaaagttc tgctatgtgg cgcggtatta tcccgtgttg acgccgggca   250
agagcaactc ggtcgccgca tacactattc tcagaatgac ttggttgagt   300
actcaccagt cacagaaaag catcttacgg atggcatgac agtaagagaa   350
ttatgcagtg ctgccataac catgagtgat aacactgcgg ccaacttact   400
tctgacaacg atcggaggac cgaaggagct aaccgctttt ttgcacaaca   450
tgggggatca tgtaactcgc cttgatcgtt gggaaccgga gctgaatgaa   500
gccataccaa acgacgagcg tgacaccacg atgcctgcag caatggcaac   550
aacgttgcgc aaactattaa ctggcgaact acttactcta gcttcccggc   600
```

-continued

```
aacaattaat agactggatg gaggcggata aagttgcagg accacttctg      650
cgctcggccc ttccggctgg ctggtttatt gctgataaat ctggagccgg      700
tgagcgtggg tctcgcggta tcattgcagc actggggcca gatggtaagc      750
cctcccgtat cgtagttatc tacacgacgg ggagtcaggc aactatggat      800
gaacgaaata gacagatcgc tgagataggt gcctcactga ttaagcattg      850
gtaactgtca gaccaagttt actcatatat actttagatt gatttaaaac      900
ttcatttta atttaaaagg atctaggtga agatccttt tgataatctc        950
atgaccaaaa tcccttaacg tgagttttcg ttccactgag cgtcagaccc     1000
cgtagaaaag atcaaaggat cttcttgaga tccttttttt ctgcgcgtaa     1050
tctgctgctt gcaaacaaaa aaaccaccgc taccagcggt ggtttgtttg     1100
ccggatcaag agctaccaac tcttttccg aaggtaactg gcttcagcag      1150
agcgcagata ccaaatactg tccttctagt gtagccgtag ttaggccacc     1200
acttcaagaa ctctgtagca ccgcctacat acctcgctct gctaatcctg     1250
ttaccagtgg ctgctgccag tggcgataag tcgtgtctta ccgggttgga     1300
ctcaagacga tagttaccgg ataaggcgca gcggtcgggc tgaacggggg     1350
gttcgtgcac acagcccagc ttggagcgaa cgacctacac cgaactgaga     1400
tacctacagc gtgagctatg agaaagcgcc acgcttcccg aagggagaaa     1450
ggcggacagg tatccggtaa gcggcagggt cggaacagga gagcgcacga     1500
gggagcttcc agggggaaac gcctggtatc tttatagtcc tgtcgggttt     1550
cgccacctct gacttgagcg tcgattttg tgatgctcgt caggggggcg      1600
gagcctatgg aaaaacgcca gcaacgcggc cttttacgg ttcctggcct      1650
tttgctggcc ttttgctcac atgttctttc ctgcgttatc ccctgattct     1700
gtggataacc gtattaccgc ctttgagtga gctgataccg ctcgccgcag     1750
ccgaacgacc gagcgcagcg agtcagtgag cgaggaagcg gaagagcgcc     1800
tgatgcggta ttttctcctt acgcatctgt gcggtatttc acaccgcata     1850
tggtgcactc tcagtacaat ctgctctgat gccgcatagt taagccagta     1900
tcctcgacat cgctctagtc tagttattaa tagtaatcaa ttacggggtc     1950
attagttcat agcccatata tggagttccg cgttacataa cttacggtaa     2000
atggcccgcc tggctgaccg cccaacgacc cccgcccatt gacgtcaata     2050
atgacgtatg ttcccatagt aacgccaata gggactttcc attgacgtca     2100
atgggtggag tatttacggt aaactgccca cttggcagta catcaagtgt     2150
atcatatgcc aagtacgccc cctattgacg tcaatgacgg taaatggccc     2200
gcctggcatt atgcccagta catgacctta tgggactttc ctacttggca     2250
gtacatctac gtattagtca tcgctattac catggtgatg cggttttggc     2300
agtacatcaa tgggcgtgga tagcggtttg actcacgggg atttccaagt     2350
ctccacccca ttgacgtcaa tgggagtttg ttttggcacc aaaatcaacg     2400
ggactttcca aaatgtcgta acaactccgc cccattgacg caaatgggcg     2450
gtaggcgtgt acggtgggag gtctatataa gcagagctct ctggctaact     2500
agagaaccca ctgcttactg gcttatcgaa attaatacga ctcactatag     2550
ggagacccaa gcttggtacc gagctcggat ccactagagc gcgcacggca     2600
agaggcgagg ggcggcgact ggtgagtacg ccggctagaa ggagagagat     2650
```

-continued

```
gggtgcgaga gcgtcagtat taagcggggg agaattagat cgatgggaaa      2700
aaattcggtt aaggccaggg ggaaagaaaa aatataaatt aaaacatata      2750
gtatgggcaa gcagggagct agaacgattc gcagttaatc ctggcctgtt      2800
agaaacatca gaaggctgta gacaaatact gggacagcta caaccatccc      2850
ttcagacagg atcagaagaa cttagatcat tatataatac agtagcaacc      2900
ctctattgtg tgcatcaaag gatagagata aaagacacca aggaagcttt      2950
agacaagata gaggaagagc aaaacaaaag taagaaaaaa gcacagcaag      3000
cagcagctga cacaggacac agcaatcagg tcagccaaaa ttaccctata      3050
gtgcagaaca tccaggggca aatggtacat caggccatat cacctagaac      3100
tttaaatgca tgggtaaaag tagtagaaga gaaggctttc agcccagaag      3150
tgatacccat gttttcagca ttatcagaag gagccacccc acaagattta      3200
aacaccatgc taaacacagt ggggggacat caagcagcca tgcaaatgtt      3250
aaaagagacc atcaatgagg aagctgcaga atgggataga gtgcatccag      3300
tgcatgcagg gcctattgca ccaggccaga tgagagaacc aaggggaagt      3350
gacatagcag gaactactag tacccttcag gaacaaatag gatggatgac      3400
aaataatcca cctatcccag taggagaaat ttataaaaga tggataatcc      3450
tgggattaaa taaaatagta agaatgtata gccctaccag cattctggac      3500
ataagacaag gaccaaaaga acccttagga ctatgtag accggttcta       3550 taaaactcta agagccgagc aagcttcaca ggaggtaaaa aattggatga      3600
cagaaaccct tgttggtccaa aatgcgaacc cagattgtaa gactatttta    3650
aaagcattgg gaccagcggc tacactagaa gaaatgatga cagcatgtca      3700
gggagtagga ggacccggcc ataaggcaag agttttggct gaagcaatga      3750
gccaagtaac aaattcagct accataatga tgcagagagg caattttagg      3800
aaccaaagaa agattgttaa gtgtttcaat tgtggcaaag aagggcacac      3850
agccagaaat tgcagggccc ctaggaaaaa gggctgttgg aaatgtggaa      3900
aggaaggaca ccaaatgaaa gattgtactg agagacaggc taattttta      3950 gggaagatct ggccttccta caagggaagg ccagggaatt ttcttcagag      4000
cagaccagag ccaacagccc caccagaaga gagcttcagg tctggggtag      4050
agacaacaac tccccctcag aagcaggagc cgatagacaa ggaactgtat      4100
cctttaactt ccctcagatc actctttggc aacgacccct cgtcacaata      4150
aagatagggg ggcaactaaa ggaagctcta ttagatacag gagcagatga      4200
tacagtatta gaagaaatga gtttgccagg aagatggaaa ccaaaaatga      4250 taggggggaat tggaggtttt atcaaagtaa gacagtatga tcagatactc     4300
atagaaatct gtggacataa agctataggt acagtattag taggacctac      4350
acctgtcaac ataattggaa gaaatctgtt gactcagatt ggttgcactt      4400
taaattttcc cattagccct attgagactg taccagtaaa attaaagcca      4450
ggaatggatg gcccaaaagt taaacaatgg ccattgacag aagaaaaaat      4500
aaaagcatta gtagaaattt gtacagagat ggaaaaggaa gggaaaattt      4550
caaaaattgg gcctgaaaat ccatacaata ctccagtatt tgccataaag      4600
aaaaaagaca gtactaaatg gagaaaatta gtagatttca gagaacttaa      4650
taagagaact caagacttct gggaagttca attaggaata ccacatcccg      4700
```

```
cagggttaaa aaagaaaaaa tcagtaacag tactggatgt gggtgatgca    4750 tattttttcag ttcccttaga tgaagacttc aggaaatata ctgcatttac   4800
catacctagt ataaacaatg agacaccagg gattagatat cagtacaatg    4850
tgcttccaca gggatggaaa ggatcaccag caatattcca aagtagcatg    4900
acaaaaatct tagagccttt tagaaaacaa aatccagaca tagttatcta    4950
tcaatacatg gatgatttgt atgtaggatc tgacttagaa ataggcagc     5000 atagaacaaa aatagaggag ctgagacaac atctgttgag gtggggactt    5050
accacaccag acaaaaaaca tcagaaagaa cctccattcc tttggatggg    5100
ttatgaactc catcctgata aatggacagt acagcctata gtgctgccag    5150
aaaaagacag ctggactgtc aatgacatac agaagttagt ggggaaattg    5200
aattgggcaa gtcagattta cccagggatt aaagtaaggc aattatgtaa    5250
actccttaga ggaaccaaag cactaacaga agtaatacca ctaacagaag    5300
aagcagagct agaactggca gaaaacgagag agattctaaaa gaaccagta   5350 catggagtgt attatgaccc atcaaaagac ttaatagcag aaatacagaa    5400
gcaggggcaa ggccaatgga catatcaaat ttatcaagag ccatttaaaa    5450
atctgaaaac aggaaaatat gcaagaatga ggggtgccca cactaatgat    5500
gtaaaacaat taacagaggc agtgcaaaaa ataaccacag aaagcatagt    5550
aatatgggga aagactccta aatttaaact gcccatacaa aaggaaacat    5600
gggaaacatg gtggacagag tattggcaag ccacctggat tcctgagtgg    5650
gagtttgtta taccccctcc tttagtgaaa ttatggtacc agttagagaa    5700
agaacccata gtaggagcag aaaccttcta tgtagatggg gcagctaaca    5750
gggagactaa attaggaaaa gcaggatatg ttactaatag aggaagacaa    5800
aaagttgtca ccctaactga cacaacaaat cagaagactg agttacaagc    5850 aattttatcta gctttgcagg attcgggatt agaagtaaac atagtaacag   5900
actcacaata tgcattagga atcattcaag cacaaccaga tcaaagtgaa    5950
tcagagttag tcaatcaaat aatagagcag ttaataaaaa aggaaaaggt    6000
ctatctggca tgggtaccag cacacaaagg aattggagga aatgaacaag    6050
tagataaatt agtcagtgct ggaatcagga aagtactatt tttagatgga    6100
atagataagg cccaagatga acatgagaaa tatcacagta attggagagc    6150
aatggctagt gattttaacc tgccacctgt agtagcaaaa gaaatagtag    6200
ccagctgtga taaatgtcag ctaaaaggag aagccatgca tggacaagta    6250
gactgtagtc caggaatatg gcaactagat tgtacacatt tagaaggaaa    6300
agttatcctg gtagcagttc atgtagccag tggatatata gaagcagaag    6350
ttattccagc agaaacaggg caggaaacag catattttct tttaaaatta    6400
gcaggaagat ggccagtaaa aacaatacat acagacaatg gcagcaattt    6450
caccagtgct acggttaagg ccgcctgttg gtgggcggga atcaagcagg    6500
aatttggaat tccctacaat ccccaaagtc aaggagtagt agaatctatg    6550
aataaagaat taaagaaaat tataggacag gtaagagatc aggctgaaca    6600
tcttaagaca gcagtacaaa tggcagtatt catccacaat tttaaaagaa    6650 aagggggat tggggggtac agtgcagggg aagaatagta gacataata    6700 gcaacagaca tacaaactaa agaattacaa aaacaaatta caaaaattca    6750
```

```
aaattttcgg gtttattaca gggacagcag aaatccactt tggaaaggac        6800
cagcaaagct cctctggaaa ggtgaagggg cagtagtaat acaagataat        6850
agtgacataa aagtagtgcc aagaagaaaa gcaaagatca ttagggatta        6900
tggaaaacag atggcaggtg atgattgtgt ggcaagtaga caggatgagg        6950
attagaacat ggaaaagttt agtaaaacac catatgtata tttcaaggaa        7000
agctaaggac tggttttata gacatcacta tgaaagtact aatccaaaaa        7050
taagttcaga agtacacatc ccactagggg atgctaaatt agtaataaca        7100
acatattggg gtctgcatac aggagaaaga gactggcatt tgggtcaggg        7150
agtctccata gaatggagga aaaagagata tagcacacaa gtagaccctg        7200
acctagcaga ccaactaatt catctgcact attttgattg tttttcagaa        7250
tctgctataa gaaataccat attaggacgt atagttagtc ctaggtgtga        7300
atatcaagca ggacataaca aggtaggatc tctacagtac ttggcactag        7350
cagcattaat aaaaccaaaa cagataaagc cacctttgcc tagtgttagg        7400
aaactgacag aggacagatg gaacaagccc cagaagacca agggccacag        7450
agggagccat acaatgaatg gacactagag cttttagagg aacttaagag        7500
tgaagctgtt agacattttc ctaggatatg gctccataac ttaggacaac        7550
atatctatga aacttacggg gatacttggg caggagtgga agccataata        7600
agaattctgc aacaactgct gtttatccat ttcagaattg ggtgtcgaca        7650
tagcagaata ggcgttactc gacagaggag agcaagaaat ggagccagta        7700
gatcctagac tagagccctg gaagcatcca ggaagtcagc ctaaaactgc        7750
ttgtaccaat tgctattgta aaaagtgttg ctttcattgc caagtttgtt        7800
tcatgacaaa agccttaggc atctcctatg gcaggaagaa gcggagacag        7850
cgacgaagag ctcatcagaa cagtcagact catcaagctt ctctatcaaa        7900
gcagtaagta gtacatgtaa tgcaacctat aatagtagca atagtagcat        7950
tagtagtagc aataataata gcaatagttg tgtggtccat agtaatcata        8000
gaatatagga aaatattaag acaaagaaaa atagacaggt taattgatag        8050
actaatagaa agagcagaag acagtggcaa tgagagtgaa ggagaagtat        8100
cagcacttgt ggagatgggg gtggaaatgg ggcaccatgc tccttgggat        8150
attgatgatc tgtagtgcta cagaaaaatt gtgggtcaca gtctattatg        8200
gggtacctgt gtggaaggaa gcaaccacca ctctattttg tgcatcagat        8250
gctaaagcat atgatacaga ggtacataat gtttgggcca cacatgcctg        8300
tgtacccaca gaccccaacc cacaagaagt agtattggta aatgtgacag        8350
aaaattttaa catgtggaaa aatgacatgg tagaacagat gcatgaggat        8400
ataatcagtt tatgggatca aagcctaaag ccatgtgtaa aattaacccc        8450
actctgtgtt agtttaaagt gcactgattt gaagaatgat actaatacca        8500
atagtagtag cgggagaatg ataatggaga aggagagat aaaaaactgc        8550 tctttcaata tcagcacaag cataagaggt aaggtgcaga agaatatgc         8600 attttttat aaacttgata taataccaat agataatgat actaccagct          8650
ataagttgac aagttgtaac acctcagtca ttacacaggc ctgtccaaag        8700
gtatcctttg agccaattcc catacattat tgtgccccgg ctggttttgc         8750
gattctaaaa tgtaataata agacgttcaa tggaacagga ccatgtacaa        8800
```

-continued

```
atgtcagcac agtacaatgt acacatgaa ttaggccagt agtatcaact      8850
caactgctgt taaatggcag tctagcagaa gaagaggtag taattagatc      8900
gatcttcaga cctggaggag gagatatgag ggacaattgg agaagtgaat      8950
tatataaata taaagtagta aaaattgaac cattaggagt agcacccacc      9000
aaggcaaaga gaagagtggt gcagagagaa aaaagagcag tgggaatagg      9050
agctttgttc cttgggttct tgggagcagc aggaagcact atgggcgcag      9100
cgtcaatgac gctgacggta caggccagac aattattgtc tggtatagtg      9150
cagcagcaga acaatttgct gagggctatt gaggcgcaac agcatctgtt      9200
gcaactcaca gtctggggca tcaagcagct ccaggcaaga atcctggctg      9250
tggaaagata cctaaaggat caacagctcc tggggatttg gggttgctct      9300
ggaaaactca tttgcaccac tgctgtgcct tggaatgcta gttggagtaa      9350
taaatctctg gaacagattt ggaatcacac gacctggatg gagtgggaca      9400
gagaaattaa caattacaca agcttaatac actccttaat tgaagaatcg      9450
caaaaccagc aagaaaagaa tgaacaagaa ttattggaat tagataaatg      9500
ggcaagtttg tggaattggt ttaacataac aaattggctg tggtatataa      9550
aattattcat aatgatagta ggaggcttgg taggtttaag aatagttttt      9600
gctgtacttt ctatagtgaa tagagttagg cagggatatt caccattatc      9650
gtttcagacc cacctcccaa ccccgagggg acccgacagg cccgaaggaa      9700
tagaagaaga aggtggagag agagacagag acagatccat tcgattagtg      9750
aacggatctt tgtgaaggaa ccttacttct gtggtgtgac ataattggac      9800
aaactaccta cagagattta aagctctaag gtaaatataa aattttttaag      9850 tgtataatgt gttaaactac tgattctaat tgtttgtgta ttttagattc      9900
caacctatgg aactgatgaa tgggagcagt ggtggaatgc ctttaatgag      9950
gaaaacctgt tttgctcaga agaaatgcca tctagtgatg atgaggctac     10000
tgctgactct caacattcta ctcctccaaa aaagaagaga aaggtagaag     10050
accccaagga cttccttca gaattgctaa gttttttgag tcatgctgtg       10100
tttagtaata gaactcttgc ttgctttgct atttacacca caaaggaaaa     10150
agctgcactg ctatacaaga aaattatgga aaaatattct gtaaccttta     10200
taagtaggca taacagttat aatcataaca tactgttttt tcttactcca     10250
cacaggcata gagtgtctgc tattaataac tatgctcaaa aattgtgtac     10300
ctttagcttt ttaatttgta aaggggttaa taaggaatat ttgatgtata     10350
gtgccttgac tagagatcat aatcagccat accacatttg tagaggtttt     10400
acttgcttta aaaaacctcc cacacctccc cctgaacctg aaacataaaa     10450
tgaatgcaat tgttgttgtt aacttgttta ttgcagctta taatggttac     10500
aaataaagca atagcatcac aaatttcaca aataaagcat tttttcact      10550 gcattctagt tgtggtttgt ccaaactcat caatgtatct tatcatgtct     10600
ggatcccgcg atgtcgaggc atctcaatta gtcagcaacc atagtcccgc     10650
ccctaactcc gcccatcccg cccctaactc cgcccagttc cgcccattct     10700 ccgcccatg gctgactaat ttttttattt tatgcagagg ccgaggccgc      10750
ctcggcctct gagctattcc agaagtagtg aggaggcttt tttggaggcc     10800
taggcttttg caaaaagctt ggcgagattt tcaggagcta aggaagctaa     10850
```

-continued

```
aatggagaaa aaaatcactg gatataccac cgttgatata tcccaatggc    10900
atcgtaaaga acattttgag gcatttcagt cagttgctca atgtacctat    10950
aaccagaccg ttcagctgga tattacggcc tttttaaaga ccgtaaagaa    11000
aaataagcac aagttttatc cggcctttat tcacattctt gcccgcctga    11050
tgaatgctca tccggaattc ttgaagacga aagggcctcg tgatacgcct    11100
atttttatag gttaatgtca tgataataat ggtttcttag acgtcaggtg    11150
gcacttttcg gggaaatgtg cgcggaaccc ctatttgttt attttctaa     11200 atacattcaa atatgtatcc gctcatgaga caataaccct gataaatgct    11250
tcaataatat tgaaaaagga agagtatgag ta                       11282
```

As will be noted, residues 1025-1613 of SEQ ID NO:44 correspond to the high-copy-number ColE1/pMB/pBR322/pUC origin of replication (SEQ ID NO:20). Residues 1981-2284 of SEQ ID NO:44 correspond to the CMV immediate early enhancer site (SEQ ID NO:29). Residues 2285-2488 of SEQ ID NO:44 correspond to the CMV immediate early promoter site (SEQ ID NO:31). Residues 2533-2551 of SEQ ID NO:44 correspond to the T7 promoter site (SEQ ID NO:12). Residues 2649-4151 of SEQ ID NO:44 correspond to a polynucleotide (SEQ ID NO:34) that encodes the HIV-1 gag protein (SEQ ID NO:33). Residues 4217-6955 of SEQ ID NO:44 correspond to a polynucleotide (SEQ ID NO:36) that encodes the HIV-1 pol protein (SEQ ID NO:35), and include a lentiviral central polypurine tract and central termination sequence (cPPT/CTS). Residues 9048-9281 of SEQ ID NO:44 correspond to a Rev response element (RRE) (SEQ ID NO:7). Residues 9831-9896 of SEQ ID NO:44 correspond to an SV40 small t intron (SEQ ID NO:39). Residues 10026-10046 of SEQ ID NO:44 correspond to a polynucleotide (SEQ ID NO:41) that encodes the nuclear localization signal of the SV40 large T antigen (SEQ ID NO:40). The nuclear localization signal is in frame with an open reading frame that encodes a protein having the sequence (SEQ ID NO:45) (the SV40 large T nuclear localization signal is underlined):

```
PKKKRKVEDP KDFPSELLSF LSHAVFSNRT LACFAIYTTK

EKAALLYKKI MEKYSVTFIS RHNSYNHNIL FFLTPHRHRV

SAINNYAQKL CTFSFLICKG VNKEYLMYSA LTRDHNQPYH

ICRGFTCFKK PPTPPPEPET
```

Residues 10471-10605 of SEQ ID NO:44 correspond to an SV40 poly(A) signal site (SEQ ID NO:42). Residues 10619-10814 of SEQ ID NO:44 correspond to an SV40 early promoter (SEQ ID NO:43), which includes an SV40 origin of replication. Residues 11171-11275 of SEQ ID NO:44 correspond to an AmpR promoter (SEQ ID NO:16). Residues 11276-11282 and residues 1-854 of SEQ ID NO:44 correspond to a polynucleotide (SEQ ID NO:24) that encodes an AmpR antibiotic resistance determinant (SEQ ID NO:23).

C. REV Vectors of the Present Invention

As used herein, the term "REV vector" is intended to denote a vector that comprises a polynucleotide that encodes a rev protein and a promoter sufficient to mediate the transcription of such gene in a mammalian cell.

Figure 14:
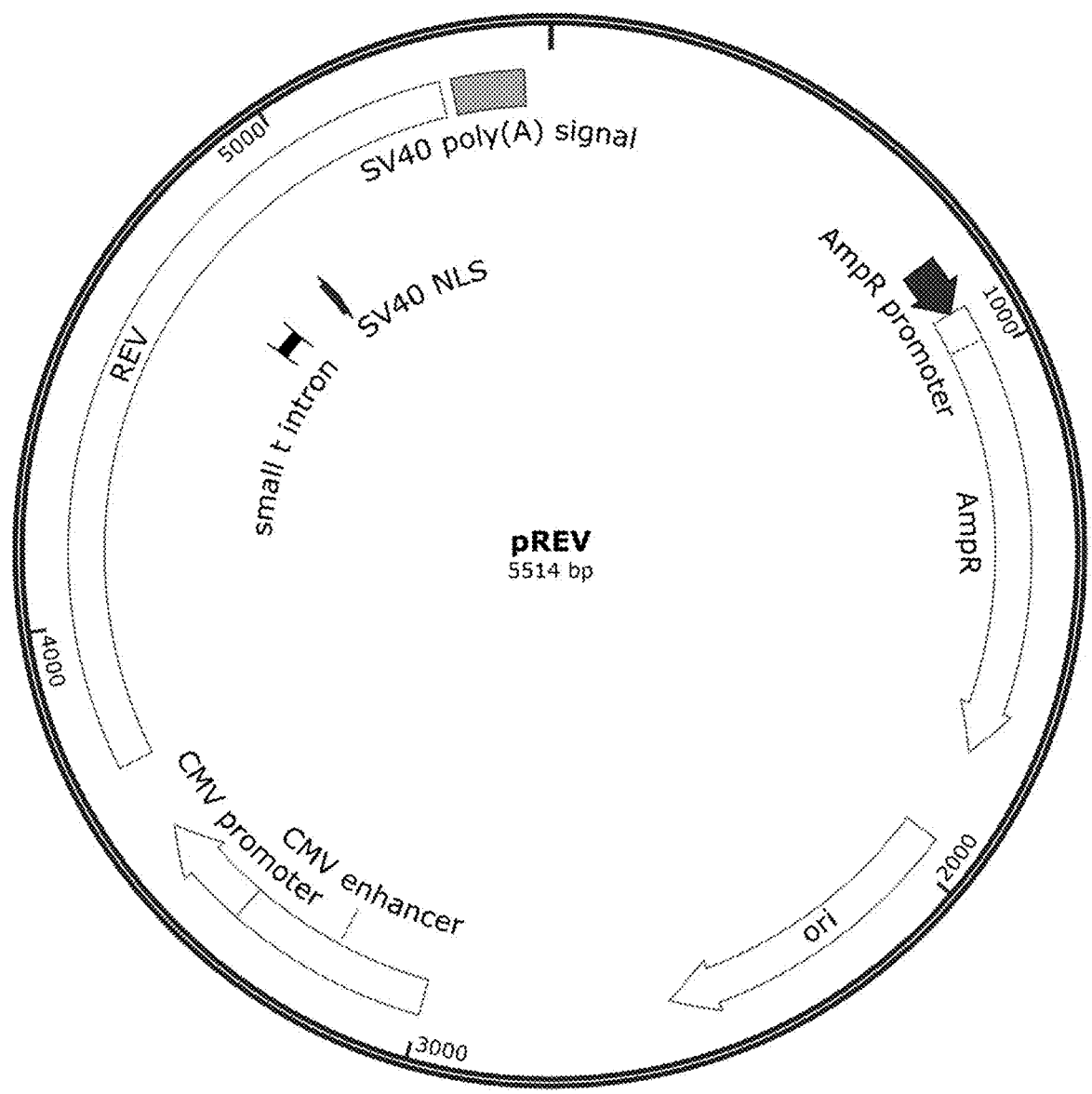
FIG. 14 provides the structure of pREV (SEQ ID NO:49) (5514 nucleotide residues), which is an example of a Rev-containing vector of the present invention.

Most preferably, the REV vector of the present invention will be a double-stranded DNA plasmid. The structure of a preferred REV vector (pREV) is shown in FIG. 14, and comprises 5,514 base pairs. The preferred REV vectors of the present invention comprise multiple features.

The first of such preferred features of the REV vectors of the present invention comprises a gene that encodes an antibiotic resistance determinant operably linked to a promoter capable of mediating its expression in a bacterial host. Polynucleotides that encode such antibiotic resistance determinants are described above. An exemplary antibiotic resistance determinant is the AmpR determinant (SEQ ID NO:23), which is encoded by a polynucleotide that comprises the sequence of SEQ ID NO:24. An exemplary AmpR promoter-containing polynucleotide has the sequence of SEQ ID NO:16.

A further preferred feature of the REV vectors of the present invention is an origin of replication capable of mediating the replication of the vector in prokaryotic cells, such as the high-copy-number ColE1/pMB1/pBR322/pUC origin of replication. Illustrative polynucleotides that comprise such an origin of replication are described above (e.g., SEQ ID NO:19, SEQ ID NO:20).

A central feature of the REV vectors of the present invention is a promoter (and an optional upstream transcriptional enhancer site) that will facilitate and mediate transcription in a mammalian host cell. Suitable promoters are described above. An exemplary promoter/enhancer site is the CMV immediate early enhancer site (SEQ ID NO:4) and the CMV immediate early promoter (SEQ ID NO:5).

A second central feature of the REV vectors of the present invention is a polynucleotide encoding a lentiviral Rev protein, operably linked to such promoter. The Rev protein, however, is encoded by a polynucleotide that contains intervening sequences and that is subject to mRNA splicing (Kammler, S. et al. (2006) "*The Strength Of The HIV-1 3' Splice Sites Affects Rev Function*," Retrovirol. 3:89:1-20). The rev gene thus consists of two coding exons that together predict a protein of 116 amino acids. An exemplary lentiviral Rev protein has the amino acid sequence (SEQ ID NO:46):

```
MAGRSGDSDE ELIRTVRLIK LLYQSNPPPN PEGTRQARRN

RRRRWRERQR QIHSISERIL GTYLGRSAEP VPLQLPPLER

LTLDCNEDCG TSGTQGVGSP QILVESPTVL ESGTKE
```

An illustrative polynucleotide that is capable of being processed to form Rev protein by transfected mammalian cells has the sequence (SEQ ID NO:47):

```
atgctgctac cattgtcaga tgtgttttct aaacaagggg ctcggaattc cccggatccg tcgactctag aggatctgca
```

-continued

```
tctcctatgg caggaagaag cggagacagc gacgaagacc tcctcaaggc agtcagactc atcaagtttc tctatcaaag caacccacct cccaatcccg aggggacccg acaggcccga aggaatagaa gaagaaggtg gagagagaga cagagacaga tccattcgat tagtgaacgg atccttagca cttatctggg acgatctgcg gagcctgtgc ctcttcagct accaccgctt gagagactta ctcttgattg taacgaggat tgtggaactt ctgggacgca gggggtggga agccctcaaa tattggtgga atctcctaca atattggagt caggagctaa agaatagtgc tgttagcttg ctcaatgcca cagctatagc agtagctgag gggacagata gggttataga agtagtacaa gaagcttata gagctattcg ccacatacct agaagaataa gacagggctt ggaaaggatt ttgctataag atgggtggca agtggtcaaa aagtagtgtg gttggatggc ctgctgtaag ggaaagaatg agacgagctg agccagcagc agatggggtg ggagcagcat ctcgagacct agaaaaacat ggagcaatca caagtagcaa cacagcagct aacaatgctg cttgtgcctg gctagaagca caagaggagg agaaggtggg ttttccagtc acacctcagg taccgagctc gaattcactc ctcaggtgca ggctgcctat cagaaggtgg tggctggtgt ggccaatgcc ctggctcaca aataccactg agatctttgt gaaggaacct tacttctgtg gtgtgacata attggacaaa ctacctacag agatttaaag ctctaaggta aatataaaat ttttaagtgt ataatgtgtt aaactactga ttctaattgt ttgtgtattt tagattccaa cctatggaac tgatgaatgg gagcagtggt ggaatgcctt taatgaggaa aacctgtttt gctcagaaga aatgccatct agtgatgatg aggctactgc tgactctcaa cattctactc
```

-continued

```
ctccaaaaaa gaagagaaag gtagaagacc ccaaggaactt tccttcagaa ttgctaagtt ttttgagtca tgctgtgttt agtaatagaa ctcttgcttg ctttgctatt tacaccacaa aggaaaaagc tgcactgcta tacaagaaaa ttatggaaaa atattctgta acctttataa gtaggcataa cagttataat cataacatac tgttttttct tactccacac aggcatagag tgtctgctat taataactat gctcaaaaat tgtgtacctt tagcttttta atttgtaaag gggttaataa ggaatatttg atgtatagtg ccttgactag agatcataat cagccatacc acatttgtag aggttttact tgctttaaaa aacctcccac acctccccct gaacctgaaa ca
```

As will be recognized, the Rev-encoding polynucleotide (SEQ ID NO:47) comprises an SV40 small t antigen intron (SEQ ID NO:48) (underlined above):

```
gtaaatataa aattttttaag tgtataatgt gttaaactac tgattctaat tgtttgtgta ttttag
```

As will also be realized, the Rev-encoding polynucleotide (SEQ ID NO:47) comprises a polynucleotide (SEQ ID NO:41) (double underlined above) that encodes the nuclear localization signal of the SV40 large T antigen (SEQ ID NO:40). The nuclear localization signal is in frame with an open reading frame (shown in bold above) that encodes a protein having the sequence of SEQ ID NO:45.

A further preferred feature of the REV vectors of the present invention is a polynucleotide that comprises a polyadenylation signal. An exemplary polynucleotide comprises the SV40 poly(A) signal site has the sequence of SEQ ID NO:42.

The double-stranded vector pREV (FIG. 14) is a preferred REV vector of the present invention that may be used with the LTR-containing vectors, packaging vectors and envelope vectors of the present invention to produce lentiviral particles that array a SARS-CoV-2 S protein on their surface. The polynucleotide sequence of the first strand of vector pREV is SEQ ID NO:49:

```
gagaggacat tccaatcata ggctgcccat ccaccctctg tgtcctcctg      50
ttaattaggt cacttaacaa aaaggaaatt gggtaggggt ttttcacaga     100
ccgctttcta agggtaattt taaaatatct gggaagtccc ttccactgct     150
gtgttccaga agtgttggta aacagcccac aaatgtcaac agcagaaaca     200
tacaagctgt cagctttgca caagggccca acaccctgct catcaagaag     250
cactgtggtt gctgtgttag taatgtgcaa aacaggaggc acattttccc     300
cacctgtgta ggttccaaaa tatctagtgt tttcattttt acttggatca     350
ggaacccagc actccactgg ataagcatta tccttatcca aaacagcctt     400
gtggtcagtg ttcatctgct gactgtcaac tgtagcattt tttggggtta     450
cagtttgagc aggatatttg gtcctgtagt ttgctaacac accctgcagc     500
tccaaaggtt cccaccaac agcaaaaaaa tgaaaatttg acccttgaat      550
gggttttcca gcaccatttt catgagtttt ttgtgtccct gaatgcaagt     600
```

-continued

| | |
|---|---|
| ttaacatagc agttacccca ataacctcag ttttaacagt aacagcttcc | 650 |
| cacatcaaaa tatttccaca ggttaagtcc tcatttaaat taggcaaagg | 700 |
| aattcttgaa gacgaaaggg cctcgtgata cgcctatttt tataggttaa | 750 |
| tgtcatgata ataatggttt cttagacgtc aggtggcact tttcggggaa | 800 |
| atgtgcgcgg aacccctatt tgtttatttt tctaaataca ttcaaatatg | 850 |
| tatccgctca tgagacaata accctgataa atgcttcaat aatattgaaa | 900 |
| aaggaagagt atgagtattc aacatttccg tgtcgccctt attccctttt | 950 |
| ttgcggcatt ttgccttcct gttttttgctc acccagaaac gctggtgaaa | 1000 |
| gtaaaagatg ctgaagatca gttgggtgca cgagtgggtt acatcgaact | 1050 |
| ggatctcaac agcggtaaga tccttgagag ttttcgcccc gaagaacgtt | 1100 |
| ttccaatgat gagcactttt aaagttctgc tatgtggcgc ggtattatcc | 1150 |
| cgtgttgacg ccgggcaaga gcaactcggt cgccgcatac actattctca | 1200 |
| gaatgacttg gttgagtact caccagtcac agaaaagcat cttacggatg | 1250 |
| gcatgacagt aagagaatta tgcagtgctg ccataaccat gagtgataac | 1300 |
| actgcggcca acttacttct gacaacgatc ggaggaccga aggagctaac | 1350 |
| cgcttttttg cacaacatgg gggatcatgt aactcgcctt gatcgttggg | 1400 |
| aaccggagct gaatgaagcc ataccaaacg acgagcgtga ccaccgcatg | 1450 |
| cctgcagcaa tggcaacaac gttgcgcaaa ctattaactg gcgaactact | 1500 |
| tactctagct tcccggcaac aattaataga ctggatggag gcggataaag | 1550 |
| ttgcaggacc acttctgcgc tcggcccttc cggctggctg gtttattgct | 1600 |
| gataaatctg gagccggtga gcgtgggtct cgcggtatca ttgcagcact | 1650 |
| ggggccagat ggtaagccct cccgtatcgt agttatctac acgacgggga | 1700 |
| gtcaggcaac tatggatgaa cgaaatagac agatcgctga gataggtgcc | 1750 |
| tcactgatta agcattggta actgtcagac caagtttact catatatact | 1800 |
| ttagattgat ttaaaacttc atttttaatt taaaaggatc taggtgaaga | 1850 |
| tcctttttga taatctcatg accaaaatcc cttaacgtga gttttcgttc | 1900 |
| cactgagcgt cagacccccgt agaaaagatc aaaggatctt cttgagatcc | 1950 |
| ttttttttctg cgcgtaatct gctgcttgca acaaaaaaa ccaccgctac | 2000 |
| cagcggtggt ttgtttgccg gatcaagagc taccaactct ttttccgaag | 2050 |
| gtaactggct tcagcagagc gcagatacca atactgtcc ttctagtgta | 2100 |
| gccgtagtta ggccaccact tcaagaactc tgtagcaccg cctacatacc | 2150 |
| tcgctctgct aatcctgtta ccagtggctg ctgccagtgg cgataagtcg | 2200 |
| tgtcttaccg ggttggactc aagacgatag ttaccggata aggcgcagcg | 2250 |
| gtcgggctga acggggggtt cgtgcacaca gcccagcttg gagcgaacga | 2300 |
| cctacaccga actgagatac ctacagcgtg agctatgaga aagcgccacg | 2350 |
| cttcccgaag ggagaaaggc ggacaggtat ccggtaagcg gcagggtcgg | 2400 |
| aacaggagag cgcacgaggg agcttccagg gggaaacgcc tggtatcttt | 2450 |
| atagtcctgt cgggtttcgc cacctctgac ttgagcgtcg attttttgtga | 2500 |
| tgctcgtcag gggggcggag cctatggaaa aacgccagca acgcggcctt | 2550 |
| tttacggttc ctggcctttt gctggccttt tgctcacatg ttctttcctg | 2600 |
| cgttatcccc tgattctgtg gataaccgta ttaccgcctt tgagtgagct | 2650 |

-continued

```
gataccgctc gccgcagccg aacgaccgag cgcagcgagt cagtgagcga      2700
ggaagcggaa gagcgcctga tgcggtattt tctccttacg catctgtgcg      2750
gtatttcaca ccgcatatgg tgcactctca gtacaatctg ctctgatgcc      2800
gcatagttaa gccagtatcc tcgaggcctc aaaaaagcc tcctcactac       2850 ttctggaata gctcagaggc cgaggcggcc tcggcctctg cataaataaa      2900
aaaaattagt cagccatgag cttggcccat tgcatacgtt gtatccatat      2950
cataatatgt acatttatat tggctcatgt ccaacattac cgccatgttg      3000
acattgatta ttgactagtt attaatagta atcaattacg gggtcattag      3050
ttcatagccc atatatggag ttccgcgtta cataacttac ggtaaatggc      3100
ccgcctggct gaccgcccaa cgacccccgc ccattgacgt caataatgac      3150
gtatgttccc atagtaacgc caatagggac tttccattga cgtcaatggg      3200
tggagtattt acggtaaact gcccacttgg cagtacatca agtgtatcat      3250
atgccaagta cgccccctat tgacgtcaat gacggtaaat ggcccgcctg      3300
gcattatgcc cagtacatga ccttatggga ctttcctact tggcagtaca      3350
tctacgtatt agtcatcgct attaccatgg tgatgcggtt ttggcagtac      3400
atcaatgggc gtggatagcg gtttgactca cggggatttc caagtctcca      3450
ccccattgac gtcaatggga gtttgttttg gcaccaaaat caacgggact      3500
ttccaaaatg tcgtaacaac tccgccccat tgacgcaaat gggcggtagg      3550
cgtgtacggt gggaggtcta taaagcaga gctcattaaa gtcctgcaac       3600 gagcccttt cacgcacttc agagcaggat gtggccactc aagaattggc       3650
cagacaaggg gaggaaatcc tctctcagct ataccgaccc ctagaaacat      3700
gcaataactc atgctattgt aagcgatgct gctaccattg tcagatgtgt      3750
tttctaaaca aggggctcgg aattccccgg atccgtcgac tctagaggat      3800
ctgcatctcc tatggcagga agaagcggag acagcgacga agacctcctc      3850
aaggcagtca gactcatcaa gtttctctat caaagcaacc cacctcccaa      3900
tcccgagggg acccgacagg cccgaaggaa tagaagaaga aggtggagag      3950
agagacagag acagatccat tcgattagtg aacggatcct tagcacttat      4000
ctgggacgat ctgcggagcc tgtgcctctt cagctaccac cgcttgagag      4050
acttactctt gattgtaacg aggattgtgg aacttctggg acgcaggggg      4100
tgggaagccc tcaaatattg gtggaatctc ctacaatatt ggagtcagga      4150
gctaaagaat agtgctgtta gcttgctcaa tgccacagct atagcagtag      4200
ctgaggggac agatagggtt atagaagtag tacaagaagc ttatagagct      4250
attcgccaca tacctagaag aataagacag gccttggaaa ggattttgct      4300
ataagatggg tggcaagtgg tcaaaaagta gtgtggttgg atggcctgct      4350
gtaagggaaa gaatgagacg agctgagcca gcagcagatg gggtgggagc      4400
agcatctcga gacctagaaa aacatggagc aatcacaagt agcaacacag      4450
cagctaacaa tgctgcttgt gcctggctag aagcacaaga ggaggagaag      4500
gtgggttttc cagtcacacc tcaggtaccg agctcgaatt cactcctcag      4550
gtgcaggctg cctatcagaa ggtggtggct ggtgtggcca atgccctggc      4600
tcacaaatac cactgagatc tttgtgaagg aaccttactt ctgtggtgtg      4650
acataattgg acaaactacc tacagagatt taaagctcta aggtaaatat      4700
```

-continued

```
aaaattttta agtgtataat gtgttaaact actgattcta attgtttgtg      4750
tattttagat tccaacctat ggaactgatg aatgggagca gtggtggaat      4800
gcctttaatg aggaaaacct gttttgctca gaagaaatgc catctagtga      4850
tgatgaggct actgctgact ctcaacattc tactcctcca aaaaagaaga      4900
gaaaggtaga agaccccaag gactttcctt cagaattgct aagtttttg       4950 agtcatgctg tgtttagtaa tagaactctt gcttgctttg ctatttacac      5000
cacaaaggaa aaagctgcac tgctatacaa gaaaattatg gaaaaatatt      5050
ctgtaacctt tataagtagg cataacagtt ataatcataa catactgttt      5100
tttcttactc cacacaggca tagagtgtct gctattaata actatgctca      5150
aaaattgtgt acctttagct ttttaatttg taaaggggtt aataaggaat      5200
atttgatgta tagtgccttg actagagatc ataatcagcc ataccacatt      5250
tgtagaggtt ttacttgctt taaaaaacct cccacacctc cccctgaacc      5300
tgaaacataa aatgaatgca attgttgttg ttaacttgtt tattgcagct      5350
tataatggtt acaaataaag caatagcatc acaaatttca caaataaagc      5400
atttttttca ctgcattcta gttgtggttt gtccaaactc atcaatgtat      5450
cttatcatgt ctggatcccc aggaagctcc tctgtgtcct cataaaccct      5500
aacctcctct actt                                             5514
```

As will be noted, residues 806-910 of SEQ ID NO:49 correspond to AmpR promoter (SEQ ID NO:16). Residues 911-1771 of SEQ ID NO:49 correspond to a polynucleotide (SEQ ID NO:24) that encodes an AmpR determinant (SEQ ID NO:23). Residues 1942-2530 of SEQ ID NO:49 correspond to a high-copy-number ColE1/pMB/pBR322/pUC origin of replication (SEQ ID NO:20). Residues 3000-3379 of SEQ ID NO:49 correspond to the CMV immediate early enhancer site (SEQ ID NO:4). Residues 3380-3583 of SEQ ID NO:49 correspond to the CMV immediate early promoter site (SEQ ID NO:5). Residues 3726-5310 of SEQ ID NO:49 correspond to a polynucleotide (SEQ ID NO:47) that is processed by mammalian cells to produce the HIV-1 Rev protein (SEQ ID NO:46). Residues 4693-4758 of such sequence includes an SV40 small t intron (SEQ ID NO:48), and residues 4888-4908 of such sequence comprises a polynucleotide (SEQ ID NO:41) that encodes the nuclear localization signal of the SV40 large T antigen (SEQ ID NO:40) and permits transcription of a protein having the sequence of SEQ ID NO:45. Residues 3726-5310 of SEQ ID NO:49 correspond to an SV40 poly(A) signal site (SEQ ID NO:42).

D. Envelope Vectors of the Present Invention

As used herein, the term "Envelope Vector" is intended to denote a vector that comprises a polynucleotide that encodes a heterologous protein (and especially the SARS-CoV-2 S protein) and a promoter sufficient to mediate the transcription of such gene in a mammalian cell.

Most preferably, the envelope vector of the present invention will be a double-stranded DNA plasmid. The structure of a preferred envelope vector (pCMV-SARS-CoV-2 S Protein) is shown in FIG. 15, and comprises 8,602 base pairs. The preferred envelope vectors of the present invention comprise multiple features.

The first of such features is optional and comprises primer binding sites to facilitate sequencing of the vector. Exemplary sites for such purpose are M13 Fwd and Rev primer binding sites. An exemplary M13 Fwd primer binding site comprises the sequence (SEQ ID NO:50):

gtaaaacgacggccagt, and hybridizes to the first strand of the vector. An exemplary M13 Rev primer binding site comprises the sequence (SEQ ID NO:51):

caggaaacagctatgac, and hybridizes to the second strand of the vector.

A further feature is a first promoter that will direct transcription in a bacterial host. Suitable promoters are described above. An exemplary promoter is the T7 promoter site, which comprises the sequence of SEQ ID NO:12.

A further feature is a promoter (and an optional upstream transcriptional enhancer site) that will facilitate and mediate transcription in a mammalian host cell. Exemplary polynucleotides that comprise suitable enhancer and promoter sites are discussed above. An exemplary CMV immediate early enhancer site comprises the sequence of SEQ ID NO:1. An exemplary CMV immediate early promoter site comprises the sequence (SEQ ID NO:52):

gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agct

A further feature is an intron capable of improving gene expression of downstream genes in a mammalian host cell.

An exemplary intron capable of such function is a beta-globin intron (Haddad-Mashadrizeh, A. et al. (2009) "*A Systematic Study Of The Function Of The Human Beta-Globin Introns On The Expression Of The Human Coagulation Factor IX In Cultured Chinese Hamster Ovary Cells,*" J. Gene. Med. 11(10):941-950). An exemplary beta-globin intron comprises the sequence (SEQ ID NO:53):

```
gtgagtttgg ggacccttga ttgttcttc tttttcgcta ttgtaaaatt catgttatat ggaggggggca aagttttcag ggtgttgttt agaatgggaa gatgtcccctt gtatcaccat ggaccctcat gataattttg tttctttcac tttctactct gttgacaacc attgtctcct cttatttct tttcattttc tgtaactttt tcgttaaact ttagcttgca tttgtaacga attttaaat tcacttttgt ttatttgtca gattgtaagt actttctcta atcacttttt tttcaaggca atcagggtat attatattgt acttcagcac agttttagag aacaattgtt ataattaaat gataaggtag aatatttctg catataaatt ctggctggcg tggaaatatt cttattggta gaaacaacta caccctggtc atcatcctgc ctttctcttt atggttacaa tgatatacac tgtttgagat gaggataaaa tactctgagt ccaaaccggg ccctctgct aaccatgttc atgccttctt ctctttccta cag
```

A further feature is a SARS-CoV-2 S protein encoding sequence that is operably controlled by the upstream mammalian-host promoter (e.g., the CMV immediate early promoter and enhancer sites) so that, upon co-transfection with the LTR-containing vectors, packaging vectors and REV vectors of the present invention, recipient host cells will produce lentiviral particles that are pseudotyped to array the SARS-CoV-2 S protein on their surfaces. An exemplary envelope vector is pseudotyped to array the SARS-CoV-2 S protein of GenBank YP_009724390.1 (Wu, F. et al. (2020) "*A New Coronavirus Associated With Human Respiratory Disease In China,*" Nature 579(7798):265-269), desirably as modified by the deletion of the C-terminal 18 amino acid residues thereof (a potential endoplasmic retention sequence) (SEQ ID NO:54), or to array a polymorphic variant thereof whose sequence differs from the sequence of SEQ ID NO:54 by less than 2%. Exemplary polymorphic variants of the SARS-CoV-2 S protein GenBank YP_009724390.1 are listed in Table 1.

SARS-CoV-2 S protein (derived from GenBank YP_009724390.1 by the removal of the C-terminal 18 amino acid residues thereof) (SEQ ID NO:54) (the S1 domain thereof shown in boldface; the S2 domain thereof is shown double underlined):

```
MFVFLVLLPL VSSQCVNLTT RTQLPPAYTN SFTRGVYYPD

KVFRSSVLHS TQDLFLPFFS NVTWFHAIHV SGTNGTKRFD

NPVLPFNDGV YFASTEKSNI IRGWIFGTTL DSKTQSLLIV

NNATNVVIKV CEFQFCNDPF LGVYYHKNNK SWMESEFRVY

SSANNCTFEY VSQPFLMDLE GKQGNFKNLR EFVFKNIDGY

FKIYSKHTPI NLVRDLPQGF SALEPLVDLP IGINITRFQT

LLALHRSYLT PGDSSSGWTA GAAAYYVGYL QPRTFLLKYN

ENGTITDAVD CALDPLSETK CTLKSFTVEK GIYQTSNFRV

QPTESIVRFP NITNLCPFGE VFNATRFASV YAWNRKRISN

CVADYSVLYN SASFSTFKCY GVSPTKLNDL CFTNVYADSF

VIRGDEVRQI APGQTGKIAD YNYKLPDDFT GCVIAWNSNN

LDSKVGGNYN YLYRLFRKSN LKPFERDIST EIYQAGSTPC

NGVEGFNCYF PLQSYGFQPT NGVGYQPYRV VVLSFELLHA

PATVCGPKKS TNLVKNKCVN FNFNGLTGTG VLTESNKKFL

PFQQFGRDIA DTTDAVRDPQ TLEILDITPC SFGGVSVITP

GTNTSNQVAV LYQDVNCTEV PVAIHADQLT PTWRVYSTGS

NVFQTRAGCL IGAEHVNNSY ECDIPIGAGI CASYQTQTNS

PRRARSVASQ SIIAYTMSLG AENSVAYSNN SIAIPTNFTI

SVTTEILPVS MTKTSVDCTM YICGDSTECS NLLLQYGSFC

TQLNRALTGI AVEQDKNTQE VFAQVKQIYK TPPIKDFGGF

NFSQILPDPS KPSKRSFIED LLFNKVTLAD AGFIKQYGDC

LGDIAARDLI CAQKFNGLTV LPPLLTDEMI AQYTSALLAG

TITSGWTFGA GAALQIPFAM QMAYRFNGIG VTQNVLYENQ

KLIANQFNSA IGKIQDSLSS TASALGKLQD VVNQNAQALN

TLVKQLSSNF GAISSVLNDI LSRLDKVEAE VQIDRLITGR

LQSLQTYVTQ QLIRAAEIRA SANLAATKMS ECVLGQSKRV

DFCGKGYHLM SFPQSAPHGV VFLHVTYVPA QEKNFTTAPA

ICHDGKAHFP REGVFVSNGT HWFVTQRNFY EPQIITTDNT

FVSGNCDVVI GIVNNTVYDP LQPELDSFKE ELDKYFKNHT

SPDVDLGDIS GINASVVNIQ KEIDRLNEVA KNLNESLIDL

QELGKYEQYI KWPWYIWLGF IAGLIAIVMV TIMLCCMTSC

CSCLKGCCSC GSCCK
```

TABLE 1

GenBank Reference of Polymorphic Variants of the SARS-CoV-2 S Protein of GenBank YP 009724390.1

| | | | |
|---|---|---|---|
| QHD43416.1 | QIS60930.1 | QIZ16197.1 | QJD47202.1 |
| (—) | (E96D) | (W258L; D614G) | (M731I) |
| QHR84449.1 | QIS60978.1 | QIZ16509.1 | QJD47358.1 |
| (S247R) | (D1168H) | (V772I) | (Y423X; D614G) |
| QHU79173.2 | QIS61254.1 | QIZ16559.1 | QJD47442.1 |
| (H49Y) | (A1078V) | (I197V) | (Y200X; D614G) |
| QHZ00379.1 | QIS61338.1 | QIZ64470.1 | QJD47718.1 |
| (S221W) | (D111N) | (D614G; A1078S) | (H49Y; S884F) |
| QIA20044.1 | QIS61422.1 | QIZ64530.1 | QJD48279.1 |
| (Y28N) | (H519Q) | (D614G; S939F) | (M1237I) |
| QIA98583.1 | QIS61468.1 | QIZ64578.1 | QJE38426.1 |
| (A930V) | (A942X) | (H146Y; D614G) | (A845S) |
| QIC53204.1 | QIT07011.1 | QIZ64624.1 | QJE38606.1 |
| (F797C) | (L8V) | (S98F) | (Y145H; D614G) |
| QII57278.1 | QIU78825.1 | QIZ97039.1 | QJE38822.1 |
| (F157L) | (G910X) | (N148S) | (S704X) |
| QII87830.1 | QIU80913.1 | QIZ97051.1 | QJF11959.1 |
| (H655Y) | (S5OL) | (Y279X; D614G) | (L752X) |

TABLE 1-continued

GenBank Reference of Polymorphic Variants of the SARS-CoV-2 S Protein of GenBank YP 009724390.1

| | | | |
|---|---|---|---|
| QIJ96493.1 (G181V) | QIU80973.1 (A27V) | QJA17276.1 (D614G; I818V) | QJF11971.1 (H655X) |
| QIK50427.1 (D614G) | QIU81585.1 (T240I) | QJA17468.1 (L5F; D614G) | QJF75467.1 (N354B) |
| QIO04367.1 (N74K) | QIU81873.2 (A653V) | QJA17524.1 (D614X; G1124X) | QJF75779.1 (V503X; D614G) |
| QIQ08810.1 (K528X) | QIU81885.1 (A570V) | QJA17596.1 (D614G; L1203F) | QJF76007.1 (S704L) |
| QIQ49882.1 (L5F; G476S) | QIV15164.1 (Q644X) | QJA42177.1 (D614G; V1065L) | QJF76438.1 (L118F; D614G) |
| QIQ50092.1 (K814X) | QIV65033.1 (Y265X) | QJC19491.1 (Q271R; D614G)) | QJF77194.1 (A27S; D614G) |
| QIS30105.1 (D614X) | QIZ13143.1 (L1152X)) | QJC20043.1 (K529E; D614G) | QJF77846.1 (Y28H) |
| QIS30115.1 (P427X; D614G) | QIZ13179.1 (S71F) | QJC20367.1 (D614G; S9291) | QJG65949.1 (G485R) |
| QIS30165.1 (V483A) | QIZ13299.1 (D80Y) | QJC20391.1 (D614G; T768I) | QJG65951.1 (A67S; F1103L) |
| QIS30295.1 (L54F; D614G) | QIZ13765.1 (D614G; V615F) | QJC20993.1 (V367F) | QJG65954.1 (S750R; L752R) |
| QIS30335.1 (A348T) | QIZ13789.1 (D614G; V6221) | QJD20632.1 (T791I) | QJG65956.1 (G838S) |
| QIS30425.1 (G476S) | QIZ13861.1 (V70F) | QJD23273.1 (V90F; D614G) | QJG65957.1 (W152R) |
| QIS60489.1 (A520S) | QIZ14569.1 (C1250Y) | QJD23524.1 (P217X) | QJI53955.1 (Q239R; D614G) |
| QIS60546.1 (T29I) | QIZ15585.1 (D614G; V1228X) | QJD24377.1 (A522S; D614G) | QJQ04352.1 (D614G; T676S) |
| QIS60582.1 (D1259H) | QIZ15717.1 (P9L) | QJD25085.1 (F220X; D614G) | QJQ27878.1 (K557X) |
| QIS60906.1 (L5F) | QIZ15969.1 (F238X; D614G) | QJD25529.1 (D614G; P631S) | QJQ28105.1 (T951; D614G) |

An exemplary polynucleotide that encodes the SARS-CoV-2 S Protein of SEQ ID NO:54 has the sequence of the S protein of SARS-CoV-2/human/USA/WA-UW-6547/2020 (Genflank: MT461658.1) (SEQ ID NO: 55):

```
atgtttgttt ttcttgtttt attgccacta gtctctagtc agtgtgttaa tcttacaacc agaactcaat taccccctgc atacactaat tctttcacac gtggtgttta ttaccctgac aaagttttca gatcctcagt tttacattca actcaggact tgttcttacc tttcttttcc aatgttactt ggttccatgc tatacatgtc tctgggacca atggtactaa gaggtttgat aaccctgtcc taccatttaa tgatggtgtt tatttgctt ccactgagaa gtctaacata ataagaggct ggattttttgg tactacttta gattcgaaga cccagtccct acttattgtt aataacgcta ctaatgttgt tattaaagtc tgtgaattc aattttgtaa tgatccattt tgggtgttt attaccacaa aaacaacaaa agttggatgg aaagtgagtt cagagtttat tctagtgcga ataattgcac ttttgaatat gtctctcagc cttttcttat ggaccttgaa ggaaaacagg gtaatttcaa aaatcttagg gaatttgtgt ttaagaatat tgatggttat ttttaaaatat attctaagca cacgcctatt aatttagtgc gtgatctccc tcagggtttt tcggcttag aaccattggt agatttgcca ataggtatta acatcactag gtttcaaact ttacttgctt tacatagaag ttatttgact cctggtgatt cttcttcagg ttggacagct ggtgctgcag cttattatgt gggttatctt caacctagga cttttctatt aaaatataat gaaaatggaa ccattacaga tgctgtagac tgtgcacttg accctctctc agaaacaaag tgtacgttga aatccttcac tgtagaaaaa ggaatctatc aaacttctaa ctttagagtc caaccaacag aatctattgt tagatttcct aatattacaa acttgtgccc ttttggtgaa gttttaacg ccaccagatt tgcatctgtt tatgcttgga acaggaagag aatcagcaac tgtgttgctg attattctgt cctatataat tccgcatcat tttccacttt taagtgttat ggagtgtctc ctactaaatt aaatgatctc tgctttacta atgtctatgc agattcattt gtaattagag gtgatgaagt cagacaaatc gctccagggc aaactggaaa gattgctgat tataattata aattaccaga tgattttaca ggctgcgtta tagcttggaa ttctaacaat cttgattcta aggttggtgg taattataat tacctgtata gattgtttag gaagtctaat ctcaaacctt ttgagagaga tatttcaact gaaatctatc aggccggtag cacaccttgt aatggtgttg aaggttttaa ttgttacttt cctttacaat catatggttt ccaacccact aatggtgttg gttaccaacc atacagagta gtagtacttt cttttgaact tctacatgca ccagcaactg tttgtggacc taaaaagtct actaatttgg ttaaaaacaa atgtgtcaat ttcaacttca atggtttaac aggcacaggt gttcttactg agtctaacaa aaagtttctg cctttccaac aatttggcag agacattgct gacactactg atgctgtccg tgatccacag acacttgaga ttcttgacat tacaccatgt tctttggtg gtgtcagtgt tataaccaca ggaacaaata cttctaacca ggttgctgtt ctttatcagg atgttaactg cacagaagtc cctgttgcta ttcatgcaga tcaacttact cctacttggc gtgtttattc tacaggttct aatgttttc aaacacgtgc aggctgttta ataggggctg aacatgtcaa caactcatat gagtgtgaca tacccattgg tgcaggtata tgcgctagtt atcagactca gactaattct cctcggcggg cacgtagtgt agctagtcaa tccatcattg cctacactat gtcacttggt gcagaaaatt cagttgctta ctctaataac tctattgcca tacccacaaa ttttactatt agtgttacca cagaaattc accagtgtct atgaccaaga catcagtaga ttgtacaatg tacatttgtg gtgattcaac tgaatgcagc aatcttttgt tgcaatatgg cagttttgt acacaattaa accgtgcttt aactggaata gctgttgaac
```

-continued

```
aagacaaaaa cacccaagaa gtttttgcac aagtcaaaca
aatttacaaa acaccaccaa ttaaagattt tggtggtttt
aattttcac aaatattacc agatccatca aaaccaagca
agaggtcatt tattgaagat ctacttttca acaaagtgac
acttgcagat gctggcttca tcaaacaata tggtgattgc
cttggtgata ttgctgctag agacctcatt tgtgcacaaa
agtttaacgg ccttactgtt ttgccaccttt tgctcacaga
tgaaatgatt gctcaataca cttctgcact gttagcgggt
acaatcactt ctggttggac ctttggtgca ggtgctgcat
tacaaatacc atttgctatg caaatggctt ataggtttaa
tggtattgga gttacacaga atgttctcta tgagaaccaa
aaattgattg ccaaccaatt taatagtgct attggcaaaa
ttcaagactc actttcttcc acagcaagtg cacttggaaa
acttcaagat gtggtcaacc aaaatgcaca agctttaaac
acgcttgtta aacaacttag ctccaatttt ggtgcaattt
caagtgtttt aaatgatatc ctttcacgtc ttgacaaagt
tgaggctgaa gtgcaaattg ataggttgat cacaggcaga
cttcaaagtt tgcagacata tgtgactcaa caattaatta
gagctgcaga aatcagagct tctgctaatc ttgctgctac
taaaatgtca gagtgtgtac ttggacaatc aaaaagagtt
gattttgtg gaaagggcta tcatcttatg tccttccctc
agtcagcacc tcatggtgta gtcttcttgc atgtgactta
tgtccctgca caagaaaaga acttcacaac tgctcctgcc
atttgtcatg atggaaaagc acactttcct cgtgaaggtg
tctttgtttc aaatggcaca cactggtttg taacacaaag
gaattttat gaaccacaaa tcattactac agacaacaca
tttgtgtctg gtaactgtga tgttgtaata ggaattgtca
acaacacagt ttatgatcct ttgcaacctg aattagactc
attcaaggag gagttagata aatattttaa gaatcataca
tcaccagatg ttgatttagg tgacatctct ggcattaatg
cttcagttgt aaacattcaa aaagaaattg accgcctcaa
tgaggttgcc aagaatttaa atgaatctct catcgatctc
caagaacttg gaaagtatga gcagtatata aaatgccat
ggtacatttg gctaggtttt atagctggct tgattgccat
agtaatggtg acaattatgc tttgctgtat gaccagttgc
tgtagttgtc tcaagggctg ttgttcttgt ggatcctgct
gcaaa
```

A second suitable polynucleotide that encodes the SARS-CoV-2 S Protein of SEQ ID NO: 54 has the sequence of SEQ ID NO:71.

A further feature is a polyadenylation (poly(A)) signal sequence. An illustrative poly(A) signal sequence is a beta-globin poly(A) signal sequence. An exemplary beta-globin poly(A) signal sequence comprises the sequence (SEQ ID NO:56):

```
aataaaggaa atttattttc attgcaatag tgtgttggaa
tttttgtgt ctctca
```

A further feature is a second promoter that will direct transcription in a bacterial host. Suitable promoters are discussed above. An illustrative polynucleotide for such purpose comprises a lac operator and a lac promoter site. An exemplary lac operator site comprises the sequence (SEQ ID NO:57):

```
ttgtgagcggataacaa
```

(positioned on the second strand of the vector). An exemplary lac promoter site comprises the sequence (SEQ ID NO:58):

```
tttacactttatgcttccggctcgtatgttg.
```

A further feature is an *E. coli* catabolite activator protein (CAP) binding site that comprises the sequence (SEQ ID NO:59):

```
taatgtgagttagctcactcat
```

(positioned on the second strand of the vector).

A further feature is an origin of replication capable of mediating the replication of the vector in prokaryotic cells. An exemplary origin or replication site for this purpose is the high-copy-number ColE1/pMB1/pBR322/pUC origin (SEQ ID NO:19).

A further feature is a gene that encodes an antibiotic resistance determinant, such as AmpR, which confers resistance to ampicillin, carbenicillin, and related antibiotics to bacterial cells transfected with the vector. The antibiotic resistance determinant is operably controlled by a promoter, such as the AmpR promoter, and both polynucleotide sequences are preferably positioned on the second stand of the vector. An exemplary AmpR antibiotic resistance determinant comprises the sequence of SEQ ID NO:21. An exemplary polynucleotide that encodes the AmpR antibiotic resistance determinant of SEQ ID NO:21 has the sequence of SEQ ID NO:22. An exemplary AmpR promoter-containing polynucleotide has the sequence of SEQ ID NO:26.

A further feature is a single-strand origin of replication, such as an origin of replication of the f1 bacteriophage, which is preferably positioned on the second stand of the vector. An exemplary polynucleotide that comprises an f1 bacteriophage origin of replication comprises the sequence (SEQ ID NO:60):

```
acgcgccctg tagcggcgca ttaagcgcgg cgggtgtggt
ggttacgcgc agcgtgaccg ctacacttgc cagcgcccta
gcgcccgctc ctttcgcttt cttcccttcc tttctcgcca
cgttcgccgg ctttccccgt caagctctaa atcgggggct
ccctttaggg ttccgattta gtgctttacg gcacctcgac
cccaaaaaac ttgattaggg tgatggttca cgtagtgggc
```

-continued

```
catcgccctg atagacggtt tttcgccctt tgacgttgga gtccacgttc tttaatagtg gactcttgtt ccaaactgga acaacactca accctatctc ggtctattct tttgatttat aagggatttt gccgatttcg gcctattggt taaaaaatga gctgatttaa caaaaattta acgcgaattt taacaaaata ttaacgctta caattt
```

Figure 15:
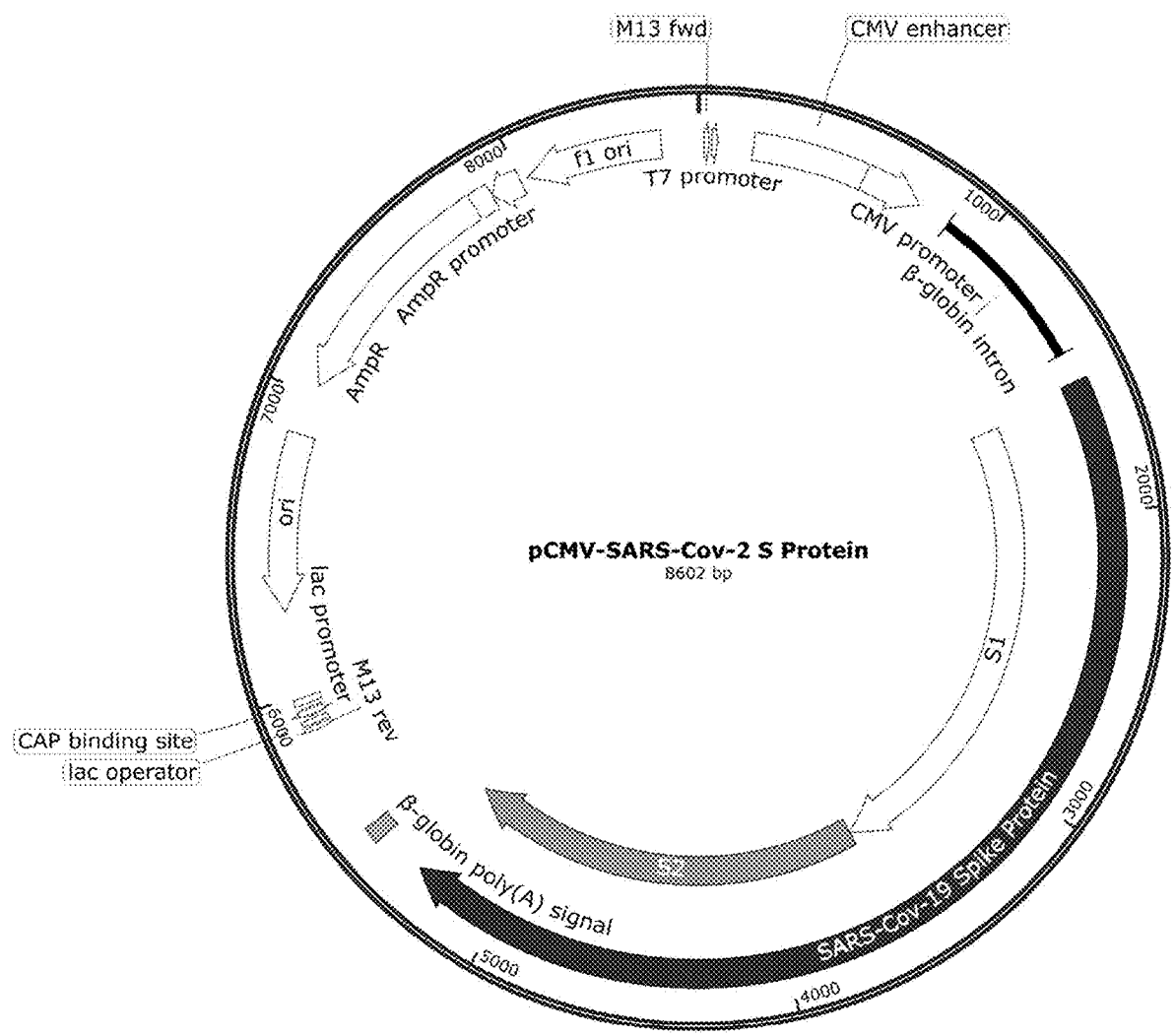
FIG. 15 provides the structure of pCMV-SARS-CoV-2 S Protein (SEQ ID NO:61) (8602 nucleotide residues), which is an example of an envelope vector of the present invention.

The vector pCMV-SARS-CoV-2 S Protein (FIG. 15) is a preferred envelope vector of the present invention that may be used with the LTR-containing vectors, packaging vectors, and REV vectors of the present invention to produce lentiviral particles that array a SARS-CoV-2 S protein on their surface. The invention contemplates that two or more different vectors may be employed in order to produce pseudotyped lentiviral particles that array both the SARS-CoV-2 S protein and one or more different proteins (e.g., the hemagglutinin (HA) protein of influenza virus, the SARS-CoV S protein, the MERS-CoV S protein, etc.).

The polynucleotide sequence of the SARS-CoV-2 S protein-coding ("first") strand of vector pCMV-SARS-CoV-2 S Protein is SEQ ID NO:61.

```
gttttcccag tcacgacgtt gtaaaacgac ggccagtgag cgcgcgtaat    50
acgactcact atagggcgaa ttggagctcc accgcggtgg cggccgctct   100
agagagcttg gcccattgca tacgttgtat ccatatcata atatgtacat   150
ttatattggc tcatgtccaa cattaccgcc atgttgacat tgattattga   200
ctagttatta atagtaatca attacggggt cattagttca tagcccatat   250
atggagttcc gcgttacata acttacggta atggcccgc ctggctgacc    300 gcccaacgac ccccgcccat tgacgtcaat aatgacgtat gttcccatag   350
taacgccaat agggactttc cattgacgtc aatgggtgga gtatttacgg   400
taaactgccc acttggcagt acatcaagtg tatcatatgc caagtacgcc   450
ccctattgac gtcaatgacg gtaaatggcc cgcctggcat tatgcccagt   500
acatgacctt atgggacttt cctacttggc agtacatcta cgtattagtc   550
atcgctatta ccatggtgat gcggttttgg cagtacatca atgggcgtgg   600
atagcggttt gactcacggg gatttccaag tctccacccc attgacgtca   650
atgggagttt gttttggcac caaaatcaac gggactttcc aaaatgtcgt   700
aacaactccg ccccattgac gcaaatgggc ggtaggcgtg tacggtggga   750
ggtctatata agcagagctc gtttagtgaa ccgtcagatc gcctggagac   800
gccatccacg ctgttttgac ctccatagaa gacaccggga ccgatccagc   850
ctccggtcga ccgatcctga aacttcagg gtgagtttgg ggacccttga    900
ttgttctttc ttttcgcta ttgtaaaatt catgttatat ggagggggca    950
aagttttcag ggtgttgttt agaatgggaa gatgtccctt gtatcaccat  1000
ggaccctcat gataattttg tttctttcac tttctactct gttgacaacc  1050
attgtctcct cttattttct tttcattttc tgtaactttt tcgttaaact  1100
ttagcttgca tttgtaacga ttttttaaat tcacttttgt ttatttgtca  1150
gattgtaagt actttctcta atcactttt tttcaaggca atcagggtat  1200
attatattgt acttcagcac agttttagag aacaattgtt ataattaaat  1250
gataaggtag aatatttctg catataaatt ctggctggcg tggaaatatt  1300
cttattggta gaaacaacta caccctggtc atcatcctgc ctttctcttt  1350
atggttacaa tgatatacac tgtttgagat gaggataaaa tactctgagt  1400
ccaaaccggg cccctctgct aaccatgttc atgccttctt ctctttccta  1450
cagctcctgg gcaacgtgct ggttgttgtg ctgtctcatc attttggcaa  1500
agaattcctc gacggatccg gtaccgagga gatctgccgc cgcgatcgcc  1550
accatgtttg tttttcttgt tttattgcca ctagtctcta gtcagtgtgt  1600
```

-continued

```
taatcttaca accagaactc aattacccc tgcatacact aattctttca    1650
cacgtggtgt ttattaccct gacaaagttt tcagatcctc agttttacat    1700
tcaactcagg acttgttctt acctttcttt tccaatgtta cttggttcca    1750
tgctatacat gtctctggga ccaatggtac taagaggttt gataaccctg    1800
tcctaccatt taatgatggt gtttattttg cttccactga gaagtctaac    1850
ataataagag gctggatttt tggtactact ttagattcga agacccagtc    1900
cctacttatt gttaataacg ctactaatgt tgttattaaa gtctgtgaat    1950
ttcaattttg taatgatcca ttttggggtg tttattacca caaaaacaac    2000
aaaagttgga tggaaagtga gttcagagtt tattctagtg cgaataattg    2050
cacttttgaa tatgtctctc agccttttct tatggacctt gaaggaaaac    2100
agggtaattt caaaaatctt agggaatttg tgtttaagaa tattgatggt    2150
tattttaaaa tatattctaa gcacacgcct attaatttag tgcgtgatct    2200
ccctcagggt ttttcggctt tagaaccatt ggtagatttg ccaataggta    2250
ttaacatcac taggtttcaa actttacttg ctttacatag aagttatttg    2300
actcctggtg attcttcttc aggttggaca gctggtgctg cagcttatta    2350
tgtgggttat cttcaaccta ggacttttct attaaaatat aatgaaaatg    2400
gaaccattac agatgctgta gactgtgcac ttgaccctct ctcagaaaca    2450
aagtgtacgt tgaaatcctt cactgtagaa aaggaatct atcaaacttc    2500 taactttaga gtccaaccaa cagaatctat tgttagattt cctaatatta    2550
caaacttgtg ccctttttggt gaagttttta acgccaccag atttgcatct    2600
gtttatgctt ggaacaggaa gagaatcagc aactgtgttg ctgattattc    2650
tgtcctatat aattccgcat cattttccac ttttaagtgt tatggagtgt    2700
ctcctactaa attaaatgat ctctgcttta ctaatgtcta tgcagattca    2750
tttgtaatta gaggtgatga agtcagacaa atcgctccag ggcaaactgg    2800
aaagattgct gattataatt ataaattacc agatgatttt acaggctgcg    2850
ttatagcttg gaattctaac aatcttgatt ctaaggttgg tggtaattat    2900
aattacctgt atagattgtt taggaagtct aatctcaaac cttttgagag    2950
agatatttca actgaaatct atcaggccgg tagcacacct tgtaatggtg    3000
ttgaaggttt taattgttac tttcctttac aatcatatgg tttccaaccc    3050
actaatggtg ttggttacca accatacaga gtagtagtac tttcttttga    3100
acttctacat gcaccagcaa ctgtttgtgg acctaaaaag tctactaatt    3150
tggttaaaaa caaatgtgtc aatttcaact tcaatggttt aacaggcaca    3200
ggtgttctta ctgagtctaa caaaaagttt ctgcctttcc aacaatttgg    3250
cagagacatt gctgacacta ctgatgctgt ccgtgatcca cagacacttg    3300
agattcttga cattacacca tgttctttg gtggtgtcag tgttataaca    3350
ccaggaacaa atacttctaa ccaggttgct gttctttatc aggatgttaa    3400
ctgcacagaa gtccctgttg ctattcatgc agatcaactt actcctactt    3450
ggcgtgttta ttctacaggt tctaatgttt ttcaaacacg tgcaggctgt    3500
ttaatagggg ctgaacatgt caacaactca tatgagtgtg acatacccat    3550
tggtgcaggt atatgcgcta gttatcagac tcagactaat tctcctcggc    3600
gggcacgtag tgtagctagt caatccatca ttgcctacac tatgtcactt    3650
```

-continued

```
ggtgcagaaa attcagttgc ttactctaat aactctattg ccatacccac    3700
aaattttact attagtgtta ccacagaaat tctaccagtg tctatgacca    3750
agacatcagt agattgtaca atgtacattt gtggtgattc aactgaatgc    3800
agcaatcttt tgttgcaata tggcagtttt tgtacacaat taaaccgtgc    3850
tttaactgga atagctgttg aacaagacaa aaacacccaa gaagttttg    3900 cacaagtcaa acaaatttac aaaacaccac caattaaaga ttttggtggt    3950
tttaattttt cacaaatatt accagatcca tcaaaaccaa gcaagaggtc    4000
atttattgaa gatctacttt tcaacaaagt gacacttgca gatgctggct    4050
tcatcaaaca atatggtgat tgccttggtg atattgctgc tagagacctc    4100
atttgtgcac aaaagtttaa cggccttact gttttgccac ctttgctcac    4150
agatgaaatg attgctcaat acacttctgc actgttagcg ggtacaatca    4200
cttctggttg gacctttggt gcaggtgctg cattacaaat accatttgct    4250
atgcaaatgg cttataggtt taatggtatt ggagttacag agaatgttct    4300
ctatgagaac caaaaattga ttgccaacca atttaatagt gctattggca    4350
aaattcaaga ctcactttct tccacagcaa gtgcacttgg aaaacttcaa    4400
gatgtggtca accaaaatgc acaagcttta acacgcttg ttaaacaact    4450 tagctccaat tttggtgcaa tttcaagtgt tttaaatgat atcctttcac    4500
gtcttgacaa agttgaggct gaagtgcaaa ttgataggtt gatcacaggc    4550
agacttcaaa gtttgcagac atatgtgact caacaattaa ttagagctgc    4600
agaaatcaga gcttctgcta atcttgctgc tactaaaatg tcagagtgtg    4650
tacttggaca atcaaaaaga gttgatttt gtggaaaggg ctatcatctt    4700
atgtccttcc ctcagtcagc acctcatggt gtagtcttct tgcatgtgac    4750
ttatgtccct gcacaagaaa agaacttcac aactgctcct gccatttgtc    4800
atgatggaaa agcacacttt cctcgtgaag gtgtctttgt ttcaaatggc    4850
acacactggt ttgtaacaca aaggaatttt tatgaaccac aaatcattac    4900
tacagacaac acatttgtgt ctggtaactg tgatgttgta ataggaattg    4950
tcaacaacac agtttatgat cctttgcaac ctgaattaga ctcattcaag    5000
gaggagttag ataaatattt taagaatcat acatcaccag atgttgattt    5050
aggtgacatc tctggcatta atgcttcagt tgtaaacatt caaaaagaaa    5100
ttgaccgcct caatgaggtt gccaagaatt taaatgaatc tctcatcgat    5150
ctccaagaac ttggaaagta tgagcagtat ataaaatggc catggtacat    5200
ttggctaggt tttatagctg gcttgattgc catagtaatg gtgacaatta    5250
tgctttgctg tatgaccagt tgctgtagtt gtctcaaggg ctgttgttct    5300
tgtggatcct gctgcaaata acctcaggtg caggctgcct atcagaaggt    5350
ggtggctggt gtggccaatg ccctggctca caaataccac tgagatcttt    5400
ttccctctgc caaaaattat ggggacatca tgaagcccct tgagcatctg    5450
acttctggct aataaaggaa atttatttc attgcaatag tgtgttggaa    5500
ttttttgtgt ctctcactcg gaaggacata tgggagggca aatcatttaa    5550
aacatcagaa tgagtatttg gtttagagtt tggcaacata tgcccatatg    5600
ctggctgcca tgaacaaagg ttggctataa agaggtcatc agtatatgaa    5650
acagccccct gctgtccatt ccttattcca tagaaaagcc ttgacttgag    5700
```

```
                                -continued
gttagattttt ttttatattt tgttttgtgt tatttttttc tttaacatcc    5750 ctaaaattttt ccttacatgt tttactagcc agatttttcc tcctctcctg    5800
actactccca gtcatagctg tccctcttct cttatggaga tccctcgacg    5850
gatcggccgc aattcgtaat catgtcatag ctgtttcctg tgtgaaattg    5900
ttatccgctc acaattccac acaacatacg agccggaagc ataaagtgta    5950
aagcctgggg tgcctaatga gtgagctaac tcacattaat tgcgttgcgc    6000
tcactgcccg ctttccagtc gggaaacctg tcgtgccagc tgcattaatg    6050
aatcggccaa cgcgcgggga gaggcggttt gcgtattggg cgctcttccg    6100
cttcctcgct cactgactcg ctgcgctcgg tcgttcggct gcggcgagcg    6150
gtatcagctc actcaaaggc ggtaatacgg ttatccacag aatcagggga    6200
taacgcagga aagaacatgt gagcaaaagg ccagcaaaag gccaggaacc    6250
gtaaaaaggc cgcgttgctg gcgtttttcc ataggctccg cccccctgac    6300
gagcatcaca aaaatcgacg ctcaagtcag aggtggcgaa acccgacagg    6350
actataaaga taccaggcgt ttccccctgg aagctccctc gtgcgctctc    6400
ctgttccgac cctgccgctt accggatacc tgtccgcctt tctcccttcg    6450
ggaagcgtgg cgctttctca tagctcacgc tgtaggtatc tcagttcggt    6500
gtaggtcgtt cgctccaagc tgggctgtgt gcacgaaccc cccgttcagc    6550
ccgaccgctg cgccttatcc ggtaactatc gtcttgagtc caacccggta    6600
agacacgact tatcgccact ggcagcagcc actggtaaca ggattagcag    6650
agcgaggtat gtaggcggtg ctacagagtt cttgaagtgg tggcctaact    6700
acggctacac tagaagaaca gtatttggta tctgcgctct gctgaagcca    6750
gttaccttcg gaaaaagagt tggtagctct tgatccggca aacaaaccac    6800
cgctggtagc ggtggttttt tgtttgcaa gcagcagatt acgcgcagaa    6850
aaaaaggatc tcaagaagat cctttgatct tttctacggg gtctgacgct    6900
cagtggaacg aaaactcacg ttaagggatt ttggtcatga gattatcaaa    6950
aaggatcttc acctagatcc ttttaaatta aaaatgaagt tttaaatcaa    7000
tctaaagtat atatgagtaa acttggtctg acagttacca atgcttaatc    7050
agtgaggcac ctatctcagc gatctgtcta tttcgttcat ccatagttgc    7100
ctgactcccc gtcgtgtaga taactacgat acgggagggc ttaccatctg    7150
gccccagtgc tgcaatgata ccgcgagacc cacgctcacc ggctccagat    7200
ttatcagcaa taaaccagcc agccggaagg gccgagcgca gaagtggtcc    7250
tgcaacttta tccgcctcca tccagtctat taattgttgc cgggaagcta    7300
gagtaagtag ttcgccagtt aatagtttgc gcaacgttgt tgccattgct    7350
acaggcatcg tggtgtcacg ctcgtcgttt ggtatggctt cattcagctc    7400
cggttcccaa cgatcaaggc gagttacatg atccccatg ttgtgcaaaa    7450 aagcggttag ctccttcggt cctccgatcg ttgtcagaag taagttggcc    7500
gcagtgttat cactcatggt tatggcagca ctgcataatt ctcttactgt    7550
catgccatcc gtaagatgct tttctgtgac tggtgagtac tcaaccaagt    7600
cattctgaga atagtgtatg cggcgaccga gttgctcttg cccggcgtca    7650
atacgggata taccgcgcc acatagcaga actttaaaag tgctcatcat    7700
tggaaaacgt tcttcggggc gaaaactctc aaggatctta ccgctgttga    7750
```

```
                                       -continued
gatccagttc gatgtaaccc actcgtgcac ccaactgatc ttcagcatct    7800
tttactttca ccagcgtttc tgggtgagca aaaacaggaa ggcaaaatgc    7850
cgcaaaaaag ggaataaggg cgacacgaaa atgttgaata ctcatactct    7900 tccttttca atattattga agcatttatc agggttattg tctcatgagc    7950
ggatacatat ttgaatgtat ttagaaaaat aaacaaatag gggttccgcg    8000
cacatttccc cgaaaagtgc cacctaaatt gtaagcgtta atattttgtt    8050
aaaattcgcg ttaaattttt gttaaatcag ctcatttttt aaccaatagg    8100
ccgaaatcgg caaaatccct tataaatcaa aagaatagac cgagataggg    8150
ttgagtgttg ttccagtttg gaacaagagt ccactattaa agaacgtgga    8200
ctccaacgtc aaagggcgaa aaaccgtcta tcagggcgat ggcccactac    8250
gtgaaccatc accctaatca agttttttgg ggtcgaggtg ccgtaaagca    8300
ctaaatcgga accctaaagg gagcccccga tttagagctt gacggggaaa    8350
gccggcgaac gtggcgagaa aggaagggaa gaaagcgaaa ggagcgggcg    8400
ctagggcgct ggcaagtgta gcggtcacgc tgcgcgtaac caccacaccc    8450
gccgcgctta atgcgccgct acagggcgcg tcccattcgc cattcaggct    8500
gcgcaactgt tgggaagggc gatcggtgcg ggcctcttcg ctattacgcc    8550
agctggcgaa aggggggatgt gctgcaaggc gattaagttg ggtaacgcca    8600
gg                                                         8602
```

As will be noted, residues 21-37 of SEQ ID NO:61 correspond to the M13 Fwd primer binding site (SEQ ID NO:50). Residues 47-65 of SEQ ID NO:61 correspond to the T7 promoter site (SEQ ID NO:12). Residues 186-565 of SEQ ID NO:61 correspond to the CMV immediate early enhancer site (SEQ ID NO:1). Residues 566-769 of SEQ ID NO:61 correspond to the CMV immediate early promoter site (SEQ ID NO:52). Residues 881-1453 of SEQ ID NO:61 correspond to the beta-globin intron site (SEQ ID NO:53). Residues 1554-5318 of SEQ ID NO:61 correspond to a polynucleotide sequence (SEQ ID NO:55) that encodes the SARS-CoV-2 S protein (SEQ ID NO:54). Residues 5461-5516 of SEQ ID NO:61 correspond to the beta-globin poly(A) signal site (SEQ ID NO:56). Residues 5874-5890 of SEQ ID NO:61 are complementary to the M13 Rev primer binding site (SEQ ID NO:51). Residues 5898-5914 of SEQ ID NO:61 are complementary to the lac operator site (SEQ ID NO:57). Residues 5922-5952 of SEQ ID NO:61 are complementary to the lac promoter site (SEQ ID NO:58). Residues 5967-5988 of SEQ ID NO:61 are complementary to the CAP binding site (SEQ ID NO:59). Residues 6276-6864 of SEQ ID NO:61 are complementary to the ColE1/pMB1/pBR322/pUC origin of replication (SEQ ID NO:19). Residues 7035-7895 of SEQ ID NO:61 are complementary to the AmpR antibiotic resistance determinant (SEQ ID NO:22). Residues 7896-8000 of SEQ ID NO:61 are complementary to the AmpR promoter (SEQ ID NO:26). Residues 8026-8481 of SEQ ID NO:61 are complementary to the f1 origin of replication (SEQ ID NO:60).

II. Methods for Producing the SARS-CoV-2 S Protein Lentiviral Particles of the Present Invention Any cell type capable of propagating a lentivirus may be employed to produce the SARS-CoV-2 S Protein Lentiviral Particle of the present invention. However, the use of HEK293 (ATCC® CRL-1573™), HEK293T, and SJ293TS human embryonic kidney cells are preferred. Such cells are widely known (e.g., Merten, O.-W. et al. (2016) "*Production Of Lentiviral Vectors*," Molec. Ther. Meth. Clin. Develop. 3:16017:1-14; Bauler, M. et al. (2020) "*Production of Lentiviral Vectors Using Suspension Cells Grown in Serum-Free Media*," Molec. Ther.: Meth. Clin. Develop. 17:58-68; Hu, J. et al. (2018) "*Human Embryonic Kidney 293 Cells: A Vehicle for Biopharmaceutical Manufacturing, Structural Biology, and Electrophysiology*," Cells Tissues Organs 205: 1-8; Thomas, P. et al. (2005) "*HEK293 Cell Line: A Vehicle For The Expression Of Recombinant Proteins*," J. Pharmacol. Toxicol. Meth. 51(3):187-200; Pear, W. S. et al. (1994) "*Production Of High-Titer Helper-Free Retroviruses By Transient Transfection*," Proc. Natl. Acad. Sci. (U.S.A.) 90:8392-8396), and are available commercially (Antibody Research Corp.; ATCC; Thermo-Fisher Scientific; Life Technologies; etc.).

Cells may be transfected with the above-described lentiviral plasmids and cultured to produce the SARS-CoV-2 S Protein Lentiviral Particle of the present invention using any of a variety of methods (Bauler, M. et al. (2020) "*Production of Lentiviral Vectors Using Suspension Cells Grown in Serum-Free Media*," Molec. Ther.: Meth. Clin. Develop. 17:58-68; Merten, O.-W. et al. (2016) "*Production Of Lentiviral Vectors*," Molec. Ther. Meth. Clin. Develop. 3:16017: 1-14; Gandara, C. et al. (2018) "*Manufacture of Third-Generation Lentivirus for Preclinical Use, with Process Development Considerations for Translation to Good Manufacturing Practice*," Hum. Gene Ther. Meth. 29(1):1-15). For example, in the method of Gandara, C. et al. (2018) ("*Manufacture of Third-Generation Lentivirus for Preclinical Use, with Process Development Considerations for Translation to Good Manufacturing Practice*," Hum. Gene Ther. Meth. 29(1):1-15), HEK293 cells are coated onto the surfaces of tissue culture dishes or flasks using poly-L-lysine and cultured at 37° C. (3% $CO_2$) to confluency in Dulbecco's modified Eagle's medium containing high glucose and containing 10% fetal bovine serum, 2 mM L-glutamine, 1 mM sodium pyruvate and 100 IU/mL of penicillin/streptomycin. Cells are then detached from the surface through the addition of Trypsin-EDTA (0.5%) and phosphate buffer. The cells are then resuspended in fresh media, cultured overnight at 37° C. (3% $CO_2$) and incubated in a 200 mM calcium chloride transfection buffer and borate-buffered saline transfection reagent for 30 minutes at room temperature in the presence of the lentiviral plasmids, and then incubated at 37° C. and 3% $CO_2$ overnight in culture media. Culture media is replaced after 18 hours, and the cells are permitted to grow for an additional 24 hours.

The amount of plasmid to be provided to such cells will vary depending on their respective lengths. Table 2 provides the mass, copy numbers and typical lengths of such plasmids that may be used to calculate the amount (µg) of plasmid that is to be provided for any particular transfection (thus, for example, if a vector has a smaller length that that indicated in Table 2, the employed amount of the plasmid will be decreased in order to maintain the indicated copy number).

TABLE 2

| Vector | Mass (µg) | Typical Length | DNA Copy Number |
|---|---|---|---|
| LTR-containing Vector | 300 | 7,537 | $3.9 \times 10^{13}$ |
| Packaging Vector | 250 | 8,890 | $2.7 \times 10^{13}$ |
| REV Vector | 125 | 4,180 | $2.9 \times 10^{13}$ |
| Envelope Vector | 150 | 5,822 | $2.5 \times 10^{13}$ |

After such culturing, the culture media is filtered using a 0.45 µm or 0.22 µm filter to obtain a culture media that comprises physical titers of between $10^{11}$ and $10^{12}$ particles/mL and functional titers of between $10^7$ and $10^{10}$ particles/mL. Additional purification can be obtained using ultracentrifugation or tangential flow filtration (Cooper, A. R. et al. (2011) "*Highly Efficient Large-Scale Lentiviral Vector Concentration By Tandem Tangential Flow Filtration*," J. Virol. Methods. 177(1):1-9; Busatto, S. et al. (2018) "*Tangential Flow Filtration for Highly Efficient Concentration of Extracellular Vesicles from Large Volumes of Fluid*," Cells 7(12): 1-11; Musumeci, T. et al. (2018) "*Tangential Flow Filtration Technique: An Overview on Nanomedicine Applications*," Pharm. Nanotechnol. 6(1):48-60; Nordin, J. Z. et al. (2019) "*Tangential Flow Filtration with or Without Subsequent Bind-Elute Size Exclusion Chromatography for Purification of Extracellular Vesicles*," Methods Mol. Biol. 1953:287-299; Tinch, S. et al. (2019) "A Scalable Lentiviral Vector Production and Purification Method Using Mustang Q Chromatography and Tangential Flow Filtration," Methods Mol. Biol. 1937:135-153).

III. Pharmaceutical Compositions

The invention provides SARS-CoV-2 S Protein Lentiviral Vaccine pharmaceutical compositions that comprise the SARS-CoV-2 S Protein Lentiviral Particles of the present invention and a pharmaceutically acceptable carrier.

In a first preferred embodiment, the SARS-CoV-2 S protein lentiviral vaccine pharmaceutical compositions of the present invention will comprise lentiviral particles that array the SARS-CoV-2 S protein on their surface. Such vaccines may be produced by transfecting cells with the packaging, REV, and envelope vectors of the present invention in concert with any of the LTR-containing vectors of the invention. In general, the lentiviral particles of such vaccines mimic the external structure of SARS-CoV-2 and thus permit the recipient subject to develop immunity to the virus.

In a second preferred embodiment, the SARS-CoV-2 S protein lentiviral vaccine pharmaceutical compositions of the present invention will comprise lentiviral particles that array the SARS-CoV-2 S protein on their surface and additionally comprise a genome that encodes all or a portion of one or more SARS-CoV-2 proteins (e.g., all or part of the SARS-CoV-2 S protein, and/or all or part of the SARS-CoV-2 N protein, etc.) ("SARS-CoV-2 Transgene-Containing SARS-CoV-2 S Protein Lentiviral Vaccines). Such vaccines may be produced by transfecting cells with the packaging, REV, and envelope vectors of the present invention in concert with an LTR-containing vector of the invention that comprises a SARS-CoV-2 protein-encoding transgene polynucleotide sequence. Such vaccines operate in multiple ways to provide enhanced immunity to recipient subjects. In a first manner, the lentiviral particles of such vaccines mimic the external structure of SARS-CoV-2 and thus permit the recipient subject to develop immunity to the virus. In a second manner, the lentiviral particles of such vaccines, particularly where the SARS-CoV-2 proteins are expressed with a secretory signal sequence (such as the IL-2 signal sequence), mediate the production and release of SARS-CoV-2 proteins into the extracellular environment, and thus provide additional antigen for eliciting immunity. In particular, lentiviral particles of such vaccines that express two or more proteins (e.g., the SARS-CoV-2 S and N proteins) would better mimic the environment seen in an actual SARS-CoV-2 infection, and thus would be expected to provide more effective immunity to recipient subjects. Even more effective immunity is anticipated to be provided by lentiviral particles of such vaccines that array two or more proteins (e.g., the SARS-CoV-2 S and N proteins) on the particle's surface.

The pharmaceutical compositions of the present invention comprise an amount of such SARS-CoV-2 S Protein Lentiviral Particles sufficient to permit the immune system of a recipient subject to initiate and preferably persistently maintain immunity to SARS-CoV-2 infection ("effective amount").

The term "pharmaceutically acceptable" means approved by a regulatory agency of the Federal or a state government or listed in the US Pharmacopeia or other generally recognized pharmacopeia for use in animals, and more particularly in humans. The term "carrier" refers to a diluent, adjuvant (e.g., Freund's adjuvant complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Suitable pharmaceutical excipients are described in U.S. Pat. Nos. 8,852,607; 8,192,975; 6,764,845; 6,759,050; and 7,598,070. The SARS-CoV-2 S Protein Lentiviral Vaccine pharmaceutical compositions of the present invention may also include one or more adjuvants to boost the immune response of a recipient so as to produce more antibodies and/or provide longer-lasting immunity. Suitable adjuvants are known in the art, and include alum, aluminum hydroxide, aluminum phosphate, calcium phosphate hydroxide, mineral oil (e.g., paraffin oil), killed *Bordetella pertussis*, killed *Mycobacterium bovis*, plant saponins from Quillaja, soybean, cytokines (e.g., IL-1, IL-2, IL-12, etc.), Freund's complete adjuvant, Freund's incomplete adjuvant, etc. Pharmaceutically acceptable carriers or diluents, adjuvants and excipients are disclosed in REMINGTON: THE SCIENCE AND PRACTICE OF PHARMACY, 21$^{st}$ Edition (2005) Hauber, Ed., Lippincott Williams & Wilkins.

Generally, the ingredients of compositions of the invention are supplied either separately or mixed together in unit dosage form, for example, as a dry lyophilized powder or water-free concentrate, or as an aqueous solution in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline, or other diluent can be provided so that the ingredients may be mixed prior to administration.

The invention also provides a pharmaceutical pack or kit comprising one or more containers of such pharmaceutical composition and instructions for the use of the included SARS-CoV-2 S Protein Lentiviral Vaccine pharmaceutical composition. Optionally associated with such container(s) can be a notice in a form prescribed by a governmental agency regulating the manufacture, use or sale of pharmaceuticals or biological products, which notice reflects approval by the agency of manufacture, use or sale for human administration.

The SARS-CoV-2 S Protein Lentiviral Vaccine pharmaceutical compositions of the present invention are preferably packaged in sterile containers, such as vials, ampoules or sachettes, indicating the provided dose. In one embodiment, such SARS-CoV-2 S Protein Lentiviral Vaccine pharmaceutical compositions are supplied as a dry sterilized lyophilized powder or water-free concentrate in a hermetically sealed container and can be reconstituted, e.g., with water, saline, or other diluent to the appropriate concentration for administration to a subject. The lyophilized material should be stored at between 2° C. and 8° C. in their original container and the material should be administered within 12 hours, preferably within 6 hours, within 5 hours, within 3 hours, or within 1 hour after being reconstituted. In another embodiment, the SARS-CoV-2 S Protein Lentiviral Vaccine pharmaceutical compositions of the present invention are supplied as an aqueous solution in a hermetically sealed container and can be diluted, e.g., with water, saline, or other diluent, to the appropriate concentration for administration to a subject.

The SARS-CoV-2 S Protein Lentiviral Vaccine pharmaceutical compositions of the present invention may further comprise one or more additional prophylactic and/or therapeutic agents useful for the treatment of the disease or condition, in one or more containers; and/or such kits can further comprise one or more additional antiviral agents or one or more anti-SARS-CoV-2 antibodies.

Thus, the invention specifically contemplates pharmaceutical compositions and kits thereof that comprise the SARS-CoV-2 S Protein Lentiviral Vaccine pharmaceutical compositions of the present invention and one or more anti-SARS-CoV-2 antiviral agents, such as, for example, Actemra (Roche), AmnioBoost (Lattice Biologics), APN01 (APEIRON Biologics), AT-100 (Airway Therapeutics), BPI-002 (BeyondSpring), Brilacidin (Innovation Pharmaceuticals), BXT-25 (BIOXYTRAN), Chloroquine and Hydroxychloroquine/Plaquenil, Darunavir (Janssen Pharmaceutical), Favilavir, Galidesivir (Biocryst Pharma), Gimsilumab (Roivant Sciences), Kevzara (Regeneron), leronlimab (CytoDyn), lopinavir (Abbvie), NP-120 (Ifenprodil) (Algernon Pharmaceuticals), OYA1 (OyaGen), PREZCOBIX® HIV (Janssen Pharmaceutical), REGN3048-3051 (Regeneron), Remdesivir (GS-5734) (Gilead Sciences), SNG001 (Synairgen Research), TJM2 (I-Mab Biopharma), TZLS-501 (Tiziana Life Sciences) be provided in prophylactically effective, or therapeutically effective, amounts. The use of such a combined composition permits a synergistic response to COVID-19 infection.

The invention also specifically contemplates pharmaceutical compositions and kits thereof that comprise the SARS-CoV-2 S Protein Lentiviral Vaccine pharmaceutical compositions of the present invention and one or more additional SARS-CoV-2 vaccines. Such additional vaccine compositions include one or more of, for example, AdCOVID (Altimmune), AdCoVID™ (Altimmune), Avian Coronavirus Infectious Bronchitis Virus (IBV) vaccine (MIGAL Research Institute), ChAdOx1 (Jenner Institute), Fusogenix DNA vaccine (Entos Pharmaceuticals), INO-4700 (GLS-5300) (Inovio Pharma), INO-4800 (Inovio Pharmaceuticals), MERS coronavirus vaccine (Novavax), mRNA-1273 (Moderna), Plant-Derived Virus-Line Particle (Medicago), TNX-1800 (Tonix Pharmaceuticals), or Trimer-Tag© recombinant subunit vaccine (Clover Biopharmaceuticals) provided in prophylactically effective, or therapeutically effective, amounts. The use of such a combined vaccine composition permits a synergistic response to COVID-19 infection.

IV. Administration and Dosage

The SARS-CoV-2 S Protein Lentiviral Particle pharmaceutical compositions of the present invention can be administered by parenteral, topical, oral or intranasal means for prophylactic and/or therapeutic treatment. Intramuscular injection (for example, into the arm or leg muscles) and intravenous infusion are preferred methods of administration of the molecules of the present invention. In some methods, such molecules are administered as a sustained release composition or device. In some methods, the SARS-CoV-2 S Protein Lentiviral Particles of the present invention are provided directly into a particular tissue, for example, into the gastrointestinal tract (small intestine, colon, etc.), or into the trachea, bronchi, lungs, or pulmonary arteries that provide oxygen to the lungs, etc.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion. Intranasal administration is preferred for eliciting IgA2 secretory antibodies. Intramuscular administration is preferred for eliciting IgG or IgM antibodies.

Such pharmaceutical compositions may be administered to a patient who does not have COVID-19 but is susceptible to, or otherwise at risk of, COVID-19. When provided for such prophylactic use, the SARS-CoV-2 S Protein Lentiviral Particle pharmaceutical compositions of the present invention are administered to a subject in an amount sufficient to initiate a protective immune response against SARS-CoV-2 and to maintain such a protective immune response for an extended period (e.g., at least about 1 month, at least about 2 months, at least about 3 months, at least about 4 months, at least about 6 months, at least about 8 months, at least about 1 year, at least about 1.5 years, at least about 2 years, at least about 2.5 years, at least about 3 years, at least about 5 years, or more than five years. As used herein, the term "protective immune response," denotes an immune response that includes the eliciting and production of neutralizing antibodies to SARS-CoV-2, so that the health of the subject is substantially preserved. Such pharmaceutical compositions may be alternatively or additionally administered to a patient who has been confirmed to suffer from SARS-CoV-2 infection, or who has been diagnosed as exhibiting COVID-19. When provided for such therapeutic use, the SARS-CoV-2 S Protein Lentiviral Particle pharmaceutical compositions of the present invention are administered to a subject in an amount sufficient to initiate a rapid protective immune response against SARS-CoV-2.

Effective doses of the SARS-CoV-2 S Protein Lentiviral Particle pharmaceutical compositions of the present invention for such prophylactic or therapeutic use may vary depending upon many different factors, including means of administration, target site, physiological state of the patient, other medications administered, and whether treatment is prophylactic or therapeutic. Treatment dosages are typically titrated to optimize their safety and efficacy. On any given day that a dosage is given, the dosage may range from about 0.0001 to about 100 mg/kg, and more usually from about 0.01 to about 10 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight A physician or veterinarian having ordinary skill in the art may readily determine and prescribe the effective amount of the pharmaceutical composition required. For example, the physician or veterinarian could start doses of the SARS-CoV-2 S Protein Lentiviral Particle pharmaceutical compositions of the present invention at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may, e.g., be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals, optionally, in unit dosage forms. While the SARS-CoV-2 S Protein Lentiviral Particle pharmaceutical compositions of the present invention may be administered alone, they may be administered with other compounds, e.g., an adjuvant, an antiviral agent, etc.

The therapeutic or prophylactic dosage may be administered repeatedly in order to ensure the continued immunity of the recipient. Relative to the initial administration of the vaccine, such subsequent administrations may be made after about 6 months, after about 1 year, after about 1.5 years, after about 2 years, after about 2.5 years, after about 3 years, after about 5 years, or after more than five years.

V. Diagnostic Utility

In addition to their therapeutic utility, the lentiviral particles of the present invention may be used diagnostically to provide antigen (e.g., SARS-CoV-2 S and/or N protein) that may be used to detect the presence of antibody in immune individuals or recovering COVID-19 patients. Such particles are superior to purified SARS-CoV-2 S and/or N protein, which may not adopt the conformation that such proteins adopt when attached to the SARS-CoV-2 surface. The conformations adopted by the SARS-CoV-2 S and/or N protein of the lentiviral particles of the present invention is expected to be closer to the native conformations of such proteins on a coronavirus.

VI. Embodiments of the Invention

Having now generally described the invention, the same will be more readily understood through reference to the following numbered Embodiments ("E"), which are provided by way of illustration and are not intended to be limiting of the present invention unless specified:

E1. A lentiviral particle that comprises a recombinantly engineered lentiviral genome and that arrays a SARS-CoV-2 spike (S) protein on its surface.

E2. The lentiviral particle of E1, wherein the recombinantly engineered lentiviral genome is non-integrating.

E3. The lentiviral particle of E1, wherein the recombinantly engineered lentiviral genome is incapable of being reverse transcribed.

E4. The lentiviral particle of E1, wherein the recombinantly engineered lentiviral genome is non-integrating and incapable of being reverse transcribed.

E5. The lentiviral particle of any one of E1-E4, wherein the recombinantly engineered lentiviral genome encodes a heterologous transgene protein.

E6. The lentiviral particle of any one of E1-E5, wherein the encoded heterologous transgene protein is an antibiotic resistance determinant, a reporter protein, a protein drug effective in treating SARS-CoV-2 infection, or a protein that comprises the epitope binding domain of an antibody that binds to a SARS-CoV-2 antigen.

E7. The lentiviral particle of E5, wherein the encoded heterologous transgene protein is a SARS-CoV-2 protein.

E8. The lentiviral particle of E7, wherein the encoded SARS-CoV-2 heterologous transgene protein is a SARS-CoV-2 Spike (S) protein or a SARS-CoV-2 Nucleocapsid (N) protein.

E9. A vaccine for the treatment of COVID-19, wherein the vaccine comprises a prophylactically effective dose of a pharmaceutical composition that comprises the lentiviral particle of any one of E1-E8 and a pharmaceutically acceptable carrier.

E10. The vaccine of E9, wherein the recombinantly engineered lentiviral genome of the lentiviral particle is non-integrating.

E11. The vaccine of E9, wherein the recombinantly engineered lentiviral genome of the lentiviral particle is incapable of being reverse transcribed.

E12. The vaccine of E9, wherein the recombinantly engineered lentiviral genome of the lentiviral particle is non-integrating and incapable of being reverse transcribed.

E13. The vaccine of E9, wherein the recombinantly engineered lentiviral genome of the lentiviral particle encodes a heterologous transgene protein.

E14. The vaccine of E13, wherein the encoded heterologous transgene protein is a SARS-CoV-2 Spike (S) protein or a SARS-CoV-2 Nucleocapsid (N) protein.

E15. The vaccine of any one of E9-E14, wherein the pharmaceutically acceptable carrier is adapted for intramuscular administration.

E16. The vaccine of any one of E9-E14, wherein the pharmaceutically acceptable carrier is adapted for intranasal administration.

E17. A method for producing the recombinant lentiviral particle of any one of E1-E16, wherein the method comprises:
(A) transfecting HEK293 cells with:
(1) an LTR-containing vector that comprises a deleted 5' LTR U3 region and a self-inactivating 3' LTR region;
(2) a packaging vector that comprises a polynucleotide that encodes gag and pol proteins;
(3) a REV vector that comprises a polynucleotide that encodes a rev protein; and
(4) an envelope vector that comprises a polynucleotide that encodes a SARS-CoV-2 spike (S) protein; and
(B) permitting the cells to produce the recombinant lentiviral particle.

E18. The method of E17, wherein the packaging vector comprises a genome that encodes a mutated integrase, wherein the transfection produces a recombinant lentiviral particle that comprises a genome that is non-integrating.

E19. The method of E17, wherein the packaging vector comprises a genome that encodes a mutated reverse transcriptase, wherein the transfection produces a recombinant lentiviral particle that comprises a genome that is incapable of being reverse transcribed.

E20. The method of E19, wherein the packaging vector comprises a genome that additionally encodes a mutated integrase, wherein the transfection produces a recombinant lentiviral particle that comprises a genome that is non-integrating and incapable of being reverse transcribed.

E21. The method of any one of E17-E20, wherein the LTR-containing vector comprises the features of any of the LTR-containing vectors: pLenti-SV40-puro (SEQ ID NO:27);
pLenti-SV40-puro (-att) (SEQ ID NO:28);
pLenti-CMV-IRES-empty (-att) (SEQ ID NO:67);
pLenti-CMV-IRES-Spike (SEQ ID NO:70);
pLenti-IgGκ-nCoV-Spike-CD8-TM (-att) (SEQ ID NO:83);
pLenti-IgGκ-nCoV-N-CD8-TM (-att) (SEQ ID NO:84); or
pLenti-IL-2 n-CoV-N(-att) (SEQ ID NO:85).

E22. The method of any one of E17-E21, wherein the packaging vector comprises the features of pGAG (SEQ ID NO:44).

E23. The method of any one of E17-E22, wherein the REV vector comprises the features of pREV (SEQ ID NO:49).

E24. The method of any one of E17-E23, wherein the envelope vector comprises the features of pCMV-SARS-CoV-2 S Protein (SEQ ID NO:61).

EXAMPLES

Having now generally described the invention, the same will be more readily understood through reference to the following examples, which are provided by way of illustration and are not intended to be limiting of the present invention unless specified.

Example 1

Production of Recombinant Lentiviral Particles that Array the SARS-CoV-2 Spike (S) Protein on their Surface HEK293 cells are co-transfected with the above-described pLenti-SV40-puro (-att), pGAG, pREV, and pCMV-SARS-CoV-2 S Protein vectors substantially as described by Gandara, C. et al. (2018) ("*Manufacture of Third-Generation Lentivirus for Preclinical Use, with Process Development Considerations for Translation to Good Manufacturing Practice*," Hum. Gene Ther. Meth. 29(1):1-15). The co-transfection yields recombinant lentiviral particles that array the SARS-CoV-2 spike (S) protein on their surface.

Example 2

Vaccine Use of Lentiviral Particles that Array the SARS-CoV-2 Spike (S) Protein on their Surface Therapeutically effective amounts of the lentiviral particles of Example 1 are injected intramuscularly or are applied intranasally to recipient human subjects. Neutralizing antibodies to SARS-CoV-2 are elicited and detected in such immunized subjects. The neutralizing antibodies protect the immunized subjects from COVID-19.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A lentiviral particle that:
(A) comprises:
  (1) a recombinantly engineered HIV-1 vector that comprises, in the 5' to 3' direction:
    (a) a human cytomegalovirus (CMV) immediate early enhancer site and promoter;
    (b) an HIV-1 5' LTR region that has been truncated to delete its U3 region;
    (c) an HIV-1 ψ region;
    (d) an HIV-1 Rev response element (RRE);
    (e) an HIV-1 central polypurine tract and central termination sequence (cPPT/CTS);
    (f) a heterologous enhancer and promoter;
    (g) a woodchuck hepatitis virus post-transcriptional regulatory element (WPRE); and
    (h) a self-inactivating HIV-1 3' LTR region;
  (2) a mutated HIV-1 integrase (IN) protein that is incapable of mediating the integration of said recombinantly engineered HIV-1 vector into the chromosome of a recipient cell; and
  (3) a mutated HIV-1 reverse transcriptase (RT) protein that is incapable of reverse transcribing said recombinantly engineered HIV-1 vector; and
(B) arrays a SARS-CoV-2 spike (S) protein on its surface.

2. The lentiviral particle of claim 1, wherein positioned 3' to said heterologous enhancer and promoter (f), and 5' to said woodchuck hepatitis virus post-transcriptional regulatory element (WPRE) (g), said recombinantly engineered HIV-1 vector additionally comprises, in the 5' to 3' direction:
  (i) an internal ribosome entry site (IRES);
  (iii) a heterologous transgene that is operably linked to said heterologous enhancer and promoter, and that encodes a heterologous transgene protein.

3. The lentiviral particle of claim 2, wherein said encoded heterologous transgene protein is an antibiotic resistance determinant, a reporter protein, a protein drug effective in treating SARS-CoV-2 infection, a viral protein, or a protein that comprises the epitope binding domain of an antibody that binds to a SARS-CoV-2 antigen.

4. The lentiviral particle of claim 2, wherein said encoded heterologous transgene protein is a SARS-CoV-2 protein.

5. The lentiviral particle of claim 4, wherein said encoded SARS-CoV-2 heterologous transgene protein is a SARS-CoV-2 Spike protein or a SARS-CoV-2 Nucleocapsid (N) protein.

6. An immunogenic composition capable of inducing neutralizing antibodies against the SARS-CoV-2 Spike (S) Protein wherein said composition comprises the lentiviral particle of claim 1 and a pharmaceutically acceptable carrier.

7. The immunogenic composition of claim 6, wherein the recombinantly engineered HIV-1 vector of said lentiviral particle encodes a heterologous transgene protein.

8. The immunogenic composition of claim 7, wherein said encoded heterologous transgene protein is a SARS-CoV-2 Spike (S) protein or a SARS-CoV-2 Nucleocapsid (N) protein.

9. The immunogenic composition of claim 6, wherein said pharmaceutically acceptable carrier is adapted for intramuscular administration.

10. The immunogenic composition of claim 6, wherein said pharmaceutically acceptable carrier is adapted for intranasal administration.

11. A method for producing the lentiviral particle of claim 1, wherein said method comprises:
(A) transfecting HEK293 cells with:
  (1) a recombinantly engineered HIV-1 vector that comprises, in the 5' to 3' direction:
    (a) a human cytomegalovirus (CMV) immediate early enhancer site and promoter;
    (b) an HIV-1 5' LTR region that has been truncated to delete its U3 region;
    (c) an HIV-1 ψ region;
    (d) an HIV-1 Rev response element (RRE);
    (e) an HIV-1 central polypurine tract and central termination sequence (cPPT/CTS);
    (f) a heterologous enhancer and promoter;
    (g) a woodchuck hepatitis virus post-transcriptional regulatory element (WPRE); and
    (h) a self-inactivating HIV-1 3' LTR region;
  (2) a packaging vector that comprises a polynucleotide that comprises an HIV-1 gag gene and an HIV-1 pol gene, wherein said HIV-1 pol gene encodes:
    (i) a mutated HIV-1 integrase (IN) protein that is incapable of mediating the integration of said recombinantly engineered HIV-1 vector into the chromosome of a recipient cell; and
    (ii) a mutated HIV-1 reverse transcriptase (RT) protein that is incapable of reverse transcribing said recombinantly engineered HIV-1 vector;
  (3) a REV vector that comprises a polynucleotide that encodes an HIV-1 rev protein; and (4) an envelope vector that comprises a polynucleotide that encodes a SARS-CoV-2 spike (S) protein; and (B) permitting said cells to produce said lentiviral particle; wherein said transfection produces said lentiviral particle that comprises:

(1) said recombinantly engineered HIV-1 vector;

(2) said mutated HIV-1 integrase (IN) protein that is incapable of mediating the integration of said recombinantly engineered HIV-1 vector into the chromosome of a recipient cell; and (3) said mutated HIV-1 reverse transcriptase (RT) protein that is incapable of reverse transcribing said recombinantly engineered HIV-1 vector;

and that arrays said SARS-CoV-2 spike (S) protein on its surface.

12. The method of claim 11, wherein said recombinantly engineered HIV-1 vector comprises the features of:

pLenti-SV40-puro (SEQ ID NO:27);
pLenti-SV40-puro (-att) (SEQ ID NO:28);
pLenti-CMV-IRES-empty (-att) (SEQ ID NO:67);
pLenti-CMV-IRES-Spike (SEQ ID NO:70);
pLenti-IgGκ-nCoV-Spike-CD8-TM (-att) (SEQ ID NO:83);
pLenti-IgGκ-nCoV-N-CD8-TM (-att) (SEQ ID NO:84); or
pLenti-IL-2 n-CoV-N(-att) (SEQ ID NO:85).

13. The method of claim 11, wherein said packaging vector comprises the features of pGAG (SEQ ID NO:44).

14. The method of claim 11, wherein said REV vector comprises the features of pREV (SEQ ID NO:49).

15. The method of claim 11, wherein said envelope vector comprises the features of pCMV-SARS-CoV-2 S Protein (SEQ ID NO:61).

16. The lentiviral particle of claim 1, wherein said arrayed SARS-CoV-2 spike (S) protein comprises the amino acid sequence of SEQ ID NO:54.

17. The lentiviral particle of claim 1, wherein said arrayed SARS-CoV-2 spike (S) protein differs from the sequence of SEQ ID NO:54 by comprising:

(A) the substitution: D614G; S247R; H49Y; S221W; Y28N; A930V; F797C; F157L; H655Y; G181V; N74K; K528X; K814X; D614X; V473A; A348T; G476S; A520S; T29I; L5F; E96D; D1168H; A1078V; D111N; H519Q; A942X; L8V; G910X; S50L; A27V; T240I; A653V; A570V; G644X; Y265X; L1152X; S71F; D80Y; V70F; C1250Y; P9L; V772I; I197V; S98F; N148S; V367F; T791I; P217X; M731I; M1237I; A845S; S704X; L752X; H655X; N354B; S704L; Y28H; G485R; G838S; W152R; or K557X; or (B) the pair of substitutions: L5F and G476S; P427X and D614G; L54F and D614G; D614G and V615F; D614G and V622I; D614G and V1228X; F238X and D614G; W258L and D614G; D614G and A1078S; D614G and S939F; H146Y and D614G; Y279X and D614G; D614G and I818V; L5F and D614G; D614X and G1124X; D614G and L1203F; D614G and V1065L; Q271R and D614G; K529E and D614G; D614G and S929I; D614G and T768I; V90F and D614G; A522S and D614G; F220X and D614G; D614G and P631S; Y423X and D614G; Y200X and D614G; H49Y and S884F; Y145H and D614G; V503X and D614G; L118F and D614G; A27S and D614G; A67S and F1103L; S750R and L752R; Q239R and D614G; D614G and T676S; or T95I and D614G.

18. The lentiviral particle of claim 1, that additionally arrays the hemagglutinin (HA) protein of influenza virus, the SARS-CoV spike (S) protein, and/or the MERS-CoV spike (S) protein on its surface.

19. The method of claim 11, wherein positioned 3' to said heterologous enhancer and promoter (f), and 5' to said woodchuck hepatitis virus post-transcriptional regulatory element (WPRE) (g), said recombinantly engineered HIV-1 vector additionally comprises, in the 5' to 3' direction:

(i) an internal ribosome entry site (IRES);

(iii) a heterologous transgene that is operably linked to said heterologous enhancer and promoter, and that encodes a heterologous transgene protein.

20. The method of claim 19, wherein said encoded heterologous transgene protein is an antibiotic resistance determinant, a reporter protein, a protein drug effective in treating SARS-CoV-2 infection, a viral protein, or a protein that comprises the epitope binding domain of an antibody that binds to a SARS-CoV-2 antigen.

21. The method of claim 19, wherein said encoded heterologous transgene protein is a SARS-CoV-2 protein.

22. The method of claim 21, wherein said encoded SARS-CoV-2 heterologous transgene protein is a SARS-CoV-2 Spike (S) protein or a SARS-CoV-2 Nucleocapsid (N) protein.

\* \* \* \* \*

SEQUENCE LISTING

<160> NUMBER OF SEQ ID NOS: 85

<210> SEQ ID NO 1
<211> LENGTH: 380
<212> TYPE: DNA
<213> ORGANISM: Human Cytomegalovirus (CMV)
<220> FEATURE:
<221> NAME/KEY: misc_feature
<222> LOCATION: (1)..(380)
<223> OTHER INFORMATION: Human Cytomegalovirus (CMV) Immediate Early
      Enhancer Site

<400> SEQUENCE: 1
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg acctatggg actttcctac ttggcagtac atctacgtat    360
tagtcatcgc tattaccatg                                                380

<210> SEQ ID NO 2
<211> LENGTH: 380
<212> TYPE: DNA
<213> ORGANISM: Human Cytomegalovirus (CMV)
<220> FEATURE:
<221> NAME/KEY: misc_feature
<222> LOCATION: (1)..(380)
<223> OTHER INFORMATION: Variant Human Cytomegalovirus (CMV) Immediate
      Early Enhancer Site

<400> SEQUENCE: 2
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt ccgcccccta ttgacgtcaa tgacggtaaa tggcccgcct    300
ggcattatgc ccagtacatg acctacggg actttcctac ttggcagtac atctacgtat    360
tagtcatcgc tattaccatg                                                380

<210> SEQ ID NO 3
<211> LENGTH: 200
<212> TYPE: DNA
<213> ORGANISM: Human Cytomegalovirus (CMV)
<220> FEATURE:
<221> NAME/KEY: misc_feature
<222> LOCATION: (1)..(200)
<223> OTHER INFORMATION: Human Cytomegalovirus (CMV) Immediate Early
      Promoter Site

<400> SEQUENCE: 3
gtgatgcggt tttggcagta catcaatggg cgtggatagc ggtttgactc acggggattt     60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag                                                200

```
<210> SEQ ID NO 4
<211> LENGTH: 204
<212> TYPE: DNA
<213> ORGANISM: Human Cytomegalovirus (CMV)
<220> FEATURE:
<221> NAME/KEY: misc_feature
<222> LOCATION: (1)..(204)
<223> OTHER INFORMATION: Variant Human Cytomegalovirus (CMV) Immediate
      Early Promoter Site

<400> SEQUENCE: 4
gtgatgcggt tttggcagta caccaatggg cgtggatagc ggtttgactc acggggattt     60
ccaagtctcc accccattga cgtcaatggg agtttgtttt ggcaccaaaa tcaacgggac    120
tttccaaaat gtcgtaataa ccccgccccg ttgacgcaaa tgggcggtag gcgtgtacgg    180
tgggaggtct atataagcag agct                                          204

<210> SEQ ID NO 5
<211> LENGTH: 181
<212> TYPE: DNA
<213> ORGANISM: Lentivirus
<220> FEATURE:
<221> NAME/KEY: misc_feature
<222> LOCATION: (1)..(181)
<223> OTHER INFORMATION: Truncated Lentiviral 5' LTR region (R and U5
      Regions)

<400> SEQUENCE: 5
gggtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga cccttttagt cagtgtggaa aatctctagc    180
a                                                                    181

<210> SEQ ID NO 6
<211> LENGTH: 126
<212> TYPE: DNA
<213> ORGANISM: Lentivirus
<220> FEATURE:
<221> NAME/KEY: misc_feature
<222> LOCATION: (1)..(126)
<223> OTHER INFORMATION: Lentiviral LTR Psi Region

<400> SEQUENCE: 6
ctctctcgac gcaggactcg gcttgctgaa gcgcgcacgg caagaggcga ggggcggcga     60
ctggtgagta cgccaaaaat tttgactagc ggaggctaga aggagagaga tgggtgcgag    120
agcgtc                                                               126

<210> SEQ ID NO 7
<211> LENGTH: 234
<212> TYPE: DNA
<213> ORGANISM: Lentivirus
<220> FEATURE:
<221> NAME/KEY: misc_feature
<222> LOCATION: (1)..(234)
<223> OTHER INFORMATION: Lentiviral REV Response Element (RRE)

<400> SEQUENCE: 7
aggagctttg ttccttgggt tcttgggagc agcaggaagc actatgggcg cagcgtcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct          234
```

<210> SEQ ID NO 8
<211> LENGTH: 118
<212> TYPE: DNA
<213> ORGANISM: Lentivirus
<220> FEATURE:
<221> NAME/KEY: misc_feature
<222> LOCATION: (1)..(118)
<223> OTHER INFORMATION: Lentiviral Central Polypurine Tract and Central
      Termination Sequence (cPPT/CTS)

<400> SEQUENCE: 8
ttttaaaaga aaggggggga ttgggggggta cagtgcaggg gaaagaatag tagacataat    60
agcaacagac atacaaacta aagaattaca aaaacaaatt acaaaaattc aaaattttt    118

<210> SEQ ID NO 9
<211> LENGTH: 330
<212> TYPE: DNA
<213> ORGANISM: SV40
<220> FEATURE:
<221> NAME/KEY: misc_feature
<222> LOCATION: (1)..(330)
<223> OTHER INFORMATION: SV40 Promoter Site

<400> SEQUENCE: 9
gtgtgtcagt tagggtgtgg aaagtcccca ggctccccag caggcagaag tatgcaaagc    60
atgcatctca attagtcagc aaccaggtgt ggaaagtccc caggctcccc agcaggcaga   120
agtatgcaaa gcatgcatct caattagtca gcaaccatag tcccgcccct aactccgccc   180
atcccgcccc taactccgcc cagttccgcc cattctccgc cccatggctg actaatttt    240 tttatttatg cagaggccga ggccgcctcg gcctctgagc tattccagaa gtagtgagga   300
ggcttttttg gaggcctagg cttttgcaaa                                   330

<210> SEQ ID NO 10
<211> LENGTH: 199
<212> TYPE: PRT
<213> ORGANISM: Streptomyces alboniger
<220> FEATURE:
<221> NAME/KEY: MISC_FEATURE
<222> LOCATION: (1)..(199)
<223> OTHER INFORMATION: Streptomyces alboniger N-acetyltransferase

<400> SEQUENCE: 10

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
                20                  25                  30

Thr Arg His Thr Val Asp Pro Asp Arg His Ile Glu Arg Val Thr Glu
            35                  40                  45

Leu Gln Glu Leu Phe Leu Thr Arg Val Gly Leu Asp Ile Gly Lys Val
        50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
                100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
        130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 11
<211> LENGTH: 600
<212> TYPE: DNA
<213> ORGANISM: Streptomyces alboniger
<220> FEATURE:
<221> NAME/KEY: misc_feature
<222> LOCATION: (1)..(600)
<223> OTHER INFORMATION: Polynucleotide Encoding Streptomyces alboniger
      N-acetyltransferase

<400> SEQUENCE: 11
atgaccgagt acaagcccac ggtgcgcctc gccacccgcg acgacgtccc ccgggcagta      60 cgcacccteg ccgccgcgtt cgccgactac cccgccacgc gccacaccgt cgatccagac     120
cgccacatcg agcgggtcac cgagctgcaa gaactcttcc tcacgcgcgt cgggctcgac     180
atcggcaagg tgtgggtcgc ggacgacggc gccgcggtgg cggtctggac cacgccggag     240
agcgtcgaag cgggggcggt gttcgccgag atcggcccgc gcatggccga gttgagcggt     300
tcccggctgg ccgcgcagca acagatggaa ggcctcctgg cgccgcaccg gcccaaggag     360
cccgcgtggt tcctggccac cgtcggcgtc tcgcccgacc accagggcaa gggtctgggc     420
agcgccgtcg tgctccccgg agtggaggcg ccgagcgcg ccggggtgcc cgccttcctg      480
gagacctccg cgccccgcaa cctccccttc tacgagcggc tcggcttcac cgtcaccgcc     540
gacgtcgagg tgcccgaagg accgcgcacc tggtgcatga cccgcaagcc cggtgcctga    600

<210> SEQ ID NO 12
<211> LENGTH: 19
<212> TYPE: DNA
<213> ORGANISM: Bacteriophage T7
<220> FEATURE:
<221> NAME/KEY: misc_feature
<222> LOCATION: (1)..(19)
<223> OTHER INFORMATION: Bacteriophage T7 Promoter

<400> SEQUENCE: 12
taatacgact cactatagg                                                   19

<210> SEQ ID NO 13
<211> LENGTH: 25
<212> TYPE: PRT
<213> ORGANISM: Artificial Sequence
<220> FEATURE:
<223> OTHER INFORMATION: Myc-FLAG Tag

<400> SEQUENCE: 13

Glu Gln Lys Leu Ile Ser Glu Glu Asp Leu Ala Ala Asn Asp Ile Leu
1               5                   10                  15

Asp Tyr Lys Asp Asp Asp Asp Lys Val
            20                  25

<210> SEQ ID NO 14
<211> LENGTH: 75

```
<212> TYPE: DNA
<213> ORGANISM: Artificial Sequence
<220> FEATURE:
<223> OTHER INFORMATION: Polynucleotide Encoding Myc-FLAG Tag

<400> SEQUENCE: 14
gagcagaaac tcatctcaga agaggatctg gcagcaaatg atatcctgga ttacaaggat      60
gacgacgata aggtt                                                      75

<210> SEQ ID NO 15
<211> LENGTH: 34
<212> TYPE: DNA
<213> ORGANISM: Bacteriophage P1
<220> FEATURE:
<221> NAME/KEY: misc_feature
<222> LOCATION: (1)..(34)
<223> OTHER INFORMATION: Bacteriophage P1 LoxP Site

<400> SEQUENCE: 15
ataacttcgt atagcataca ttatacgaag ttat                                  34

<210> SEQ ID NO 16
<211> LENGTH: 589
<212> TYPE: DNA
<213> ORGANISM: Woodchuck Hepatitis Virus
<220> FEATURE:
<221> NAME/KEY: misc_feature
<222> LOCATION: (1)..(589)
<223> OTHER INFORMATION: Woodchuck Hepatitis Virus Post-Transcriptional
      Regulatory Element (WPRE)

<400> SEQUENCE: 16
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct     300
attgccacgg cggaactcat cgccgcctgc cttgcccgct gctggacagg gctcggctg      360 ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                 589

<210> SEQ ID NO 17
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Factor Xa Cleavage Site

<400> SEQUENCE: 17
tcggccctca at                                                         12

<210> SEQ ID NO 18
<211> LENGTH: 17
<212> TYPE: DNA
<213> ORGANISM: Artificial Sequence
<220> FEATURE:
<223> OTHER INFORMATION: KS Primer Binding Site
```

<400> SEQUENCE: 18
cgaggtcgac ggtatcg                                                      17

<210> SEQ ID NO 19
<211> LENGTH: 589
<212> TYPE: DNA
<213> ORGANISM: Artificial Sequence
<220> FEATURE:
<223> OTHER INFORMATION: ColE1/pMB1/pBR322/pUC Origin of Replication

<400> SEQUENCE: 19
ttgagatcct ttttttctgc gcgtaatctg ctgcttgcaa acaaaaaaac caccgctacc      60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttgtgat gctcgtcagg ggggcggagc ctatggaaa                 589

<210> SEQ ID NO 20
<211> LENGTH: 589
<212> TYPE: DNA
<213> ORGANISM: Artificial Sequence
<220> FEATURE:
<223> OTHER INFORMATION: Variant ColE1/pMB1/pBR322/pUC Origin of
      Replication

<400> SEQUENCE: 20
ttgagatcct ttttttctgc gcgtaatctg ctgcttgcaa acaaaaaaac caccgctacc      60
agcggtggtt tgtttgccgg atcaagagct accaactctt tttccgaagg taactggctt    120
cagcagagcg cagataccaa atactgtcct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttgtgat gctcgtcagg ggggcggagc ctatggaaa                 589

<210> SEQ ID NO 21
<211> LENGTH: 286
<212> TYPE: PRT
<213> ORGANISM: Escherichia coli
<220> FEATURE:
<221> NAME/KEY: MISC_FEATURE
<222> LOCATION: (1)..(286)
<223> OTHER INFORMATION: AmpR Antibiotic Resistance Determinant

<400> SEQUENCE: 21

Met Ser Ile Gln His Phe Arg Val Ala Leu Ile Pro Phe Phe Ala Ala

```
   1               5              10              15
 Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
             35                  40                  45

Leu Asn Ser Gly Lys Ile Leu Glu Ser Phe Arg Pro Glu Glu Arg Phe
  50                  55                  60

Pro Met Met Ser Thr Phe Lys Val Leu Cys Gly Ala Val Leu Ser
  65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
                115                 120                 125

Asp Asn Thr Ala Ala Asn Leu Leu Leu Thr Thr Ile Gly Gly Pro Lys
             130                 135                 140

Glu Leu Thr Ala Phe Leu His Asn Met Gly Asp His Val Thr Arg Leu
 145                 150                 155                 160

Asp Arg Trp Glu Pro Glu Leu Asn Glu Ala Ile Pro Asn Asp Glu Arg
                 165                 170                 175

Asp Thr Thr Met Pro Val Ala Met Ala Thr Thr Leu Arg Lys Leu Leu
                 180                 185                 190

Thr Gly Glu Leu Leu Thr Leu Ala Ser Arg Gln Gln Leu Ile Asp Trp
             195                 200                 205

Met Glu Ala Asp Lys Val Ala Gly Pro Leu Leu Arg Ser Ala Leu Pro
 210                 215                 220

Ala Gly Trp Phe Ile Ala Asp Lys Ser Gly Ala Gly Glu Arg Gly Ser
 225                 230                 235                 240

Arg Gly Ile Ile Ala Ala Leu Gly Pro Asp Gly Lys Pro Ser Arg Ile
                 245                 250                 255

Val Val Ile Tyr Thr Thr Gly Ser Gln Ala Thr Met Asp Glu Arg Asn
                 260                 265                 270

Arg Gln Ile Ala Glu Ile Gly Ala Ser Leu Ile Lys His Trp
                 275                 280                 285

<210> SEQ ID NO 22
<211> LENGTH: 858
<212> TYPE: DNA
<213> ORGANISM: Escherichia coli
<220> FEATURE:
<221> NAME/KEY: misc_feature
<222> LOCATION: (1)..(858)
<223> OTHER INFORMATION: Polynucleotide Encoding AmpR Antibiotic
      Resistance Determinant

<400> SEQUENCE: 22
atgagtattc aacatttccg tgtcgccctt attcccttttt ttgcggcatt ttgccttcct      60 gttttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
```

```
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattgg                                                  858
```

<210> SEQ ID NO 23
<211> LENGTH: 286
<212> TYPE: PRT
<213> ORGANISM: Escherichia coli
<220> FEATURE:
<221> NAME/KEY: MISC_FEATURE
<222> LOCATION: (1)..(286)
<223> OTHER INFORMATION: Variant AmpR Antibiotic Resistance Determinant

<400> SEQUENCE: 23

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270
```

Arg Gln Ile Ala Glu Ile Gly Ala Ser Leu Ile Lys His Trp
            275                 280                 285

```
<210> SEQ ID NO 24
<211> LENGTH: 858
<212> TYPE: DNA
<213> ORGANISM: Escherichia coli
<220> FEATURE:
<221> NAME/KEY: misc_feature
<222> LOCATION: (1)..(861)
<223> OTHER INFORMATION: Polynucleotide Encoding Varinat AmpR Antibiotic
      Resistance Determinant

<400> SEQUENCE: 24
atgagtattc aacatttccg tgtcgccctt attccctttt ttgcggcatt ttgccttcct      60 gttttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtgttgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga caccacgatg   540
cctgcagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
tcactgatta agcattgg                                                  858

<210> SEQ ID NO 25
<211> LENGTH: 105
<212> TYPE: DNA
<213> ORGANISM: Escherichia coli
<220> FEATURE:
<221> NAME/KEY: misc_feature
<222> LOCATION: (1)..(105)
<223> OTHER INFORMATION: AmpR Promoter-Containing Polynucleotide

<400> SEQUENCE: 25
cgcgggaccc ctatttgttt attttctaa atacattcaa atatgtatcc gctcatgaga      60
caataaccct gataaatgct tcaataatat tgaaaaagga agagt                    105

<210> SEQ ID NO 26
<211> LENGTH: 105
<212> TYPE: DNA
<213> ORGANISM: Escherichia coli
<220> FEATURE:
<221> NAME/KEY: misc_feature
<222> LOCATION: (1)..(105)
<223> OTHER INFORMATION: Variant AmpR Promoter-Containing Polynucleotide

<400> SEQUENCE: 26
cgcggaaccc ctatttgttt attttctaa atacattcaa atatgtatcc gctcatgaga      60
caataaccct gataaatgct tcaataatat tgaaaaagga agagt                    105
```

<210> SEQ ID NO 27
<211> LENGTH: 7705
<212> TYPE: DNA
<213> ORGANISM: Artificial Sequence
<220> FEATURE:
<223> OTHER INFORMATION: pLenti-SV40-puro Vector

<400> SEQUENCE: 27

| | | | | | |
|---|---|---|---|---|---|
| gtcgacggat | cgggagatct | cccgatcccc | tatggtgcac | tctcagtaca | atctgctctg | 60 |
| atgccgcata | gttaagccag | tatctgctcc | ctgcttgtgt | gttggaggtc | gctgagtagt | 120 |
| gcgcgagcaa | aatttaagct | acaacaaggc | aaggcttgac | cgacaattgc | atgaagaatc | 180 |
| tgcttagggt | taggcgtttt | gcgctgcttc | gcgatgtacg | ggccagatat | cgcgttgaca | 240 |
| ttgattattg | actagttatt | aatagtaatc | aattacgggg | tcattagttc | atagcccata | 300 |
| tatggagttc | cgcgttacat | aacttacggt | aaatggcccg | cctggctgac | cgcccaacga | 360 |
| cccccgccca | ttgacgtcaa | taatgacgta | tgttcccata | gtaacgccaa | tagggacttt | 420 |
| ccattgacgt | caatgggtgg | agtatttacg | gtaaactgcc | cacttggcag | tacatcaagt | 480 |
| gtatcatatg | ccaagtacgc | cccctattga | cgtcaatgac | ggtaaatggc | ccgcctggca | 540 |
| ttatgcccag | tacatgacct | tatgggactt | tcctacttgg | cagtacatct | acgtattagt | 600 |
| catcgctatt | accatggtga | tgcggttttg | gcagtacatc | aatgggcgtg | gatagcggtt | 660 |
| tgactcacgg | ggatttccaa | gtctccaccc | cattgacgtc | aatgggagtt | tgttttggca | 720 |
| ccaaaatcaa | cgggactttc | caaaatgtcg | taacaactcc | gccccattga | cgcaaatggg | 780 |
| cggtaggcgt | gtacggtggg | aggtctatat | aagcagcgcg | ttttgcctgt | actgggtctc | 840 |
| tctggttaga | ccagatctga | gcctgggagc | tctctggcta | actagggaac | ccactgctta | 900 |
| agcctcaata | aagcttgcct | tgagtgcttc | aagtagtgtg | tgcccgtctg | ttgtgtgact | 960 |
| ctggtaacta | gagatccctc | agaccctttt | agtcagtgtg | gaaaatctct | agcagtggcg | 1020 |
| cccgaacagg | gacttgaaag | cgaaagggaa | accagaggag | ctctctcgac | gcaggactcg | 1080 |
| gcttgctgaa | gcgcgcacgg | caagaggcga | ggggcggcga | ctggtgagta | cgccaaaaat | 1140 |
| tttgactagc | ggaggctaga | aggagagaga | tgggtgcgag | agcgtcagta | ttaagcgggg | 1200 |
| gagaattaga | tcgcgatggg | aaaaaattcg | gttaaggcca | gggggaaaga | aaaaatataa | 1260 |
| attaaaacat | atagtatggg | caagcaggga | gctagaacga | ttcgcagtta | atcctggcct | 1320 |
| gttagaaaca | tcagaaggct | gtagacaaat | actgggacag | ctacaaccat | cccttcagac | 1380 |
| aggatcagaa | gaacttagat | cattatataa | tacagtagca | accctctatt | gtgtgcatca | 1440 |
| aaggatagag | ataaaagaca | ccaaggaagc | tttagacaag | atagaggaag | agcaaaacaa | 1500 |
| aagtaagacc | accgcacagc | aagcggccgg | ccgctgatct | tcagacctgg | aggaggagat | 1560 |
| atgagggaca | attggagaag | tgaattatat | aaatataaag | tagtaaaaat | tgaaccatta | 1620 |
| ggagtagcac | ccaccaaggc | aaagagaaga | gtggtgcaga | gagaaaaaag | agcagtggga | 1680 |
| ataggagctt | tgttccttgg | gttcttggga | gcagcaggaa | gcactatggg | cgcagcgtca | 1740 |
| atgacgctga | cggtacaggc | cagacaatta | ttgtctggta | tagtgcagca | gcagaacaat | 1800 |
| ttgctgaggg | ctattgaggc | gcaacagcat | ctgttgcaac | tcacagtctg | ggcatcaag | 1860 |
| cagctccagg | caagaatcct | ggctgtggaa | agatacctaa | aggatcaaca | gctcctgggg | 1920 |
| atttggggtt | gctctggaaa | actcatttgc | accactgctg | tgccttggaa | tgctagttgg | 1980 |
| agtaataaat | ctctggaaca | gatttggaat | cacacgacct | ggatggagtg | ggacagaaa | 2040 |
| attaacaatt | acacaagctt | aatacactcc | ttaattgaag | aatcgcaaaa | ccagcaagaa | 2100 |

```
aagaatgaac aagaattatt ggaattagat aaatgggcaa gtttgtggaa ttggtttaac    2160
ataacaaatt ggctgtggta tataaaatta ttcataatga tagtaggagg cttggtaggt    2220
ttaagaatag ttttttgctgt actttctata gtgaatagag ttaggcaggg atattcacca   2280
ttatcgtttc agacccacct cccaaccccg aggggacccg acaggcccga aggaatagaa    2340
gaagaaggtg gagagagaga cagagacaga tccattcgat tagtgaacgg atcggcactg    2400
cgtgcgccaa ttctgcagac aaatggcagt attcatccac aattttaaaa gaaaaggggg    2460
gattgggggg tacagtgcag gggaaagaat agtagacata atagcaacag acatacaaac    2520
taaagaatta caaaaacaaa ttacaaaaat tcaaaatttt cgggtttatt acagggacag    2580
cagagatcca gtttggttag taccgggccc gctctagaat gtgtgtcagt tagggtgtgg    2640
aaagtcccca ggctcccccag caggcagaag tatgcaaagc atgcatctca attagtcagc   2700
aaccaggtgt ggaaagtccc caggctcccc agcaggcaga agtatgcaaa gcatgcatct    2760
caattagtca gcaaccatag tcccgcccct aactccgccc atcccgcccc taactccgcc    2820
cagttccgcc cattctccgc cccatggctg actaatttt tttatttatg cagaggccga     2880
ggccgcctcg gcctctgagc tattccagaa gtagtgagga ggcttttttg gaggcctagg    2940
cttttgcaaa aagctcccgg gagcttgtat atccattttc ggatctgatc aagagacacg    3000
tacgaccatg accgagtaca agcccacggt gcgcctcgcc accgcgacg acgtcccccg     3060 ggcagtacgc accctcgccg ccgcgttcgc cgactacccc gccacgcgcc acaccgtcga    3120
tccagaccgc cacatcgagc gggtcaccga gctgcaagaa ctcttcctca cgcgcgtcgg    3180
gctcgacatc ggcaaggtgt gggtcgcgga cgacggcgcc gcggtggcgg tctggaccac    3240 gccgagagc gtcgaagcgg gggcggtgtt cgccgagatc ggcccgcgca tggccgagtt    3300
gagcggttcc cggctggccg cgcagcaaca gatggaaggc ctcctggcgc cgcaccggcc    3360
caaggagccc gcgtggttcc tggccaccgt cggcgtctcg cccgaccacc agggcaaggg    3420
tctgggcagc gccgtcgtgc tccccggagt ggaggcggcc gagcgcgccg gggtgcccgc    3480
cttcctggag acctccgcgc cccgcaacct cccccttctac gagcggctcg gcttcaccgt    3540
caccgccgac gtcgaggtgc ccgaaggacc gcgcacctgg tgcatgaccc gcaagcccgg    3600
tgcctgattt ctagacatgt ccaatatgac cgccatgttg acattgatta ttgactagtt    3660
attaatagta atcaattacg gggtcattag ttcatagccc atatatggag ttccgcgtta    3720
cataacttac ggtaaatggc ccgcctggct gaccgcccaa cgacccccgc ccattgacgt    3780
caataatgac gtatgttccc atagtaacgc caatagggac tttccattga cgtcaatggg    3840
tggagtattt acggtaaact gcccacttgg cagtacatca agtgtatcat atgccaagtc    3900
cgccccctat tgacgtcaat gacggtaaat ggcccgcctg gcattatgcc cagtacatga    3960
ccttacggga ctttcctact tggcagtaca tctacgtatt agtcatcgct attaccatgg    4020
tgatgcggtt ttggcagtac accaatgggc gtggatagcg gtttgactca cggggatttc    4080
caagtctcca ccccattgac gtcaatggga gtttgttttg gcaccaaaat caacgggact    4140
ttccaaaatg tcgtaataac cccgccccgt tgacgcaaat gggcggtagg cgtgtacggt    4200
gggaggtcta tataagcaga gctcgtttag tgaaccgtca gaattttgta atacgactca    4260
ctatagggcg gccgggaatt cgtcgactgg atccggtacc gaggagatct gccgccgcga    4320
tcgccggcgc gccagatctc aagcttaact agctagcgga ccgacgcgta cgcggccgct    4380
cgagcagaaa ctcatctcag aagaggatct ggcagcaaat gatatcctgg attacaagga    4440
```

-continued

```
tgacgacgat aaggtttaaa cggccggccg cggtctgtac aagtaggatt cgtcgaggga      4500
cctaataact tcgtatagca tacattatac gaagttatac atgtttaagg gttccggttc      4560
cactaggtac aattcgatat caagcttatc gataatcaac ctctggatta caaaatttgt      4620
gaaagattga ctggtattct taactatgtt gctcctttta cgctatgtgg atacgctgct      4680
ttaatgcctt tgtatcatgc tattgcttcc cgtatggctt tcattttctc ctccttgtat      4740
aaatcctggt tgctgtctct ttatgaggag ttgtggcccg ttgtcaggca acgtggcgtg      4800
gtgtgcactg tgtttgctga cgcaaccccc actggttggg gcattgccac cacctgtcag      4860
ctcctttccg ggactttcgc tttcccctc cctattgcca cggcggaact catcgccgcc       4920
tgccttgccc gctgctggac aggggctcgg ctgttgggca ctgacaattc cgtggtgttg      4980
tcggggaaat catcgtcctt ccttggctg ctcgcctgtg ttgccacctg gattctgcgc       5040
gggacgtcct tctgctacgt cccttcggcc ctcaatccag cggaccttcc ttcccgcggc      5100
ctgctgccgg ctctgcggcc tcttccgcgt cttcgccttc gccctcagac gagtcggatc      5160
tccctttggg ccgcctcccc gcatcgatac cgtcgacctc gatcgagacc tagaaaaaca     5220
tggagcaatc acaagtagca atacagcagc taccaatgct gattgtgcct ggctagaagc      5280
acaagaggag gaggaggtgg gttttccagt cacacctcag gtacctttaa gaccaatgac      5340
ttacaaggca gctgtagatc ttagccactt tttaaaagaa agggggggac tggaagggct      5400
aattcactcc caacgaagac aagatatcct tgatctgtgg atctaccaca cacaaggcta      5460
cttccctgat tggcagaact acacaccagg gccagggatc agatatccac tgacctttgg      5520
atggtgctac aagctagtac cagttgagca agagaaggta gaagaagcca atgaaggaga      5580 gaacaccgc ttgttacacc ctgtgagcct gcatgggatg gatgacccgg agagagaagt       5640
attagagtgg aggtttgaca gccgcctagc atttcatcac atggcccgag agctgcatcc      5700
ggactgtact gggtctctct ggttagacca gatctgagcc tgggagctct ctggctaact      5760
agggaaccca ctgcttaagc ctcaataaag cttgccttga gtgcttcaag tagtgtgtgc      5820
ccgtctgttg tgtgactctg gtaactagag atccctcaga cccttttagt cagtgtggaa      5880
aatctctagc agcatgtgag caaaaggcca gcaaaggcc aggaaccgta aaaaggccgc       5940
gttgctggcg tttttccata ggctccgccc ccctgacgag catcacaaaa atcgacgctc      6000
aagtcagagg tggcgaaacc cgacaggact ataaagatac caggcgtttc ccctggaag      6060 ctccctcgtg cgctctcctg ttccgaccct gccgcttacc ggatacctgt ccgcctttct      6120
cccttcggga agcgtggcgc tttctcatag ctcacgctgt aggtatctca gttcggtgta      6180
ggtcgttcgc tccaagctgg gctgtgtgca cgaaccccc gttcagcccg accgctgcgc       6240
cttatccggt aactatcgtc ttgagtccaa cccggtaaga cacgacttat cgccactggc      6300
agcagccact ggtaacagga ttagcagagc gaggtatgta ggcggtgcta cagagttctt      6360
gaagtggtgg cctaactacg gctacactag aagaacagta tttggtatct gcgtctgct      6420 gaagccagtt accttcggaa aaagagttgg tagctcttga tccggcaaac aaaccaccgc      6480
tggtagcggt ggtttttttg tttgcaagca gcagattacg cgcagaaaaa aaggatctca     6540
agaagatcct ttgatctttt ctacggggtc tgacgctcag tggaacgaaa actcacgtta      6600
agggattttg gtcatgagat tatcaaaaag gatcttcacc tagatccttt taaattaaaa      6660
atgaagtttt aaatcaatct aaagtatata tgagtaaact tggtctgaca gttaccaatg      6720
cttaatcagt gaggcaccta tctcagcgat ctgtctattt cgttcatcca tagttgcctg      6780
actccccgtc gtgtagataa ctacgatacg ggagggctta ccatctggcc ccagtgctgc      6840
```

-continued

```
aatgataccg cgagacccac gctcaccggc tccagattta tcagcaataa accagccagc    6900
cggaagggcc gagcgcagaa gtggtcctgc aactttatcc gcctccatcc agtctattaa    6960
ttgttgccgg gaagctagag taagtagttc gccagttaat agtttgcgca acgttgttgc    7020
cattgctaca ggcatcgtgg tgtcacgctc gtcgtttggt atggcttcat tcagctccgg    7080
ttcccaacga tcaaggcgag ttacatgatc ccccatgttg tgcaaaaaag cggttagctc    7140
cttcggtcct ccgatcgttg tcagaagtaa gttggccgca gtgttatcac tcatggttat    7200
ggcagcactg cataattctc ttactgtcat gccatccgta agatgctttt ctgtgactgg    7260
tgagtactca accaagtcat tctgagaata gtgtatgcgg cgaccgagtt gctcttgccc    7320
ggcgtcaata cgggataata ccgcgccaca tagcagaact ttaaaagtgc tcatcattgg    7380
aaaacgttct cggggcgaaa actctcaag gatcttaccg ctgttgagat ccagttcgat    7440
gtaacccact cgtgcaccca actgatcttc agcatctttt actttcacca gcgtttctgg    7500
gtgagcaaaa acaggaaggc aaaatgccgc aaaaaaggga ataagggcga cacggaaatg    7560
ttgaatactc atactcttcc tttttcaata ttattgaagc atttatcagg gttattgtct    7620
catgagcgga tacatatttg aatgtattta gaaaaataaa caaatagggg tcccgcgcac    7680
atttccccga aaagtgccac ctgac                                         7705
```

<210> SEQ ID NO 28
<211> LENGTH: 7701
<212> TYPE: DNA
<213> ORGANISM: Artificial Sequence
<220> FEATURE:
<223> OTHER INFORMATION: pLenti-SV40-puro (-att) Vector

<400> SEQUENCE: 28

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360
cccccgccca ttgacgtcaa taatgacgta tgttcccata gtaacgccaa tagggacttt     420
ccattgacgt caatgggtgg agtatttacg gtaaactgcc cacttggcag tacatcaagt     480
gtatcatatg ccaagtacgc cccctattga cgtcaatgac ggtaaatggc ccgcctggca     540
ttatgcccag tacatgacct tatgggactt tcctacttgg cagtacatct acgtattagt     600
catcgctatt accatggtga tgcggttttg gcagtacatc aatgggcgtg atagcggtt     660
tgactcacgg ggatttccaa gtctccaccc cattgacgtc aatgggagtt tgttttggca     720
ccaaaatcaa cgggactttc caaaatgtcg taacaactcc gccccattga cgcaaatggg     780
cggtaggcgt gtacggtggg aggtctatat aagcagcgcg ttttgcctgt actgggtctc     840
tctggttaga ccagatctga gcctgggagc tctctggcta actagggaac ccactgctta     900
agcctcaata aagcttgcct tgagtgcttc aagtagtgtg tgcccgtctg ttgtgtgact     960
ctggtaacta gagatccctc agacccttttt agtcagtgtg gaaaatctct aggtggcgcc    1020
cgaacaggga cttgaaagcg aaagggaaac cagaggagct ctctcgacgc aggactcggc    1080
ttgctgaagc gcgcacggca agaggcgagg ggcggcgact ggtgagtacg ccaaaaattt    1140
```

```
tgactagcgg aggctagaag gagagagatg ggtgcgagag cgtcagtatt aagcggggga    1200
gaattagatc gcgatgggaa aaaattcggt taaggccagg gggaaagaaa aaatataaat    1260
taaaacatat agtatgggca agcagggagc tagaacgatt cgcagttaat cctggcctgt    1320
tagaaacatc agaaggctgt agacaaatac tgggacagct acaaccatcc cttcagacag    1380
gatcagaaga acttagatca ttatataata cagtagcaac cctctattgt gtgcatcaaa    1440
ggatagagat aaaagacacc aaggaagctt tagacaagat agaggaagag caaaacaaaa    1500
gtaagaccac cgcacagcaa gcggccggcc gctgatcttc agacctggag gaggagatat    1560
gagggacaat tggagaagtg aattatataa atataaagta gtaaaaattg aaccattagg    1620
agtagcaccc accaaggcaa agagaagagt ggtgcagaga gaaaaaagag cagtgggaat    1680
aggagctttg ttccttgggt tcttgggagc agcaggaagc actatgggcg cagcgtcaat    1740
gacgctgacg gtacaggcca gacaattatt gtctggtata gtgcagcagc agaacaattt    1800
gctgagggct attgaggcgc aacagcatct gttgcaactc acagtctggg gcatcaagca    1860
gctccaggca agaatcctgg ctgtggaaag atacctaaag gatcaacagc tcctgggat    1920 ttggggttgc tctggaaaac tcatttgcac cactgctgtg ccttggaatg ctagttggag    1980
taataaatct ctgaacaga tttggaatca cacgacctgg atggagtggg acagagaaat    2040
taacaattac acaagcttaa tacactcctt aattgaagaa tcgcaaaacc agcaagaaaa    2100
gaatgaacaa gaattattgg aattagataa atgggcaagt ttgtggaatt ggtttaacat    2160
aacaaattgg ctgtggtata taaaattatt cataatgata gtaggaggct tggtaggttt    2220
aagaatagtt tttgctgtac tttctatagt gaatagagtt aggcagggat attcaccatt    2280
atcgtttcag acccacctcc caaccccgag gggacccgac aggcccgaag gaatagaaga    2340
agaaggtgga gagagagaca gagacagatc cattcgatta gtgaacggat cggcactgcg    2400
tgcgccaatt ctgcagacaa atggcagtat tcatccacaa ttttaaaaga aaaggggga    2460 ttgggggta cagtgcaggg gaaagaatag tagacataat agcaacagac atacaaacta    2520
aagaattaca aaaacaaatt acaaaaattc aaaattttcg ggtttattac agggacagca    2580
gagatccagt ttggttagta ccgggcccgc tctagaatgt gtgtcagtta gggtgtggaa    2640
agtccccagg ctccccagca ggcagaagta tgcaaagcat gcatctcaat tagtcagcaa    2700
ccaggtgtgg aaagtcccca ggctccccag caggcagaag tatgcaaagc atgcatctca    2760
attagtcagc aaccatagtc ccgcccctaa ctccgcccat cccgccccta actccgccca    2820
gttccgccca ttctccgccc catggctgac taatttttt tatttatgca gaggccgagg    2880
ccgcctcggc ctctgagcta ttccagaagt agtgaggagg cttttttgga ggcctaggct    2940
tttgcaaaaa gctcccggga gcttgtatat ccattttcgg atctgatcaa gagacacgta    3000
cgaccatgac cgagtacaag cccacggtgc gcctcgccac ccgcgacgac gtccccgggg    3060
cagtacgcac cctcgccgcc gcgttcgccg actaccccgc cacgcgccac accgtcgatc    3120
cagaccgcca catcgagcgg gtcaccgagc tgcaagaact cttcctcacg cgcgtcgggc    3180
tcgacatcgg caaggtgtgg gtcgcggacg acggcgccgc ggtggcggtc tggaccacgc    3240
cggagagcgt cgaagcgggg gcggtgttcg ccgagatcgg cccgcgcatg ccgagttga    3300 gcggttcccg gctggccgcg cagcaacaga tggaaggcct cctggcgccg caccggccca    3360
aggagcccgc gtggttcctg gccaccgtcg gcgtctcgcc cgaccaccag ggcaagggtc    3420
tgggcagcgc cgtcgtgctc cccggagtgg aggcggccga gcgcgccggg gtgcccgcct    3480
tcctggagac ctccgcgccc cgcaacctcc ccttctacga gcggctcggc ttcaccgtca    3540
```

```
ccgccgacgt cgaggtgccc gaaggaccgc gcacctggtg catgacccgc aagcccggtg      3600
cctgatttct agacatgtcc aatatgaccg ccatgttgac attgattatt gactagttat      3660
taatagtaat caattacggg gtcattagtt catagcccat atatggagtt ccgcgttaca      3720
taacttacgg taaatggccc gcctggctga ccgcccaacg acccccgccc attgacgtca      3780
ataatgacgt atgttcccat agtaacgcca tagggacttt ccattgacg tcaatgggtg      3840 gagtatttac ggtaaactgc ccacttggca gtacatcaag tgtatcatat gccaagtccg      3900 cccctattg acgtcaatga cggtaaatgg cccgcctggc attatgccca gtacatgacc      3960
ttacgggact ttcctacttg gcagtacatc tacgtattag tcatcgctat taccatggtg      4020
atgcggtttt ggcagtacac caatgggcgt ggatagcggt ttgactcacg ggatttcca      4080 agtctccacc ccattgacgt caatgggagt ttgttttggc accaaaatca acgggacttt      4140
ccaaaatgtc gtaataaccc cgccccgttg acgcaaatgg gcggtaggcg tgtacggtgg      4200
gaggtctata taagcagagc tcgtttagtg aaccgtcaga attttgtaat acgactcact      4260
atagggcggc cgggaattcg tcgactggat ccggtaccga ggagatctgc cgccgcgatc      4320
gccggcgcgc cagatctcaa gcttaactag ctagcggacc gacgcgtacg cggccgctcg      4380
agcagaaact catctcagaa gaggatctgg cagcaaatga tatcctggat tacaaggatg      4440
acgacgataa ggtttaaacg gccggccgcg gtctgtacaa gtaggattcg tcagggacc      4500 taataacttc gtatagcata cattatacga agttatacat gtttaagggt tccggttcca      4560
ctaggtacaa ttcgatatca agcttatcga taatcaacct ctggattaca aaatttgtga      4620
aagattgact ggtattctta actatgttgc tccttttacg ctatgtggat acgctgcttt      4680
aatgcctttg tatcatgcta ttgcttcccg tatggctttc attttctcct ccttgtataa      4740
atcctggttg ctgtctcttt atgaggagtt gtggcccgtt gtcaggcaac gtggcgtggt      4800
gtgcactgtg tttgctgacg caaccccac tggttgggc attgccacca cctgtcagct      4860
cctttccggg actttcgctt tccccctccc tattgccacg gcggaactca tcgccgcctg      4920
ccttgcccgc tgctggacag gggctcggct gttgggcact gacaattccg tggtgttgtc      4980
ggggaaatca tcgtcctttc cttggctgct cgcctgtgtt gccacctgga ttctgcgcgg      5040
gacgtccttc tgctacgtcc cttcggccct caatccagcg gaccttcctt cccgcggcct      5100
gctgccggct ctgcggcctc ttccgcgtct tcgccttcgc cctcagacga gtcggatctc      5160
cctttgggcc gcctccccgc atcgataccg tcgacctcga tcagaccta gaaaaacatg      5220 gagcaatcac aagtagcaat acagcagcta ccaatgctga ttgtgcctgg ctagaagcac      5280
aagaggagga ggaggtgggt tttccagtca cacctcaggt acctttaaga ccaatgactt      5340
acaaggcagc tgtagatctt agccactttt taaaagaaaa ggggggacga agggctaatt      5400
cactcccaac gaagacaaga tctgcttgat ctgtggatct accacacaca aggctacttc      5460
cctgattggc agaactacac accagggcca gggatcagat atccactgac ctttggatgg      5520
tgctacaagc tagtaccagt tgagcaagag aaggtagaag aagccaatga aggagagaac      5580
acccgcttgt tacaccctgt gagcctgcat gggatggatg acccggagag agaagtatta      5640
gagtggaggt ttgacagccg cctagcattt catcacatgg cccgagagct gcatccggac      5700
tgtactgggt ctctctggtt agaccagatc tgagcctggg agctctctgg ctaactaggg      5760
aacccactgc ttaagcctca ataaagcttg ccttgagtgc ttcaagtagt gtgtgcccgt      5820
ctgttgtgtg actctggtaa ctagagatcc ctcagaccct tttagtcagt gtggaaaatc      5880
```

```
tctagcagca tgtgagcaaa aggccagcaa aaggccagga accgtaaaaa ggccgcgttg      5940
ctggcgtttt tccataggct ccgcccccct gacgagcatc acaaaaatcg acgctcaagt      6000
cagaggtggc gaaacccgac aggactataa agataccagg cgtttccccc tggaagctcc      6060
ctcgtgcgct ctcctgttcc gaccctgccg cttaccggat acctgtccgc ctttctccct      6120
tcgggaagcg tggcgctttc tcatagctca cgctgtaggt atctcagttc ggtgtaggtc      6180
gttcgctcca agctgggctg tgtgcacgaa ccccccgttc agcccgaccg ctgcgcctta      6240
tccggtaact atcgtcttga gtccaacccg gtaagacacg acttatcgcc actggcagca      6300
gccactggta acaggattag cagagcgagg tatgtaggcg gtgctacaga gttcttgaag      6360
tggtggccta actacggcta cactagaaga acagtatttg gtatctgcgc tctgctgaag      6420
ccagttacct tcggaaaaag agttggtagc tcttgatccg gcaaacaaac caccgctggt      6480
agcggtggtt tttttgtttg caagcagcag attacgcgca gaaaaaaagg atctcaagaa      6540
gatcctttga tcttttctac ggggtctgac gctcagtgga acgaaaactc acgttaaggg      6600
attttggtca tgagattatc aaaaaggatc ttcacctaga tccttttaaa ttaaaaatga      6660
agttttaaat caatctaaag tatatatgag taaacttggt ctgacagtta ccaatgctta      6720
atcagtgagg cacctatctc agcgatctgt ctatttcgtt catccatagt tgcctgactc      6780
cccgtcgtgt agataactac gatacgggag ggcttaccat ctggccccag tgctgcaatg      6840
ataccgcgag acccacgctc accggctcca gatttatcag caataaacca gccagccgga      6900
agggccgagc gcagaagtgg tcctgcaact ttatccgcct ccatccagtc tattaattgt      6960
tgccgggaag ctagagtaag tagttcgcca gttaatagtt tgcgcaacgt tgttgccatt      7020
gctacaggca tcgtggtgtc acgctcgtcg tttggtatgg cttcattcag ctccggttcc      7080
caacgatcaa ggcgagttac atgatccccc atgttgtgca aaaaagcggt tagctccttc      7140
ggtcctccga tcgttgtcag aagtaagttg gccgcagtgt tatcactcat ggttatggca      7200
gcactgcata attctcttac tgtcatgcca tccgtaagat gcttttctgt gactggtgag      7260
tactcaacca agtcattctg agaatagtgt atgcggcgac cgagttgctc ttgcccggcg      7320
tcaatacggg ataataccgc gccacatagc agaactttaa aagtgctcat cattggaaaa      7380
cgttcttcgg ggcgaaaact ctcaaggatc ttaccgctgt tgagatccag ttcgatgtaa      7440
cccactcgtg cacccaactg atcttcagca tcttttactt tcaccagcgt ttctgggtga      7500
gcaaaaacag gaaggcaaaa tgccgcaaaa aagggaataa gggcgacacg gaaatgttga      7560
atactcatac tcttcctttt tcaatattat tgaagcattt atcagggtta ttgtctcatg      7620
agcggataca tatttgaatg tatttagaaa aataaacaaa taggggtccc gcgcacattt      7680
ccccgaaaag tgccacctga c                                               7701
```

<210> SEQ ID NO 29
<211> LENGTH: 304
<212> TYPE: DNA
<213> ORGANISM: Artificial Sequence
<220> FEATURE:
<223> OTHER INFORMATION: Truncated Variant of Human Cytomegalovirus
      (CMV) Immediate Early Enhancer Site

<400> SEQUENCE: 29

```
cgttacataa cttacggtaa atggcccgcc tggctgaccg cccaacgacc cccgcccatt       60
gacgtcaata atgacgtatg ttcccatagt aacgccaata gggactttcc attgacgtca      120
atgggtggag tatttacggt aaactgccca cttggcagta catcaagtgt atcatatgcc      180
```

```
aagtacgccc cctattgacg tcaatgacgg taaatggccc gcctggcatt atgcccagta    240
catgacctta tgggactttc ctacttggca gtacatctac gtattagtca tcgctattac    300
catg                                                                 304

<210> SEQ ID NO 30
<211> LENGTH: 304
<212> TYPE: DNA
<213> ORGANISM: Artificial Sequence
<220> FEATURE:
<223> OTHER INFORMATION: Truncated Variant of Variant Human
      Cytomegalovirus (CMV) Immediate Early Enhancer Site

<400> SEQUENCE: 30
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtccgccc cctattgacg tcaatgacgg taaatggccc gcctggcatt atgcccagta    240
catgacctta cgggactttc ctacttggca gtacatctac gtattagtca tcgctattac    300
catg                                                                 304

<210> SEQ ID NO 31
<211> LENGTH: 204
<212> TYPE: DNA
<213> ORGANISM: Artificial Sequence
<220> FEATURE:
<223> OTHER INFORMATION: Variant Human Cytomegalovirus (CMV) Immediate
      Early Enhancer Site

<400> SEQUENCE: 31
gtgatgcggt tttggcagta catcaatggg cgtggatagc ggtttgactc acggggattt    60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag agct                                          204

<210> SEQ ID NO 32
<211> LENGTH: 200
<212> TYPE: DNA
<213> ORGANISM: Artificial Sequence
<220> FEATURE:
<223> OTHER INFORMATION: Variant Human Cytomegalovirus (CMV) Immediate
      Early Enhancer Site

<400> SEQUENCE: 32
gtgatgcggt tttggcagta caccaatggg cgtggatagc ggtttgactc acggggattt    60
ccaagtctcc accccattga cgtcaatggg agtttgtttt ggcaccaaaa tcaacgggac    120
tttccaaaat gtcgtaataa ccccgccccg ttgacgcaaa tgggcggtag cgtgtacgg    180 tgggaggtct atataagcag                                               200

<210> SEQ ID NO 33
<211> LENGTH: 500
<212> TYPE: PRT
<213> ORGANISM: HIV-1
<220> FEATURE:
<221> NAME/KEY: MISC_FEATURE
<222> LOCATION: (1)..(500)
<223> OTHER INFORMATION: HIV-1 GAG Protein

<400> SEQUENCE: 33
```

```
Met Gly Ala Arg Ala Ser Val Leu Ser Gly Glu Leu Asp Arg Trp
1               5                   10                  15

Glu Lys Ile Arg Leu Arg Pro Gly Gly Lys Lys Tyr Lys Leu Lys
            20                  25              30

His Ile Val Trp Ala Ser Arg Glu Leu Glu Arg Phe Ala Val Asn Pro
                35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
```

```
             420              425              430
Phe Leu Gly Lys Ile Trp Pro Ser Tyr Lys Gly Arg Pro Gly Asn Phe
            435              440              445

Leu Gln Ser Arg Pro Glu Pro Thr Ala Pro Pro Glu Glu Ser Phe Arg
        450              455              460

Ser Gly Val Glu Thr Thr Thr Pro Pro Gln Lys Gln Glu Pro Ile Asp
465              470              475              480

Lys Glu Leu Tyr Pro Leu Thr Ser Leu Arg Ser Leu Phe Gly Asn Asp
            485              490              495

Pro Ser Ser Gln
            500
```

<210> SEQ ID NO 34
<211> LENGTH: 1500
<212> TYPE: DNA
<213> ORGANISM: HIV-1
<220> FEATURE:
<221> NAME/KEY: misc_feature
<222> LOCATION: (1)..(1500)
<223> OTHER INFORMATION: Polynucleotide Encoding HIV-1 GAG Protein

<400> SEQUENCE: 34

| | | |
|---|---|---|
| atgggtgcga gagcgtcagt attaagcggg ggagaattag atcgatggga aaaaattcgg | 60 |
| ttaaggccag gggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtgggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaaa gaacccttta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt cagggagtag gaggacccgg ccataaggca | 1080 |
| agagttttgg ctgaagcaat gagccaagta acaaattcag ctaccataat gatgcagaga | 1140 |
| ggcaatttta ggaaccaaag aaagattgtt aagtgtttca attgtggcaa agaagggcac | 1200 |
| acagccagaa attgcagggc ccctaggaaa aagggctgtt ggaaatgtgg aaaggaagga | 1260 |
| caccaaatga aagattgtac tgagagacag gctaattttt tagggaagat ctggccttcc | 1320 |
| tacaagggaa ggccagggaa ttttcttcag agcagaccag agccaacagc cccaccagaa | 1380 |
| gagagcttca ggtctggggt agagacaaca actccccctc agaagcagga gccgatagac | 1440 |
| aaggaactgt atcctttaac ttccctcaga tcactctttg gcaacgaccc ctcgtcacaa | 1500 |

-continued

```
<210> SEQ ID NO 35
<211> LENGTH: 912
<212> TYPE: PRT
<213> ORGANISM: HIV-1
<220> FEATURE:
<221> NAME/KEY: MISC_FEATURE
<222> LOCATION: (1)..(912)
<223> OTHER INFORMATION: HIV-1 POL Protein

<400> SEQUENCE: 35

Met Ser Leu Pro Gly Arg Trp Lys Pro Lys Met Ile Gly Gly Ile Gly
1               5                   10                  15

Gly Phe Ile Lys Val Arg Gln Tyr Asp Gln Ile Leu Ile Glu Ile Cys
            20                  25                  30

Gly His Lys Ala Ile Gly Thr Val Leu Val Gly Pro Thr Pro Val Asn
        35                  40                  45

Ile Ile Gly Arg Asn Leu Leu Thr Gln Ile Gly Cys Thr Leu Asn Phe
    50                  55                  60

Pro Ile Ser Pro Ile Glu Thr Val Pro Val Lys Leu Lys Pro Gly Met
65                  70                  75                  80

Asp Gly Pro Lys Val Lys Gln Trp Pro Leu Thr Glu Glu Lys Ile Lys
                85                  90                  95

Ala Leu Val Glu Ile Cys Thr Glu Met Glu Lys Glu Gly Lys Ile Ser
            100                 105                 110

Lys Ile Gly Pro Glu Asn Pro Tyr Asn Thr Pro Val Phe Ala Ile Lys
        115                 120                 125

Lys Lys Asp Ser Thr Lys Trp Arg Lys Leu Val Asp Phe Arg Glu Leu
    130                 135                 140

Asn Lys Arg Thr Gln Asp Phe Trp Glu Val Gln Leu Gly Ile Pro His
145                 150                 155                 160

Pro Ala Gly Leu Lys Lys Lys Ser Val Thr Val Leu Asp Val Gly
                165                 170                 175

Asp Ala Tyr Phe Ser Val Pro Leu Asp Glu Asp Phe Arg Lys Tyr Thr
            180                 185                 190

Ala Phe Thr Ile Pro Ser Ile Asn Asn Glu Thr Pro Gly Ile Arg Tyr
        195                 200                 205

Gln Tyr Asn Val Leu Pro Gln Gly Trp Lys Gly Ser Pro Ala Ile Phe
    210                 215                 220

Gln Ser Ser Met Thr Lys Ile Leu Glu Pro Phe Arg Lys Gln Asn Pro
225                 230                 235                 240

Asp Ile Val Ile Tyr Gln Tyr Met Asp Asp Leu Tyr Val Gly Ser Asp
                245                 250                 255

Leu Glu Ile Gly Gln His Arg Thr Lys Ile Glu Glu Leu Arg Gln His
            260                 265                 270

Leu Leu Arg Trp Gly Leu Thr Thr Pro Asp Lys Lys His Gln Lys Glu
        275                 280                 285

Pro Pro Phe Leu Trp Met Gly Tyr Glu Leu His Pro Asp Lys Trp Thr
    290                 295                 300

Val Gln Pro Ile Val Leu Pro Glu Lys Asp Ser Trp Thr Val Asn Asp
305                 310                 315                 320

Ile Gln Lys Leu Val Gly Lys Leu Asn Trp Ala Ser Gln Ile Tyr Pro
                325                 330                 335

Gly Ile Lys Val Arg Gln Leu Cys Lys Leu Leu Arg Gly Thr Lys Ala
            340                 345                 350

Leu Thr Glu Val Ile Pro Leu Thr Glu Glu Ala Glu Leu Glu Leu Ala
```

-continued

```
            355                 360                 365
Glu Asn Arg Glu Ile Leu Lys Glu Pro Val His Gly Val Tyr Tyr Asp
        370                 375                 380
Pro Ser Lys Asp Leu Ile Ala Glu Ile Gln Lys Gln Gly Gln Gly Gln
385                 390                 395                 400
Trp Thr Tyr Gln Ile Tyr Gln Glu Pro Phe Lys Asn Leu Lys Thr Gly
                405                 410                 415
Lys Tyr Ala Arg Met Arg Gly Ala His Thr Asn Asp Val Lys Gln Leu
            420                 425                 430
Thr Glu Ala Val Gln Lys Ile Thr Thr Glu Ser Ile Val Ile Trp Gly
        435                 440                 445
Lys Thr Pro Lys Phe Lys Leu Pro Ile Gln Lys Glu Thr Trp Glu Thr
        450                 455                 460
Trp Trp Thr Glu Tyr Trp Gln Ala Thr Trp Ile Pro Glu Trp Glu Phe
465                 470                 475                 480
Val Asn Thr Pro Pro Leu Val Lys Leu Trp Tyr Gln Leu Glu Lys Glu
                485                 490                 495
Pro Ile Val Gly Ala Glu Thr Phe Tyr Val Asp Gly Ala Ala Asn Arg
            500                 505                 510
Glu Thr Lys Leu Gly Lys Ala Gly Tyr Val Thr Asn Arg Gly Arg Gln
        515                 520                 525
Lys Val Val Thr Leu Thr Asp Thr Thr Asn Gln Lys Thr Glu Leu Gln
530                 535                 540
Ala Ile Tyr Leu Ala Leu Gln Asp Ser Gly Leu Glu Val Asn Ile Val
545                 550                 555                 560
Thr Asp Ser Gln Tyr Ala Leu Gly Ile Ile Gln Ala Gln Pro Asp Gln
                565                 570                 575
Ser Glu Ser Glu Leu Val Asn Gln Ile Ile Glu Gln Leu Ile Lys Lys
            580                 585                 590
Glu Lys Val Tyr Leu Ala Trp Val Pro Ala His Lys Gly Ile Gly Gly
        595                 600                 605
Asn Glu Gln Val Asp Lys Leu Val Ser Ala Gly Ile Arg Lys Val Leu
        610                 615                 620
Phe Leu Asp Gly Ile Asp Lys Ala Gln Asp Glu His Glu Lys Tyr His
625                 630                 635                 640
Ser Asn Trp Arg Ala Met Ala Ser Asp Phe Asn Leu Pro Pro Val Val
                645                 650                 655
Ala Lys Glu Ile Val Ala Ser Cys Asp Lys Cys Gln Leu Lys Gly Glu
            660                 665                 670
Ala Met His Gly Gln Val Asp Cys Ser Pro Gly Ile Trp Gln Leu Asp
        675                 680                 685
Cys Thr His Leu Glu Gly Lys Val Ile Leu Val Ala Val His Val Ala
        690                 695                 700
Ser Gly Tyr Ile Glu Ala Glu Val Ile Pro Ala Glu Thr Gly Gln Glu
705                 710                 715                 720
Thr Ala Tyr Phe Leu Leu Lys Leu Ala Gly Arg Trp Pro Val Lys Thr
                725                 730                 735
Ile His Thr Asp Asn Gly Ser Asn Phe Thr Ser Ala Thr Val Lys Ala
            740                 745                 750
Ala Cys Trp Trp Ala Gly Ile Lys Gln Glu Phe Gly Ile Pro Tyr Asn
        755                 760                 765
Pro Gln Ser Gln Gly Val Val Glu Ser Met Asn Lys Glu Leu Lys Lys
        770                 775                 780
```

```
Ile Ile Gly Gln Val Arg Asp Gln Ala Glu His Leu Lys Thr Ala Val
785                 790                 795                 800

Gln Met Ala Val Phe Ile His Asn Phe Lys Arg Lys Gly Gly Ile Gly
                805                 810                 815

Gly Tyr Ser Ala Gly Glu Arg Ile Val Asp Ile Ile Ala Thr Asp Ile
            820                 825                 830

Gln Thr Lys Glu Leu Gln Lys Gln Ile Thr Lys Ile Gln Asn Phe Arg
        835                 840                 845

Val Tyr Tyr Arg Asp Ser Arg Asn Pro Leu Trp Lys Gly Pro Ala Lys
850                 855                 860

Leu Leu Trp Lys Gly Glu Gly Ala Val Val Ile Gln Asp Asn Ser Asp
865                 870                 875                 880

Ile Lys Val Val Pro Arg Arg Lys Ala Lys Ile Ile Arg Asp Tyr Gly
                885                 890                 895

Lys Gln Met Ala Gly Asp Asp Cys Val Ala Ser Arg Gln Asp Glu Asp
            900                 905                 910

<210> SEQ ID NO 36
<211> LENGTH: 2736
<212> TYPE: DNA
<213> ORGANISM: HIV-1
<220> FEATURE:
<221> NAME/KEY: misc_feature
<222> LOCATION: (1)..(2736)
<223> OTHER INFORMATION: Polynucleotide Encoding HIV-1 POL Protein

<400> SEQUENCE: 36
atgagtttgc caggaagatg gaaaccaaaa atgataggggg gaattggagg tttatcaaa      60 gtaagacagt atgatcagat actcatagaa atctgtggac ataaagctat aggtacagta    120
ttagtaggac ctacacctgt caacataatt ggaagaaatc tgttgactca gattggttgc    180
actttaaatt ttcccattag ccctattgag actgtaccag taaaattaaa gccaggaatg    240
gatggcccaa aagttaaaca atggccattg acagaagaaa aaataaaagc attagtagaa    300
atttgtacag agatggaaaa ggaagggaaa atttcaaaaa ttgggcctga aaatccatac    360
aatactccag tatttgccat aaagaaaaaa gacagtacta atggagaaaa attagtagat    420
ttcagagaac ttaataagag aactcaagac ttctgggaag ttcaattagg aataccacat    480
cccgcagggt taaaaagaa aaaatcagta acagtactgg atgtgggtga tgcatatttt    540
tcagttccct tagatgaaga cttcaggaaa tatactgcat ttaccatacc tagtataaac    600
aatgagacac cagggattag atatcagtac aatgtgcttc cacagggatg aaaggatca    660 ccagcaatat tccaaagtag catgacaaaa atcttagagc cttttagaaa acaaaatcca    720
gacatagtta tctatcaata catggatgat ttgtatgtag gatctgactt agaaataggg    780
cagcatagaa caaaaataga ggagctgaga caacatctgt tgaggtgggg acttaccaca    840
ccagacaaaa aacatcagaa agaacctcca ttcctttgga tgggttatga actccatcct    900
gataaatgga cagtacagcc tatagtgctg ccagaaaaag acagctggac tgtcaatgac    960
atacagaagt tagtgggaa attgaattgg gcaagtcaga tttacccagg gattaaagta   1020
aggcaattat gtaaactcct tagaggaacc aaagcactaa cagaagtaat accactaaca   1080
gaagaagcag agctagaact ggcagaaaac agagagattc taaaagaacc agtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
```

```
atgagggtg cccacactaa tgatgtaaaa caattaacag aggcagtgca aaaaataacc    1320
acagaaagca tagtaatatg gggaaagact cctaaattta aactgcccat acaaaaggaa    1380
acatgggaaa catggtggac agagtattgg caagccacct ggattcctga gtgggagttt    1440
gttaataccc ctcctttagt gaaattatgg taccagttag agaaagaacc catagtagga    1500
gcagaaacct tctatgtaga tggggcagct aacagggaga ctaaattagg aaaagcagga    1560
tatgttacta atagaggaag acaaaaagtt gtcaccctaa ctgacacaac aaatcagaag    1620
actgagttac aagcaattta tctagctttg caggattcgg gattagaagt aaacatagta    1680
acagactcac aatatgcatt aggaatcatt caagcacaac cagatcaaag tgaatcagag    1740
ttagtcaatc aaataataga gcagttaata aaaaaggaaa aggtctatct ggcatgggta    1800
ccagcacaca aaggaattgg aggaaatgaa caagtagata aattagtcag tgctggaatc    1860
aggaaagtac tatttttaga tggaatagat aaggcccaag atgaacatga aaatatcac    1920 agtaattgga gagcaatggc tagtgatttt aacctgccac ctgtagtagc aaaagaaata    1980
gtagccagct gtgataaatg tcagctaaaa ggagaagcca tgcatggaca agtagactgt    2040
agtccaggaa tatggcaact agattgtaca catttagaag gaaaagttat cctggtagca    2100
gttcatgtag ccagtggata tatagaagca gaagttattc cagcagaaac agggcaggaa    2160
acagcatatt ttcttttaaa attagcagga agatggccag taaaaacaat acatacagac    2220
aatggcagca atttcaccag tgctacggtt aaggccgcct gttggtgggc gggaatcaag    2280
caggaatttg gaattcccta caatccccaa agtcaaggag tagtagaatc tatgaataaa    2340
gaattaaaga aaattatagg acaggtaaga gatcaggctg aacatcttaa gacagcagta    2400
caaatggcag tattcatcca catttttaaa agaaaagggg ggattggggg gtacagtgca    2460
ggggaaagaa tagtagacat aatagcaaca gacatacaaa ctaaagaatt acaaaaacaa    2520
attacaaaaa ttcaaaattt tcgggtttat tacagggaca gcagaaatcc actttggaaa    2580
ggaccagcaa agctcctctg gaaaggtgaa ggggcagtag taatacaaga taatagtgac    2640
ataaaagtag tgccaagaag aaaagcaaag atcattaggg attatggaaa acagatggca    2700
ggtgatgatt gtgtggcaag tagacaggat gaggat                              2736
```

```
<210> SEQ ID NO 37
<211> LENGTH: 912
<212> TYPE: PRT
<213> ORGANISM: Artificial Sequence
<220> FEATURE:
<223> OTHER INFORMATION: Variant HIV-1 POL Protein Comprising D249V,
      D250V and D688V Substitutions

<400> SEQUENCE: 37

Met Ser Leu Pro Gly Arg Trp Lys Pro Lys Met Ile Gly Gly Ile Gly
1               5                   10                  15

Gly Phe Ile Lys Val Arg Gln Tyr Asp Gln Ile Leu Ile Glu Ile Cys
                20                  25                  30

Gly His Lys Ala Ile Gly Thr Val Leu Val Gly Pro Thr Pro Val Asn
            35                  40                  45

Ile Ile Gly Arg Asn Leu Leu Thr Gln Ile Gly Cys Thr Leu Asn Phe
        50                  55                  60

Pro Ile Ser Pro Ile Glu Thr Val Pro Val Lys Leu Lys Pro Gly Met
65                  70                  75                  80

Asp Gly Pro Lys Val Lys Gln Trp Pro Leu Thr Glu Glu Lys Ile Lys
                85                  90                  95
```

```
Ala Leu Val Glu Ile Cys Thr Glu Met Glu Lys Glu Gly Lys Ile Ser
                100                 105                 110

Lys Ile Gly Pro Glu Asn Pro Tyr Asn Thr Pro Val Phe Ala Ile Lys
            115                 120                 125

Lys Lys Asp Ser Thr Lys Trp Arg Lys Leu Val Asp Phe Arg Glu Leu
130                 135                 140

Asn Lys Arg Thr Gln Asp Phe Trp Glu Val Gln Leu Gly Ile Pro His
145                 150                 155                 160

Pro Ala Gly Leu Lys Lys Lys Ser Val Thr Val Leu Asp Val Gly
                165                 170                 175

Asp Ala Tyr Phe Ser Val Pro Leu Asp Glu Asp Phe Arg Lys Tyr Thr
            180                 185                 190

Ala Phe Thr Ile Pro Ser Ile Asn Asn Glu Thr Pro Gly Ile Arg Tyr
        195                 200                 205

Gln Tyr Asn Val Leu Pro Gln Gly Trp Lys Gly Ser Pro Ala Ile Phe
    210                 215                 220

Gln Ser Ser Met Thr Lys Ile Leu Glu Pro Phe Arg Lys Gln Asn Pro
225                 230                 235                 240

Asp Ile Val Ile Tyr Gln Tyr Met Val Val Leu Tyr Val Gly Ser Asp
                245                 250                 255

Leu Glu Ile Gly Gln His Arg Thr Lys Ile Glu Glu Leu Arg Gln His
            260                 265                 270

Leu Leu Arg Trp Gly Leu Thr Thr Pro Asp Lys Lys His Gln Lys Glu
        275                 280                 285

Pro Pro Phe Leu Trp Met Gly Tyr Glu Leu His Pro Asp Lys Trp Thr
    290                 295                 300

Val Gln Pro Ile Val Leu Pro Glu Lys Asp Ser Trp Thr Val Asn Asp
305                 310                 315                 320

Ile Gln Lys Leu Val Gly Lys Leu Asn Trp Ala Ser Gln Ile Tyr Pro
                325                 330                 335

Gly Ile Lys Val Arg Gln Leu Cys Lys Leu Leu Arg Gly Thr Lys Ala
            340                 345                 350

Leu Thr Glu Val Ile Pro Leu Thr Glu Glu Ala Glu Leu Glu Leu Ala
        355                 360                 365

Glu Asn Arg Glu Ile Leu Lys Glu Pro Val His Gly Val Tyr Tyr Asp
    370                 375                 380

Pro Ser Lys Asp Leu Ile Ala Glu Ile Gln Lys Gln Gly Gln Gly Gln
385                 390                 395                 400

Trp Thr Tyr Gln Ile Tyr Gln Glu Pro Phe Lys Asn Leu Lys Thr Gly
                405                 410                 415

Lys Tyr Ala Arg Met Arg Gly Ala His Thr Asn Asp Val Lys Gln Leu
            420                 425                 430

Thr Glu Ala Val Gln Lys Ile Thr Thr Glu Ser Ile Val Ile Trp Gly
        435                 440                 445

Lys Thr Pro Lys Phe Lys Leu Pro Ile Gln Lys Glu Thr Trp Glu Thr
    450                 455                 460

Trp Trp Thr Glu Tyr Trp Gln Ala Thr Trp Ile Pro Glu Trp Glu Phe
465                 470                 475                 480

Val Asn Thr Pro Pro Leu Val Lys Leu Trp Tyr Gln Leu Glu Lys Glu
                485                 490                 495

Pro Ile Val Gly Ala Glu Thr Phe Tyr Val Asp Gly Ala Ala Asn Arg
            500                 505                 510

Glu Thr Lys Leu Gly Lys Ala Gly Tyr Val Thr Asn Arg Gly Arg Gln
```

```
                515                 520                 525
Lys Val Val Thr Leu Thr Asp Thr Thr Asn Gln Lys Thr Glu Leu Gln
530                 535                 540

Ala Ile Tyr Leu Ala Leu Gln Asp Ser Gly Leu Glu Val Asn Ile Val
545                 550                 555                 560

Thr Asp Ser Gln Tyr Ala Leu Gly Ile Ile Gln Ala Gln Pro Asp Gln
                565                 570                 575

Ser Glu Ser Glu Leu Val Asn Gln Ile Ile Glu Gln Leu Ile Lys Lys
            580                 585                 590

Glu Lys Val Tyr Leu Ala Trp Val Pro Ala His Lys Gly Ile Gly Gly
        595                 600                 605

Asn Glu Gln Val Asp Lys Leu Val Ser Ala Gly Ile Arg Lys Val Leu
610                 615                 620

Phe Leu Asp Gly Ile Asp Lys Ala Gln Asp His Glu Lys Tyr His
625                 630                 635                 640

Ser Asn Trp Arg Ala Met Ala Ser Asp Phe Asn Leu Pro Pro Val Val
                645                 650                 655

Ala Lys Glu Ile Val Ala Ser Cys Asp Lys Cys Gln Leu Lys Gly Glu
            660                 665                 670

Ala Met His Gly Gln Val Asp Cys Ser Pro Gly Ile Trp Gln Leu Val
        675                 680                 685

Cys Thr His Leu Glu Gly Lys Val Ile Leu Val Ala Val His Val Ala
690                 695                 700

Ser Gly Tyr Ile Glu Ala Glu Val Ile Pro Ala Glu Thr Gly Gln Glu
705                 710                 715                 720

Thr Ala Tyr Phe Leu Leu Lys Leu Ala Gly Arg Trp Pro Val Lys Thr
                725                 730                 735

Ile His Thr Asp Asn Gly Ser Asn Phe Thr Ser Ala Thr Val Lys Ala
            740                 745                 750

Ala Cys Trp Trp Ala Gly Ile Lys Gln Glu Phe Gly Ile Pro Tyr Asn
        755                 760                 765

Pro Gln Ser Gln Gly Val Val Glu Ser Met Asn Lys Glu Leu Lys Lys
770                 775                 780

Ile Ile Gly Gln Val Arg Asp Gln Ala Glu His Leu Lys Thr Ala Val
785                 790                 795                 800

Gln Met Ala Val Phe Ile His Asn Phe Lys Arg Lys Gly Gly Ile Gly
                805                 810                 815

Gly Tyr Ser Ala Gly Glu Arg Ile Val Asp Ile Ile Ala Thr Asp Ile
            820                 825                 830

Gln Thr Lys Glu Leu Gln Lys Gln Ile Thr Lys Ile Gln Asn Phe Arg
        835                 840                 845

Val Tyr Tyr Arg Asp Ser Arg Asn Pro Leu Trp Lys Gly Pro Ala Lys
850                 855                 860

Leu Leu Trp Lys Gly Glu Gly Ala Val Val Ile Gln Asp Asn Ser Asp
865                 870                 875                 880

Ile Lys Val Val Pro Arg Arg Lys Ala Lys Ile Ile Arg Asp Tyr Gly
                885                 890                 895

Lys Gln Met Ala Gly Asp Asp Cys Val Ala Ser Arg Gln Asp Glu Asp
            900                 905                 910

<210> SEQ ID NO 38
<211> LENGTH: 2739
<212> TYPE: DNA
<213> ORGANISM: Artificial Sequence
```

<220> FEATURE:
<223> OTHER INFORMATION: Polynucleotide Encoding Variant HIV-1 POL
    Protein Comprising D249V, D250V and D688V Substitutions

<400> SEQUENCE: 38

```
atgagtttgc caggaagatg gaaaccaaaa atgatagggg gaattggagg ttttatcaaa     60
gtaagacagt atgatcagat actcatagaa atctgtggac ataaagctat aggtacagta    120
ttagtaggac ctacacctgt caacataatt ggaagaaatc tgttgactca gattggttgc    180
actttaaatt ttcccattag ccctattgag actgtaccag taaaattaaa gccaggaatg    240
gatggcccaa aagttaaaca atggccattg acagaagaaa aaataaaagc attagtagaa    300
atttgtacag agatggaaaa ggaagggaaa atttcaaaaa ttgggcctga aaatccatac    360
aatactccag tatttgccat aaagaaaaaa gacagtacta aatggagaaa attagtagat    420
ttcagagaac ttaataagag aactcaagac ttctgggaag ttcaattagg aataccacat    480
cccgcagggt taaaaaagaa aaaatcagta acagtactgg atgtgggtga tgcatatttt    540
tcagttccct tagatgaaga cttcaggaaa tatactgcat ttaccatacc tagtataaac    600
aatgagacac cagggattag atatcagtac aatgtgcttc cacagggatg gaaaggatca    660
ccagcaatat tccaaagtag catgacaaaa atcttagagc cttttagaaa acaaaatcca    720
gacatagtta tctatcaata catggtcgtg ttgtatgtag gatctgactt agaaataggg    780
cagcatagaa caaaaataga ggagctgaga caacatctgt tgaggtgggg acttaccaca    840
ccagacaaaa aacatcagaa agaacctcca ttcctttgga tgggttatga actccatcct    900
gataaatgga cagtacagcc tatagtgctg ccagaaaaag acagctggac tgtcaatgac    960
atacagaagt tagtggggaa attgaattgg gcaagtcaga tttacccagg gattaaagta   1020
aggcaattat gtaaactcct tagaggaacc aaagcactaa cagaagtaat accactaaca   1080
gaagaagcag agctagaact ggcagaaaac agagagattc taaaagaacc agtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
atgaggggtg cccacactaa tgatgtaaaa caattaacag aggcagtgca aaaaataacc   1320
acagaaagca tagtaatatg gggaaagact cctaaattta aactgcccat acaaaaggaa   1380
acatgggaaa catggtggac agagtattgg caagccacct ggattcctga gtgggagttt   1440
gttaataccc ctcctttagt gaaattatgg taccagttag agaaagaacc catagtagga   1500
gcagaaacct tctatgtaga tggggcagct aacagggaga ctaaattagg aaaagcagga   1560
tatgttacta atagaggaag acaaaaagtt gtcaccctaa ctgacacaac aaatcagaag   1620
actgagttac aagcaattta tctagctttg caggattcgg gattagaagt aaacatagta   1680
acagactcac aatatgcatt aggaatcatt caagcacaac cagatcaaag tgaatcagag   1740
ttagtcaatc aaataataga gcagttaata aaaaaggaaa aggtctatct ggcatgggta   1800
ccagcacaca aaggaattgg aggaaatgaa caagtagata aattagtcag tgctggaatc   1860
aggaaagtac tatttttaga tggaatagat aaggcccaag atgaacatga gaaatatcac   1920
agtaattgga gagcaatggc tagtgatttt aacctgccac ctgtagtagc aaaagaaata   1980
gtagccagct gtgataaatg tcagctaaaa ggagaagcca tgcatggaca agtagactgt   2040
agtccaggaa tatggcaact agtctgtaca catttagaag gaaaagttat cctggtagca   2100
gttcatgtag ccagtggata tatagaagca gaagttattc cagcagaaac agggcaggaa   2160
acagcatatt ttcttttaaa attagcagga agatggccag taaaaacaat acatacagac   2220
```

```
aatggcagca atttcaccag tgctacggtt aaggccgcct gttggtgggc gggaatcaag    2280
caggaatttg gaattcccta caatccccaa agtcaaggag tagtagaatc tatgaataaa    2340
gaattaaaga aaattatagg acaggtaaga gatcaggctg aacatcttaa gacagcagta    2400
caaatggcag tattcatcca caattttaaa agaaaagggg ggattggggg gtacagtgca    2460
ggggaaagaa tagtagacat aatagcaaca gacatacaaa ctaaagaatt acaaaaacaa    2520
attacaaaaa ttcaaaattt tcgggtttat tacagggaca gcagaaatcc actttggaaa    2580
ggaccagcaa agctcctctg gaaaggtgaa ggggcagtag taatacaaga taatagtgac    2640
ataaaagtag tgccaagaag aaaagcaaag atcattaggg attatggaaa acagatggca    2700
ggtgatgatt gtgtggcaag tagacaggat gaggattag                          2739

<210> SEQ ID NO 39
<211> LENGTH: 66
<212> TYPE: DNA
<213> ORGANISM: SV40
<220> FEATURE:
<221> NAME/KEY: misc_feature
<222> LOCATION: (1)..(66)
<223> OTHER INFORMATION: Polynucleotide That Comprises SV40 Small t
      Intron

<400> SEQUENCE: 39
gtaaatataa aatttttaag tgtataatgt gttaaactac tgattctaat tgtttgtgta    60
ttttag                                                               66

<210> SEQ ID NO 40
<211> LENGTH: 7
<212> TYPE: PRT
<213> ORGANISM: SV40
<220> FEATURE:
<221> NAME/KEY: MISC_FEATURE
<222> LOCATION: (1)..(7)
<223> OTHER INFORMATION: Nuclear Localization Signal of SV40 Large T
      Antigen

<400> SEQUENCE: 40

Pro Lys Lys Lys Arg Lys Val
1               5

<210> SEQ ID NO 41
<211> LENGTH: 21
<212> TYPE: DNA
<213> ORGANISM: SV40
<220> FEATURE:
<221> NAME/KEY: misc_feature
<222> LOCATION: (1)..(21)
<223> OTHER INFORMATION: Polynucleotide Encoding Nuclear Localization
      Signal of SV40 Large T Antigen

<400> SEQUENCE: 41
ccaaaaaaga agagaaaggt a                                              21

<210> SEQ ID NO 42
<211> LENGTH: 135
<212> TYPE: DNA
<213> ORGANISM: SV40
<220> FEATURE:
<221> NAME/KEY: misc_feature
<222> LOCATION: (1)..(135)
<223> OTHER INFORMATION: SV40 Poly(A) Polyadenylation Signal Site

<400> SEQUENCE: 42
```

| aacttgttta ttgcagctta taatggttac aaataaagca atagcatcac aaatttcaca | 60 |
| aataaagcat tttttcact gcattctagt tgtggtttgt ccaaactcat caatgtatct | 120 |
| tatcatgtct ggatc | 135 |

```
<210> SEQ ID NO 43
<211> LENGTH: 196
<212> TYPE: DNA
<213> ORGANISM: SV40
<220> FEATURE:
<221> NAME/KEY: misc_feature
<222> LOCATION: (1)..(196)
<223> OTHER INFORMATION: SV40 Early Promoter

<400> SEQUENCE: 43
```

| gcatctcaat tagtcagcaa ccatagtccc gcccctaact ccgcccatcc cgcccctaac | 60 |
| tccgcccagt tccgcccatt ctccgcccca tggctgacta atttttttta tttatgcaga | 120 |
| ggccgaggcc gcctcggcct ctgagctatt ccagaagtag tgaggaggct ttttggagg | 180 |
| cctaggcttt tgcaaa | 196 |

```
<210> SEQ ID NO 44
<211> LENGTH: 11282
<212> TYPE: DNA
<213> ORGANISM: Artificial Sequence
<220> FEATURE:
<223> OTHER INFORMATION: pGAG Vector

<400> SEQUENCE: 44
```

| ttcaacattt ccgtgtcgcc cttattccct ttttgcggc attttgcctt cctgttttg | 60 |
| ctcacccaga aacgctggtg aaagtaaaag atgctgaaga tcagttgggt gcacgagtgg | 120 |
| gttacatcga actggatctc aacagcggta agatccttga gttttcgc cccgaagaac | 180 |
| gttttccaat gatgagcact tttaaagttc tgctatgtgg cgcggtatta tcccgtgttg | 240 |
| acgccgggca agagcaactc ggtcgccgca tacactattc tcagaatgac ttggttgagt | 300 |
| actcaccagt cacagaaaag catcttacgg atggcatgac agtaagagaa ttatgcagtg | 360 |
| ctgccataac catgagtgat aacactgcgg ccaacttact tctgacaacg atcggaggac | 420 |
| cgaaggagct aaccgctttt ttgcacaaca tgggggatca tgtaactcgc cttgatcgtt | 480 |
| gggaaccgga gctgaatgaa gccataccaa acgacgagcg tgacaccacg atgcctgcag | 540 |
| caatggcaac aacgttgcgc aaactattaa ctggcgaact acttactcta gcttcccggc | 600 |
| aacaattaat agactggatg gaggcggata aagttgcagg accacttctg cgctcggccc | 660 |
| ttccggctgg ctggtttatt gctgataaat ctggagccgg tgagcgtggg tctcgcggta | 720 |
| tcattgcagc actggggcca gatggtaagc cctcccgtat cgtagttatc tacacgacgg | 780 |
| ggagtcaggc aactatggat gaacgaaata gacagatcgc tgagataggt gcctcactga | 840 |
| ttaagcattg gtaactgtca gaccaagttt actcatatat actttagatt gatttaaaac | 900 |
| ttcatttta atttaaaagg atctaggtga agatcctttt tgataatctc atgaccaaaa | 960 |
| tcccttaacg tgagttttcg ttccactgag cgtcagaccc cgtagaaaag atcaaaggat | 1020 |
| cttcttgaga tcctttttt ctgcgcgtaa tctgctgctt gcaaacaaaa aaaccaccgc | 1080 |
| taccagcggt ggtttgtttg ccggatcaag agctaccaac tctttttccg aaggtaactg | 1140 |
| gcttcagcag agcgcagata ccaaatactg tccttctagt gtagccgtag ttaggccacc | 1200 |
| acttcaagaa ctctgtagca ccgcctacat acctcgctct gctaatcctg ttaccagtgg | 1260 |
| ctgctgccag tggcgataag tcgtgtctta ccgggttgga ctcaagacga tagttaccgg | 1320 |

```
ataaggcgca gcggtcgggc tgaacggggg gttcgtgcac acagcccagc ttggagcgaa      1380
cgacctacac cgaactgaga tacctacagc gtgagctatg agaaagcgcc acgcttcccg      1440
aagggagaaa ggcggacagg tatccggtaa gcggcagggt cggaacagga gagcgcacga      1500
gggagcttcc aggggaaac gcctggtatc tttatagtcc tgtcgggttt cgccacctct       1560
gacttgagcg tcgattttg tgatgctcgt caggggggcg gagcctatgg aaaaacgcca       1620
gcaacgcggc cttttacgg ttcctggcct tttgctggcc ttttgctcac atgttctttc       1680
ctgcgttatc ccctgattct gtggataacc gtattaccgc ctttgagtga gctgataccg      1740
ctcgccgcag ccgaacgacc gagcgcagcg agtcagtgag cgaggaagcg gaagagcgcc      1800
tgatgcggta ttttctcctt acgcatctgt gcggtatttc acaccgcata tggtgcactc      1860
tcagtacaat ctgctctgat gccgcatagt taagccagta tcctcgacat cgctctagtc      1920
tagttattaa tagtaatcaa ttacggggtc attagttcat agcccatata tggagttccg      1980
cgttacataa cttacggtaa atggcccgcc tggctgaccg cccaacgacc cccgcccatt      2040
gacgtcaata atgacgtatg ttcccatagt aacgccaata gggactttcc attgacgtca      2100
atgggtggag tatttacggt aaactgccca cttggcagta catcaagtgt atcatatgcc      2160
aagtacgccc cctattgacg tcaatgacgg taaatggccc gcctggcatt atgcccagta      2220
catgacctta tgggactttc ctacttggca gtacatctac gtattagtca tcgctattac      2280
catggtgatg cggttttggc agtacatcaa tgggcgtgga tagcggtttg actcacgggg      2340
atttccaagt ctccacccca ttgacgtcaa tgggagtttg ttttggcacc aaaatcaacg      2400
ggactttcca aatgtcgta acaactccgc cccattgacg caaatgggcg taggcgtgt        2460 acggtgggag gtctatataa gcagagctct ctggctaact agagaaccca ctgcttactg      2520
gcttatcgaa attaatacga ctcactatag ggagacccaa gcttggtacc gagctcggat      2580
ccactagagc gcgcacggca agaggcgagg ggcggcgact ggtgagtacg ccggctagaa      2640
ggagagagat gggtgcgaga gcgtcagtat taagcggggg agaattagat cgatgggaaa      2700
aaattcggtt aaggccaggg ggaaagaaaa aatataaatt aaaacatata gtatgggcaa      2760
gcagggagct agaacgattc gcagttaatc ctggcctgtt agaaacatca gaaggctgta      2820
gacaaatact gggacagcta caaccatccc ttcagacagg atcagaagaa cttagatcat      2880
tatataatac agtagcaacc ctctattgtg tgcatcaaag gatagagata aaagacacca      2940
aggaagcttt agacaagata gaggaagagc aaaacaaaag taagaaaaaa gcacagcaag      3000
cagcagctga cacaggacac agcaatcagg tcagccaaaa ttaccctata gtgcagaaca      3060
tccaggggca aatggtacat caggccatat cacctagaac tttaaatgca tgggtaaaag      3120
tagtagaaga gaaggctttc agcccagaag tgatacccat gttttcagca ttatcagaag      3180
gagccacccc acaagattta aacaccatgc taaacacagt ggggggacat caagcagcca      3240
tgcaaatgtt aaaagagacc atcaatgagg aagctgcaga atgggataga gtgcatccag      3300
tgcatgcagg gcctattgca ccaggccaga tgagagaacc aaggggaagt gacatagcag      3360
gaactactag taccctttcag gaacaaatag gatggatgac aaataatcca cctatcccag      3420
taggagaaat ttataaaaga tggataatcc tgggattaaa taaaatagta agaatgtata      3480
gccctaccag cattctggac ataagacaag gaccaaaaga accctttaga gactatgtag      3540
accggttcta taaaactcta agagccgagc aagcttcaca ggaggtaaaa aattggatga      3600
cagaaacctt gttggtccaa aatgcgaacc cagattgtaa gactatttta aaagcattgg      3660
```

```
gaccagcggc tacactagaa gaaatgatga cagcatgtca gggagtagga ggacccggcc   3720
ataaggcaag agttttggct gaagcaatga gccaagtaac aaattcagct accataatga   3780
tgcagagagg caattttagg aaccaaagaa agattgttaa gtgtttcaat tgtggcaaag   3840
aagggcacac agccagaaat tgcagggccc ctaggaaaaa gggctgttgg aaatgtggaa   3900
aggaaggaca ccaaatgaaa gattgtactg agagacaggc taattttta gggaagatct   3960
ggccttccta caagggaagg ccagggaatt ttcttcagag cagaccagag ccaacagccc   4020
caccagaaga gagcttcagg tctggggtag agacaacaac tcccctcag aagcaggagc   4080
cgatagacaa ggaactgtat cctttaactt ccctcagatc actctttggc aacgacccct   4140
cgtcacaata aagatagggg ggcaactaaa ggaagctcta ttagatacag gagcagatga   4200
tacagtatta gaagaaatga gtttgccagg aagatggaaa ccaaaaatga taggggaat   4260
tggaggtttt atcaaagtaa gacagtatga tcagatactc atagaaatct gtggacataa   4320
agctataggt acagtattag taggacctac acctgtcaac ataattggaa gaaatctgtt   4380
gactcagatt ggttgcactt taaattttcc cattagccct attgagactg taccagtaaa   4440
attaaagcca ggaatggatg gcccaaaagt taaacaatgg ccattgacag aagaaaaaat   4500
aaaagcatta gtagaaattt gtacagagat ggaaaaggaa gggaaaattt caaaaattgg   4560
gcctgaaaat ccatacaata ctccagtatt tgccataaag aaaaaagaca gtactaaatg   4620
gagaaaatta gtagatttca gagaacttaa taagagaact caagacttct gggaagttca   4680
attaggaata ccacatcccg cagggttaaa aagaaaaaa tcagtaacag tactggatgt   4740
gggtgatgca tattttcag ttcccttaga tgaagacttc aggaaatata ctgcatttac   4800
catacctagt ataaacaatg agacaccagg gattagatat cagtacaatg tgcttccaca   4860
gggatggaaa ggatcaccag caatattcca aagtagcatg acaaaaatct tagagccttt   4920
tagaaaacaa aatccagaca tagttatcta tcaatacatg gatgatttgt atgtaggatc   4980
tgacttagaa ataggcagc atagaacaaa aatagaggag ctgagacaac atctgttgag   5040
gtggggactt accacaccag acaaaaaaca tcagaaagaa cctccattcc tttggatggg   5100
ttatgaactc catcctgata atgtgacagt acagcctata gtgctgccag aaaaagacag   5160
ctggactgtc aatgacatac agaagttagt ggggaaattg aattgggcaa gtcagattta   5220
cccagggatt aaagtaaggc aattatgtaa actccttaga ggaaccaaag cactaacaga   5280
agtaatacca ctaacagaag aagcagagct agaactggca gaaaacagag agattctaaa   5340
agaaccagta catggagtgt attatgaccc atcaaaagac ttaatagcag aaatacagaa   5400
gcagggcaa ggccaatgga catatcaaat ttatcaagag ccatttaaaa atctgaaaac   5460
aggaaaatat gcaagaatga ggggtgccca cactaatgat gtaaaacaat aacagaggc   5520
agtgcaaaaa ataaccacag aaagcatagt aatatgggga aagactccta aatttaaact   5580
gcccatacaa aaggaaacat gggaaacatg tggacagagta tattggcaag ccacctggat   5640
tcctgagtgg gagtttgtta ataccctcc tttagtgaaa ttatggtacc agttagaaaa   5700
agaacccata gtaggagcag aaaccttcta tgtagatggg gcagctaaca gggagactaa   5760
attaggaaaa gcaggatatg ttactaatag aggaagacaa aaagttgtca ccctaactga   5820
cacaacaaat cagaagactg agttacaagc aatttatcta gctttgcagg attcgggatt   5880
agaagtaaac atagtaacag actcacaata tgcattagga atcattcaag cacaaccaga   5940
tcaaagtgaa tcagagttag tcaatcaaat aatagagcag ttaataaaaa aggaaaaggt   6000
ctatctggca tgggtaccag cacacaaagg aattggagga aatgaacaag tagataaatt   6060
```

```
agtcagtgct ggaatcagga aagtactatt tttagatgga atagataagg cccaagatga   6120
acatgagaaa tatcacagta attggagagc aatggctagt gattttaacc tgccacctgt   6180
agtagcaaaa gaaatagtag ccagctgtga taaatgtcag ctaaaaggag aagccatgca   6240
tggacaagta gactgtagtc caggaatatg gcaactagat tgtacacatt tagaaggaaa   6300
agttatcctg gtagcagttc atgtagccag tggatatata gaagcagaag ttattccagc   6360
agaaacaggg caggaaacag catattttct tttaaaatta gcaggaagat ggccagtaaa   6420
aacaatacat acagacaatg gcagcaattt caccagtgct acggttaagg ccgcctgttg   6480
gtgggcggga atcaagcagg aatttggaat tccctacaat ccccaaagtc aaggagtagt   6540
agaatctatg aataaagaat taagaaaat tataggacag gtaagagatc aggctgaaca   6600
tcttaagaca gcagtacaaa tggcagtatt catccacaat tttaaaagaa aaggggggat   6660
tggggggtac agtgcagggg aaagaatagt agacataata gcaacagaca tacaaactaa   6720
agaattacaa aaacaaatta caaaaattca aaattttcgg gtttattaca gggacagcag   6780
aaatccactt tggaaaggac cagcaaagct cctctggaaa ggtgaagggg cagtagtaat   6840
acaagataat agtgacataa aagtagtgcc aagaagaaaa gcaaagatca ttagggatta   6900
tggaaaacag atggcaggtg atgattgtgt ggcaagtaga caggatgagg attagaacat   6960
ggaaaagttt agtaaaacac catatgtata tttcaaggaa agctaaggac tggttttata   7020
gacatcacta tgaaagtact aatccaaaaa taagttcaga agtacacatc ccactagggg   7080
atgctaaatt agtaataaca acatattggg gtctgcatac aggagaaaga gactggcatt   7140
tgggtcaggg agtctccata gaatggagga aaaagagata tagcacacaa gtagaccctg   7200
acctagcaga ccaactaatt catctgcact attttgattg ttttttcagaa tctgctataa   7260 gaaataccat attaggacgt atagttagtc ctaggtgtga atatcaagca ggacataaca   7320
aggtaggatc tctacagtac ttggcactag cagcattaat aaaaccaaaa cagataaagc   7380 caccctttgcc tagtgttagg aaactgacag aggacagatg gaacaagccc cagaagacca   7440
agggccacag agggagccat acaatgaatg gacactagag cttttagagg aacttaagag   7500
tgaagctgtt agacattttc ctaggatatg gctccataac ttaggacaac atatctatga   7560
aacttacggg gatacttggg caggagtgga agccataata agaattctgc aacaactgct   7620
gtttatccat ttcagaattg ggtgtcgaca tagcagaata ggcgttactc gacagaggag   7680
agcaagaaat ggagccagta gatcctagac tagagccctg gaagcatcca ggaagtcagc   7740
ctaaaactgc ttgtaccaat tgctattgta aaaagtgttg ctttcattgc caagtttgtt   7800
tcatgacaaa agccttaggc atctcctatg gcaggaagaa gcggagacag cgacgaagag   7860
ctcatcagaa cagtcagact catcaagctt ctctatcaaa gcagtaagta gtacatgtaa   7920
tgcaacctat aatagtagca atagtagcat tagtagtagc aataataata gcaatagttg   7980
tgtggtccat agtaatcata gaatatagga aaatattaag acaagaaaaa atagacaggt   8040
taattgatag actaatagaa agagcagaag acagtggcaa tgagagtgaa ggagaagtat   8100
cagcacttgt ggagatgggg gtggaaatgg ggcaccatgc tccttgggat attgatgatc   8160
tgtagtgcta cagaaaaatt gtgggtcaca gtctattatg gggtacctgt gtggaaggaa   8220
gcaaccacca ctctattttg tgcatcagat gctaaagcat atgatacaga ggtacataat   8280
gtttgggcca cacatgcctg tgtacccaca gaccccaacc cacaagaagt agtattggta   8340
aatgtgacag aaaattttaa catgtggaaa aatgacatgg tagaacagat gcatgaggat   8400
```

```
ataatcagtt tatgggatca aagcctaaag ccatgtgtaa aattaacccc actctgtgtt    8460
agtttaaagt gcactgattt gaagaatgat actaatacca atagtagtag cgggagaatg    8520
ataatggaga aaggagagat aaaaaactgc tctttcaata tcagcacaag cataagaggt    8580
aaggtgcaga aagaatatgc atttttttat aaacttgata taataccaat agataatgat    8640
actaccagct ataagttgac aagttgtaac acctcagtca ttacacaggc ctgtccaaag    8700
gtatcctttg agccaattcc catacattat tgtgccccgg ctggttttgc gattctaaaa    8760
tgtaataata agacgttcaa tggaacagga ccatgtacaa atgtcagcac agtacaatgt    8820
acacatggaa ttaggccagt agtatcaact caactgctgt taaatggcag tctagcagaa    8880
gaagaggtag taattagatc gatcttcaga cctggaggag gagatatgag ggacaattgg    8940
agaagtgaat tatataaata taaagtagta aaaattgaac cattaggagt agcacccacc    9000
aaggcaaaga gaagagtggt gcagagagaa aaaagagcag tgggaatagg agctttgttc    9060
cttgggttct tgggagcagc aggaagcact atgggcgcag cgtcaatgac gctgacggta    9120
caggccagac aattattgtc tggtatagtg cagcagcaga acaatttgct gagggctatt    9180
gaggcgcaac agcatctgtt gcaactcaca gtctggggca tcaagcagct ccaggcaaga    9240
atcctggctg tggaaagata cctaaaggat caacagctcc tggggatttg gggttgctct    9300
ggaaaactca tttgcaccac tgctgtgcct tggaatgcta gttggagtaa taaatctctg    9360
gaacagattt ggaatcacac gacctggatg gagtgggaca gagaaattaa caattacaca    9420
agcttaatac actccttaat tgaagaatcg caaaaccagc aagaaaagaa tgaacaagaa    9480
ttattggaat tagataaatg ggcaagtttg tggaattggt ttaacataac aaattggctg    9540
tggtatataa aattattcat aatgatagta ggaggcttgg taggtttaag aatagttttt    9600
gctgtacttt ctatagtgaa tagagttagg cagggatatt caccattatc gtttcagacc    9660
cacctcccaa ccccgagggg acccgacagg cccgaaggaa tagaagaaga aggtggagag    9720
agagacagag acagatccat tcgattagtg aacggatctt gtgaaggaa ccttacttct    9780 gtggtgtgac ataattggac aaactaccta cagagattta aagctctaag gtaaatataa    9840
aatttttaag tgtataatgt gttaaactac tgattctaat tgtttgtgta ttttagattc    9900
caacctatgg aactgatgaa tgggagcagt ggtggaatgc ctttaatgag gaaaacctgt    9960
tttgctcaga gaaatgcca tctagtgatg atgaggctac tgctgactct caacattcta   10020
ctcctccaaa aagaagaga aaggtagaag accccaagga ctttccttca gaattgctaa   10080 gtttttgag tcatgctgtg tttagtaata gaactcttgc ttgctttgct atttacacca   10140
caaaggaaaa agctgcactg ctatacaaga aaattatgga aaaatattct gtaacccttta   10200 taagtaggca taacagttat aatcataaca tactgttttt tcttactcca cacaggcata   10260
gagtgtctgc tattaataac tatgctcaaa aattgtgtac ctttagcttt ttaatttgta   10320
aaggggttaa taaggaatat ttgatgtata gtgccttgac tagagatcat aatcagccat   10380
accacatttg tagaggtttt acttgcttta aaaaacctcc cacacctccc cctgaacctg   10440
aaacataaaa tgaatgcaat tgttgttgtt aacttgttta ttgcagctta taatggttac   10500
aaataaagca atagcatcac aaatttcaca ataaagcat ttttttcact gcattctagt   10560
tgtggtttgt ccaaactcat caatgtatct tatcatgtct ggatcccgcg atgtcgaggc   10620
atctcaatta gtcagcaacc atagtcccgc ccctaactcc gcccatcccg ccctaactc    10680 cgcccagttc cgcccattct ccgccccatg gctgactaat tttttttatt tatgcagagg   10740
ccgaggccgc ctcggcctct gagctattcc agaagtagtg aggaggcttt tttggaggcc   10800
```

-continued

```
taggcttttg caaaaagctt ggcgagattt tcaggagcta aggaagctaa aatggagaaa    10860
aaaatcactg gatataccac cgttgatata tcccaatggc atcgtaaaga acattttgag    10920
gcatttcagt cagttgctca atgtacctat aaccagaccg ttcagctgga tattacggcc    10980 ttttaaaga ccgtaaagaa aaataagcac aagtttatc cggcctttat tcacattctt     11040
gcccgcctga tgaatgctca tccggaattc ttgaagacga agggcctcg tgatacgcct     11100 atttttatag gttaatgtca tgataataat ggtttcttag acgtcaggtg gcacttttcg    11160
gggaaatgtg cgcggaaccc ctatttgttt attttctaa atacattcaa atatgtatcc     11220
gctcatgaga caataacct gataaatgct tcaataatat tgaaaaagga agagtatgag     11280
ta                                                                  11282
```

<210> SEQ ID NO 45
<211> LENGTH: 140
<212> TYPE: PRT
<213> ORGANISM: Artificial Sequence
<220> FEATURE:
<223> OTHER INFORMATION: Fusion Protein Comprising Nuclear Localization
      Signal of SV40 Large T Antigen

<400> SEQUENCE: 45

Pro Lys Lys Lys Arg Lys Val Glu Asp Pro Lys Asp Phe Pro Ser Glu
1               5                   10                  15

Leu Leu Ser Phe Leu Ser His Ala Val Phe Ser Asn Arg Thr Leu Ala
            20                  25                  30

Cys Phe Ala Ile Tyr Thr Thr Lys Glu Lys Ala Ala Leu Leu Tyr Lys
        35                  40                  45

Lys Ile Met Glu Lys Tyr Ser Val Thr Phe Ile Ser Arg His Asn Ser
    50                  55                  60

Tyr Asn His Asn Ile Leu Phe Phe Leu Thr Pro His Arg His Arg Val
65                  70                  75                  80

Ser Ala Ile Asn Asn Tyr Ala Gln Lys Leu Cys Thr Phe Ser Phe Leu
                85                  90                  95

Ile Cys Lys Gly Val Asn Lys Glu Tyr Leu Met Tyr Ser Ala Leu Thr
            100                 105                 110

Arg Asp His Asn Gln Pro Tyr His Ile Cys Arg Gly Phe Thr Cys Phe
        115                 120                 125

Lys Lys Pro Pro Thr Pro Pro Glu Pro Glu Thr
    130                 135                 140

<210> SEQ ID NO 46
<211> LENGTH: 116
<212> TYPE: PRT
<213> ORGANISM: Lentivirus
<220> FEATURE:
<221> NAME/KEY: MISC_FEATURE
<222> LOCATION: (1)..(116)
<223> OTHER INFORMATION: Lentiviral REV Protein

<400> SEQUENCE: 46

Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Asn Pro Glu
            20                  25                  30

Gly Thr Arg Gln Ala Arg Arg Asn Arg Arg Arg Trp Arg Glu Arg
        35                  40                  45

Gln Arg Gln Ile His Ser Ile Ser Glu Arg Ile Leu Gly Thr Tyr Leu

```
                50                  55                  60
Gly Arg Ser Ala Glu Pro Val Pro Leu Gln Leu Pro Pro Leu Glu Arg
 65                  70                  75                  80

Leu Thr Leu Asp Cys Asn Glu Asp Cys Gly Thr Ser Thr Gln Gly
                 85                  90                  95

Val Gly Ser Pro Gln Ile Leu Val Glu Ser Pro Thr Val Leu Glu Ser
            100                 105                 110

Gly Thr Lys Glu
        115

<210> SEQ ID NO 47
<211> LENGTH: 1582
<212> TYPE: DNA
<213> ORGANISM: Lentivirus
<220> FEATURE:
<221> NAME/KEY: misc_feature
<222> LOCATION: (1)..(1582)
<223> OTHER INFORMATION: Polynucleotide Capable of Being Processed to
      Form Lentiviral Rev Protein

<400> SEQUENCE: 47
atgctgctac cattgtcaga tgtgttttct aaacaagggg ctcggaattc cccggatccg      60
tcgactctag aggatctgca tctcctatgg caggaagaag cggagacagc gacgaagacc     120
tcctcaaggc agtcagactc atcaagtttc tctatcaaag caaccacct cccaatcccg      180 aggggacccg acaggcccga aggaatagaa gaagaaggtg agagagagag cagagacaga    240
tccattcgat tagtgaacgg atccttagca cttatctggg acgatctgcg gagcctgtgc    300
ctcttcagct accaccgctt gagagactta ctcttgattg taacgaggat gtggaactt     360 ctgggacgca gggggtggga agccctcaaa tattggtgga atctcctaca atattggagt    420
caggagctaa agaatagtgc tgttagcttg ctcaatgcca cagctatagc agtagctgag    480
gggacagata gggttataga agtagtacaa gaagcttata gagctattcg ccacatacct    540
agaagaataa gacagggctt ggaaaggatt ttgctataag atgggtggca agtggtcaaa    600
aagtagtgtg gttggatggc ctgctgtaag ggaaagaatg agacgagctg agccagcagc    660
agatggggtg ggagcagcat ctcgagacct agaaaaacat ggagcaatca caagtagcaa    720
cacagcagct aacaatgctg cttgtgcctg gctagaagca caagaggagg agaaggtggg    780
ttttccagtc acacctcagg taccgagctc gaattcactc tcaggtgca ggctgcctat    840 cagaaggtgg tggctggtgt ggccaatgcc ctggctcaca ataccactg agatctttgt     900 gaaggaacct tacttctgtg gtgtgacata attggacaaa ctacctacag agatttaaag    960
ctctaaggta aatataaat ttttaagtgt ataatgtgtt aaactactga ttctaattgt    1020
ttgtgtattt tagattccaa cctatggaac tgatgaatgg gagcagtggt ggaatgcctt    1080
taatgaggaa aacctgttt gctcagaaga aatgccatct agtgatgatg aggctactgc    1140
tgactctcaa cattctactc ctccaaaaaa gaagagaaag gtagaagacc caaggactt    1200 tccttcagaa ttgctaagtt ttttgagtca tgctgtgttt agtaatagaa ctcttgcttg    1260
ctttgctatt tacaccacaa aggaaaaagc tgcactgcta tacaagaaaa ttatggaaaa    1320
atattctgta accttttataa gtaggcataa cagttataat cataacatac tgttttttct     1380
tactccacac aggcatagag tgtctgctat taataactat gctcaaaaat tgtgtacctt    1440
tagcttttta atttgtaaag gggttaataa ggaatatttg atgtatagtg ccttgactag    1500
agatcataat cagccatacc acatttgtag aggttttact tgctttaaaa aacctcccac    1560
``` acctcccct gaacctgaaa ca        1582

<210> SEQ ID NO 48
<211> LENGTH: 66
<212> TYPE: DNA
<213> ORGANISM: SV40
<220> FEATURE:
<221> NAME/KEY: misc_feature
<222> LOCATION: (1)..(66)
<223> OTHER INFORMATION: SV40 Small t Antigen Intron

<400> SEQUENCE: 48
gtaaatataa aattttttaag tgtataatgt gttaaactac tgattctaat tgtttgtgta        60
ttttag        66

<210> SEQ ID NO 49
<211> LENGTH: 5514
<212> TYPE: DNA
<213> ORGANISM: Artificial Sequence
<220> FEATURE:
<223> OTHER INFORMATION: pREV Vector

<400> SEQUENCE: 49
gagaggacat tccaatcata ggctgcccat ccaccctctg tgtcctcctg ttaattaggt        60
cacttaacaa aaaggaaatt gggtaggggt ttttcacaga ccgctttcta agggtaattt        120
taaaatatct gggaagtccc ttccactgct gtgttccaga agtgttggta acagcccac        180 aaatgtcaac agcagaaaca tacaagctgt cagctttgca caagggccca acaccctgct        240
catcaagaag cactgtggtt gctgtgttag taatgtgcaa acaggaggc acattttccc        300 cacctgtgta ggttccaaaa tatctagtgt tttcattttt acttggatca ggaacccagc        360
actccactgg ataagcatta tccttatcca aaacagcctt gtggtcagtg ttcatctgct        420
gactgtcaac tgtagcattt tttggggtta cagtttgagc aggatatttg gtcctgtagt        480
ttgctaacac accctgcagc tccaaaggtt ccccaccaac agcaaaaaaa tgaaaatttg        540
acccttgaat gggttttcca gcaccatttt catgagtttt ttgtgtccct gaatgcaagt        600
ttaacatagc agttacccca ataacctcag ttttaacagt aacagcttcc cacatcaaaa        660
tatttccaca ggttaagtcc tcatttaaat taggcaaagg aattcttgaa gacgaaaggg        720
cctcgtgata cgcctatttt tataggttaa tgtcatgata ataatggttt cttagacgtc        780
aggtggcact tttcggggaa atgtgcgcgg aaccctatt tgtttatttt tctaaataca        840
ttcaaatatg tatccgctca tgagacaata accctgataa atgcttcaat aatattgaaa        900
aaggaagagt atgagtattc aacatttccg tgtcgccctt attcccttt ttgcggcatt        960 ttgccttcct gttttgctc acccagaaac gctggtgaaa gtaaaagatg ctgaagatca        1020
gttgggtgca cgagtgggtt acatcgaact ggatctcaac agcggtaaga tccttgagag        1080
ttttcgcccc gaagaacgtt ttccaatgat gagcactttt aaagttctgc tatgtggcgc        1140
ggtattatcc cgtgttgacg ccgggcaaga gcaactcggt cgccgcatac actattctca        1200
gaatgacttg gttgagtact caccagtcac agaaaagcat cttacggatg gcatgacagt        1260
aagagaatta tgcagtgctg ccataaccat gagtgataac actgcggcca acttacttct        1320
gacaacgatc ggaggaccga aggagctaac cgcttttttg cacaacatgg ggatcatgt        1380 aactcgcctt gatcgttggg aaccggagct gaatgaagcc ataccaaacg acgagcgtga        1440
caccacgatg cctgcagcaa tggcaacaac gttgcgcaaa ctattaactg gcgaactact        1500
tactctagct tcccggcaac aattaataga ctggatggag gcggataaag ttgcaggacc        1560

```
acttctgcgc tcggcccttc cggctggctg gtttattgct gataaatctg gagccggtga    1620
gcgtgggtct cgcggtatca ttgcagcact ggggccagat ggtaagccct cccgtatcgt    1680
agttatctac acgacgggga gtcaggcaac tatggatgaa cgaaatagac agatcgctga    1740
gataggtgcc tcactgatta agcattggta actgtcagac caagtttact catatatact    1800
ttagattgat ttaaaacttc attttttaatt taaaaggatc taggtgaaga tcctttttga    1860
taatctcatg accaaaatcc cttaacgtga gttttcgttc cactgagcgt cagacccgt    1920 agaaaagatc aaaggatctt cttgagatcc ttttttttctg cgcgtaatct gctgcttgca    1980
aacaaaaaaa ccaccgctac cagcggtggt ttgtttgccg gatcaagagc taccaactct    2040 tttttccgaag gtaactggct tcagcagagc gcagatacca aatactgtcc ttctagtgta    2100
gccgtagtta ggccaccact tcaagaactc tgtagcaccg cctacatacc tcgctctgct    2160
aatcctgtta ccagtggctg ctgccagtgg cgataagtcg tgtcttaccg ggttggactc    2220
aagacgatag ttaccggata aggcgcagcg gtcgggctga acggggggtt cgtgcacaca    2280
gcccagcttg gagcgaacga cctacaccga actgagatac ctacagcgtg agctatgaga    2340
aagcgccacg cttcccgaag ggagaaaggc ggacaggtat ccggtaagcg cagggtcgg    2400 aacaggagag cgcacgaggg agcttccagg gggaaacgcc tggtatcttt atagtcctgt    2460
cgggtttcgc cacctctgac ttgagcgtcg attttttgtga tgctcgtcag ggggggcggag    2520 cctatggaaa aacgccagca acgcggcctt tttacggttc ctggccttttt gctggccttt    2580 tgctcacatg ttctttcctg cgttatcccc tgattctgtg gataaccgta ttaccgcctt    2640
tgagtgagct gataccgctc gccgcagccg aacgaccgag cgcagcgagt cagtgagcga    2700
ggaagcggaa gagcgcctga tgcggtattt tctccttacg catctgtgcg gtatttcaca    2760
ccgcatatgg tgcactctca gtacaatctg ctctgatgcc gcatagttaa gccagtatcc    2820
tcgaggcctc caaaaaagcc tcctcactac ttctggaata gctcagaggc cgaggcggcc    2880
tcggcctctg cataaataaa aaaaattagt cagccatgag cttggcccat tgcatacgtt    2940
gtatccatat cataatatgt acatttatat tggctcatgt ccaacattac cgccatgttg    3000
acattgatta ttgactagtt attaatagta atcaattacg gggtcattag ttcatagccc    3060
atatatggag ttccgcgtta cataacttac ggtaaatggc ccgcctggct gaccgcccaa    3120
cgacccccgc ccattgacgt caataatgac gtatgttccc atagtaacgc caatagggac    3180
tttccattga cgtcaatggg tggagtattt acggtaaact gcccacttgg cagtacatca    3240
agtgtatcat atgccaagta cgccccctat tgacgtcaat gacggtaaat ggcccgcctg    3300
gcattatgcc cagtacatga ccttatggga ctttcctact tggcagtaca tctacgtatt    3360
agtcatcgct attaccatgg tgatgcggtt ttggcagtac atcaatgggc gtggatagcg    3420
gtttgactca cggggatttc caagtctcca ccccattgac gtcaatggga gtttgttttg    3480
gcaccaaaat caacgggact ttccaaaatg tcgtaacaac tccgccccat tgacgcaaat    3540
gggcggtagg cgtgtacggt gggaggtcta tataagcaga gctcattaaa gtcctgcaac    3600
gagccctttt cacgcacttc agagcaggat gtggccactc aagaattggc cagacaaggg    3660
gaggaaatcc tctctcagct ataccgaccc ctagaaacat gcaataactc atgctattgt    3720
aagcgatgct gctaccattg tcagatgtgt tttctaaaca aggggctcgg aattccccgg    3780
atccgtcgac tctagaggat ctgcatctcc tatggcagga agaagcggag acagcgacga    3840
agacctcctc aaggcagtca gactcatcaa gtttctctat caaagcaacc cacctcccaa    3900
```

-continued

```
tcccgagggg acccgacagg cccgaaggaa tagaagaaga aggtggagag agagacagag    3960
acagatccat tcgattagtg aacggatcct tagcacttat ctgggacgat ctgcggagcc    4020
tgtgcctctt cagctaccac cgcttgagag acttactctt gattgtaacg aggattgtgg    4080
aacttctggg acgcaggggg tgggaagccc tcaaatattg gtggaatctc ctacaatatt    4140
ggagtcagga gctaaagaat agtgctgtta gcttgctcaa tgccacagct atagcagtag    4200
ctgaggggac agatagggtt atagaagtag tacaagaagc ttatagagct attcgccaca    4260
tacctagaag aataagacag ggcttggaaa ggattttgct ataagatggg tggcaagtgg    4320
tcaaaaagta gtgtggttgg atggcctgct gtaagggaaa gaatgagacg agctgagcca    4380
gcagcagatg gggtgggagc agcatctcga gacctagaaa aacatggagc aatcacaagt    4440
agcaacacag cagctaacaa tgctgcttgt gcctggctag aagcacaaga ggaggagaag    4500
gtgggttttc cagtcacacc tcaggtaccg agctcgaatt cactcctcag gtgcaggctg    4560
cctatcagaa ggtggtggct ggtgtggcca atgccctggc tcacaaatac cactgagatc    4620
tttgtgaagg aaccttactt ctgtggtgtg acataattgg acaaactacc tacagagatt    4680
taaagctcta aggtaaatat aaaattttta agtgtataat gtgttaaact actgattcta    4740
attgtttgtg tattttagat tccaacctat ggaactgatg aatgggagca gtggtggaat    4800
gcctttaatg aggaaaacct gttttgctca gaagaaatgc catctagtga tgatgaggct    4860
actgctgact ctcaacattc tactcctcca aaaaagaaga gaaggtagaa gaccccaag     4920 gactttcctt cagaattgct aagttttttg agtcatgctg tgtttagtaa tagaactctt    4980
gcttgctttg ctatttacac cacaaaggaa aaagctgcac tgctatacaa gaaaattatg    5040
gaaaaatatt ctgtaaccct tataagtagg cataacagtt ataatcataa catactgttt    5100
tttcttactc cacacaggca tagagtgtct gctattaata actatgctca aaaattgtgt    5160
acctttagct ttttaatttg taaggggtt aataaggaat atttgatgta tagtgccttg     5220
actagagatc ataatcagcc ataccacatt tgtagaggtt ttacttgctt taaaaaacct    5280
cccacacctc cccctgaacc tgaaacataa aatgaatgca attgttgttg ttaacttgtt    5340
tattgcagct tataatggtt acaaataaag caatagcatc acaaatttca caaataaagc    5400 attttttttca ctgcattcta gttgtggttt gtccaaactc atcaatgtat cttatcatgt    5460
ctggatcccc aggaagctcc tctgtgtcct cataaaccct aacctcctct actt          5514
```

<210> SEQ ID NO 50
<211> LENGTH: 17
<212> TYPE: DNA
<213> ORGANISM: Bacteriophage M13
<220> FEATURE:
<221> NAME/KEY: misc_feature
<222> LOCATION: (1)..(17)
<223> OTHER INFORMATION: Forward Primer Binding Site

<400> SEQUENCE: 50
gtaaaacgac ggccagt                                                     17

<210> SEQ ID NO 51
<211> LENGTH: 17
<212> TYPE: DNA
<213> ORGANISM: Bacteriophage M13
<220> FEATURE:
<221> NAME/KEY: misc_feature
<223> OTHER INFORMATION: Reverse Primer Binding Site
<220> FEATURE:
<221> NAME/KEY: misc_feature
<222> LOCATION: (1)..(17)

<223> OTHER INFORMATION: Reverse Primer Binding Site

<400> SEQUENCE: 51
caggaaacag ctatgac                                                       17

<210> SEQ ID NO 52
<211> LENGTH: 204
<212> TYPE: DNA
<213> ORGANISM: Human Cytomegalovirus (CMV)
<220> FEATURE:
<221> NAME/KEY: misc_feature
<222> LOCATION: (1)..(204)
<223> OTHER INFORMATION: Human Cytomegalovirus (CMV) Immediate Early
      Promoter Site

<400> SEQUENCE: 52
gtgatgcggt tttggcagta catcaatggg cgtggatagc ggtttgactc acggggattt        60
ccaagtctcc accccattga cgtcaatggg agtttgtttt ggcaccaaaa tcaacgggac       120
tttccaaaat gtcgtaacaa ctccgcccca ttgacgcaaa tgggcggtag cgtgtacgg        180 tgggaggtct atataagcag agct                                              204

<210> SEQ ID NO 53
<211> LENGTH: 573
<212> TYPE: DNA
<213> ORGANISM: Homo sapiens
<220> FEATURE:
<221> NAME/KEY: misc_feature
<222> LOCATION: (1)..(573)
<223> OTHER INFORMATION: Beta-Globin Intron

<400> SEQUENCE: 53
gtgagtttgg ggacccttga ttgttctttc tttttcgcta ttgtaaaatt catgttatat        60 ggaggggca aagttttcag ggtgttgttt agaatgggaa gatgtccctt gtatcaccat       120
ggaccctcat gataattttg tttctttcac tttctactct gttgacaacc attgtctcct      180 cttatttct tttcattttc tgtaactttt tcgttaaact ttagcttgca tttgtaacga       240 attttaaat tcacttttgt ttatttgtca gattgtaagt actttctcta atcacttttt       300
tttcaaggca atcagggtat attatattgt acttcagcac agttttagag aacaattgtt      360
ataattaaat gataaggtag aatatttctg catataaatt ctggctggcg tggaaatatt      420
cttattggta gaaacaacta caccctggtc atcatcctgc ctttctcttt atggttacaa     480
tgatatacac tgtttgagat gaggataaaa tactctgagt ccaaaccggg cccctctgct     540
aaccatgttc atgccttctt ctctttccta cag                                   573

<210> SEQ ID NO 54
<211> LENGTH: 1255
<212> TYPE: PRT
<213> ORGANISM: SARS-CoV-2
<220> FEATURE:
<221> NAME/KEY: MISC_FEATURE
<222> LOCATION: (1)..(1255)
<223> OTHER INFORMATION: SARS-CoV-2 S Protein Lacking C-Terminal 18
      Amino Acid Residues

<400> SEQUENCE: 54

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser

-continued

His Ser Thr Gln Asp Leu Phe Leu Pro Phe Phe Ser Asn Val Thr Trp
            35                  40                  45
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

```
                    -continued

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880
```

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys
    1250                1255

<210> SEQ ID NO 55
<211> LENGTH: 3765
<212> TYPE: DNA

```
<213> ORGANISM: SARS-CoV-2
<220> FEATURE:
<221> NAME/KEY: misc_feature
<222> LOCATION: (1)..(3765)
<223> OTHER INFORMATION: Polynucleotide Encoding SARS-CoV-2 S Protein
      Lacking C-Terminal 18 Amino Acid Residues

<400> SEQUENCE: 55
atgtttgttt ttcttgtttt attgccacta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
```

```
gcagaaaatt cagttgctta ctctaataac tctattgcca tacccacaaa tttactatt      2160 agtgttacca cagaaattct accagtgtct atgaccaaga catcagtaga ttgtacaatg     2220
tacatttgtg gtgattcaac tgaatgcagc aatcttttgt tgcaatatgg cagttttgt     2280 acacaattaa accgtgcttt aactggaata gctgttgaac aagacaaaaa cacccaagaa     2340 gttttgcac aagtcaaaca aatttacaaa acaccaccaa ttaaagattt tggtggtttt      2400
aatttttcac aaatattacc agatccatca aaaccaagca agaggtcatt tattgaagat     2460 ctactttca caaagtgac acttgcagat gctggcttca tcaaacaata tggtgattgc      2520
cttggtgata ttgctgctag agacctcatt tgtgcacaaa agtttaacgg ccttactgtt     2580
ttgccacctt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga atgttctcta tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agctttaaac    2880
acgcttgtta aacaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120 gattttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaatttttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatatttaa gaatcataca     3480 tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaccagttgc    3720
tgtagttgtc tcaagggctg ttgttcttgt ggatcctgct gcaaa                    3765

<210> SEQ ID NO 56
<211> LENGTH: 56
<212> TYPE: DNA
<213> ORGANISM: Homo sapiens
<220> FEATURE:
<221> NAME/KEY: misc_feature
<222> LOCATION: (1)..(56)
<223> OTHER INFORMATION: Beta-Globin Poly(A) Polyadenylation Signal
      Sequence

<400> SEQUENCE: 56
aataaaggaa atttattttc attgcaatag tgtgttggaa ttttttgtgt ctctca           56

<210> SEQ ID NO 57
<211> LENGTH: 17
<212> TYPE: DNA
<213> ORGANISM: Escherichia coli
<220> FEATURE:
<221> NAME/KEY: misc_feature
<222> LOCATION: (1)..(17)
```

<223> OTHER INFORMATION: Lac Operator Site

<400> SEQUENCE: 57
ttgtgagcgg ataacaa                                                    17

<210> SEQ ID NO 58
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Lac Promoter Site

<400> SEQUENCE: 58 tttacactttt atgcttccgg ctcgtatgtt g                                   31

<210> SEQ ID NO 59
<211> LENGTH: 22
<212> TYPE: DNA
<213> ORGANISM: Escherichia coli
<220> FEATURE:
<221> NAME/KEY: misc_feature
<222> LOCATION: (1)..(22)
<223> OTHER INFORMATION: Catabolite Activator Protein (CAP) Binding Site

<400> SEQUENCE: 59
taatgtgagt tagctcactc at                                              22

<210> SEQ ID NO 60
<211> LENGTH: 456
<212> TYPE: DNA
<213> ORGANISM: Bacteriophage f1
<220> FEATURE:
<221> NAME/KEY: misc_feature
<222> LOCATION: (1)..(456)
<223> OTHER INFORMATION: Origin of Replication

<400> SEQUENCE: 60
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca    120
cgttcgccgg ctttccccgt caagctctaa atcgggggct ccctttaggg ttccgattta    180
gtgctttacg gcacctcgac cccaaaaaac ttgattaggg tgatggttca cgtagtgggc    240
catcgccctg atagacggtt tttcgccctt tgacgttgga gtccacgttc tttaatagtg    300
gactcttgtt ccaaactgga acaacactca accctatctc ggtctattct tttgatttat    360
aagggatttt gccgatttcg gcctattggt taaaaaatga gctgatttaa caaaaattta    420
acgcgaattt taacaaaata ttaacgctta caattt                              456

<210> SEQ ID NO 61
<211> LENGTH: 8602
<212> TYPE: DNA
<213> ORGANISM: Artificial Sequence
<220> FEATURE:
<223> OTHER INFORMATION: pCMV-SARS-CoV-2 S Protein Vector

<400> SEQUENCE: 61
gttttcccag tcacgacgtt gtaaaacgac ggccagtgag cgcgcgtaat acgactcact 60
atagggcgaa ttggagctcc accgcggtgg cggccgctct agagagcttg gcccattgca 120
tacgttgtat ccatatcata atatgtacat ttatattggc tcatgtccaa cattaccgcc 180
atgttgacat tgattattga ctagttatta atagtaatca attacggggt cattagttca 240

```
tagcccatat atggagttcc gcgttacata acttacggta aatggcccgc ctggctgacc    300
gcccaacgac ccccgcccat tgacgtcaat aatgacgtat gttcccatag taacgccaat    360
agggactttc cattgacgtc aatgggtgga gtatttacgg taaactgccc acttggcagt    420
acatcaagtg tatcatatgc caagtacgcc ccctattgac gtcaatgacg gtaaatggcc    480
cgcctggcat tatgcccagt acatgacctt atgggacttt cctacttggc agtacatcta    540
cgtattagtc atcgctatta ccatggtgat gcggttttgg cagtacatca atgggcgtgg    600
atagcggttt gactcacggg gatttccaag tctccacccc attgacgtca atgggagttt    660
gttttggcac caaaatcaac gggactttcc aaaatgtcgt aacaactccg ccccattgac    720
gcaaatgggc ggtaggcgtg tacggtggga ggtctatata agcagagctc gtttagtgaa    780
ccgtcagatc gcctggagac gccatccacg ctgttttgac ctccatagaa gacaccggga    840
ccgatccagc ctccggtcga ccgatcctga aacttcagg gtgagtttgg ggacccttga    900
ttgttctttc tttttcgcta ttgtaaaatt catgttatat ggagggggca aagttttcag    960
ggtgttgttt agaatgggaa gatgtccctt gtatcaccat ggaccctcat gataaattttg   1020
tttctttcac tttctactct gttgacaacc attgtctcct cttatttttct tttcatttttc   1080
tgtaacttt tcgttaaact ttagcttgca tttgtaacga atttttaaat tcacttttgt    1140
ttatttgtca gattgtaagt actttctcta atcactttt tttcaaggca atcagggtat    1200
attatattgt acttcagcac agttttagag aacaattgtt ataattaaat gataaggtag    1260
aatatttctg catataaatt ctggctggcg tggaaatatt cttattggta gaaacaacta    1320
caccctggtc atcatcctgc ctttctcttt atggttacaa tgatatacac tgtttgagat    1380
gaggataaaa tactctgagt ccaaaccggg cccctctgct aaccatgttc atgccttctt    1440
ctcttttccta cagctcctgg gcaacgtgct ggttgttgtg ctgtctcatc attttggcaa    1500
agaattcctc gacggatccg gtaccgagga gatctgccgc cgcgatcgcc accatgtttg    1560
ttttttcttgt tttattgcca ctagtctcta gtcagtgtgt taatcttaca accagaactc    1620
aattacccccc tgcatacact aattctttca cacgtggtgt ttattaccct gacaaagttt    1680
tcagatcctc agttttacat tcaactcagg acttgttctt acctttcttt tccaatgtta    1740
cttggttcca tgctatacat gtctctggga ccaatggtac taagaggttt gataaccctg    1800
tcctaccatt taatgatggt gtttattttg cttccactga gaagtctaac ataataagag    1860
gctggatttt tggtactact ttagattcga agacccagtc cctacttatt gttaataacg    1920
ctactaatgt tgttattaaa gtctgtgaat ttcaattttg taatgatcca ttttttgggtg   1980
tttattacca caaaaacaac aaaagttgga tggaaagtga gttcagagtt tattctagtg    2040
cgaataattg cactttgaa tatgtctctc agccttttct tatggacctt gaaggaaaac    2100
agggtaattt caaaaatctt agggaatttg tgtttaagaa tattgatggt tattttaaaa    2160
tatattctaa gcacacgcct attaatttag tgcgtgatct ccctcagggt ttttcggctt    2220
tagaaccatt ggtagatttg ccaataggta ttaacatcac taggtttcaa acttacttg    2280
ctttacatag aagttatttg actcctggtg attcttcttc aggttggaca gctggtgctg    2340
cagcttatta tgtgggttat cttcaaccta ggacttttct attaaaatat aatgaaaatg    2400
gaaccattac agatgctgta gactgtgcac ttgaccctct ctcagaaaca aagtgtacgt    2460
tgaaatcctt cactgtagaa aaaggaatct atcaaacttc taactttaga gtccaaccaa    2520
cagaatctat tgttagattt cctaatatta caaacttgtg cccttttggt gaagttttta    2580
```

```
acgccaccag atttgcatct gtttatgctt ggaacaggaa gagaatcagc aactgtgttg    2640
ctgattattc tgtcctatat aattccgcat cattttccac ttttaagtgt tatggagtgt    2700
ctcctactaa attaaatgat ctctgcttta ctaatgtcta tgcagattca tttgtaatta    2760
gaggtgatga agtcagacaa atcgctccag ggcaaactgg aaagattgct gattataatt    2820
ataaattacc agatgatttt acaggctgcg ttatagcttg gaattctaac aatcttgatt    2880
ctaaggttgg tggtaattat aattaccgt atagattgtt taggaagtct aatctcaaac     2940
cttttgagag agatatttca actgaaatct atcaggccgg tagcacacct tgtaatggtg    3000
ttgaaggttt taattgttac tttccttac aatcatatgg tttccaaccc actaatggtg     3060
ttggttacca accatacaga gtagtagtac tttcttttga acttctacat gcaccagcaa    3120
ctgtttgtgg acctaaaaag tctactaatt tggttaaaaa caatgtgtc aatttcaact     3180 tcaatggttt aacaggcaca ggtgttctta ctgagtctaa caaaagtttt ctgccttcc     3240 aacaatttgg cagagacatt gctgacacta ctgatgctgt ccgtgatcca cagacacttg    3300
agattcttga cattacacca tgttcttttg gtggtgtcag tgttataaca ccaggaacaa    3360
atacttctaa ccaggttgct gttctttatc aggatgttaa ctgcacagaa gtccctgttg    3420
ctattcatgc agatcaactt actccctactt ggcgtgttta ttctacaggt tctaatgttt    3480
ttcaaacacg tgcaggctgt ttaataggg ctgaacatgt caacaactca tatgagtgtg     3540 acataccct tggtgcaggt atatgcgcta gttatcagac tcagactaat tctcctcggc     3600
gggcacgtag tgtagctagt caatccatca ttgcctacac tatgtcactt ggtgcagaaa    3660
attcagttgc ttactctaat aactctattg ccatacccac aaattttact attagtgtta    3720
ccacagaaat tctaccagtg tctatgacca agacatcagt agattgtaca atgtacattt    3780
gtggtgattc aactgaatgc agcaatcttt tgttgcaata tggcagtttt tgtacacaat    3840
taaaccgtgc tttaactgga atagctgttg aacaagacaa aaacacccaa gaagtttttg    3900
cacaagtcaa acaaatttac aaaacaccac caattaaaga ttttggtggt tttaattttt    3960
cacaaatatt accagatcca tcaaaaccaa gcaagaggtc atttattgaa gatctacttt    4020
tcaacaaagt gacacttgca gatgctggct tcatcaaaca atatggtgat tgccttggtg    4080
atattgctgc tagagacctc atttgtgcac aaaagtttaa cggccttact gttttgccac    4140
ctttgctcac agatgaaatg attgctcaat acacttctgc actgttagcg ggtacaatca    4200
cttctggttg gacctttggt gcaggtgctg cattacaaat accatttgct atgcaaatgg    4260
cttataggtt taatggtatt ggagttacac agaatgttct ctatgagaac caaaaattga    4320
ttgccaacca atttaatagt gctattggca aaattcaaga ctcactttct tccacagcaa    4380
gtgcacttgg aaaacttcaa gatgtggtca accaaaatgc acaagcttta aacacgcttg    4440
ttaaacaact tagctccaat tttggtgcaa tttcaagtgt tttaaatgat atcctttcac    4500
gtcttgacaa agttgaggct gaagtgcaaa ttgataggtt gatcacaggc agacttcaaa    4560
gtttgcagac atatgtgact caacaattaa ttagagctga gaaatcaga gcttctgcta     4620 atcttgctgc tactaaaatg tcagagtgtg tacttggaca atcaaaaaga gttgattttt    4680
gtggaaaggg ctatcatctt atgtccttcc ctcagtcagc acctcatggt gtagtcttct    4740
tgcatgtgac ttatgtccct gcacaagaaa agaacttcac aactgctcct gccatttgtc    4800
atgatggaaa agcacacttt cctcgtgaag gtgtctttgt ttcaaatggc acacactggt    4860
ttgtaacaca aaggaatttt tatgaaccac aaatcattac tacagacaac acatttgtgt    4920
ctggtaactg tgatgttgta ataggaattg tcaacaacac agtttatgat cctttgcaac    4980
```

```
ctgaattaga ctcattcaag gaggagttag ataaatattt taagaatcat acatcaccag    5040
atgttgattt aggtgacatc tctggcatta atgcttcagt tgtaaacatt caaaagaaa     5100 ttgaccgcct caatgaggtt gccaagaatt taaatgaatc tctcatcgat ctccaagaac    5160
ttggaaagta tgagcagtat ataaaatggc catggtacat ttggctaggt tttatagctg    5220
gcttgattgc catagtaatg gtgacaatta tgctttgctg tatgaccagt tgctgtagtt    5280
gtctcaaggg ctgttgttct tgtggatcct gctgcaaata acctcaggtg caggctgcct    5340
atcagaaggt ggtggctggt gtggccaatg ccctggctca caaataccac tgagatcttt    5400
ttccctctgc caaaattat ggggacatca tgaagcccct tgagcatctg acttctggct      5460
aataaaggaa atttattttc attgcaatag tgtgttggaa ttttttgtgt ctctcactcg     5520
gaaggacata tgggagggca aatcatttaa aacatcagaa tgagtatttg gtttagagtt    5580
tggcaacata tgcccatatg ctggctgcca tgaacaaagg ttggctataa agaggtcatc    5640
agtatatgaa acagcccct gctgtccatt ccttattcca tagaaaagcc ttgacttgag      5700
gttagatttt ttttatattt tgttttgtgt tatttttttc tttaacatcc ctaaaatttt    5760
ccttacatgt tttactagcc agatttttcc tcctctcctg actactccca gtcatagctg    5820
tccctcttct cttatggaga tccctcgacg gatcggccgc aattcgtaat catgtcatag    5880
ctgtttcctg tgtgaaattg ttatccgctc acaattccac acaacatacg agccggaagc    5940
ataaagtgta aagcctgggg tgcctaatga gtgagctaac tcacattaat tgcgttgcgc    6000
tcactgcccg ctttccagtc gggaaacctg tcgtgccagc tgcattaatg aatcggccaa    6060
cgcgcgggga gaggcggttt gcgtattggg cgctcttccg cttcctcgct cactgactcg    6120
ctgcgctcgg tcgttcggct gcggcgagcg gtatcagctc actcaaaggc ggtaatacgg    6180
ttatccacag aatcagggga taacgcagga agaacatgt gagcaaaagg ccagcaaaag      6240
gccaggaacc gtaaaaaggc cgcgttgctg gcgttttttcc ataggctccg cccccctgac    6300
gagcatcaca aaaatcgacg ctcaagtcag aggtggcgaa acccgacagg actataaaga    6360
taccaggcgt ttccccctgg aagctccctc gtgcgctctc ctgttccgac cctgccgctt    6420
accggatacc tgtccgcctt tctcccttcg ggaagcgtgg cgctttctca tagctcacgc    6480
tgtaggtatc tcagttcggt gtaggtcgtt cgctccaagc tgggctgtgt gcacgaaccc    6540
cccgttcagc ccgaccgctg cgccttatcc ggtaactatc gtcttgagtc aacccggta    6600 agacacgact tatcgccact ggcagcagcc actggtaaca ggattagcag agcgaggtat    6660
gtaggcggtg ctacagagtt cttgaagtgg tggcctaact acggctacac tagaagaaca    6720
gtatttggta tctgcgctct gctgaagcca gttaccttcg gaaaaagagt ggtagctct    6780 tgatccggca acaaaccac cgctggtagc ggtggttttt ttgtttgcaa gcagcagatt      6840
acgcgcagaa aaaaggatc tcaagaagat cctttgatct tttctacggg gtctgacgct      6900
cagtggaacg aaaactcacg ttaagggatt ttggtcatga gattatcaaa aaggatcttc    6960
acctagatcc ttttaaatta aaaatgaagt tttaaatcaa tctaaagtat atatgagtaa    7020
acttggtctg acagttacca atgcttaatc agtgaggcac ctatctcagc gatctgtcta    7080
tttcgttcat ccatagttgc ctgactcccc gtcgtgtaga taactacgat acgggagggc    7140
ttaccatctg gccccagtgc tgcaatgata ccgcgagacc cacgctcacc ggctccagat    7200
ttatcagcaa taaccagcc agccggaagg gccgagcgca gaagtggtcc tgcaacttta    7260
tccgcctcca tccagtctat taattgttgc cgggaagcta gagtaagtag ttcgccagtt    7320
```

-continued

```
aatagtttgc gcaacgttgt tgccattgct acaggcatcg tggtgtcacg ctcgtcgttt      7380
ggtatggctt cattcagctc cggttcccaa cgatcaaggc gagttacatg atcccccatg      7440
ttgtgcaaaa aagcggttag ctccttcggt cctccgatcg ttgtcagaag taagttggcc      7500
gcagtgttat cactcatggt tatggcagca ctgcataatt ctcttactgt catgccatcc      7560
gtaagatgct tttctgtgac tggtgagtac tcaaccaagt cattctgaga atagtgtatg      7620
cggcgaccga gttgctcttg cccggcgtca atacgggata ataccgcgcc acatagcaga      7680
actttaaaag tgctcatcat tggaaaacgt tcttcgggg gaaaactctc aaggatctta      7740
ccgctgttga gatccagttc gatgtaaccc actcgtgcac ccaactgatc ttcagcatct      7800
tttactttca ccagcgtttc tgggtgagca aaaacaggaa ggcaaaatgc cgcaaaaaag      7860
ggaataaggg cgacacggaa atgttgaata ctcatactct tcctttttca atattattga      7920
agcatttatc agggttattg tctcatgagc ggatacatat ttgaatgtat ttagaaaaat      7980
aaacaaatag gggttccgcg cacatttccc cgaaaagtgc cacctaaatt gtaagcgtta      8040
atattttgtt aaaattcgcg ttaaattttt gttaaatcag ctcattttt aaccaatagg      8100 ccgaaatcgg caaaatccct tataaatcaa agaatagac cgagataggg ttgagtgttg      8160
ttccagtttg gaacaagagt ccactattaa agaacgtgga ctccaacgtc aaagggcgaa      8220
aaaccgtcta tcagggcgat ggcccactac gtgaaccatc accctaatca agttttttgg      8280
ggtcgaggtg ccgtaaagca ctaaatcgga acccctaaagg gagcccccga tttagagctt      8340
gacggggaaa gccggcgaac gtggcgagaa aggaagggaa gaaagcgaaa ggagcgggcg      8400
ctagggcgct ggcaagtgta gcggtcacgc tgcgcgtaac caccacaccc gccgcgctta      8460
atgcgccgct acagggcgcg tcccattcgc cattcaggct gcgcaactgt tgggaagggc      8520
gatcggtgcg ggcctcttcg ctattacgcc agctggcgaa aggggatgt gctgcaaggc      8580 gattaagttg ggtaacgcca gg                                              8602
```

<210> SEQ ID NO 62
<211> LENGTH: 453
<212> TYPE: DNA
<213> ORGANISM: Lentivirus
<220> FEATURE:
<221> NAME/KEY: misc_feature
<222> LOCATION: (1)..(453)
<223> OTHER INFORMATION: Native Lentiviral LTR U3 Region

<400> SEQUENCE: 62

```
tggaagggct aattcactcc caacgaagac aagatatcct tgatctgtgg atctaccaca        60
cacaaggcta cttccctgat tggcagaact acacaccagg gccagggatc agatatccac       120
tgacctttgg atggtgctac aagctagtac cagttgagca agagaaggta gaagaagcca       180
atgaaggaga gaacacccgc ttgttacacc ctgtgagcct gcatgggatg gatgacccgg       240
agagagaagt attagagtgg aggtttgaca gccgcctagc atttcatcac atggcccgag       300
agctgcatcc ggagtacttc aagaactgct gacatcgagc ttgctacaag gactttccg        360 ctggggactt tccagggagg cgtggcctgg gcgggactgg ggagtggcga gccctcagat       420
cctgcatata agcagctgct ttttgcctgt act                                    453
```

<210> SEQ ID NO 63
<211> LENGTH: 320
<212> TYPE: DNA
<213> ORGANISM: Artificial Sequence
<220> FEATURE:
<223> OTHER INFORMATION: Lentiviral LTR U3 Region Comprising Internal Deletion of 133 Residues

<400> SEQUENCE: 63

```
tggaagggct aattcactcc caacgaagac aagatatcct tgatctgtgg atctaccaca    60
cacaaggcta cttccctgat tggcagaact acacaccagg gccagggatc agatatccac   120
tgacctttgg atggtgctac aagctagtac cagttgagca agagaaggta agaagccaa    180
atgaaggaga gaacacccgc ttgttacacc ctgtgagcct gcatgggatg gatgacccgg   240
agagagaagt attagagtgg aggtttgaca gccgcctagc atttcatcac atggcccgag   300
agctgcatcc ggactgtact                                               320
```

<210> SEQ ID NO 64
<211> LENGTH: 318
<212> TYPE: DNA
<213> ORGANISM: Artificial Sequence
<220> FEATURE:
<223> OTHER INFORMATION: Variant Lentiviral LTR U3 Region Comprising
      Internal Deletion of 133 Residues

<400> SEQUENCE: 64

```
gaagggctaa ttcactccca acgaagacaa gatctgcttg atctgtggat ctaccacaca    60
caaggctact tccctgattg gcagaactac acaccagggc cagggatcag atatccactg   120
acctttggat ggtgctacaa gctagtacca gttgagcaag agaaggtaga agaagccaat   180
gaaggagaga cacccgctt gttacaccct gtgagcctgc atgggatgga tgacccggag   240
agagaagtat tagagtggag gtttgacagc cgcctagcat ttcatcacat ggcccgagag   300
ctgcatccgg actgtact                                                 318
```

<210> SEQ ID NO 65
<211> LENGTH: 288
<212> TYPE: PRT
<213> ORGANISM: Lentivirus
<220> FEATURE:
<221> NAME/KEY: MISC_FEATURE
<222> LOCATION: (1)..(288)
<223> OTHER INFORMATION: Wildtype Lentiviral Integrase Protein

<400> SEQUENCE: 65

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
            85                  90                  95

Thr Ala Tyr Phe Leu Leu Lys Leu Ala Gly Arg Trp Pro Val Lys Thr
        100                 105                 110

Ile His Thr Asp Asn Gly Ser Asn Phe Thr Ser Ala Thr Val Lys Ala
    115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
```

```
                    145                 150                 155                 160
Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Ile Gly
            180                 185                 190

Gly Tyr Ser Ala Gly Glu Arg Ile Val Asp Ile Ile Ala Thr Asp Ile
            195                 200                 205

Gln Thr Lys Glu Leu Gln Lys Gln Ile Thr Lys Ile Gln Asn Phe Arg
210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
                260                 265                 270

Lys Gln Met Ala Gly Asp Asp Cys Val Ala Ser Arg Gln Asp Glu Asp
            275                 280                 285
```

<210> SEQ ID NO 66
<211> LENGTH: 864
<212> TYPE: DNA
<213> ORGANISM: Lentivirus
<220> FEATURE:
<221> NAME/KEY: misc_feature
<222> LOCATION: (1)..(864)
<223> OTHER INFORMATION: Polynucleotide Encoding Wildtype Lentiviral
      Integrase Protein

<400> SEQUENCE: 66

```
tttttagatg gaatagataa ggcccaagat gaacatgaga aatatcacag taattggaga      60
gcaatggcta gtgattttaa cctgccacct gtagtagcaa aagaaatagt agccagctgt     120
gataaatgtc agctaaaagg agaagccatg catggacaag tagactgtag tccaggaata     180
tggcaactag attgtacaca tttagaagga aaagttatcc tggtagcagt tcatgtagcc     240
agtggatata tagaagcaga agttattcca gcagaaacag ggcaggaaac agcatatttt     300
cttttaaaat tagcaggaag atggccagta aaaacaatac atacagacaa tggcagcaat     360
ttcaccagtg ctacggttaa ggccgcctgt tggtgggcgg gaatcaagca ggaatttgga     420
attccctaca atccccaaag tcaaggagta gtagaatcta tgaataaaga attaagaaa      480 attataggac aggtaagaga tcaggctgaa catcttaaga cagcagtaca aatggcagta     540
ttcatccaca attttaaaag aaaagggggg attggggggt acagtgcagg ggaaagaata     600
gtagacataa tagcaacaga catacaaact aaagaattac aaaaacaaat tacaaaaatt     660
caaaattttc gggtttatta cagggacagc agaaatccac tttggaaagg accagcaaag     720
ctcctctgga aaggtgaagg ggcagtagta atacaagata atagtgacat aaaagtagtg     780
ccaagaagaa aagcaaagat cattagggat tatggaaaac agatggcagg tgatgattgt     840
gtggcaagta gacaggatga ggat                                            864
```

<210> SEQ ID NO 67
<211> LENGTH: 7267
<212> TYPE: DNA
<213> ORGANISM: Artificial Sequence
<220> FEATURE:
<223> OTHER INFORMATION: pLenti-CMV-IRES-empty (-att) Vector

<400> SEQUENCE: 67

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360 ccccccgccca ttgacgtcaa taatgacgta tgttcccata gtaacgccaa tagggacttt     420
ccattgacgt caatgggtgg agtatttacg gtaaactgcc cacttggcag tacatcaagt     480
gtatcatatg ccaagtacgc cccctattga cgtcaatgac ggtaaatggc ccgcctggca     540
ttatgcccag tacatgacct tatgggactt tcctacttgg cagtacatct acgtattagt     600
catcgctatt accatggtga tgcggttttg gcagtacatc aatgggcgtg gatagcggtt     660
tgactcacgg ggatttccaa gtctccaccc cattgacgtc aatgggagtt tgttttggca     720
ccaaaatcaa cgggactttc caaaatgtcg taacaactcc gccccattga cgcaaatggg     780
cggtaggcgt gtacggtggg aggtctatat aagcagcgcg ttttgcctgt actgggtctc     840
tctggttaga ccagatctga gcctgggagc tctctggcta actagggaac ccactgctta     900
agcctcaata aagcttgcct tgagtgcttc aagtagtgtg tgcccgtctg ttgtgtgact     960
ctggtaacta gagatccctc agacccttt  agtcagtgtg aaaatctct  aggtggcgcc    1020 cgaacaggga cttgaaagcg aaagggaaac cagaggagct ctctcgacgc aggactcggc    1080
ttgctgaagc gcgcacggca agaggcgagg gcggcgact  ggtgagtacg ccaaaaattt    1140
tgactagcgg aggctagaag gagagagatg ggtgcgagag cgtcagtatt aagcggggga    1200
gaattagatc gcgatgggaa aaaattcggt taaggccagg gggaagaaa  aaatataaat    1260 taaaacatat agtatgggca agcagggagc tagaacgatt cgcagttaat cctggcctgt    1320
tagaaacatc agaaggctgt agacaaatac tgggacagct acaaccatcc cttcagacag    1380
gatcagaaga acttagatca ttatataata cagtagcaac cctctattgt gtgcatcaaa    1440
ggatagagat aaaagacacc aaggaagctt tagacaagat agaggaagag caaaacaaaa    1500
gtaagaccac cgcacagcaa gcggccggcc gctgatcttc agacctggag gaggagatat    1560
gagggacaat tggagaagtg aattatataa atataaagta gtaaaaattg aaccattagg    1620
agtagcaccc accaaggcaa agagaagagt ggtgcagaga gaaaaaagag cagtgggaat    1680
aggagctttg ttccttgggt tcttgggagc agcaggaagc actatgggcg cagcgtcaat    1740
gacgctgacg gtacaggcca gacaattatt gtctggtata gtgcagcagc agaacaattt    1800
gctgagggct attgaggcgc aacagcatct gttgcaactc acagtctggg gcatcaagca    1860
gctccaggca agaatcctgg ctgtggaaag atacctaaag gatcaacagc tcctggggat    1920
ttggggttgc tctggaaaac tcatttgcac cactgctgtg ccttggaatg ctagttggag    1980
taataaatct ctggaacaga tttggaatca cacgacctgg atggagtggg acagagaaat    2040
taacaattac acaagcttaa tacactcctt aattgaagaa tcgcaaaacc agcaagaaaa    2100
gaatgaacaa gaattattgg aattagataa atgggcaagt ttgtggaatt ggtttaacat    2160
aacaaattgg ctgtggtata taaaattatt cataatgata gtaggaggct tggtaggttt    2220
aagaatagtt tttgctgtac tttctatagt gaatagagtt aggcagggat attcaccatt    2280
atcgtttcag acccacctcc caaccccgag gggacccgac aggcccgaag gaatagaaga    2340
agaaggtgga gagagagaca gagacagatc cattcgatta gtgaacggat cggcactgcg    2400
```

```
tgcgccaatt ctgcagacaa atggcagtat tcatccacaa ttttaaaaga aagggggga      2460
ttgggggta  cagtgcaggg gaaagaatag tagacataat agcaacagac atacaaacta    2520
aagaattaca aaaacaaatt acaaaaattc aaaattttcg ggtttattac agggacagca    2580
gagatccagt ttggttagta ccgggcccgc tctagacatg tccaatatga ccgccatgtt    2640
gacattgatt attgactagt tattaatagt aatcaattac ggggtcatta gttcatagcc    2700
catatatgga gttccgcgtt acataactta cggtaaatgg cccgcctggc tgaccgccca    2760
acgaccccg  cccattgacg tcaataatga cgtatgttcc catagtaacg ccaataggga    2820
ctttccattg acgtcaatgg gtggagtatt tacggtaaac tgcccacttg gcagtacatc    2880
aagtgtatca tatgccaagt ccgcccccta ttgacgtcaa tgacggtaaa tggcccgcct    2940
ggcattatgc ccagtacatg accttacggg actttcctac ttggcagtac atctacgtat    3000
tagtcatcgc tattaccatg gtgatgcggt tttggcagta caccaatggg cgtggatagc    3060
ggtttgactc acggggattt ccaagtctcc accccattga cgtcaatggg agtttgtttt    3120
ggcaccaaaa tcaacgggac tttccaaaat gtcgtaataa ccccgcccg  ttgacgcaaa    3180
tgggcggtag gcgtgtacgg tgggaggtct atataagcag agctcgttta gtgaaccgtc    3240
agaattttgt aatacgactc actatagggc ggccgggaat tcgtcgactg cccccccccc    3300
taacgttact ggccgaagcc gcttggaata aggccggtgt gcgtttgtct atatgttatt    3360
ttccaccata ttgccgtctt ttggcaatgt gagggcccgg aaacctggcc ctgtcttctt    3420
gacgagcatt cctaggggtc tttccctct  cgccaaagga atgcaaggtc tgttgaatgt    3480
cgtgaaggaa gcagttcctc tggaagcttc ttgaagacaa acaacgtctg tagcgaccct    3540
ttgcaggcag cggaaccccc cacctggcga caggtgcctc tgcggccaaa agccacgtgt    3600
ataagataca cctgcaaagg cggcacaacc ccagtgccac gttgtgagtt ggatagttgt    3660
ggaaagagtc aaatggctct cctcaagcgt attcaacaag gggctgaagg atgcccagaa    3720
ggtaccccat tgtatgggat ctgatctggg gcctcggtgc acatgcttta catgtgttta    3780
gtcgaggtta aaaaacgtct aggccccccg aaccacgggg acgtggtttt cctttgaaaa    3840
acacgatgat aatgatccgg taccgaggag atctgccgcc gcgatcgccg gcgcgccaga    3900
tctcaagctt aactagctag cggaccgacg cgtacgcggc cgctcgagca gaaactcatc    3960
tcagaagagg atctggcagc aaatgatatc ctggattaca aggatgacga cgataaggtt    4020
taaacggccg ccgcggtct  gtacaagtag gattcgtcga gggacctaat aacttcgtat    4080
agcatacatt atacgaagtt atacatgttt aagggttccg gttccactag gtacaattcg    4140
atatcaagct tatcgataat caacctctgg attacaaaat ttgtgaaaga ttgactggta    4200
ttcttaacta tgttgctcct tttacgctat gtggatacgc tgctttaatg cctttgtatc    4260
atgctattgc ttcccgtatg gctttcattt tctcctcctt gtataaatcc tggttgctgt    4320
ctctttatga ggagttgtgg cccgttgtca ggcaacgtgg cgtggtgtgc actgtgtttg    4380
ctgacgcaac cccactggt  tggggcattg ccaccacctg tcagctcctt tccgggactt    4440
tcgctttccc cctccctatt gccacggcgg aactcatcgc cgcctgcctt gcccgctgct    4500
ggacaggggc tcggctgttg ggcactgaca attccgtggt gttgtcgggg aaatcatcgt    4560
ccttccttg  gctgctcgcc tgtgttgcca cctggattct gcgcgggacg tccttctgct    4620
acgtcccttc ggccctcaat ccagcggacc ttccttcccg cggcctgctg ccggctctgc    4680
ggcctcttcc gcgtcttcgc cttcgccctc agacgagtcg gatctcccct tgggccgcct    4740
```

```
ccccgcatcg ataccgtcga cctcgatcga gacctagaaa acatggagc  aatcacaagt   4800
agcaatacag cagctaccaa tgctgattgt gcctggctag aagcacaaga ggaggaggag   4860
gtgggttttc cagtcacacc tcaggtacct ttaagaccaa tgacttacaa ggcagctgta   4920
gatcttagcc actttttaaa agaaaagggg ggacgaaggg ctaattcact cccaacgaag   4980
acaagatctg cttgatctgt ggatctacca cacacaaggc tacttccctg attggcagaa   5040
ctacacacca gggccaggga tcagatatcc actgaccttt ggatggtgct acaagctagt   5100
accagttgag caagagaagg tagaagaagc caatgaagga gagaacaccc gcttgttaca   5160
ccctgtgagc ctgcatggga tggatgaccc ggagagagaa gtattagagt ggaggtttga   5220
cagccgccta gcatttcatc acatggcccg agagctgcat ccggactgta ctgggtctct   5280
ctggttagac cagatctgag cctgggagct ctctggctaa ctagggaacc cactgcttaa   5340
gcctcaataa agcttgcctt gagtgcttca agtagtgtgt gcccgtctgt tgtgtgactc   5400
tggtaactag agatccctca gaccctttta gtcagtgtgg aaaatctcta gcagcatgtg   5460
agcaaaaggc cagcaaaagg ccaggaaccg taaaaaggcc gcgttgctgg cgttttccca   5520
taggctccgc cccctgacg agcatcacaa aaatcgacgc tcaagtcaga ggtggcgaaa    5580
cccgacagga ctataaagat accaggcgtt tcccctgga  agctccctcg tgcgctctcc   5640
tgttccgacc ctgccgctta ccggatacct gtccgccttt ctcccttcgg aagcgtggc   5700
gctttctcat agctcacgct gtaggtatct cagttcggtg taggtcgttc gctccaagct   5760
gggctgtgtg cacgaacccc ccgttcagcc cgaccgctgc gccttatccg gtaactatcg   5820
tcttgagtcc aacccggtaa gacacgactt atcgccactg gcagcagcca ctggtaacag   5880
gattagcaga gcgaggtatg taggcggtgc tacagagttc ttgaagtggt ggcctaacta   5940
cggctacact agaagaacag tatttggtat ctgcgctctg ctgaagccag ttaccttcgg   6000
aaaaagagtt ggtagctctt gatccggcaa acaaaccacc gctggtagcg gtggttttt   6060
tgtttgcaag cagcagatta cgcgcagaaa aaaaggatct caagaagatc ctttgatctt   6120
ttctacgggg tctgacgctc agtggaacga aaactcacgt taagggattt tggtcatgag   6180
attatcaaaa aggatcttca cctagatcct ttaaattaa  aaatgaagtt ttaaatcaat   6240
ctaaagtata tatgagtaaa cttggtctga cagttaccaa tgcttaatca gtgaggcacc   6300
tatctcagcg atctgtctat ttcgttcatc catagttgcc tgactccccg tcgtgtagat   6360
aactacgata cgggagggct taccatctgg ccccagtgct gcaatgatac cgcgagaccc   6420
acgctcaccg gctccagatt tatcagcaat aaaccagcca gccggaaggg ccgagcgcag   6480
aagtggtcct gcaactttat ccgcctccat ccagtctatt aattgttgcc gggaagctag   6540
agtaagtagt tcgccagtta atagtttgcg caacgttgtt gccattgcta caggcatcgt   6600
ggtgtcacgc tcgtcgtttg gtatggcttc attcagctcc ggttcccaac gatcaaggcg   6660
agttacatga tcccccatgt tgtgcaaaaa agcggttagc tccttcggtc ctccgatcgt   6720
tgtcagaagt aagttggccg cagtgttatc actcatggtt atggcagcac tgcataattc   6780
tcttactgtc atgccatccg taagatgctt ttctgtgact ggtgagtact caaccaagtc   6840
attctgagaa tagtgtatgc ggcgaccgag ttgctcttgc ccggcgtcaa tacgggataa   6900
taccgcgcca catagcagaa ctttaaaagt gctcatcatt ggaaaacgtt cttcggggcg   6960
aaaactctca aggatcttac cgctgttgag atccagttcg atgtaaccca ctcgtgcacc   7020
caactgatct tcagcatctt ttactttcac cagcgtttct gggtgagcaa aaacaggaag   7080
gcaaaatgcc gcaaaaaagg gaataagggc gacacggaaa tgttgaatac tcatactctt   7140
```

```
ccttttttcaa tattattgaa gcatttatca gggttattgt ctcatgagcg gatacatatt    7200
tgaatgtatt tagaaaaata aacaaatagg ggtcccgcgc acatttcccc gaaaagtgcc    7260
acctgac                                                              7267
```

<210> SEQ ID NO 68
<211> LENGTH: 179
<212> TYPE: DNA
<213> ORGANISM: Lentivirus
<220> FEATURE:
<221> NAME/KEY: misc_feature
<223> OTHER INFORMATION: Alternative 5' LTR Region Lacking Two 3'
      Residues

<400> SEQUENCE: 68

```
gggtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga ccctttagt cagtgtggaa aatctctag    179
```

<210> SEQ ID NO 69
<211> LENGTH: 462
<212> TYPE: DNA
<213> ORGANISM: Encephalomyocarditis Virus (EMCV)
<220> FEATURE:
<221> NAME/KEY: misc_feature
<222> LOCATION: (1)..(462)
<223> OTHER INFORMATION: Internal Ribosome Entry Site of
      Encephalomyocarditis Virus (EMCV)

<400> SEQUENCE: 69

```
gagggcccgg aaacctggcc ctgtcttctt gacgagcatt cctaggggtc tttcccctct     60
cgccaaagga atgcaaggtc tgttgaatgt cgtgaaggaa gcagttcctc tggaagcttc    120
ttgaagacaa acaacgtctg tagcgaccct ttgcaggcag cggaaccccc cacctggcga    180
caggtgcctc tgcggccaaa agccacgtgt ataagataca cctgcaaagg cggcacaacc    240
ccagtgccac gttgtgagtt ggatagttgt ggaaagagtc aaatggctct cctcaagcgt    300
attcaacaag gggctgaagg atgcccagaa ggtaccccat tgtatgggat ctgatctggg    360
gcctcggtgc acatgcttta catgtgttta gtcgaggtta aaaaacgtct aggccccccg    420
aaccacgggg acgtggtttt cctttgaaaa acacgatgat aa                      462
```

<210> SEQ ID NO 70
<211> LENGTH: 11060
<212> TYPE: DNA
<213> ORGANISM: Artificial Sequence
<220> FEATURE:
<223> OTHER INFORMATION: pLenti-CMV-IRES-Spike (-att) Vector

<400> SEQUENCE: 70

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt cgctgcttc gcgatgtacg ggccagatat cgcgttgaca    240
ttgattattg actagttatt aatagtaatc aattacgggg tcattagttc atagcccata    300
tatggagttc cgcgttacat aacttacggt aaatggcccg cctggctgac cgcccaacga    360
ccccccgcca ttgacgtcaa taatgacgta tgttcccata gtaacgccaa tagggacttt    420
ccattgacgt caatgggtgg agtatttacg gtaaactgcc cacttggcag tacatcaagt    480
```

```
gtatcatatg ccaagtacgc ccctattga cgtcaatgac ggtaaatggc ccgcctggca      540
ttatgcccag tacatgacct tatgggactt tcctacttgg cagtacatct acgtattagt      600
catcgctatt accatggtga tgcggttttg gcagtacatc aatgggcgtg gatagcggtt      660
tgactcacgg ggatttccaa gtctccaccc cattgacgtc aatgggagtt tgttttggca      720
ccaaaatcaa cgggactttc caaaatgtcg taacaactcc gccccattga cgcaaatggg      780
cggtaggcgt gtacggtggg aggtctatat aagcagcgcg ttttgcctgt actgggtctc      840
tctggttaga ccagatctga gcctgggagc tctctggcta actagggaac ccactgctta      900
agcctcaata aagcttgcct tgagtgcttc aagtagtgtg tgcccgtctg ttgtgtgact      960
ctggtaacta gagatccctc agacccttttt agtcagtgtg aaaatctct aggtggcgcc     1020 cgaacaggga cttgaaagcg aaagggaaac cagaggagct ctctcgacgc aggactcggc     1080
ttgctgaagc gcgcacggca agaggcgagg ggcggcgact ggtgagtacg ccaaaaattt     1140
tgactagcgg aggctagaag gagagagatg ggtgcgagag cgtcagtatt aagcggggga     1200
gaattagatc gcgatgggaa aaaattcggt taaggccagg gggaaagaaa aaatataaat     1260
taaaacatat agtatgggca agcagggagc tagaacgatt cgcagttaat cctggcctgt     1320
tagaaacatc agaaggctgt agacaaatac tgggacagct acaaccatcc cttcagacag     1380
gatcagaaga acttagatca ttatataata cagtagcaac cctctattgt gtgcatcaaa     1440
ggatagagat aaaagacacc aaggaagctt tagacaagat agaggaagag caaaacaaaa     1500
gtaagaccac cgcacagcaa gcggccggcc gctgatcttc agacctggag gaggagatat     1560
gagggacaat tggagaagtg aattatataa atataaagta gtaaaaattg aaccattagg     1620
agtagcaccc accaaggcaa agagaagagt ggtgcagaga gaaaaaagag cagtgggaat     1680
aggagctttg ttccttgggt tcttgggagc agcaggaagc actatgggcg cagcgtcaat     1740
gacgctgacg gtacaggcca gacaattatt gtctggtata gtgcagcagc agaacaattt     1800
gctgagggct attgaggcgc aacagcatct gttgcaactc acagtctggg gcatcaagca     1860
gctccaggca agaatcctgg ctgtggaaag ataccctaaag gatcaacagc tcctggggat     1920
ttggggttgc tctggaaaac tcatttgcac cactgctgtg ccttggaatg ctagttggag     1980
taataaatct ctggaacaga tttggaatca cacgacctgg atggagtggg acagagaaat     2040
taacaattac acaagcttaa tacactcctt aattgaagaa tcgcaaaacc agcaagaaaa     2100
gaatgaacaa gaattattgg aattagataa atgggcaagt ttgtggaatt ggtttaacat     2160
aacaaattgg ctgtggtata taaaattatt cataatgata gtaggaggct tggtaggttt     2220
aagaatagtt tttgctgtac tttctatagt gaatagagtt aggcagggat attcaccatt     2280
atcgtttcag acccacctcc caaccccgag gggacccgac aggcccgaag gaatagaaga     2340
agaaggtgga gagagagaca gagacagatc cattcgatta gtgaacggat cggcactgcg     2400
tgcgccaatt ctgcagacaa atggcagtat tcatccacaa ttttaaaaga aaaggggggga     2460 ttgggggta cagtgcaggg gaaagaatag tagacataat agcaacagac atacaaacta     2520
aagaattaca aaaacaaatt acaaaaattc aaaattttcg ggtttattac agggacagca     2580
gagatccagt ttggttagta ccgggcccgc tctagacatg tccaatatga ccgccatgtt     2640
gacattgatt attgactagt tattaatagt aatcaattac ggggtcatta gttcatagcc     2700
catatatgga gttccgcgtt acataactta cggtaaatgg cccgcctggc tgaccgccca     2760
acgacccccg cccattgacg tcaataatga cgtatgttcc catagtaacg ccaataggga     2820
```

```
ctttccattg acgtcaatgg gtggagtatt tacggtaaac tgcccacttg gcagtacatc    2880
aagtgtatca tatgccaagt ccgcccccta ttgacgtcaa tgacggtaaa tggcccgcct    2940
ggcattatgc ccagtacatg accttacggg actttcctac ttggcagtac atctacgtat    3000
tagtcatcgc tattaccatg gtgatgcggt tttggcagta caccaatggg cgtggatagc    3060
ggtttgactc acggggattt ccaagtctcc accccattga cgtcaatggg agtttgtttt    3120
ggcaccaaaa tcaacgggac tttccaaaat gtcgtaataa ccccgccccg ttgacgcaaa    3180
tgggcggtag gcgtgtacgg tgggaggtct atataagcag agctcgttta gtgaaccgtc    3240
agaattttgt aatacgactc actatagggc ggccgggaat tcgtcgactg ccccccccc    3300 taacgttact ggccgaagcc gcttggaata aggccggtgt gcgtttgtct atatgttatt    3360
ttccaccata ttgccgtctt ttggcaatgt gagggcccgg aaacctggcc ctgtcttctt    3420
gacgagcatt cctaggggtc tttcccctct cgccaaagga atgcaaggtc tgttgaatgt    3480
cgtgaaggaa gcagttcctc tggaagcttc ttgaagacaa acaacgtctg tagcgaccct    3540
ttgcaggcag cggaaccccc cacctggcga caggtgcctc tgcggccaaa agccacgtgt    3600
ataagataca cctgcaaagg cggcacaacc ccagtgccac gttgtgagtt ggatagttgt    3660
ggaaagagtc aaatggctct cctcaagcgt attcaacaag ggctgaagg atgcccagaa     3720 ggtaccccat tgtatgggat ctgatctggg gcctcggtgc acatgcttta catgtgttta    3780
gtcgaggtta aaaacgtct aggccccccg aaccacgggg acgtggtttt cctttgaaaa     3840
acacgatgat aatgatccgg taccgaggag atctgccgcc gcgatcgcca ccatgtacag    3900
gatgcaactc ctgtcttgca ttgcactaag tcttgcactt gtcacaaaca gtatgtttgt    3960
gttcctggtg ctgctgccac tggtgtccag ccagtgtgtg aacctgacca ccaggaccca    4020
acttcctcct gcctacacca actccttcac caggggagtc tactaccctg acaaggtgtt    4080
caggtcctct gtgctgcaca gcacccagga cctgttcctg ccattcttca gcaatgtgac    4140
ctggttccat gccatccatg tgtctggcac caatggcacc aagagggttg acaaccctgt    4200
gctgccattc aatgatggag tctactttgc cagcacagag aagagcaaca tcatcagggg    4260
ctggattttt ggcaccaccc tggacagcaa gacccagtcc ctgctgattg tgaacaatgc    4320
caccaatgtg gtgattaagg tgtgtgagtt ccagttctgt aatgacccat tcctgggagt    4380
ctactaccac aagaacaaca gtcctggat ggagtctgag ttcagggtct actcctctgc     4440
caacaactgt acctttgaat atgtgagcca accattcctg atggacttgg agggcaagca    4500
gggcaacttc aagaacctga gggagttttgt gttcaagaac attgatggct acttcaagat    4560
ttacagcaaa cacacaccaa tcaacctggt gagggacctg ccacagggct tctctgcctt    4620
ggaaccactg gtggacctgc caattggcat caacatcacc aggttccaga ccctgctggc    4680
tctgcacagg tcctacctga cacctggaga ctcctcctct ggctggacag caggagcagc    4740
agcctactat gtgggctacc tccaaccaag gaccttcctg ctgaaataca atgagaatgg    4800
caccatcaca gatgctgtgg actgtgccct ggacccactg tctgagacca gtgtaccct     4860 gaaatccttc acagtggaga agggcatcta ccagaccagc aacttcaggg tccaaccaac    4920
agagagcatt gtgaggtttc caaacatcac caacctgtgt ccatttggag aggtgttcaa    4980
tgccaccagg tttgcctctg tctatgcctg gaacaggaag aggattagca actgtgtggc    5040
tgactactct gtgctctaca actctgcctc cttcagcacc ttcaagtgtt atggagtgag    5100
cccaaccaaa ctgaatgacc tgtgtttcac caatgtctat gctgactcct tgtgattag    5160 gggagatgag gtgagacaga ttgcccctgg acaaacaggc aagattgctg actacaacta    5220
```

```
caaactgcct gatgacttca caggctgtgt gattgcctgg aacagcaaca acctggacag   5280
caaggtggga ggcaactaca actacctcta cagactgttc aggaagagca acctgaaacc   5340
atttgagagg gacatcagca cagagattta ccaggctggc agcacaccat gtaatggagt   5400
ggagggcttc aactgttact ttccactcca atcctatggc ttccaaccaa ccaatggagt   5460
gggctaccaa ccatacaggg tggtggtgct gtcctttgaa ctgctccatg cccctgccac   5520
agtgtgtgga ccaaagaaga gcaccaacct ggtgaagaac aagtgtgtga acttcaactt   5580
caatggactg acaggcacag gagtgctgac agagagcaac aagaagttcc tgccattcca   5640
acagtttggc agggacattg ctgacaccac agatgctgtg agggacccac agaccttgga   5700
gattctggac atcacaccat gttcctttgg aggagtgtct gtgattacac ctggcaccaa   5760
caccagcaac caggtggctg tgctctacca ggatgtgaac tgtactgagg tgcctgtggc   5820
tatccatgct gaccaactta caccaacctg gagggtctac agcacaggca gcaatgtgtt   5880
ccagaccagg gctggctgtc tgattggagc agagcatgtg aacaactcct atgagtgtga   5940
catcccaatt ggagcaggca tctgtgcctc ctaccagacc cagaccaaca gcccaaggag   6000
ggcaaggtct gtggcaagcc agagcatcat tgcctacaca atgagtctgg gagcagagaa   6060
ctctgtggct tacagcaaca acagcattgc catcccaacc aacttcacca tctctgtgac   6120
cacagagatt ctgcctgtga gtatgaccaa gacctctgtg gactgtacaa tgtatatctg   6180
tggagacagc acagagtgta gcaacctgct gctccaatat ggctccttct gtacccaact   6240
taacagggct ctgacaggca ttgctgtgga acaggacaag aacacccagg aggtgtttgc   6300
ccaggtgaag cagatttaca agacacctcc aatcaaggac tttggaggct caacttcag   6360 ccagattctg cctgacccaa gcaagccaag caagaggtcc ttcattgagg acctgctgtt   6420
caacaaggtg accctggctg atgctggctt catcaagcaa tatggagact gtctgggaga   6480
cattgctgcc agggacctga tttgtgccca gaagttcaat ggactgacag tgctgcctcc   6540
actgctgaca gatgagatga ttgcccaata cacctctgcc ctgctggctg gcaccatcac   6600
ctctggctgg acctttggag caggagcagc cctccaaatc ccatttgcta tgcagatggc   6660
ttacaggttc aatggcattg gagtgaccca gaatgtgctc tatgagaacc agaaactgat   6720
tgccaaccag ttcaactctg ccattggcaa gattcaggac tccctgtcca gcacagcctc   6780
tgccctgggc aaactccaag atgtggtgaa ccagaatgcc caggctctga acaccctggt   6840
gaagcaactt tccagcaact ttggagccat ctcctctgtg ctgaatgaca tcctgagcag   6900
actggacaag gtggaggctg aggtccagat tgacagactg attacaggca gactccaatc   6960
cctccaaacc tatgtgaccc aacaacttat cagggctgct gagattaggg catctgccaa   7020
cctggctgcc accaagatga gtgagtgtgt gctgggacaa agcaagaggg tggacttctg   7080
tggcaagggc taccacctga tgagttttcc acagtctgcc cctcatggag tggtgttcct   7140
gcatgtgacc tatgtgcctg cccaggagaa gaacttcacc acagcccctg ccatctgcca   7200
tgatggcaag gctcactttc aagggaggg agtgtttgtg agcaatggca cccactggtt   7260
tgtgacccag aggaacttct atgaaccaca gattatcacc acagacaaca cctttgtgtc   7320
tggcaactgt gatgtggtga ttggcattgt gaacaacaca gtctatgacc cactccaacc   7380
tgaactggac tccttcaagg aggaactgga caaatacttc aagaaccaca ccagccctga   7440
tgtggacctg ggagacatct ctggcatcaa tgcctctgtg gtgaacatcc agaaggagat   7500
tgacagactg aatgaggtgg ctaagaacct gaatgagtcc ctgattgacc tccaagaact   7560
```

```
gggcaaatat gaacaataca tcaagtgggcc atggtacatc tggctgggct tcattgctgg    7620
actgattgcc attgtgatgg tgaccataat gctgtgttgt atgacctcct gttgttcctg    7680
tctgaaaggc tgttgttcct gtggctcctg ttgtaagtga acgcgtacgc ggccgctcga    7740
gcagaaactc atctcagaag aggatctggc agcaaatgat atcctggatt acaaggatga    7800
cgacgataag gtttaaacgg ccggccgcgg tctgtacaag taggattcgt cgagggacct    7860
aataacttcg tatagcatac attatacgaa gttatacatg tttaagggtt ccggttccac    7920
taggtacaat tcgatatcaa gcttatcgat aatcaacctc tggattacaa aatttgtgaa    7980
agattgactg gtattcttaa ctatgttgct cctttttacgc tatgtggata cgctgcttta    8040
atgcctttgt atcatgctat tgcttcccgt atggctttca ttttctcctc cttgtataaa    8100
tcctggttgc tgtctcttta tgaggagttg tgggccgttg tcaggcaacg tggcgtggtg    8160
tgcactgtgt ttgctgacgc aacccccact ggttggggca ttgccaccac ctgtcagctc    8220
ctttccggga ctttcgcttt ccccctccct attgccacgg cggaactcat cgccgcctgc    8280
cttgcccgct gctggacagg ggctcggctg ttgggcactg acaattccgt ggtgttgtcg    8340
gggaaatcat cgtcctttcc ttggctgctc gcctgtgttg ccacctggat tctgcgcggg    8400
acgtccttct gctacgtccc ttcggccctc aatccagcgg accttccttc ccgcggcctg    8460
ctgccggctc tgcggcctct tccgcgtctt cgccttcgcc ctcagacgag tcggatctcc    8520
ctttgggccg cctccccgca tcgataccgt cgacctcgat cgagacctag aaaaacatgg    8580
agcaatcaca gtagcaata cagcagctac caatgctgat tgtgcctggc tagaagcaca    8640
agaggaggag gaggtgggtt ttccagtcac acctcaggta cctttaagac caatgactta    8700
caaggcagct gtagatctta gccactttt aaagaaaag gggggacgaa gggctaattc    8760
actcccaacg aagacaagat ctgcttgatc tgtggatcta ccacacacaa ggctacttcc    8820
ctgattggca gaactacaca ccagggccag ggatcagata tccactgacc tttggatggt    8880
gctacaagct agtaccagtt gagcaagaga aggtagaaga agccaatgaa ggagagaaca    8940
cccgcttgtt acaccctgtg agcctgcatg ggatggatga cccggagaga gaagtattag    9000
agtggaggtt tgacagccgc ctagcatttc atcacatggc ccgagagctg catccggact    9060
gtactgggtc tctctggtta gaccagatct gagcctggga gctctctggc taactaggga    9120
acccactgct taagcctcaa taaagcttgc cttgagtgct tcaagtagtg tgtgcccgtc    9180
tgttgtgtga ctctggtaac tagagatccc tcagaccctt ttagtcagtg tggaaaatct    9240
ctagcagcat gtgagcaaaa ggccagcaaa aggccaggaa ccgtaaaaag gccgcgttgc    9300
tggcgttttt ccataggctc cgcccccctg acgagcatca caaaaatcga cgctcaagtc    9360
agaggtggcg aaacccgaca ggactataaa gataccaggc gtttccccct ggaagctccc    9420
tcgtgcgctc tcctgttccg accctgccgc ttaccggata cctgtccgcc tttctccctt    9480
cgggaagcgt ggcgctttct catagctcac gctgtaggta tctcagttcg gtgtaggtcg    9540
ttcgctccaa gctgggctgt gtgcacgaac cccccgttca gcccgaccgc tgcgccttat    9600
ccggtaacta tcgtcttgag tccaacccgg taagacacga cttatcgcca ctggcagcag    9660
ccactggtaa caggattagc agagcgaggt atgtaggcgg tgctacagag ttcttgaagt    9720
ggtggcctaa ctacggctac actagaagaa cagtatttgg tatctgcgct ctgctgaagc    9780
cagttacctt cggaaaaaga gttggtagct cttgatccgg caaacaaacc accgctggta    9840
gcggtggttt ttttgtttgc aagcagcaga ttacgcgcag aaaaaaagga tctcaagaag    9900
atcctttgat cttttctacg gggtctgacg ctcagtggaa cgaaaactca cgttaaggga    9960
```

-continued

```
ttttggtcat gagattatca aaaggatct tcacctagat cctttaaat taaaaatgaa    10020
gttttaaatc aatctaaagt atatatgagt aaacttggtc tgacagttac caatgcttaa    10080
tcagtgaggc acctatctca gcgatctgtc tatttcgttc atccatagtt gcctgactcc    10140
ccgtcgtgta gataactacg atacgggagg gcttaccatc tggccccagt gctgcaatga    10200
taccgcgaga cccacgctca ccggctccag atttatcagc aataaaccag ccagccggaa    10260
gggccgagcg cagaagtggt cctgcaactt tatccgcctc catccagtct attaattgtt    10320
gccgggaagc tagagtaagt agttcgccag ttaatagttt gcgcaacgtt gttgccattg    10380
ctacaggcat cgtggtgtca cgctcgtcgt ttggtatggc ttcattcagc tccggttccc    10440
aacgatcaag gcgagttaca tgatccccca tgttgtgcaa aaaagcggtt agctccttcg    10500
gtcctccgat cgttgtcaga agtaagttgg ccgcagtgtt atcactcatg gttatggcag    10560
cactgcataa ttctcttact gtcatgccat ccgtaagatg cttttctgtg actggtgagt    10620
actcaaccaa gtcattctga gaatagtgta tgcggcgacc gagttgctct tgcccggcgt    10680
caatacggga taataccgcg ccacatagca gaactttaaa agtgctcatc attggaaaac    10740
gttcttcggg gcgaaaactc tcaaggatct taccgctgtt gagatccagt tcgatgtaac    10800
ccactcgtgc acccaactga tcttcagcat cttttacttt caccagcgtt tctgggtgag    10860
caaaaacagg aaggcaaaat gccgcaaaaa agggaataag ggcgacacgg aaatgttgaa    10920
tactcatact cttccttttt caatattatt gaagcattta tcagggttat tgtctcatga    10980
gcggatacat atttgaatgt atttagaaaa ataaacaaat aggggtcccg cgcacatttc    11040
cccgaaaagt gccacctgac                                                11060
```

<210> SEQ ID NO 71
<211> LENGTH: 3765
<212> TYPE: DNA
<213> ORGANISM: Artificial Sequence
<220> FEATURE:
<223> OTHER INFORMATION: Codon-Optimized Polynucleotide Encoding
  SARS-CoV-2 S Protein Lacking Terminal 18 Amino Acid Residues

<400> SEQUENCE: 71

```
atgtttgtgt tcctggtgct gctgccactg gtgtccagcc agtgtgtgaa cctgaccacc      60
aggacccaac ttcctcctgc ctacaccaac tccttcacca ggggagtcta ctaccctgac     120
aaggtgttca ggtcctctgt gctgcacagc acccaggacc tgttcctgcc attcttcagc     180
aatgtgacct ggttccatgc catccatgtg tctggcacca atggcaccaa gaggtttgac     240
aaccctgtgc tgccattcaa tgatggagtc tactttgcca gcacagagaa gagcaacatc     300
atcaggggct ggattttttgg caccaccctg gacagcaaga cccagtccct gctgattgtg     360
aacaatgcca ccaatgtggt gattaaggtg tgtgagttcc agttctgtaa tgacccattc     420
ctggagtctc tactaccaca agacaacaag tcctggatgg agtctgagtt cagggtctac     480
tcctctgcca acaactgtac ctttgaatat gtgagccaac cattcctgat ggacttggag     540
ggcaagcagg gcaacttcaa gaacctgagg gagtttgtgt tcaagaacat tgatggctac     600
ttcaagattt acagcaaaca caccccaatc aacctggtga ggacctgcc acagggcttc     660
tctgccttgg aaccactggt ggacctgcca attggcatca acatcaccag gttccagacc     720
ctgctggctc tgcacaggtc ctacctgaca cctggagact cctcctctgg ctggacagca     780
ggagcagcag cctactatgt gggctaccte caaccaagga ccttcctgct gaaatacaat     840
gagaatggca ccatcacaga tgctgtggac tgtgccctgg acccactgtc tgagaccaag     900
```

```
tgtaccctga aatccttcac agtggagaag ggcatctacc agaccagcaa cttcagggtc    960
caaccaacag agagcattgt gaggtttcca aacatcacca acctgtgtcc atttggagag   1020
gtgttcaatg ccaccaggtt tgcctctgtc tatgcctgga acaggaagag gattagcaac   1080
tgtgtggctg actactctgt gctctacaac tctgcctcct tcagcacctt caagtgttat   1140
ggagtgagcc caaccaaact gaatgacctg tgtttcacca atgtctatgc tgactccttt   1200
gtgattaggg gagatgaggt gagacagatt gcccctggac aaacaggcaa gattgctgac   1260
tacaactaca aactgcctga tgacttcaca ggctgtgtga ttgcctggaa cagcaacaac   1320
ctggacagca aggtgggagg caactacaac tacctctaca gactgttcag gaagagcaac   1380
ctgaaaccat ttgagaggga catcagcaca gagatttacc aggctggcag cacaccatgt   1440
aatggagtgg agggcttcaa ctgttacttt ccactccaat cctatggctt ccaaccaacc   1500
aatggagtgg gctaccaacc atacaggtg tggtgctgt cctttgaact gctccatgcc   1560
cctgccacag tgtgtggacc aaagaagagc accaacctgg tgaagaacaa gtgtgtgaac   1620
ttcaacttca atggactgac aggcacagga gtgctgacag agagcaacaa gaagttcctg   1680
ccattccaac agtttggcag ggacattgct gacaccacag atgctgtgag ggacccacag   1740
accttggaga ttctggacat cacaccatgt tcctttggag gagtgtctgt gattacacct   1800
ggcaccaaca ccagcaacca ggtggctgtg ctctaccagg atgtgaactg tactgaggtg   1860
cctgtggcta tccatgctga ccaacttaca ccaacctgga gggtctacag cacaggcagc   1920
aatgtgttcc agaccagggc tggctgtctg attggagcag agcatgtgaa caactcctat   1980
gagtgtgaca tcccaattgg agcaggcatc tgtgcctcct accagaccca gaccaacagc   2040
ccaaggaggg caaggtctgt ggcaagccag agcatcattg cctacacaat gagtctggga   2100
gcagagaact ctgtggctta cagcaacaac agcattgcca tcccaaccaa cttcaccatc   2160
tctgtgacca cagagattct gcctgtgagt atgaccaaga cctctgtgga ctgtacaatg   2220
tatatctgtg gagacagcac agagtgtagc aacctgctgc tccaatatgg ctccttctgt   2280
acccaactta cagggctct gacaggcatt gctgtggaac aggacaagaa cacccaggag   2340
gtgtttgccc aggtgaagca gatttacaag acacctccaa tcaaggactt ggaggcttc   2400
aacttcagcc agattctgcc tgacccaagc aagccaagca gaggtccctt cattgaggac   2460
ctgctgttca caaggtgac cctggctgat gctggcttca tcaagcaata tggagactgt   2520
ctgggagaca ttgctgccag ggacctgatt tgtgcccaga gttcaatgg actgacagtg   2580
ctgcctccac tgctgacaga tgagatgatt gcccaataca cctctgccct gctggctggc   2640
accatcacct ctggctggac ctttggagca ggagcagccc tccaaatccc atttgctatg   2700
cagatggctt acaggttcaa tggcattgga gtgacccaga atgtgctcta tgagaaccag   2760
aaactgattg ccaaccagtt caactctgcc attggcaaga ttcaggactc cctgtccagc   2820
acagcctctg ccctgggcaa actccaagat gtggtgaacc agaatgccca ggctctgaac   2880
accctggtga agcaacttc cagcaacttt ggagccatct cctctgtgct gaatgacatc   2940
ctgagcagac tggacaaggt ggaggctgag gtccagattg acagactgat tacaggcaga   3000
ctccaatccc tccaaaccta tgtgacccaa caacttatca ggctgctga gattagggca   3060
tctgccaacc tggctgccac caagatgagt gagtgtgtgc tgggacaaag caagagggtg   3120
gacttctgtg gcaagggcta ccacctgatg agttttccac agtctgcccc tcatggagtg   3180
gtgttcctgc atgtgaccta tgtgcctgcc caggagaaga acttcaccac agcccctgcc   3240
```

```
atctgccatg atggcaaggc tcactttcca agggagggag tgtttgtgag caatggcacc      3300
cactggtttg tgacccagag gaacttctat gaaccacaga ttatcaccac agacaacacc      3360
tttgtgtctg gcaactgtga tgtggtgatt ggcattgtga acaacacagt ctatgaccca      3420
ctccaacctg aactggactc cttcaaggag gaactggaca atacttcaa gaaccacacc       3480 agccctgatg tggacctggg agacatctct ggcatcaatg cctctgtggt gaacatccag      3540
aaggagattg acagactgaa tgaggtggct aagaacctga atgagtccct gattgacctc      3600
caagaactgg gcaaatatga acaatacatc aagtggccat ggtacatctg gctgggcttc      3660
attgctggac tgattgccat tgtgatggtg accataatgc tgtgttgtat gacctcctgt      3720
tgttcctgtc tgaaaggctg ttgttcctgt ggctcctgtt gtaag                      3765
```

<210> SEQ ID NO 72
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: IL-2 Signal Sequence

<400> SEQUENCE: 72

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 73
<211> LENGTH: 60
<212> TYPE: DNA
<213> ORGANISM: Homo sapiens
<220> FEATURE:
<221> NAME/KEY: misc_feature
<222> LOCATION: (1)..(60)
<223> OTHER INFORMATION: Polynucleotide Encoding IL-2 Signal Sequence

<400> SEQUENCE: 73

```
atgtacagga tgcaactcct gtcttgcatt gcactaagtc ttgcacttgt cacaaacagt      60
```

<210> SEQ ID NO 74
<211> LENGTH: 18
<212> TYPE: DNA
<213> ORGANISM: Artificial Sequence
<220> FEATURE:
<223> OTHER INFORMATION: Polynucleotide Complementary to Polynucleotide
      That Encodes a Tetracysteine Peptide

<400> SEQUENCE: 74

```
gcaacaacct ggacagca                                                    18
```

<210> SEQ ID NO 75
<211> LENGTH: 6
<212> TYPE: PRT
<213> ORGANISM: Artificial Sequence
<220> FEATURE:
<223> OTHER INFORMATION: Tetracysteine Peptide

<400> SEQUENCE: 75

```
Cys Cys Pro Gly Cys Cys
1               5
```

<210> SEQ ID NO 76
<211> LENGTH: 98

```
<212> TYPE: DNA
<213> ORGANISM: Lentivirus
<220> FEATURE:
<221> NAME/KEY: misc_feature
<222> LOCATION: (1)..(98)
<223> OTHER INFORMATION: Lentiviral LTR R Region

<400> SEQUENCE: 76
gggtctctct ggttagacca gatctgagcc tgggagctct ctggctaact agggaaccca    60
ctgcttaagc ctcaataaag cttgccttga gtgcttca                           98

<210> SEQ ID NO 77
<211> LENGTH: 83
<212> TYPE: DNA
<213> ORGANISM: Lentivirus
<220> FEATURE:
<221> NAME/KEY: misc_feature
<222> LOCATION: (1)..(83)
<223> OTHER INFORMATION: Lentiviral U5 LTR Region

<400> SEQUENCE: 77
agtagtgtgt gcccgtctgt tgtgtgactc tggtaactag agatccctca gaccctttta    60
gtcagtgtgg aaaatctcta gca                                           83

<210> SEQ ID NO 78
<211> LENGTH: 419
<212> TYPE: PRT
<213> ORGANISM: SARS-CoV-2
<220> FEATURE:
<221> NAME/KEY: MISC_FEATURE
<222> LOCATION: (1)..(419)
<223> OTHER INFORMATION: SARS-CoV-2 Nucleocapsid (N) Protein

<400> SEQUENCE: 78
```

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

```
Arg Met Ala Gly Asn Gly Gly Asp Ala Ala Leu Ala Leu Leu Leu Leu
        210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
                260                 265                 270

Ala Phe Gly Arg Arg Gly Pro Glu Gln Thr Gln Gly Asn Phe Gly Asp
            275                 280                 285

Gln Glu Leu Ile Arg Gln Gly Thr Asp Tyr Lys His Trp Pro Gln Ile
        290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
                340                 345                 350

Leu Asn Lys His Ile Asp Ala Tyr Lys Thr Phe Pro Pro Thr Glu Pro
            355                 360                 365

Lys Lys Asp Lys Lys Lys Lys Ala Asp Glu Thr Gln Ala Leu Pro Gln
        370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 79
<211> LENGTH: 1257
<212> TYPE: DNA
<213> ORGANISM: SARS-CoV-2
<220> FEATURE:
<221> NAME/KEY: misc_feature
<222> LOCATION: (1)..(1257)
<223> OTHER INFORMATION: Polynucleotide Encoding SARS-CoV-2 Nucleocapsid
      (N) Protein

<400> SEQUENCE: 79
atgtctgata atggacccca aaatcagcga atgcacccc gcattacgtt tggtggaccc      60
tcagattcaa ctggcagtaa ccagaatgga gaacgcagtg gggcgcgatc aaaacaacgt    120
cggccccaag gtttacccaa taatactgcg tcttggttca ccgctctcac tcaacatggc    180
aaggaagacc ttaaattccc tcaggacaa ggcgttccaa ttaacaccaa tagcagtcca    240
gatgaccaaa ttggctacta ccgaagagct accagacgaa ttcgtggtgg tgacggtaaa    300
atgaaagatc tcagtccaag atggtatttc tactacctag aactgggcc agaagctgga    360 cttccctatg gtgctaacaa agacggcatc atatgggttg caactgaggg agccttgaat    420
acaccaaaag atcacattgg cacccgcaat cctgctaaca atgctgcaat cgtgctacaa    480
cttcctcaag gaacaacatt gccaaaaggc ttctacgcag aagggagcag aggcggcagt    540
caagcctctt ctcgttcctc atcacgtagt cgcaacagtt caagaaattc aactccaggc    600
agcagtaggg gaacttctcc tgctagaatg gctggcaatg gcggtgatgc tgctcttgct    660
ttgctgctgc ttgacagatt gaaccagctt gagagcaaaa tgtctggtaa aggccaacaa    720
```

```
caacaaggcc aaactgtcac taagaaatct gctgctgagg cttctaagaa gcctcggcaa      780
aaacgtactg ccactaaagc atacaatgta acacaagctt tcggcagacg tggtccagaa      840
caaacccaag gaaattttgg ggaccaggaa ctaatcagac aaggaactga ttacaaacat      900
tggccgcaaa ttgcacaatt tgccccagc gcttcagcgt tcttcggaat gtcgcgcatt       960
ggcatggaag tcacaccttc gggaacgtgg ttgacctaca caggtgccat caaattggat     1020
gacaaagatc caatttcaa agatcaagtc attttgctga ataagcatat tgacgcatac     1080
aaaacattcc caccaacaga gcctaaaaag gacaaaaaga gaaggctga tgaaactcaa      1140 gccttaccgc agagacagaa gaaacagcaa actgtgactc ttcttcctgc tgcagatttg     1200 gatgattttct ccaaacaatt gcaacaatcc atgagcagtg ctgactcaac tcaggcc      1257
```

<210> SEQ ID NO 80
<211> LENGTH: 1257
<212> TYPE: DNA
<213> ORGANISM: Artificial Sequence
<220> FEATURE:
<223> OTHER INFORMATION: Codon-Optimized Polynucleotide Encoding
      SARS-CoV-2 Nucleocapsid (N) Protein

<400> SEQUENCE: 80

```
atgtctgata atggaccaca aaaccagcgc aatgctccga ggataacatt cggtgggccc       60
tccgactcta ctggaagcaa tcaaaatggg gagcggtcag gagccaggtc taaacgagg      120 cgacctcagg ggctgcctaa taatactgcc agctggttca ctgctctgac ccagcatggc     180
aaggaggact tgaagttccc cagggtcag ggtgtaccaa tcaacactaa ttcttcccca      240
gacgaccaga ttggttatta cagaagggct acccggagga ttaggggagg ggatggcaag    300
atgaaggatc ttagtccacg ctggtatttt tactacctg gtacaggacc agaggctgga     360
cttccttatg gagcaaacaa agatggaatc atctgggtgg ccacggaggg agccctcaat    420
accccaaaag accatatcgg gacccggaac cccgccaata atgccgcgat agtactgcaa    480
ttgccccaag ggactactct gccaaaaggc ttttatgcag aagggtctcg aggagggtct    540
caggcctcca gtcgctcatc ttcccggtcc agaaacagca gccggaattc cacacccggg    600
agtagcagag cactagcccc tgcacgaatg ctggcaatg aggagatgc cgcccttgca     660 ctgctgcttc tggatcgcct gaaccagttg gagtccaaaa tgagtggcaa ggggcagcaa   720
cagcagggcc agacagtcac caagaagtct gccgcagaag cttccaaaaa gccaaggcag  780
aagaggacag caactaaagc ttataacgtg acgcaggctt tcggtaggcg gggaccagaa    840
cagacccagg gtaacttcgg cgatcaggag cttattagac aggggacaga ctataaacac   900 tggcccaga tcgcccaatt tgccccccagt gcatccgcct tcttcgggat gagtagaatc    960
ggcatggagg tgactcctag tggcacgtgg ctcacctata ccggcgctat caagcttgat   1020
gacaaagatc taatttcaa agatcaggtc atactgctga ataagcacat tgacgcatac    1080
aaaacctttc ccctaccga accgaagaag acaagaaga aaaaggccga tgagacgcaa    1140
gctctgcctc agaggcagaa gaaacagcaa acagtcactc tgttgcctgc ggcggacctt   1200
gatgactttt ctaaacagct gcagcagagt atgagcagcg ccgactccac ccaggcg      1257
```

<210> SEQ ID NO 81
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)

<223> OTHER INFORMATION: IgGk Signal Sequence

<400> SEQUENCE: 81

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 82
<211> LENGTH: 66
<212> TYPE: DNA
<213> ORGANISM: Homo sapiens
<220> FEATURE:
<221> NAME/KEY: misc_feature
<222> LOCATION: (1)..(66)
<223> OTHER INFORMATION: Polynucleotide Encoding IgGk Signal Sequence

<400> SEQUENCE: 82

```
atggacatga gggtccctgc tcagctcctg gggctcctgc tgctctggct ctcaggtgcc      60
agatgt                                                                 66
```

<210> SEQ ID NO 83
<211> LENGTH: 11381
<212> TYPE: DNA
<213> ORGANISM: Artificial Sequence
<220> FEATURE:
<223> OTHER INFORMATION: pLenti-IgG?-nCoV-Spike-CD8-TM (-att) Vector

<400> SEQUENCE: 83

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360 ccccccgccca ttgacgtcaa taatgacgta tgttcccata gtaacgccaa tagggacttt     420
ccattgacgt caatgggtgg agtatttacg gtaaactgcc cacttggcag tacatcaagt     480
gtatcatatg ccaagtacgc ccctattga cgtcaatgac ggtaaatggc ccgcctggca     540
ttatgcccag tacatgacct tatgggactt tcctacttgg cagtacatct acgtattagt     600
catcgctatt accatggtga tgcggttttg gcagtacatc aatgggcgtg gatagcggtt     660
tgactcacgg ggatttccaa gtctccaccc cattgacgtc aatgggagtt tgttttggca     720
ccaaaatcaa cgggactttc caaaatgtcg taacaactcc gccccattga cgcaaatggg     780
cggtaggcgt gtacggtggg aggtctatat aagcagcgcg ttttgcctgt actgggtctc     840
tctggttaga ccagatctga gcctgggagc tctctggcta actagggaac ccactgctta     900
agcctcaata aagcttgcct tgagtgcttc aagtagtgtg tgcccgtctg ttgtgtgact     960
ctggtaacta gagatccctc agacccttt agtcagtgtg aaaatctct aggtggcgcc    1020 cgaacaggga cttgaaagcg aaagggaaac cagaggagct ctctcgacgc aggactcggc    1080
ttgctgaagc gcgcacggca agaggcgagg ggcggcgact ggtgagtacg ccaaaaattt    1140
tgactagcgg aggctagaag gagagagatg ggtgcgagag cgtcagtatt aagcggggga    1200
gaattagatc gcgatgggaa aaaattcggt taaggccagg gggaaagaaa aaatataaat    1260
taaaacatat agtatgggca agcagggagc tagaacgatt cgcagttaat cctggcctgt    1320
```

```
tagaaacatc agaaggctgt agacaaatac tgggacagct acaaccatcc cttcagacag   1380
gatcagaaga acttagatca ttatataata cagtagcaac cctctattgt gtgcatcaaa   1440
ggatagagat aaaagacacc aaggaagctt tagacaagat agaggaagag caaaacaaaa   1500
gtaagaccac cgcacagcaa gcggccggcc gctgatcttc agacctggag gaggagatat   1560
gagggacaat tggagaagtg aattatataa atataaagta gtaaaaattg aaccattagg   1620
agtagcaccc accaaggcaa agagaagagt ggtgcagaga gaaaaagag cagtgggaat   1680 aggagctttg ttccttgggt tcttgggagc agcaggaagc actatgggcg cagcgtcaat   1740
gacgctgacg gtacaggcca gacaattatt gtctggtata gtgcagcagc agaacaattt   1800
gctgagggct attgaggcgc aacagcatct gttgcaactc acagtctggg gcatcaagca   1860
gctccaggca agaatcctgg ctgtggaaag atacctaaag gatcaacagc tcctggggat   1920
ttggggttgc tctggaaaac tcatttgcac cactgctgtg ccttggaatg ctagttggag   1980
taataaatct ctggaacaga tttggaatca cacgacctgg atggagtggg acagagaaat   2040
taacaattac acaagcttaa tacactcctt aattgaagaa tcgcaaaacc agcaagaaaa   2100
gaatgaacaa gaattattgg aattagataa atgggcaagt ttgtggaatt ggtttaacat   2160
aacaaattgg ctgtggtata taaaattatt cataatgata gtaggaggct tggtaggttt   2220
aagaatagtt tttgctgtac tttctatagt gaatagagtt aggcagggat attcaccatt   2280
atcgtttcag acccacctcc caaccccgag gggacccgac aggcccgaag gaatagaaga   2340
agaaggtgga gagagagaca gagacagatc cattcgatta gtgaacggat cggcactgcg   2400
tgcgccaatt ctgcagacaa atggcagtat tcatccacaa ttttaaaaga aaggggggga   2460
ttggggggta cagtgcaggg gaaagaatag tagacataat agcaacagac atacaaacta   2520
aagaattaca aaacaaatt acaaaaattc aaaattttcg ggtttattac agggacagca   2580
gagatccagt ttggttagta ccgggcccgc tctagacatg tccaatatga ccgccatgtt   2640
gacattgatt attgactagt tattaatagt aatcaattac ggggtcatta gttcatagcc   2700
catatatgga gttccgcgtt acataactta cggtaaatgg cccgcctggc tgaccgccca   2760
acgacccccg cccattgacg tcaataatga cgtatgttcc catagtaacg ccaatagggac   2820 ctttccattg acgtcaatgg gtggagtatt tacggtaaac tgcccacttg gcagtacatc   2880
aagtgtatca tatgccaagt ccgccccta ttgacgtcaa tgacggtaaa tggcccgcct   2940
ggcattatgc ccagtacatg accttacggg actttcctac ttggcagtac atctacgtat   3000
tagtcatcgc tattaccatg gtgatgcggt tttggcagta caccaatggg cgtggatagc   3060
ggtttgactc acggggattt ccaagtctcc accccattga cgtcaatggg agtttgtttt   3120
ggcaccaaaa tcaacgggac tttccaaaat gtcgtaataa ccccgccccg ttgacgcaaa   3180
tgggcggtag gcgtgtacgg tgggaggtct atataagcag agctcgttta gtgaaccgtc   3240
agatttttgt aatacgactc actatagggc ggccgggaat tcgtcgactg ccccccccc   3300 taacgttact ggccgaagcc gcttggaata aggccggtgt gcgtttgtct atatgttatt   3360
ttccaccata ttgccgtctt ttggcaatgt gagggcccgg aaacctggcc ctgtcttctt   3420
gacgagcatt cctaggggtc tttccctct cgccaaagga atgcaaggtc tgttgaatgt   3480
cgtgaaggaa gcagttcctc tggaagcttc ttgaagacaa acaacgtctg tagcgaccct   3540
ttgcaggcag cggaaccccc cacctggcga caggtgcctc tgcggccaaa agccacgtgt   3600
ataagataca cctgcaaagg cggcacaacc ccagtgccac gttgtgagtt ggatagttgt   3660
```

```
ggaaagagtc aaatggctct cctcaagcgt attcaacaag gggctgaagg atgcccagaa      3720
ggtaccccat tgtatgggat ctgatctggg gcctcggtgc acatgcttta catgtgttta      3780
gtcgaggtta aaaaacgtct aggccccccg aaccacgggg acgtggtttt cctttgaaaa      3840
acacgatgat aatgatccgg taccgaggag atctgccgcc gcgatcgcca ccatggacat      3900
gagggtccct gctcagctcc tggggctcct gctgctctgg ctctcaggtg ccagatgtat      3960
gtttgtgttc ctggtgctgc tgccactggt gtccagccag tgtgtgaacc tgaccaccag      4020
gacccaactt cctcctgcct acaccaactc cttcaccagg ggagtctact accctgacaa      4080
ggtgttcagg tcctctgtgc tgcacagcac ccaggacctg ttcctgccat tcttcagcaa      4140
tgtgacctgg ttccatgcca tccatgtgtc tggcaccaat ggcaccaaga ggtttgacaa      4200
ccctgtgctg ccattcaatg atggagtcta ctttgccagc acagagaaga gcaacatcat      4260
caggggctgg attttggca ccaccctgga cagcaagacc cagtccctgc tgattgtgaa      4320
caatgccacc aatgtggtga ttaaggtgtg tgagttccag ttctgtaatg acccattcct      4380
gggagtctac taccacaaga caacaagtc ctggatggag tctgagttca gggtctactc      4440
ctctgccaac aactgtacct ttgaatatgt gagccaacca ttcctgatgg acttggaggg      4500
caagcagggc aacttcaaga acctgaggga gtttgtgttc aagaacattg atggctactt      4560
caagatttac agcaaacaca ccaatcaa cctggtgagg gacctgccac agggcttctc      4620
tgccttggaa ccactggtgg acctgccaat tggcatcaac atcaccaggt tccagaccct      4680
gctggctctg cacaggtcct acctgacacc tggagactcc tcctctggct ggacagcagg      4740
agcagcagcc tactatgtgg gctacctcca accaaggacc ttcctgctga aatacaatga      4800
gaatggcacc atcacagatg ctgtggactg tgccctggac ccactgtctg agaccaagtg      4860
taccctgaaa tccttcacag tggagaaggg catctaccag accagcaact tcagggtcca      4920
accaacagag agcattgtga ggtttccaaa catcaccaac ctgtgtccat tggagaggt      4980 gttcaatgcc accaggtttg cctctgtcta tgcctggaac aggaagagga ttagcaactg      5040
tgtggctgac tactctgtgc tctacaactc tgcctccttc agcaccttca gtgttatgg      5100 agtgagccca accaaactga atgacctgtg tttcaccaat gtctatgctg actccttgt      5160 gattagggga gatgaggtga gacagattgc ccctggacaa acaggcaaga ttgctgacta      5220
caactacaaa ctgcctgatg acttcacagg ctgtgtgatt gcctggaaca gcaacaacct      5280
ggacagcaag gtgggaggca actacaacta cctctacaga ctgttcagga gagcaacct      5340 gaaaccattt gagagggaca tcagcacaga gatttaccag gctggcagca ccatgtaa      5400 tggagtggag ggcttcaact gttactttcc actccaatcc tatggcttcc aaccaaccaa      5460
tggagtgggc taccaaccat acaggtggt ggtgctgtcc tttgaactgc tccatgcccc      5520
tgccacagtg tgtggaccaa agaagagcac caacctggtg aagaacaagt gtgtgaactt      5580
caacttcaat ggactgacag gcacaggagt gctgacagag agcaacaaga agttcctgcc      5640
attccaacag tttggcaggg acattgctga caccacagat gctgtgaggg acccacagac      5700
cttggagatt ctggacatca ccatgttcc ctttggagga gtgtctgtga ttacacctgg      5760
caccaacacc agcaaccagg tggctgtgct ctaccaggat gtgaactgta ctgaggtgcc      5820
tgtggctatc catgctgacc aacttacacc aacctggagg gtctacagca caggcagcaa      5880
tgtgttccag accagggctg gctgtctgat tggagcagag catgtgaaca actcctatga      5940
gtgtgacatc ccaattggag caggcatctg tgcctcctac cagacccaga ccaacagccc      6000 aaggaggca aggtctgtgg caagccagag catcattgcc tacacaatga gtctgggagc      6060
```

```
agagaactct gtggcttaca gcaacaacag cattgccatc ccaaccaact tcaccatctc    6120
tgtgaccaca gagattctgc ctgtgagtat gaccaagacc tctgtggact gtacaatgta    6180
tatctgtgga gacagcacag agtgtagcaa cctgctgctc caatatggct ccttctgtac    6240
ccaacttaac agggctctga caggcattgc tgtggaacag gacaagaaca cccaggaggt    6300
gtttgcccag gtgaagcaga tttacaagac acctccaatc aaggactttg gaggcttcaa    6360
cttcagccag attctgcctg acccaagcaa gccaagcaag aggtccttca ttgaggacct    6420
gctgttcaac aaggtgaccc tggctgatgc tggcttcatc aagcaatatg gagactgtct    6480
gggagacatt gctgccaggg acctgatttg tgcccagaag ttcaatggac tgacagtgct    6540
gcctccactg ctgacagatg agatgattgc caatacacc tctgccctgc tggctggcac    6600
catcacctct ggctggacct ttggagcagg agcagccctc caaatcccat ttgctatgca    6660
gatggcttac aggttcaatg gcattggagt gacccagaat gtgctctatg agaaccagaa    6720
actgattgcc aaccagttca actctgccat tggcaagatt caggactccc tgtccagcac    6780
agcctctgcc ctgggcaaac tccaagatgt ggtgaaccag aatgcccagg ctctgaacac    6840
cctggtgaag caacttttcca gcaactttgg agccatctcc tctgtgctga atgacatcct    6900
gagcagactg gacaaggtgg aggctgaggt ccagattgac agactgatta caggcagact    6960
ccaatccctc caaacctatg tgacccaaca acttatcagg gctgctgaga ttagggcatc    7020
tgccaacctg gctgccacca gatgagtgaa gtgtgtgctg ggacaaagca agagggtgga    7080
cttctgtggc aagggctacc acctgatgag ttttccacag tctgcccctc atggagtggt    7140
gttcctgcat gtgacctatg tgcctgccca ggagaagaac ttcaccacag cccctgccat    7200
ctgccatgat ggcaaggctc actttccaag ggagggagtg tttgtgagca atggcaccca    7260
ctggtttgtg acccagagga acttctatga accacagatt atcaccacag acaacacctt    7320
tgtgtctggc aactgtgatg tggtgattgg cattgtgaac aacacagtct atgacccact    7380
ccaacctgaa ctggactcct tcaaggagga actggacaaa tacttcaaga accacaccag    7440
ccctgatgtg gacctgggag acatctctgg catcaatgcc tctgtggtga acatccagaa    7500
ggagattgac agactgaatg aggtggctaa gaacctgaat gagtccctga ttgacctcca    7560
agaactgggc aaatatgaac aatacatcaa gtggccatgg tacatctggc tgggcttcat    7620
tgctggactg attgccattg tgatggtgac cataatgctg tgttgtatga cctcctgttg    7680
ttcctgtctg aaaggctgtt gttcctgtgg ctcctgttgt aagtttgatg aggatgactc    7740
tgaacctgtg ctgaaaggag tgaaactgca ctacaccgcc ctgagcaact ccatcatgta    7800
cttcagccac ttcgtgccgg tcttcctgcc agcgaagccc accacgacgc cagcgccgcg    7860
accaccaaca ccggcgccca ccatcgcgtc gcagcccctg tccctgcgcc cagaggcgtg    7920
ccggccagcg gcggggggcg cagtgcacac gaggggctg gacttcgcct gtgatatcta    7980
catctgggcg cccttggccg ggacttgtgg ggtccttctc ctgtcactgg ttatcacctg    8040
aacgcgtacg cggccgctcg agcagaaact catctcagaa gaggatctgg cagcaaatga    8100
tatcctggat tacaaggatg acgacgataa ggtttaaacg gccggccgcg gtctgtacaa    8160
gtaggattcg tcgagggacc taataacttc gtatagcata cattatacga agttatacat    8220
gtttaagggt tccggttcca ctaggtacaa ttcgatatca agcttatcga taatcaacct    8280
ctggattaca aaatttgtga aagattgact ggtattctta actatgttgc tccttttacg    8340
ctatgtggat acgctgcttt aatgcctttg tatcatgcta ttgcttcccg tatggctttc    8400
```

-continued

```
attttctcct ccttgtataa atcctggttg ctgtctcttt atgaggagtt gtggcccgtt    8460
gtcaggcaac gtggcgtggt gtgcactgtg tttgctgacg caaccccac tggttggggc     8520 attgccacca cctgtcagct cctttccggg actttcgctt tcccctccc tattgccacg     8580 gcggaactca tcgccgcctg ccttgccgc tgctggacag gggctcggct gttgggcact    8640
gacaattccg tggtgttgtc ggggaaatca tcgtcctttc cttggctgct cgcctgtgtt    8700
gccacctgga ttctgcgcgg gacgtccttc tgctacgtcc cttcggccct caatccagcg    8760
gaccttcctt cccgcggcct gctgccggct ctgcggcctc ttccgcgtct tcgccttcgc    8820
cctcagacga gtcggatctc cctttgggcc gcctccccgc atcgataccg tcgacctcga    8880
tcgagaccta gaaaaacatg gagcaatcac aagtagcaat acagcagcta ccaatgctga    8940
ttgtgcctgg ctagaagcac aagaggagga ggaggtgggt tttccagtca cacctcaggt    9000
acctttaaga ccaatgactt acaaggcagc tgtagatctt agccactttt taaaagaaaa    9060 gggggggacga agggctaatt cactcccaac gaagacaaga tctgcttgat ctgtggatct    9120
accacacaca aggctacttc cctgattggc agaactacac accagggcca gggatcagat    9180
atccactgac ctttggatgg tgctacaagc tagtaccagt tgagcaagag aaggtagaag    9240
aagccaatga aggagagaac acccgcttgt tacaccctgt gagcctgcat gggatggatg    9300
acccggagag agaagtatta gagtggaggt ttgacagccg cctagcattt catcacatgg    9360
cccgagagct gcatccggac tgtactgggt ctctctggtt agaccagatc tgagcctggg    9420
agctctctgg ctaactaggg aacccactgc ttaagcctca ataaagcttg ccttgagtgc    9480
ttcaagtagt gtgtgcccgt ctgttgtgtg actctggtaa ctagagatcc ctcagaccct    9540
tttagtcagt gtggaaaatc tctagcagca tgtgagcaaa aggccagcaa aaggccagga    9600
accgtaaaaa ggccgcgttg ctggcgtttt tccataggct ccgcccccct gacgagcatc    9660
acaaaaatcg acgctcaagt cagaggtggc gaaacccgac aggactataa agataccagg    9720
cgtttccccc tggaagctcc ctcgtgcgct ctcctgttcc gaccctgccg cttaccggat    9780
acctgtccgc ctttctccct tcgggaagcg tggcgctttc tcatagctca cgctgtaggt    9840
atctcagttc ggtgtaggtc gttcgctcca agctgggctg tgtgcacgaa ccccccgttc    9900
agcccgaccg ctgcgcctta tccggtaact atcgtcttga gtccaacccg gtaagacacg    9960
acttatcgcc actggcagca gccactggta acaggattag cagagcgagg tatgtaggcg   10020
gtgctacaga gttcttgaag tggtggccta actacggcta cactagaaga acagtatttg   10080
gtatctgcgc tctgctgaag ccagttacct tcggaaaaag agttggtagc tcttgatccg   10140
gcaaacaaac caccgctggt agcggtggtt tttttgtttg caagcagcag attacgcgca   10200
gaaaaaaagg atctcaagaa gatcctttga tcttttctac ggggtctgac gctcagtgga   10260
acgaaaactc acgttaaggg attttggtca tgagattatc aaaaaggatc ttcacctaga   10320
tccttttaaa ttaaaaatga agttttaaat caatctaaag tatatatgag taaacttggt   10380
ctgacagtta ccaatgctta atcagtgagg cacctatctc agcgatctgt ctatttcgtt   10440
catccatagt tgcctgactc cccgtcgtgt agataactac gatacgggag ggcttaccat   10500
ctggccccag tgctgcaatg ataccgcgag acccacgctc accggctcca gatttatcag   10560
caataaacca gccagccgga agggccgagc gcagaagtgg tcctgcaact ttatccgcct   10620
ccatccagtc tattaattgt tgccgggaag ctagagtaag tagttcgcca gttaatagtt   10680
tgcgcaacgt tgttgccatt gctacaggca tcgtggtgtc acgctcgtcg tttggtatgg   10740
cttcattcag ctccggttcc caacgatcaa ggcgagttac atgatccccc atgttgtgca   10800
```

```
aaaaagcggt tagctccttc ggtcctccga tcgttgtcag aagtaagttg gccgcagtgt    10860
tatcactcat ggttatggca gcactgcata attctcttac tgtcatgcca tccgtaagat    10920
gcttttctgt gactggtgag tactcaacca agtcattctg agaatagtgt atgcggcgac    10980
cgagttgctc ttgcccggcg tcaatacggg ataataccgc gccacatagc agaactttaa    11040
aagtgctcat cattggaaaa cgttcttcgg ggcgaaaact ctcaaggatc ttaccgctgt    11100
tgagatccag ttcgatgtaa cccactcgtg cacccaactg atcttcagca tcttttactt    11160
tcaccagcgt ttctgggtga gcaaaaacag gaaggcaaaa tgccgcaaaa aagggaataa    11220
gggcgacacg gaaatgttga atactcatac tcttcctttt tcaatattat tgaagcattt    11280
atcagggtta ttgtctcatg agcggataca tatttgaatg tatttagaaa aataaacaaa    11340 tagggggtccc gcgcacattt ccccgaaaag tgccacctga c                       11381

<210> SEQ ID NO 84
<211> LENGTH: 8819
<212> TYPE: DNA
<213> ORGANISM: Artificial Sequence
<220> FEATURE:
<223> OTHER INFORMATION: pLenti-IgG?-nCoV-N-CD8-TM (-att) Vector

<400> SEQUENCE: 84
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360 ccccccgccca ttgacgtcaa taatgacgta tgttcccata gtaacgccaa tagggacttt     420
ccattgacgt caatgggtgg agtatttacg gtaaactgcc cacttggcag tacatcaagt     480
gtatcatatg ccaagtacgc ccctattga cgtcaatgac ggtaaatggc ccgcctggca     540
ttatgcccag tacatgacct tatgggactt tcctacttgg cagtacatct acgtattagt     600
catcgctatt accatggtga tgcggttttg gcagtacatc aatgggcgtg atagcggtt     660 tgactcacgg ggatttccaa gtctccaccc cattgacgtc aatgggagtt tgttttggca     720
ccaaaatcaa cgggactttc caaaatgtcg taacaactcc gccccattga cgcaaatggg     780
cggtaggcgt gtacggtggg aggtctatat aagcagcgcg ttttgcctgt actgggtctc     840
tctggttaga ccagatctga gcctgggagc tctctggcta actagggaac ccactgctta     900
agcctcaata aagcttgcct tgagtgcttc aagtagtgtg tgcccgtctg ttgtgtgact     960
ctggtaacta gagatccctc agaccctttt agtcagtgtg aaaatctct aggtggcgcc    1020 cgaacaggga cttgaaagcg aaagggaaac cagaggagct ctctcgacgc aggactcggc    1080
ttgctgaagc gcgcacggca agaggcgagg ggcggcgact ggtgagtacg ccaaaaattt    1140
tgactagcgg aggctagaag gagagagatg ggtgcgagag cgtcagtatt aagcggggga    1200
gaattagatc gcgatgggaa aaaattcggt taaggccagg gggaaagaaa aaatataaat    1260
taaaacatat agtatgggca agcagggagc tagaacgatt cgcagttaat cctggcctgt    1320
tagaaacatc agaaggctgt agacaaatac tgggacagct acaaccatcc cttcagacag    1380
gatcagaaga acttagatca ttatataata cagtagcaac cctctattgt gtgcatcaaa    1440
```

```
ggatagagat aaaagacacc aaggaagctt tagacaagat agaggaagag caaaacaaaa   1500
gtaagaccac cgcacagcaa gcggccggcc gctgatcttc agacctggag gaggagatat   1560
gagggacaat tggagaagtg aattatataa atataaagta gtaaaaattg aaccattagg   1620
agtagcaccc accaaggcaa agagaagagt ggtgcagaga gaaaaaagag cagtgggaat   1680
aggagctttg ttccttgggt tcttgggagc agcaggaagc actatgggcg cagcgtcaat   1740
gacgctgacg gtacaggcca gacaattatt gtctggtata gtgcagcagc agaacaattt   1800
gctgagggct attgaggcgc aacagcatct gttgcaactc acagtctggg gcatcaagca   1860
gctccaggca agaatcctgg ctgtggaaag atacctaaag gatcaacagc tcctggggat   1920
ttggggttgc tctggaaaac tcatttgcac cactgctgtg ccttggaatg ctagttggag   1980
taataaatct ctggaacaga tttggaatca cacgacctgg atggagtggg acagagaaat   2040
taacaattac acaagcttaa tacactcctt aattgaagaa tcgcaaaacc agcaagaaaa   2100
gaatgaacaa gaattattgg aattagataa atgggcaagt ttgtggaatt ggtttaacat   2160
aacaaattgg ctgtggtata taaaattatt cataatgata gtaggaggct tggtaggttt   2220
aagaatagtt tttgctgtac tttctatagt gaatagagtt aggcagggat attcaccatt   2280
atcgtttcag acccacctcc caaccccgag gggacccgac aggcccgaag gaatagaaga   2340
agaaggtgga gagagagaca gagacagatc cattcgatta gtgaacggat cggcactgcg   2400
tgcgccaatt ctgcagacaa atggcagtat tcatccacaa ttttaaaaga aaaggggggga   2460 ttggggggta cagtgcaggg gaaagaatag tagacataat agcaacagac atacaaacta   2520
aagaattaca aaaacaaatt acaaaaattc aaaattttcg ggtttattac agggacagca   2580
gagatccagt ttggttagta ccgggcccgc tctagacatg tccaatatga ccgccatgtt   2640
gacattgatt attgactagt tattaatagt aatcaattac gggtcatta gttcatagcc   2700 catatatgga gttccgcgtt acataactta cggtaaatgg cccgcctggc tgaccgccca   2760 acgaccccg cccattgacg tcaataatga cgtatgttcc catagtaacg ccaatagggga   2820 ctttccattg acgtcaatgg gtggagtatt tacggtaaac tgcccacttg gcagtacatc   2880
aagtgtatca tatgccaagt ccgccccccta ttgacgtcaa tgacggtaaa tggcccgcct   2940
ggcattatgc ccagtacatg accttacggg actttcctac ttggcagtac atctacgtat   3000
tagtcatcgc tattaccatg gtgatgcggt tttggcagta caccaatggg cgtggatagc   3060
ggtttgactc acggggattt ccaagtctcc accccattga cgtcaatggg agtttgtttt   3120
ggcaccaaaa tcaacgggac tttccaaaat gtcgtaataa ccccgccccg ttgacgcaaa   3180
tgggcggtag gcgtgtacgg tgggaggtct atataagcag agctcgttta gtgaaccgtc   3240
agaattttgt aatacgactc actatagggc ggcgggaat tcgtcgactg ccccccccccc   3300 taacgttact ggccgaagcc gcttggaata aggccggtgt gcgtttgtct atatgttatt   3360
ttccaccata ttgccgtctt ttggcaatgt gagggcccgg aaacctggcc ctgtcttctt   3420
gacgagcatt cctaggggtc tttccccctct cgccaaagga atgcaaggtc tgttgaatgt   3480
cgtgaaggaa gcagttcctc tggaagcttc ttgaagacaa acaacgtctg tagcgaccct   3540
ttgcaggcag cggaaccccc cacctggcga caggtgcctc tgcggccaaa agccacgtgt   3600
ataagataca cctgcaaagg cggcacaacc ccagtgccac gttgtgagtt ggatagttgt   3660
ggaaagagtc aaatggctct cctcaagcgt attcaacaag ggctgaagg atgcccagaa   3720 ggtacccat tgtatgggat ctgatctggg gcctcggtgc acatgcttta catgtgttta   3780
gtcgaggtta aaaaacgtct aggccccccg aaccacgggg acgtggtttt cctttgaaaa   3840
```

```
acacgatgat aatgatccgg taccgaggag atctgccgcc gcgatcgcca ccatggacat   3900
gagggtccct gctcagctcc tggggctcct gctgctctgg ctctcaggtg ccagatgtat   3960
gtctgataat ggaccccaaa atcagcgaaa tgcaccccgc attacgtttg gtggaccctc   4020
agattcaact ggcagtaacc agaatggaga acgcagtggg gcgcgatcaa acaacgtcg    4080 gccccaaggt ttacccaata atactgcgtc ttggttcacc gctctcactc aacatggcaa   4140
ggaagacctt aaattccctc gaggacaagg cgttccaatt aacaccaata gcagtccaga   4200
tgaccaaatt ggctactacc gaagagctac cagacgaatt cgtggtggtg acggtaaaat   4260
gaaagatctc agtccaagat ggtatttcta ctacctagga actgggccag aagctggact   4320
tccctatggt gctaacaaag acggcatcat atgggttgca actgagggag ccttgaatac   4380
accaaaagat cacattggca cccgcaatcc tgctaacaat gctgcaatcg tgctacaact   4440
tcctcaagga acaacattgc caaaaggctt ctacgcagaa gggagcagag gcggcagtca   4500
agcctcttct cgttcctcat cacgtagtcg caacagttca agaaattcaa ctccaggcag   4560
cagtagggga acttctcctg ctagaatggc tggcaatggc ggtgatgctg ctcttgcttt   4620
gctgctgctt gacagattga accagcttga gagcaaaatg tctggtaaag ccaacaaca   4680 acaaggccaa actgtcacta agaaatctgc tgctgaggct tctaagaagc ctcggcaaaa   4740
acgtactgcc actaaagcat acaatgtaac acaagctttc ggcagacgtg gtccagaaca   4800
aacccaagga aattttgggg accaggaact aatcagacaa ggaactgatt acaaacattg   4860
gccgcaaatt gcacaatttg cccccagcgc ttcagcgttc ttcggaatgt cgcgcattgg   4920
catggaagtc acaccttcgg gaacgtggtt gacctacaca ggtgccatca aattggatga   4980
caaagatcca aatttcaaag atcaagtcat tttgctgaat aagcatattg acgcatacaa   5040
aacattccca ccaacagagc ctaaaaagga caaaaagaag aaggctgatg aaactcaagc   5100
cttaccgcag agacagaaga acagcaaac tgtgactctt cttcctgctg cagatttgga   5160
tgatttctcc aaacaattgc aacaatccat gagcagtgct gactcaactc aggccgccct   5220
gagcaactcc atcatgtact tcagccactt cgtgccggtc ttcctgccag cgaagcccac   5280
cacgacgcca gcgccgcgac caccaacacc ggcgcccacc atcgcgtcgc agcccctgtc   5340
cctgcgccca gaggcgtgcc ggccagcggc gggggcgca gtgcacacga ggggctgga   5400 cttcgcctgt gatatctaca tctgggcgcc cttggccggg acttgtgggg tccttctcct   5460
gtcactggtt atcacctgaa cgcgtacgcg gccgctcgag cagaaactca tctcagaaga   5520
ggatctggca gcaaatgata tcctggatta caaggatgac gacgataagg tttaaacggc   5580
cggccgcggt ctgtacaagt aggattcgtc gagggaccta ataacttcgt atagcataca   5640
ttatacgaag ttatacatgt ttaagggttc cggttccact aggtacaatt cgatatcaag   5700
cttatcgata atcaacctct ggattacaaa atttgtgaaa gattgactgg tattcttaac   5760
tatgttgctc cttttacgct atgtggatac gctgctttaa tgcctttgta tcatgctatt   5820
gcttcccgta tggctttcat tttctcctcc ttgtataaat cctggttgct gtctctttat   5880
gaggagttgt ggcccgttgt caggcaacgt ggcgtggtgt gcactgtgtt tgctgacgca   5940
acccccactg gttggggcat tgccaccacc tgtcagctcc tttccgggac tttcgctttc   6000
cccctcccta ttgccacggc ggaactcatc gccgcctgcc ttgcccgctg ctggacaggg   6060
gctcggctgt tgggcactga caattccgtg gtgttgtcgg ggaaatcatc gtcctttcct   6120
tggctgctcg cctgtgttgc cacctggatt ctgcgcggga cgtccttctg ctacgtccct   6180
```

```
tcggccctca atccagcgga ccttccttcc cgcggcctgc tgccggctct gcggcctctt    6240
ccgcgtcttc gccttcgccc tcagacgagt cggatctccc tttgggccgc ctccccgcat    6300
cgataccgtc gacctcgatc gagacctaga aaacatggag gcaatcacaa gtagcaatac    6360
agcagctacc aatgctgatt gtgcctggct agaagcacaa gaggaggagg aggtgggttt    6420
tccagtcaca cctcaggtac ctttaagacc aatgacttac aaggcagctg tagatcttag    6480
ccacttttta aaagaaaagg ggggacgaag ggctaattca ctcccaacga agacaagatc    6540
tgcttgatct gtggatctac cacacacaag gctacttccc tgattggcag aactacacac    6600
cagggccagg gatcagatat ccactgacct ttggatggtg ctacaagcta gtaccagttg    6660
agcaagagaa ggtagaagaa gccaatgaag gagagaacac ccgcttgtta cccctgtga    6720
gcctgcatgg gatggatgac ccggagagag aagtattaga gtggaggttt gacagccgcc    6780
tagcatttca tcacatggcc cgagagctgc atccggactg tactgggtct ctctggttag    6840
accagatctg agcctgggag ctctctggct aactagggaa cccactgctt aagcctcaat    6900
aaagcttgcc ttgagtgctt caagtagtgt gtgcccgtct gttgtgtgac tctggtaact    6960
agagatccct cagacccttt tagtcagtgt ggaaaatctc tagcagcatg tgagcaaaag    7020
gccagcaaaa ggccaggaac cgtaaaaagg ccgcgttgct ggcgttttc cataggctcc    7080
gcccccctga cgagcatcac aaaaatcgac gctcaagtca gaggtggcga acccgacag    7140
gactataaag ataccaggcg tttccccctg gaagctccct cgtgcgctct cctgttccga    7200
ccctgccgct taccggatac ctgtccgcct ttctcccttc gggaagcgtg gcgctttctc    7260
atagctcacg ctgtaggtat ctcagttcgg tgtaggtcgt tcgctccaag ctgggctgtg    7320
tgcacgaacc ccccgttcag cccgaccgct gcgccttatc cggtaactat cgtcttgagt    7380
ccaacccggt aagacacgac ttatcgccac tggcagcagc cactggtaac aggattagca    7440
gagcgaggta tgtaggcggt gctacagagt tcttgaagtg gtggcctaac tacggctaca    7500
ctagaagaac agtatttggt atctgcgctc tgctgaagcc agttaccttc ggaaaaagag    7560
ttggtagctc ttgatccggc aaacaaacca ccgctggtag cggtggtttt tttgtttgca    7620
agcagcagat tacgcgcaga aaaaaaggat ctcaagaaga tcctttgatc ttttctacgg    7680
ggtctgacgc tcagtggaac gaaaactcac gttaagggat tttggtcatg agattatcaa    7740
aaaggatctt cacctagatc cttttaaatt aaaaatgaag ttttaaatca atctaaagta    7800
tatatgagta aacttggtct gacagttacc aatgcttaat cagtgaggca cctatctcag    7860
cgatctgtct atttcgttca tccatagttg cctgactccc cgtcgtgtag ataactacga    7920
tacgggaggg cttaccatct ggccccagtg ctgcaatgat accgcgagac ccacgctcac    7980
cggctccaga tttatcagca ataaaccagc cagccggaag ggccgagcgc agaagtggtc    8040
ctgcaacttt atccgcctcc atccagtcta ttaattgttg ccgggaagct agagtaagta    8100
gttcgccagt taatagtttg cgcaacgttg ttgccattgc tacaggcatc gtggtgtcac    8160
gctcgtcgtt tggtatggct tcattcagct ccggttccca acgatcaagg cgagttacat    8220
gatccccat gttgtgcaaa aaagcggtta gctccttcgg tcctccgatc gttgtcagaa    8280
gtaagttggc cgcagtgtta tcactcatgg ttatggcagc actgcataat tctcttactg    8340
tcatgccatc cgtaagatgc ttttctgtga ctggtgagta ctcaaccaag tcattctgag    8400
aatagtgtat gcggcgaccg agttgctctt gcccggcgtc aatacgggat aataccgcgc    8460
cacatagcag aactttaaaa gtgctcatca ttggaaaacg ttcttcgggg cgaaaactct    8520
caaggatctt accgctgttg agatccagtt cgatgtaacc cactcgtgca cccaactgat    8580
```

```
cttcagcatc ttttactttc accagcgttt ctgggtgagc aaaaacagga aggcaaaatg    8640
ccgcaaaaaa gggaataagg gcgacacgga aatgttgaat actcatactc ttccttttc     8700 aatattattg aagcatttat cagggttatt gtctcatgag cggatacata tttgaatgta    8760
tttagaaaaa taaacaaata ggggtcccgc gcacatttcc ccgaaaagtg ccacctgac     8819
```

<210> SEQ ID NO 85
<211> LENGTH: 10
<212> TYPE: DNA
<213> ORGANISM: Artificial Sequence
<220> FEATURE:
<223> OTHER INFORMATION: Kozak Consensus Sequence for Strong Initiation
      of Translation

<400> SEQUENCE: 85

```
gccaccatgg                                                              10
```